US007910315B2

(12) United States Patent
Modiano et al.

(10) Patent No.: US 7,910,315 B2
(45) Date of Patent: Mar. 22, 2011

(54) EARLY DETECTION OF HEMANGIOSARCOMA AND ANGIOSARCOMA

(75) Inventors: Jaime F. Modiano, Littleton, CO (US); Stuart C. Helfand, Madison, WI (US)

(73) Assignee: The Regents of the University of Colorado, a body corporate, Boulder, CO (US)

( * ) Notice: Subject to any disclaimer, the term of this patent is extended or adjusted under 35 U.S.C. 154(b) by 599 days.

(21) Appl. No.: 11/662,529

(22) PCT Filed: Sep. 9, 2005

(86) PCT No.: PCT/US2005/031753

§ 371 (c)(1), (2), (4) Date: Oct. 25, 2007

(87) PCT Pub. No.: WO2006/031524

PCT Pub. Date: Mar. 23, 2006

(65) Prior Publication Data

US 2008/0050730 A1 Feb. 28, 2008

Related U.S. Application Data

(60) Provisional application No. 60/608,745, filed on Sep. 10, 2004.

(51) Int. Cl.
*G01N 33/53* (2006.01)
*G01N 33/574* (2006.01)
*C12Q 1/68* (2006.01)

(52) U.S. Cl. .............................. 435/7.1; 435/6; 435/7.23

(58) Field of Classification Search ......................... None
See application file for complete search history.

(56) References Cited

U.S. PATENT DOCUMENTS 7,354,729 B2 * 4/2008 Rich .................................. 435/8
2002/0009759 A1 1/2002 Terstappen et al.

FOREIGN PATENT DOCUMENTS

WO WO 03/037172 A2 5/2003
WO WO 03/095977 A2 11/2003
WO WO 2005/043121 A2 5/2005

OTHER PUBLICATIONS

Arber et al. American Journal of Surgical Pathology. 1997. vol. 21, No. 7; p. 827-835 (IDS).*
Tockman et al (Cancer Res., 1992, 52:2711s-2718s).*
Kern et al (Cytometry Part B, Clinical Cytometry, 2003, 55B:29-36).*
Escribano et al (Analyitical Cellular Pathology, 1998, 16:151-159).*
Paietta et al (Cytometry Part B, Clinical Cytometry, 2004, 59B:1-9).*
Arber et al., "Splenic vascular tumors: A histologic, immunophenotypic, and virologic study", *American Journal of Surgical Pathology*, 21:827-835 (1997).
Breiteneder-Geleff et al., "Angiosarcomas express mixed endothelial phenotypes of blood and lymphatic capillaries", *American Journal of Pathology*, 154:385-394 (1999).
Brown et al., "Canine hemangiosarcoma: retrospective analysis of 104 cases", *J. Am. Vet. Med. Assoc.*, 186:56-58 (1985).
Budd G. T., "Management of angiosarcoma", *Curr. Oncol. Rep.*, 4:515-519 (2002).
Clifford et al., "Treatment of canine hemangiosarcoma: 2000 and beyond", *J. Vet. Intern. Med.*, 14:479-485 (2000).
Del Papa et al., "Circulating endothelial cells as a marker of ongoing vascular disease in systemic sclerosis", *Arthritis & Rheumatism*, 50:1296-1304 (2004).
Eghbali-Fatourechi et al., "Circulating osteoblast-lineage cells in humans", *N. Engl J. Med*, 352:1959-1966 (2005).
Fedok et al., "Angiosarcoma: current review", *Am J. Otolaryngol.*, 20:223-231 (1999).
Fosmire et al., "Canine malignant hemangiosarcoma as a model of primitive angiogenic endothelium", *Laboratory Investigation*, 84:562-572 (2004).
Hai et al., "Primary splenic angiosarcoma: case report and literature review", *J. Natl. Med. Assoc.*, 92:143-146 (2000).
Hur et al., "Characterization of two types of endothelial progenitor cells and their different contributions to neovasculogenesis", *Arterioscler Thromb Vasc Biol.*, 24:288-293 (2004).
Khan et al., "Detection of circulating endothelial cells and endothelial progenitor cells by flow cytometry", *Cytometry Part B (Clinical Cytometry)*, 64B:1-8 (2005).
Liu et al., "Changes in cell surface molecules associated with in vitro culture of prostatic stromal cells", *The Prostate*, 45:303-312 (2000).
Martin-Padura et al., "Expression of VE (vascular endothelial)-cadherin and other endothelial-specific markers in haemangiomas", *Journal of Pathology*, 175:51-57 (1995).
Oksanen A., "Hemangiosarcoma in dogs", *J. Comp. Pathol.*, 88:585-595 (1978).
PCT International Search Report and Written Opinion mailed Mar. 11, 2008 for PCT/US05/31753.
Poblet et al., "Different immunoreactivity of endothelial markers in well and poorly differentiated areas of angiosarcomas", *Virchows Arch*, 428:217-221 (1996).
Shaw et al., "Hemapoietic stem cells and endothelial cell precursors express Tie-2, CD31 and CD45", *Blood Cells, Molecules, & Diseases*, 32:168-175 (2004).
Sorenmo et al., "Canine hemangiosarcoma treated with standard chemotherapy and minocycline", *J. Vet. Intern. Med.*, 14:395-398 (2000).
Sorenmo et al., "Chemotherapy of canine hemangiosarcoma with doxorubicin and cyclophosphamide", *J. Vet. Intern. Med.*, 7:370-376 (1993).
Weiss DJ., "Flow Cytometric evaluation of hemophagocytic disorders in canine bone marrow", *Veterinary Clinical Pathology*, 31:36-41 (2002).

* cited by examiner

*Primary Examiner* — Laura B Goddard
(74) *Attorney, Agent, or Firm* — Kilpatrick Townsend & Stockton LLP

(57) ABSTRACT

A variety of methods, compositions and kits are provided for the early detection, diagnosis and treatment of hemangiosarcoma in dogs and angiosarcomas in humans.

14 Claims, 7 Drawing Sheets

Fig. 5A Splenic Hematoma
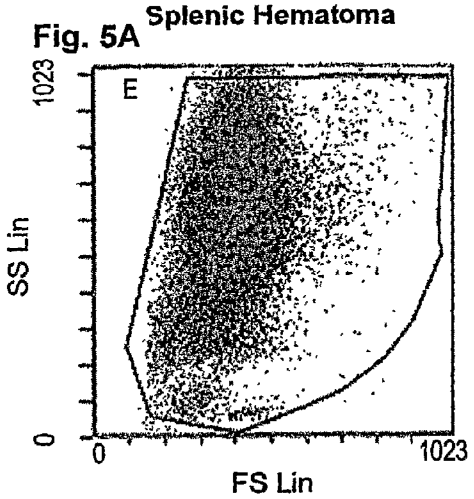
Fig. 5D Hemangiosarcoma
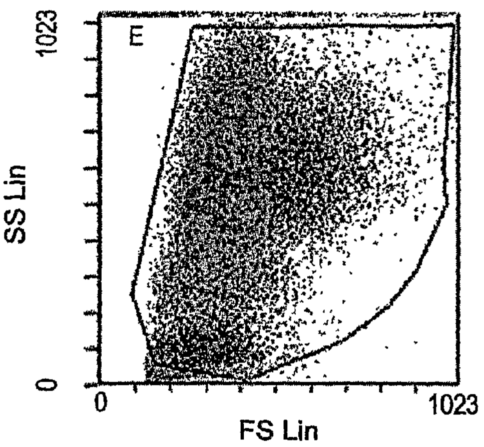
Fig. 5B
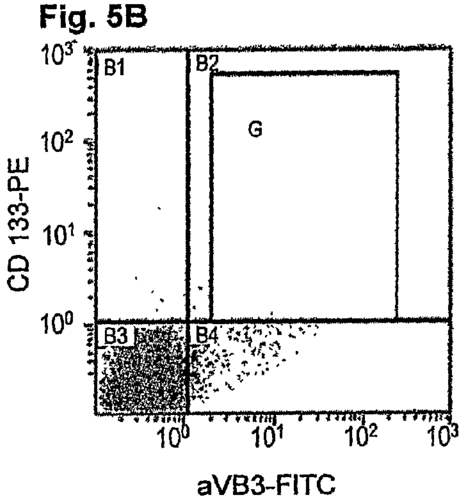
Fig. 5E
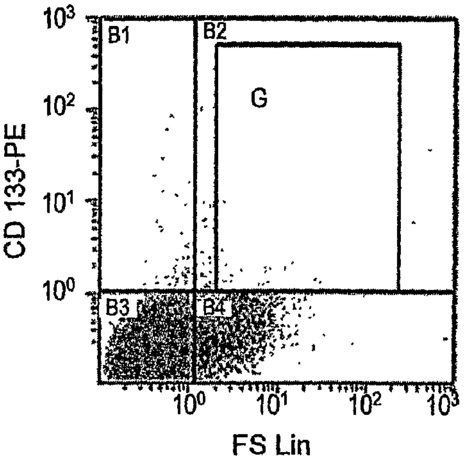
Fig. 5C
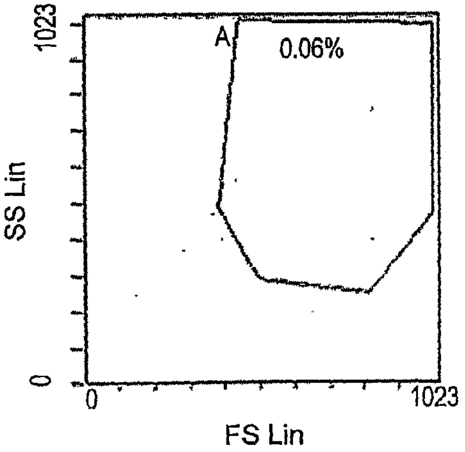
Fig. 5F
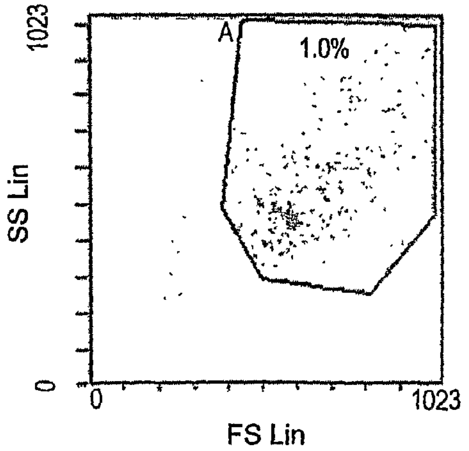

```
                          SEQUENCE LISTING

<160> NUMBER OF SEQ ID NOS: 45

<210> SEQ ID NO 1
<211> LENGTH: 3154
<212> TYPE: DNA
<213> ORGANISM: Canis familiaris

<400> SEQUENCE: 1

gagctcagag tctatcgcag ccaccgcgat gagaggcgct cgcggcgcct gggattttct     60

ctgcgtcctg ctcctgctgc tgctgctcgg cgtccggaca ggctcttctc aaccatctgt    120

gagtccaggg gaaccgtctc tcccatccat ccatccagca aaatcagagt taatagtcag    180

tgtcggcgac gagcttaggc tgtcctgcac cgacccagga tttgtcaagt ggactttga    240

gaccctgggt caactgaatg agaacacaca caacgaatgg atcacagaga aggcagaggc    300

tggccacacg ggcaattaca cgtgcaccaa cagagatggc ttgagcaggt ccatttatgt    360

gtttgtcaga gatcctgcaa agcttttcct cgttgacctt cccttgtatg ggaaagaagg    420

caatgatacg ctggtccgct gccctctgac ggacccagaa gtgaccaatt actccctcag    480

ggggtgcgag gggaagcctc ttcccaagga cttgacgttc gtcgctgatc ccaaagctgg    540

catcacgatc agaaacgtga agcgcgagta tcatcggctc tgcttgcact gctctgcgga    600

ccagaagggc aggacggtgc tgtccaagaa attcaccctg aaagtgaggg cagccatcag    660

agctgtacca gttgtgtcag tatccaaaac aagctctctc ctgaaggaag gggaagcctt    720

ctctgtgatg tgctttataa aagatgtgtc tagtttcgtg gactcgatgt ggataaagga    780

gaacagccag cagactaatg cacagacaca gagtaatagc tggcatcatg gtgacttcaa    840

ttttgaacgt caggaaaagt tgattatcag ctcagcaaga gttaatgatt ctggagtgtt    900

catgtgttac gccaataata cttttggatc agcaaatgtc acaacaacct tggaagtagt    960

agataaagga ttcattaata tcttccccat gatgagtact acaatatttg taaatgatgg   1020

acagaatgtg gatctgattg ttgaatatga ggcatatccc aaaccggagc accagcagtg   1080

gatctatatg aacagaacct tcactgataa atgggaagat tatcccaagt ctgacaatga   1140

aagtaatatc agatatgtga gtgaacttca tctaaccaga ttaaaaggga acgaaggagg   1200

cacttacaca tttcaagtgt ccaattccga tgtcaattct tcggtgacat ttaatgttta   1260

tgtgaacaca aaaccagaaa tcctgactca tgaaagtctc acgaatggca tgctccagtg   1320

tgtggttgca ggattcccag agcccgcagt aggttggtat ttctgtccag gagctgagca   1380

gagatgttct gtccctattg ggccaatgga tgtgcagatg caaaactcgt ctctgtcacc   1440

gtctggaaaa ctagtggttc agagttccat cgattatagt gccttcaagc acaatggcac   1500
```

-continued agtcgagtgt agggcttaca acaatgtagg caggagttct gccttttta actttgcatt 1560 taaagaacaa atccatcccc acaccctgtt cacacctttg ctgattggct ttgtgatcgc 1620
agctggaatg atgtgcatta tcgtgatgat tcttacctac aagtatctac agaaacccat 1680
gtatgaagta cagtggaagg ttgttgagga gatcaatgga aacaattatg tttacataga 1740
cccaacacag cttccttacg atcacaaatg ggagtttccc agaaacaggc tgagctttgg 1800
gaaaactttg ggtgctggtg ccttcgggaa agtggttgaa gccaccgcat atggcctgat 1860
taagtcggat gcggccatga ctgttgccgt taagatgctc aaaccaagtg cccatttaac 1920
cgaacgagaa gccctaatgt ctgagctcaa agtcttgagt tacctcggta atcatatgaa 1980
tattgtgaat cttcttggag cgtgcaccgt tggagggccc accttggtca ttacagaata 2040
ttgttgctat ggtgatcttt tgaatttttt gcgaaggaaa cgtgattcat ttatttgctc 2100
aaagcaggaa gatcacggag aagtggcact ttataagaac cttctgcatt caaaggagtc 2160
ttcctgcagt gacagtacta atgaatacat ggacatgaaa cccggcgttt cttacgttgt 2220
gccaaccaag gcagacaaaa ggagatctgc gagaataggc tcatacatag aaagggatgt 2280
gactcctgcc atcatggaag atgatgagtt ggctctagat ctagaggact tgctgagctt 2340
ttcttaccag gtggccaagg gtatggcatt cctggcctcg aagaattgta ttcacagaga 2400
cttggctgct agaaatatcc tccttactca tggtcgaatc acaaagattt gtgattttgg 2460
tctagccaga gacatcaaga atgattctaa ttatgtggtc aaaggaaacg ctcggctacc 2520
tgtgaagtgg atggcccctg agagcatttt caactgtgtg tacacatttg aaagtgatgt 2580
ctggtcctat gggatttttc tgtgggagct cttctcttta ggaagcagcc cctaccctgg 2640
gatgccagtc gattcaaagt tctacaagat gatcaaggaa gggttccgga tgctcagccc 2700
tgagcatgca cctgctgaaa tgtatgacat catgaagacg tgctgggatg ctgatcccct 2760
gaaaaggccg acgttcaagc agatcgtgca gctaattgag aagcagattt cagatagcac 2820
caatcatatt tattccaacc tcgcgaactg cagccccaac ccagagcgcc ccgtggtgga 2880
ccattccgtg cggatcaatt ccgtgggcag cagcgcgtct tccacccagc ctctgctggt 2940
acacgaagat gtgtgaagca ggaggagtgc cgggggtctc cccaacaaga gcgatccctg 3000
ttcttttggt tcctatactg gttattctgt cctccttcgg cttgcatcct attccagggt 3060
agcggacacc cctctgtccc tccctcttta cgagcacacc ctaattagtg gccagtgact 3120
tttgtcatca gccaccatcc tattgcaaag gttc 3154

<210> SEQ ID NO 2
<211> LENGTH: 975
<212> TYPE: PRT
<213> ORGANISM: Canis familiaris

<400> SEQUENCE: 2

Met Arg Gly Ala Arg Gly Ala Trp Asp Phe Leu Cys Val Leu Leu Leu
1 5 10 15

Leu Leu Leu Leu Gly Val Arg Thr Gly Ser Ser Gln Pro Ser Val Ser
20 25 30

Pro Gly Glu Pro Ser Leu Pro Ser Ile His Pro Ala Lys Ser Glu Leu
35 40 45

Ile Val Ser Val Gly Asp Glu Leu Arg Leu Ser Cys Thr Asp Pro Gly
50 55 60

Phe Val Lys Trp Thr Phe Glu Thr Leu Gly Gln Leu Asn Glu Asn Thr
65 70 75 80

His Asn Glu Trp Ile Thr Glu Lys Ala Glu Ala Gly His Thr Gly Asn

-continued

```
                85                  90                  95

Tyr Thr Cys Thr Asn Arg Asp Gly Leu Ser Arg Ser Ile Tyr Val Phe
            100                 105                 110

Val Arg Asp Pro Ala Lys Leu Phe Leu Val Asp Leu Pro Leu Tyr Gly
        115                 120                 125

Lys Glu Gly Asn Asp Thr Leu Val Arg Cys Pro Leu Thr Asp Pro Glu
    130                 135                 140

Val Thr Asn Tyr Ser Leu Arg Gly Cys Glu Gly Lys Pro Leu Pro Lys
145                 150                 155                 160

Asp Leu Thr Phe Val Ala Asp Pro Lys Ala Gly Ile Thr Ile Arg Asn
                165                 170                 175

Val Lys Arg Glu Tyr His Arg Leu Cys Leu His Cys Ser Ala Asp Gln
            180                 185                 190

Lys Gly Arg Thr Val Leu Ser Lys Lys Phe Thr Leu Lys Val Arg Ala
        195                 200                 205

Ala Ile Arg Ala Val Pro Val Val Ser Val Ser Lys Thr Ser Ser Leu
    210                 215                 220

Leu Lys Glu Gly Glu Ala Phe Ser Val Met Cys Phe Ile Lys Asp Val
225                 230                 235                 240

Ser Ser Phe Val Asp Ser Met Trp Ile Lys Glu Asn Ser Gln Gln Thr
                245                 250                 255

Asn Ala Gln Thr Gln Ser Asn Ser Trp His His Gly Asp Phe Asn Phe
            260                 265                 270

Glu Arg Gln Glu Lys Leu Ile Ile Ser Ser Ala Arg Val Asn Asp Ser
        275                 280                 285

Gly Val Phe Met Cys Tyr Ala Asn Asn Thr Phe Gly Ser Ala Asn Val
    290                 295                 300

Thr Thr Thr Leu Glu Val Val Asp Lys Gly Phe Ile Asn Ile Phe Pro
305                 310                 315                 320

Met Met Ser Thr Thr Ile Phe Val Asn Asp Gly Gln Asn Val Asp Leu
                325                 330                 335

Ile Val Glu Tyr Glu Ala Tyr Pro Lys Pro Glu His Gln Gln Trp Ile
            340                 345                 350

Tyr Met Asn Arg Thr Phe Thr Asp Lys Trp Glu Asp Tyr Pro Lys Ser
        355                 360                 365

Asp Asn Glu Ser Asn Ile Arg Tyr Val Ser Glu Leu His Leu Thr Arg
    370                 375                 380

Leu Lys Gly Asn Glu Gly Gly Thr Tyr Thr Phe Gln Val Ser Asn Ser
385                 390                 395                 400

Asp Val Asn Ser Ser Val Thr Phe Asn Val Tyr Val Asn Thr Lys Pro
                405                 410                 415

Glu Ile Leu Thr His Glu Ser Leu Thr Asn Gly Met Leu Gln Cys Val
            420                 425                 430

Val Ala Gly Phe Pro Glu Pro Ala Val Gly Trp Tyr Phe Cys Pro Gly
        435                 440                 445

Ala Glu Gln Arg Cys Ser Val Pro Ile Gly Pro Met Asp Val Gln Met
    450                 455                 460

Gln Asn Ser Ser Leu Ser Pro Ser Gly Lys Leu Val Val Gln Ser Ser
465                 470                 475                 480

Ile Asp Tyr Ser Ala Phe Lys His Asn Gly Thr Val Glu Cys Arg Ala
                485                 490                 495

Tyr Asn Asn Val Gly Arg Ser Ser Ala Phe Phe Asn Phe Ala Phe Lys
            500                 505                 510
```

-continued

```
Glu Gln Ile His Pro His Thr Leu Phe Thr Pro Leu Leu Ile Gly Phe
        515                 520                 525

Val Ile Ala Ala Gly Met Met Cys Ile Ile Val Met Ile Leu Thr Tyr
    530                 535                 540

Lys Tyr Leu Gln Lys Pro Met Tyr Glu Val Gln Trp Lys Val Val Glu
545                 550                 555                 560

Glu Ile Asn Gly Asn Asn Tyr Val Tyr Ile Asp Pro Thr Gln Leu Pro
                565                 570                 575

Tyr Asp His Lys Trp Glu Phe Pro Arg Asn Arg Leu Ser Phe Gly Lys
            580                 585                 590

Thr Leu Gly Ala Gly Ala Phe Gly Lys Val Val Glu Ala Thr Ala Tyr
        595                 600                 605

Gly Leu Ile Lys Ser Asp Ala Ala Met Thr Val Ala Val Lys Met Leu
    610                 615                 620

Lys Pro Ser Ala His Leu Thr Glu Arg Glu Ala Leu Met Ser Glu Leu
625                 630                 635                 640

Lys Val Leu Ser Tyr Leu Gly Asn His Met Asn Ile Val Asn Leu Leu
                645                 650                 655

Gly Ala Cys Thr Val Gly Gly Pro Thr Leu Val Ile Thr Glu Tyr Cys
            660                 665                 670

Cys Tyr Gly Asp Leu Leu Asn Phe Leu Arg Arg Lys Arg Asp Ser Phe
        675                 680                 685

Ile Cys Ser Lys Gln Glu Asp His Gly Glu Val Ala Leu Tyr Lys Asn
    690                 695                 700

Leu Leu His Ser Lys Glu Ser Ser Cys Ser Asp Ser Thr Asn Glu Tyr
705                 710                 715                 720

Met Asp Met Lys Pro Gly Val Ser Tyr Val Val Pro Thr Lys Ala Asp
                725                 730                 735

Lys Arg Arg Ser Ala Arg Ile Gly Ser Tyr Ile Glu Arg Asp Val Thr
            740                 745                 750

Pro Ala Ile Met Glu Asp Asp Glu Leu Ala Leu Asp Leu Glu Asp Leu
        755                 760                 765

Leu Ser Phe Ser Tyr Gln Val Ala Lys Gly Met Ala Phe Leu Ala Ser
    770                 775                 780

Lys Asn Cys Ile His Arg Asp Leu Ala Ala Arg Asn Ile Leu Leu Thr
785                 790                 795                 800

His Gly Arg Ile Thr Lys Ile Cys Asp Phe Gly Leu Ala Arg Asp Ile
                805                 810                 815

Lys Asn Asp Ser Asn Tyr Val Val Lys Gly Asn Ala Arg Leu Pro Val
            820                 825                 830

Lys Trp Met Ala Pro Glu Ser Ile Phe Asn Cys Val Tyr Thr Phe Glu
        835                 840                 845

Ser Asp Val Trp Ser Tyr Gly Ile Phe Leu Trp Glu Leu Phe Ser Leu
    850                 855                 860

Gly Ser Ser Pro Tyr Pro Gly Met Pro Val Asp Ser Lys Phe Tyr Lys
865                 870                 875                 880

Met Ile Lys Glu Gly Phe Arg Met Leu Ser Pro Glu His Ala Pro Ala
                885                 890                 895

Glu Met Tyr Asp Ile Met Lys Thr Cys Trp Asp Ala Asp Pro Leu Lys
            900                 905                 910

Arg Pro Thr Phe Lys Gln Ile Val Gln Leu Ile Glu Lys Gln Ile Ser
        915                 920                 925

Asp Ser Thr Asn His Ile Tyr Ser Asn Leu Ala Asn Cys Ser Pro Asn
    930                 935                 940
```

-continued

Pro Glu Arg Pro Val Val Asp His Ser Val Arg Ile Asn Ser Val Gly
945 950 955 960

Ser Ser Ala Ser Ser Thr Gln Pro Leu Leu Val His Glu Asp Val
965 970 975

<210> SEQ ID NO 3
<211> LENGTH: 2952
<212> TYPE: DNA
<213> ORGANISM: Homo sapiens

<400> SEQUENCE: 3
gatcccatcg cagctaccgc gatgagaggc gctcgcggcg cctgggattt tctctgcgtt 60
ctgctcctac tgcttcgcgt ccagacaggc tcttctcaac catctgtgag tccaggggaa 120
ccgtctccac catccatcca tccaggaaaa tcagacttaa tagtccgcgt gggcgacgag 180
attaggctgt tatgcactga tccgggcttt gtcaaatgga cttttgagat cctggatgaa 240
acgaatgaga ataagcagaa tgaatggatc acggaaaagg cagaagccac caacaccggc 300
aaatacacgt gcaccaacaa acacggctta agcaattcca tttatgtgtt tgttagagat 360
cctgccaagc ttttccttgt tgaccgctcc ttgtatggga aagaagacaa cgacacgctg 420
gtccgctgtc ctctcacaga cccagaagtg accaattatt ccctcaaggg gtgccagggg 480
aagcctcttc ccaaggactt gaggtttatt cctgacccca aggcgggcat catgatcaaa 540
agtgtgaaac gcgcctacca tcggctctgt ctgcattgtt ctgtggacca ggagggcaag 600
tcagtgctgt cggaaaaatt catcctgaaa gtgaggccag ccttcaaagc tgtgcctgtt 660
gtgtctgtgt ccaaagcaag ctatcttctt agggaagggg aagaattcac agtgacgtgc 720
acaataaaag atgtgtctag ttctgtgtac tcaacgtgga aaagagaaaa cagtcagact 780
aaactacagg agaaatataa tagctggcat cacggtgact tcaattatga acgtcaggca 840
acgttgacta tcagttcagc gagagttaat gattctggag tgttcatgtg ttatgccaat 900
aatacttttg gatcagcaaa tgtcacaaca accttggaag tagtagataa aggattcatt 960
aatatcttcc ccatgataaa cactacagta tttgtaaacg atggagaaaa tgtagatttg 1020
attgttgaat atgaagcatt ccccaaacct gaacaccagc agtggatcta tatgaacaga 1080
accttcactg ataaatggga agattatccc aagtctgaga atgaaagtaa tatcagatac 1140
gtaagtgaac ttcatctaac gagattaaaa ggcaccgaag gaggcactta cacattccta 1200
gtgtccaatt ctgacgtcaa tgctgccata gcatttaatg tttatgtgaa tacaaaacca 1260
gaaatcctga cttacgacag gctcgtgaat ggcatgctcc aatgtgtggc agcaggattc 1320
ccagagccca caatagattg gtatttttgt ccaggaactg agcagagatg ctctgcttct 1380
gtactgccag tggatgtgca gacactaaac tcatctgggc caccgtttgg aaagctagtg 1440
gttcagagtt ctatagattc tagtgcattc aagcacaatg gcacggttga atgtaaggct 1500
tacaacgatg tgggcaagac ttctgcctat tttaactttg catttaaagg taacaacaaa 1560
gagcaaatcc atccccacac cctgttcact cctttgctga ttggtttcgt aatcgtagct 1620
ggcatgatgt gcattattgt gatgattctg acctacaaat atttacagaa acccatgtat 1680
gaagtacagt ggaaggttgt tgaggagata aatggaaaca attatgttta catagaccca 1740
acacaacttc cttatgatca caaatgggag tttcccagaa acaggctgag ttttgggaaa 1800
accctgggtg ctggagcttt cgggaaggtt gttgaggcaa ctgcttatgg cttaattaag 1860
tcagatgcgg ccatgactgt cgctgtaaag atgctcaagc cgagtgccca tttgacagaa 1920
cgggaagccc tcatgtctga actcaaagtc ctgagttacc ttggtaatca catgaatatt 1980
gtgaatctac ttggagcctg caccattgga gggcccaccc tggtcattac agaatattgt 2040
tgctatggtg atcttttgaa tttttgaga agaaaacgtg attcatttat ttgttcaaag 2100
caggaagatc atgcagaagc tgcactttat aagaatcttc tgcattcaaa ggagtcttcc 2160
tgcagcgata gtactaatga gtacatggac atgaaacctg gagtttctta tgttgtccca 2220
accaaggccg acaaaaggag atctgtgaga ataggctcat acatagaaag agatgtgact 2280
cccgccatca tggaggatga cgagttggcc ctagacttag aagacttgct gagcttttct 2340
taccaggtgg caaagggcat ggctttcctc gcctccaaga attgtattca cagagacttg 2400
gcagccagaa atatcctcct tactcatggt cggatcacaa agatttgtga ttttggtcta 2460
gccagagaca tcaagaatga ttctaattat gtggttaaag gaaacgctcg actacctgtg 2520
aagtggatgg cacctgaaag cattttcaac tgtgtataca cgtttgaaag tgacgtctgg 2580
tcctatggga tttttctttg ggagctgttc tctttaggaa gcagccccta tcctggaatg 2640
ccggtcgatt ctaagttcta caagatgatc aaggaaggct tccggatgct cagccctgaa 2700
cacgcacctg ctgaaatgta tgacataatg aagacttgct gggatgcaga tcccctaaaa 2760
agaccaacat tcaagcaaat tgttcagcta attgagaagc agatttcaga gagcaccaat 2820
catatttact ccaacttagc aaactgcagc cccaaccgac agaagcccgt ggtagaccat 2880
tctgtgcgga tcaattctgt cggcagcacc gcttcctcct cccagcctct gcttgtgcac 2940
gacgatgtct ga 2952

<210> SEQ ID NO 4
<211> LENGTH: 976
<212> TYPE: PRT
<213> ORGANISM: Homo sapiens

<400> SEQUENCE: 4

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe

-continued

```
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
    370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
    450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
        515                 520                 525

Phe Val Ile Val Ala Gly Met Met Cys Ile Ile Val Met Ile Leu Thr
    530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
        595                 600                 605

Tyr Gly Leu Ile Lys Ser Asp Ala Ala Met Thr Val Ala Val Lys Met
    610                 615                 620
```

```
Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
        675                 680                 685

Phe Ile Cys Ser Lys Gln Glu Asp His Ala Glu Ala Ala Leu Tyr Lys
    690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
        755                 760                 765

Leu Leu Ser Phe Ser Tyr Gln Val Ala Lys Gly Met Ala Phe Leu Ala
    770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
        835                 840                 845

Glu Ser Asp Val Trp Ser Tyr Gly Ile Phe Leu Trp Glu Leu Phe Ser
    850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
    930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975
```

<210> SEQ ID NO 5
<211> LENGTH: 2956
<212> TYPE: DNA
<213> ORGANISM: Canis familiaris

<400> SEQUENCE: 5

```
cccccctcgg cctccagggc ggcggcaacc ccggcccccg ctcccgtccc ccgcctgcgg      60

ggctgagccg agcgctcgcg gtggcggcgg ccaagcggag gggccggcct tgccaggaac     120

gcggagggag gggtggggag agacagccag ctcgcccacc ccgctccggg cggagggcgg     180
```

-continued agggcggcgg gcggcgggcg gcggcgcgtc ccggggccga gcgcgtctgt ccggagccga 240
gcggagcggc gcgggaagga tgctggcggg caggggcgcg cgcgcgggcg gcgggctgcc 300
gcggggctgg accgcgctct gcctgctcag tctgctgccc tttgggttca caaacacaga 360
aaccgtgatt actcctacca cagtgccaac ctccacagaa ataatgtcag ctgtttctga 420
gaatacatcc aaacgggaag ccatcacact aactccttct ggaactacca ccctgtactc 480
tgtctctcaa gacagcagtg ggaccacagc aaccatctca gagactacag tccatgtcac 540
atctacctct gagatcaccc taacgcctgg gaccatgaac tcttctgttc agtcgcagac 600
ctctttagct atcacggtat cttttacccc aaccaacttt tcaacttcaa gtgtgacctt 660
ggagcccagc ctgctacctg gaaatggttc ggatcccccc tacaacagca ccagccttgt 720
gacatccccc acggaatatt atacatcact ttctcctacc ccaagtagaa atgacacccc 780
aagtaccatc aagggagaaa tcaaatgttc cggagtcaaa gaagtgaaat tgaaccaagg 840
tatctgccta gagctaaatg agacctccag ctgtgaggac tttaagaaag ataacgaaga 900
aaaactgacc caagtcctgt gtgagaagga gccagctgag gctggggccg gggtgtgctc 960
cctgcttctg gcccagtctg aggtgaggcc tcactgcctg ctgctggtct tggccaacaa 1020
aacagaactt ttcagtaaac tccaacttct gagaaagcac cagtctgacc tgaaaaagct 1080
ggggatccga gacttcactg aacaagatgt tgggagccac cagagctatt cccgcaagac 1140
cctgattgca ctggtcacct cagggatcct gctggctgtc ttgggcacca ctggttactt 1200
cctgatgaac cgccgcagtt ggagccctac aggagaaagg ctgggcgaag acccttatta 1260
cacggagaac ggtggaggcc agggctatag ctcaggccct ggggtctccc ctgaggctca 1320
gggaaaggcc agtgtgaacc gtgggcctca ggagaacggg accggccagg ccacgtccag 1380
aaacggccat tcagcaagac aacacatggt ggctgataca gaattgtgac tctggggggg 1440
gagtaaggct gggcagggtc tggggaaggg gcccctccca gcacctgacc acatgctgcc 1500
tctgtgctgg agctgccacc acttacattc tagcctttcc tgctgcacac accctccgag 1560
gccattcctg gggccctgca ctgcaccagg ccgaggggtt ctctccatcc tggggcccgg 1620
gaggtaaccc ctacctttta tacattcatc tcactaagcc tagagtctgg tctcctttga 1680
gaaaagacat gagggagacg tgccaaagta tagagaagct accagagttg ggggggtggg 1740
gggtgatgat ctcacatcat tcacgtgtgg gcttcttccc tcttcctcct ctctgcctta 1800
ttaaaagaac ttccaggggg aagcatggcc ttttctgggc tacaatgtcc tcctgggagg 1860
ctttgtcttt tcctgtgtct tcctcatgtc tgtctcctct actttaggga aaccaaagca 1920
cctgctcctt tgtaatgcta tagccagcaa gacttgttgt cttaaaccgt ctcccttgtg 1980
ctcacaccag ctcactgtgg attcaggcaa ccggcttccc tcatgctctc cgggctccct 2040
gagctccaca ccttctccct gcacctctgt gtacagaagc ctgcactgtt ctctggctga 2100
gcctggaacg agactccaag ttttgaacaa tgtcttgtgt ctatgtttgg gagacagcat 2160
agggatgcgt ggacacatgc gttcctatct ttggggacaa atgaaggaga ggggatggct 2220
cagtccttgt ctctctgggg ctcacagagt ctcatcttgg gcccccgttt ctccctgtga 2280
gtctcagtga acgggaccaa gggaccagat cttggagcca agcctcttga cccatgcacc 2340
tctgaagaag cccctcgctc gaaggctagg tcctggcctt gccctctgat cctgatggct 2400
tcctccttcc tccctctgac tcctgggtga gctgtggact cagactccca gcagactcct 2460
ttctgtctca gcctccccga ccccaacccc ctcactgttc tgtacccccca tatagtcagg 2520 gcccccgaca tctccagagg accttcatca caagccatct cctctgtagg tggcccaggt 2580

-continued

```
tctcatttat tttttaggt attttttttt tccagagggg tgagcagaga tcttggtttc   2640

aatgacggtt ggaaatagaa ctttccagag ataggaagac tgggtggatt ttatttctga   2700

atacaaaaat ggtgtgtgta aatactgtaa ttaaagtgat accgagacac atctgttctg   2760

tgtcgctgcc ccagccaggt gtgtctgaat gccacggcgg tgtccctggt gtcccggtca   2820

gacccggcca gacttcccaa tgatgtggta gagaggggtg accctggaaa gaggtgggcc   2880

catctcgggg gatacaggca aaagccaggg tgctgcccct tggccaagtg tccctatggg   2940

tgggggggt tggagg                                                    2956


<210> SEQ ID NO 6
<211> LENGTH: 389
<212> TYPE: PRT
<213> ORGANISM: Canis familiaris

<400> SEQUENCE: 6

Met Leu Ala Gly Arg Gly Ala Arg Ala Gly Gly Gly Leu Pro Arg Gly
1               5                   10                  15

Trp Thr Ala Leu Cys Leu Leu Ser Leu Leu Pro Phe Gly Phe Thr Asn
            20                  25                  30

Thr Glu Thr Val Ile Thr Pro Thr Thr Val Pro Thr Ser Thr Glu Ile
        35                  40                  45

Met Ser Ala Val Ser Glu Asn Thr Ser Lys Arg Glu Ala Ile Thr Leu
    50                  55                  60

Thr Pro Ser Gly Thr Thr Thr Leu Tyr Ser Val Ser Gln Asp Ser Ser
65                  70                  75                  80

Gly Thr Thr Ala Thr Ile Ser Glu Thr Thr Val His Val Thr Ser Thr
                85                  90                  95

Ser Glu Ile Thr Leu Thr Pro Gly Thr Met Asn Ser Ser Val Gln Ser
            100                 105                 110

Gln Thr Ser Leu Ala Ile Thr Val Ser Phe Thr Pro Thr Asn Phe Ser
        115                 120                 125

Thr Ser Ser Val Thr Leu Glu Pro Ser Leu Leu Pro Gly Asn Gly Ser
    130                 135                 140

Asp Pro Pro Tyr Asn Ser Thr Ser Leu Val Thr Ser Pro Thr Glu Tyr
145                 150                 155                 160

Tyr Thr Ser Leu Ser Pro Thr Pro Ser Arg Asn Asp Thr Pro Ser Thr
                165                 170                 175

Ile Lys Gly Glu Ile Lys Cys Ser Gly Val Lys Glu Val Lys Leu Asn
            180                 185                 190

Gln Gly Ile Cys Leu Glu Leu Asn Glu Thr Ser Ser Cys Glu Asp Phe
        195                 200                 205

Lys Lys Asp Asn Glu Glu Lys Leu Thr Gln Val Leu Cys Glu Lys Glu
    210                 215                 220

Pro Ala Glu Ala Gly Ala Gly Val Cys Ser Leu Leu Leu Ala Gln Ser
225                 230                 235                 240

Glu Val Arg Pro His Cys Leu Leu Leu Val Leu Ala Asn Lys Thr Glu
                245                 250                 255

Leu Phe Ser Lys Leu Gln Leu Leu Arg Lys His Gln Ser Asp Leu Lys
            260                 265                 270

Lys Leu Gly Ile Arg Asp Phe Thr Glu Gln Asp Val Gly Ser His Gln
        275                 280                 285

Ser Tyr Ser Arg Lys Thr Leu Ile Ala Leu Val Thr Ser Gly Ile Leu
    290                 295                 300

Leu Ala Val Leu Gly Thr Thr Gly Tyr Phe Leu Met Asn Arg Arg Ser
```

-continued

```
305                 310                 315                 320

Trp Ser Pro Thr Gly Glu Arg Leu Gly Glu Asp Pro Tyr Tyr Thr Glu
                325                 330                 335

Asn Gly Gly Gly Gln Gly Tyr Ser Ser Gly Pro Gly Val Ser Pro Glu
            340                 345                 350

Ala Gln Gly Lys Ala Ser Val Asn Arg Gly Pro Gln Glu Asn Gly Thr
        355                 360                 365

Gly Gln Ala Thr Ser Arg Asn Gly His Ser Ala Arg Gln His Met Val
    370                 375                 380

Ala Asp Thr Glu Leu
385


<210> SEQ ID NO 7
<211> LENGTH: 2657
<212> TYPE: DNA
<213> ORGANISM: Homo sapiens

<400> SEQUENCE: 7

cccgggcgga gggggcggga agagcgcgtc ctggccaagc cgagtagtgt cttccactcg     60

gtgcgtctct ctaggagccg cgcgggaagg atgctggtcc gcaggggcgc gcgcgcaggg    120

cccaggatgc cgcggggctg gaccgcgctt tgcttgctga gtttgctgcc ttctgggttc    180

atgagtcttg acaacaacgg tactgctacc ccagagttac ctacccaggg aacattttca    240

aatgtttcta caaatgtatc ctaccaagaa actacaacac ctagtaccct tggaagtacc    300

agcctgcacc ctgtgtctca acatggcaat gaggccacaa caaacatcac agaaacgaca    360

gtcaaattca catctacctc tgtgataacc tcagtttatg gaaacacaaa ctcttctgtc    420

cagtcacaga cctctgtaat cagcacagtg ttcaccaccc cagccaacgt ttcaactcca    480

gagacaacct tgaagcctag cctgtcacct ggaaatgttt cagacctttc aaccactagc    540

actagccttg caacatctcc cactaaaccc tatacatcat cttctcctat cctaagtgac    600

atcaaggcag aaatcaaatg ttcaggcatc agagaagtga aattgactca gggcatctgc    660

ctggagcaaa ataagacctc cagctgtgcg gagtttaaga aggacagggg agagggcctg    720

gcccgagtgc tgtgtgggga ggagcaggct gatgctgatg ctggggccca ggtatgctcc    780

ctgctccttg cccagtctga ggtgaggcct cagtgtctac tgctggtctt ggccaacaga    840

acagaaattt ccagcaaact ccaacttatg aaaaagcacc aatctgacct gaaaaagctg    900

gggatcctag atttcactga gcaagatgtt gcaagccacc agagctattc ccaaaagacc    960

ctgattgcac tggtcacctc gggagccctg ctggctgtct tgggcatcac tggctatttc   1020

ctgatgaatc gccgcagctg gagccccaca ggagaaaggc tggagctgga accctgacca   1080

ctcttcagga agaaaggagt ctgcacatgc agctgcaccc tccctccgat ccttcctccc   1140

acctccccct ccccttctc ccacccctgc cccacttcc tgtttgggcc ctctcccatc   1200

cagtgtctca cagccctgct taccagataa tgctacttta tttatacact gtctagggcg   1260

aagaccctta ttacacggaa aacggtggag gccagggcta tagctcagga cctgggacct   1320

cccctgaggc tcagggaaag gccagtgtga accgaggggc tcaggaaaac gggaccggcc   1380

aggccacctc cagaaacggc cattcagcaa gacaacacgt ggtggctgat accgaattgt   1440

gactcggcta ggtggggcaa ggctgggcag tgtccgagag agcacccctc tctgcatctg   1500

accacgtgct acccccatgc tggaggtgac atctcttacg cccaaccctt ccccactgca   1560

cacacctcag aggctgttct tggggcccta caccttgagg aggggcaggt aaactcctgt   1620

cctttacaca ttcgctccct ggagcagact ctggtcttct ttgggtaaac gtgtgacggg   1680
```

```
ggaaagccaa ggtctggaga agctcccagg aacaactgat ggccttgcag cactcacaca   1740

ggaccccctt cccctacccc ctcctctctg ccgcaataca ggaaccccca ggggaaagat   1800

gagcttttct aggctacaat ttctcccag gaagctttga tttttaccgt ttcttccctg    1860

tattttcttt ctctactttg aggaaaccaa agtaaccttt tgcacctgct ctcttgtaat   1920

gatatagcca gaaaaacgtg ttgccttgaa ccacttccct catctctcct ccaagacact   1980

gtggacttgg tcaccagctc ctcccttgtt ctctaagttc cactgagctc catgtgcccc   2040

ctctaccatt tgcagagtcc tgcacagttt tctggctgga gcctagaaca ggcctcccaa   2100

gttttaggac aaacagctca gttctagtct ctctggggcc acacagaaac tctttttggg   2160

ctcttttttc tccctctgga tcaaagtagg caggaccatg ggaccaggtc ttggagctga   2220

gcctctcacc tgtactcttc cgaaaaatcc tcttcctctg aggctggatc ctagccttat   2280

cctctgatct ccatggcttc ctcctccctc ctgccgactc ctgggttgag ctgttgcctc   2340

agtcccccaa cagatgcttt tctgtctctg cctccctcac cctgagcccc ttccttgctc   2400

tgcaccccca tatggtcata gcccagatca gctcctaacc cttatcacca gctgcctctt   2460

ctgtgggtga cccaggtcct tgtttgctgt tgatttcttt ccagaggggt tgaacaggga   2520

tcctggtttc aatgacggtt ggaaatagaa atttccagag aagagagtat tgggtagata   2580

ttttttctga atacaaagtg atgtgtttaa atactgcaat taaagtgata ctgaaacaca   2640

aaaaaaaaaa aaaaaaa                                                  2657
```

<210> SEQ ID NO 8
<211> LENGTH: 328
<212> TYPE: PRT
<213> ORGANISM: Homo sapiens

<400> SEQUENCE: 8

```
Met Leu Val Arg Arg Gly Ala Arg Ala Gly Pro Arg Met Pro Arg Gly
1               5                   10                  15

Trp Thr Ala Leu Cys Leu Leu Ser Leu Leu Pro Ser Gly Phe Met Ser
            20                  25                  30

Leu Asp Asn Asn Gly Thr Ala Thr Pro Glu Leu Pro Thr Gln Gly Thr
        35                  40                  45

Phe Ser Asn Val Ser Thr Asn Val Ser Tyr Gln Glu Thr Thr Thr Pro
    50                  55                  60

Ser Thr Leu Gly Ser Thr Ser Leu His Pro Val Ser Gln His Gly Asn
65                  70                  75                  80

Glu Ala Thr Thr Asn Ile Thr Glu Thr Thr Val Lys Phe Thr Ser Thr
                85                  90                  95

Ser Val Ile Thr Ser Val Tyr Gly Asn Thr Asn Ser Ser Val Gln Ser
            100                 105                 110

Gln Thr Ser Val Ile Ser Thr Val Phe Thr Thr Pro Ala Asn Val Ser
        115                 120                 125

Thr Pro Glu Thr Thr Leu Lys Pro Ser Leu Ser Pro Gly Asn Val Ser
    130                 135                 140

Asp Leu Ser Thr Thr Ser Thr Ser Leu Ala Thr Ser Pro Thr Lys Pro
145                 150                 155                 160

Tyr Thr Ser Ser Ser Pro Ile Leu Ser Asp Ile Lys Ala Glu Ile Lys
                165                 170                 175

Cys Ser Gly Ile Arg Glu Val Lys Leu Thr Gln Gly Ile Cys Leu Glu
            180                 185                 190

Gln Asn Lys Thr Ser Ser Cys Ala Glu Phe Lys Lys Asp Arg Gly Glu
```

```
        195                 200                 205

Gly Leu Ala Arg Val Leu Cys Gly Glu Glu Gln Ala Asp Ala Asp Ala
    210                 215                 220

Gly Ala Gln Val Cys Ser Leu Leu Leu Ala Gln Ser Glu Val Arg Pro
225                 230                 235                 240

Gln Cys Leu Leu Leu Val Leu Ala Asn Arg Thr Glu Ile Ser Ser Lys
                245                 250                 255

Leu Gln Leu Met Lys Lys His Gln Ser Asp Leu Lys Lys Leu Gly Ile
            260                 265                 270

Leu Asp Phe Thr Glu Gln Asp Val Ala Ser His Gln Ser Tyr Ser Gln
        275                 280                 285

Lys Thr Leu Ile Ala Leu Val Thr Ser Gly Ala Leu Leu Ala Val Leu
    290                 295                 300

Gly Ile Thr Gly Tyr Phe Leu Met Asn Arg Arg Ser Trp Ser Pro Thr
305                 310                 315                 320

Gly Glu Arg Leu Glu Leu Glu Pro
                325
```

<210> SEQ ID NO 9
<211> LENGTH: 2265
<212> TYPE: DNA
<213> ORGANISM: Artificial
<220> FEATURE:
<223> OTHER INFORMATION: Predicted nucleic acid sequence for dog CD51

<400> SEQUENCE: 9

```
gatgggcttt tttaaacgtg tccggccacc gcaggaagag caagaaaggg aacagcttca     60

acctcatgaa aatggcgaag gaaactcaga aacttaacgg tcatttttaa gtcatgctac    120

gctctgaccc gtcagagttt ccgacttcat cataggtttc agtttccttt gcgaggaata    180

aaaattccaa gactgtactg ctgatggtgc ccattggtgt taaccacaca acaagggcaa    240

tgggtgtcaa ctttttgtc attactaagt tcaaacgtac gtgtaataca caccactgac    300

ttgcgttttt aggtatttaa ataatgaaat tttaagcaat agtcgttctt caatgtacat    360

aagacaagga gcacctgagt taccactttc tataagatag gacctcctac gatgattatt    420

tctgattttg tgtgattttg tgtgttgttg cttttgtggt tttaaggcaa tccatatttg    480

gaccttagga gccacatctt ttgtacagga gcttactgtt aatacacatt acactacagt    540

tgagttttta agctactaac tttataactg catgaacttg gattttaata ttacctgtgt    600

cgtagaactt taaaaaaaaa aaaaaaagca tgatccatcc aggttctttc ctgtaatagc    660

aaaggtatag tattttaata tgaaagttgg gtacatgcta ttgtgttttt atttttgttt    720

aatccactcc atttccttac atttcagttt gtatacgttt aggttctatt tcaaatcctt    780

taagccaacc tatactaaaa attctatgat caaaaatgcc tcttttgtgt aatagtttta    840

atttccgcta ctcatcatca tgcttaaagc catatgcgtt tggaaatcat ttctgaagta    900

cagaaattcc attgtattag tctggctatc tgcaatacaa aaaaaaaaat atatatatat    960

atatatcatt taagttaaaa gactgtagtt ctttgataga cttgcttatt aatcgtacgc   1020

tcttagagca agaattttga gtctagatta atttattttc ttcctatata tgtaatcttc   1080

cttattatct ctaaaacttt actgagaatg ggttaagatc aatgaagaat ctttataatg   1140

tgcaggaacc tgcacccgac ctccaacccc atgagaaatg cgtggaattg aaattcttaa   1200

agtagcttgc tggtttgctt ccggcaataa tagcatgatg ctcacacgga cattacctta   1260

gcttagcaag ggtatcatct gtaaaaccag tctcagctac caaaataacg tagagtagtg   1320
```

-continued

```
acttttataa gcaatacaag ttattgggag ccttttaaaa cttttatagt tttattaaca   1380

taaattactt ttttagaatt tttatataac agctgcacag gtagcacatt gtaattttat   1440

ctgcctggag ggtgatgatt cttctagagg aataatgtga tttagtcaca gttcctcaag   1500

gtctgggaac gactattaat tatacctatt tttgtgcaat tacatcatgt tgtgctttag   1560

aaattgagag tttaataggt ttttaactgc tgtcctcatt aggcaaggat aaatatttcc   1620

cttaaataat tgaatatttt tctatgattt aaaaataatt gaaatttatc gtgccatgtc   1680

ttgtgttcga attcctcaca caaggggcta agctagaata tatttgtaaa acagaggaac   1740

gtgagttata tacgttagaa cgtgacaaga ccctgtattc agcttagatg aatttcaaaa   1800

ttaatagatt ttgtagcata ggttttgcta gtagctcaaa agatcttagt catatgcaat   1860

aactattttt attaccagta agtctaaagt tttttaagaa aaaatatttt tatcctagga   1920

tcttcaccaa acagtcacta agttgacgac tttcacttta tacctgtttc cccactgaat   1980

ggtagtcatc cctgaaagta gatgttggat agaaatccac tcttcacaag aaatgttagt   2040

ttgcttttgc acggtctgtt cctcctgtgg cctgtagctc aaggtataat catgtgtggg   2100

agactgaagg atattggtgt tggaagcatg atgttttaag ttccctttta tgaaatgtag   2160

ttttgagcaa tagtattttc ttttaaaaaa tgaaaacgtg tatctctacg gaactatggt   2220

agaagtatga tttggaagct tacacttcga ggaaaatgtt tggga                   2265
```

<210> SEQ ID NO 10
<211> LENGTH: 7037
<212> TYPE: DNA
<213> ORGANISM: Homo sapiens

<400> SEQUENCE: 10

```
gctgcgtgga gcggcggagc cggagggaag caaaggaccg tctgcgctgc tgtccccgcc     60

ccgcgcgctc tgcgcccctc gtccctggcg gtcgctccga agctcagccc tcttgcctgc    120

cccggagctg tcccgggcta gccgagaaga gagcggccgg caagtttggg cgcgcgcagg    180

cggcgggccg cgggcactgg gcgcctcgct ggggcggggg gaggtggcta ccgctcccgg    240

cttggcgtcc cgcgcgcact tcggcgatgg cttttccgcc gcggcgacgg ctgcgcctcg    300

gtccccgcgg cctcccgctt cttctctcgg gactcctgct acctctgtgc cgcgccttca    360

acctagacgt ggacagtcct gccgagtact ctggccccga gggaagttac ttcggcttcg    420

ccgtggattt cttcgtgccc agcgcgtctt cccggatgtt tcttctcgtg ggagctccca    480

aagcaaacac cacccagcct gggattgtgg aaggagggca ggtcctcaaa tgtgactggt    540

cttctacccg ccggtgccag ccaattgaat ttgatgcaac aggcaataga gattatgcca    600

aggatgatcc attggaattt aagtcccatc agtggtttgg agcatctgtg aggtcgaaac    660

aggataaaat tttggcctgt gccccattgt accattggag aactgagatg aaacaggagc    720

gagagcctgt tggaacatgc tttcttcaag atggaacaaa gactgttgag tatgctccat    780

gtagatcaca agatattgat gctgatggac agggattttg tcaaggagga ttcagcattg    840

attttactaa agctgacaga gtacttcttg gtggtcctgg tagcttttat tggcaaggtc    900

agcttatttc ggatcaagtg gcagaaatcg tatctaaata cgaccccaat gtttacagca    960

tcaagtataa taaccaatta gcaactcgga ctgcacaagc tatttttgat gacagctatt   1020

tgggttattc tgtggctgtc ggagatttca atggtgatgg catagatgac tttgtttcag   1080

gagttccaag agcagcaagg actttgggaa tggtttatat ttatgatggg aagaacatgt   1140

cctccttata caattttact ggcgagcaga tggctgcata tttcggattt tctgtagctg   1200
```

-continued ccactgacat taatggagat gattatgcag atgtgtttat tggagcacct ctcttcatgg 1260
atcgtggctc tgatggcaaa ctccaagagg tggggcaggt ctcagtgtct ctacagagag 1320
cttcaggaga cttccagacg acaaagctga atggatttga ggtctttgca cggtttggca 1380
gtgccatagc tcctttggga gatctggacc aggatggttt caatgatatt gcaattgctg 1440
ctccatatgg gggtgaagat aaaaaaggaa ttgtttatat cttcaatgga agatcaacag 1500
gcttgaacgc agtcccatct caaatccttg aagggcagtg ggctgctcga agcatgccac 1560
caagctttgg ctattcaatg aaaggagcca cagatataga caaaaatgga tatccagact 1620
taattgtagg agcttttggt gtagatcgag ctatcttata cagggccaga ccagttatca 1680
ctgtaaatgc tggtcttgaa gtgtacccta gcattttaaa tcaagacaat aaaacctgct 1740
cactgcctgg aacagctctc aaagtttcct gttttaatgt taggttctgc ttaaaggcag 1800
atggcaaagg agtacttccc aggaaactta atttccaggt ggaacttctt ttggataaac 1860
tcaagcaaaa gggagcaatt cgacgagcac tgtttctcta cagcaggtcc ccaagtcact 1920
ccaagaacat gactatttca aggggggggac tgatgcagtg tgaggaattg atagcgtatc 1980
tgcgggatga atctgaattt agagacaaac tcactccaat tactattttt atggaatatc 2040
ggttggatta tagaacagct gctgatacaa caggcttgca acccattctt aaccagttca 2100
cgcctgctaa cattagtcga caggctcaca ttctacttga ctgtggtgaa gacaatgtct 2160
gtaaacccaa gctggaagtt tctgtagata gtgatcaaaa gaagatctat attggggatg 2220
acaaccctct gacattgatt gttaaggctc agaatcaagg agaaggtgcc tacgaagctg 2280
agctcatcgt ttccattcca ctgcaggctg atttcatcgg ggttgtccga aacaatgaag 2340
ccttagcaag actttcctgt gcatttaaga cagaaaacca aactcgccag gtggtatgtg 2400
accttggaaa cccaatgaag gctggaactc aactcttagc tggtcttcgt ttcagtgtgc 2460
accagcagtc agagatggat acttctgtga aatttgactt acaaatccaa agctcaaatc 2520
tatttgacaa agtaagccca gttgtatctc acaaagttga tcttgctgtt ttagctgcag 2580
ttgagataag aggagtctcg agtcctgatc atatctttct tccgattcca aactgggagc 2640
acaaggagaa ccctgagact gaagaagatg ttgggccagt tgttcagcac atctatgagc 2700
tgagaaacaa tggtccaagt tcattcagca aggcaatgct ccatcttcag tggccttaca 2760
aatataataa taacactctg ttgtatatcc ttcattatga tattgatgga ccaatgaact 2820
gcacttcaga tatggagatc aaccctttga gaattaagat ctcatctttg caaacaactg 2880
aaaagaatga cacggttgcc gggcaaggtg agcgggacca tctcatcact aagcgggatc 2940
ttgccctcag tgaaggagat attcacactt tgggttgtgg agttgctcag tgcttgaaga 3000
ttgtctgcca agttgggaga ttagacagag gaaagagtgc aatcttgtac gtaaagtcat 3060
tactgtggac tgagactttt atgaataaag aaaatcagaa tcattcctat tctctgaagt 3120
cgtctgcttc atttaatgtc atagagtttc cttataagaa tcttccaatt gaggatatca 3180
ccaactccac attggttacc actaatgtca cctggggcat tcagccagcg cccatgcctg 3240
tgcctgtgtg ggtgatcatt ttagcagttc tagcaggatt gttgctactg gctgttttgg 3300
tatttgtaat gtacaggatg ggctttttta aacgggtccg gccacctcaa gaagaacaag 3360
aaagggagca gcttcaacct catgaaaatg gtgaaggaaa ctcagaaact taactgcagt 3420
ttttaagtta tgctacatct tgacccacta gaattagcaa ctttattata gatttaaact 3480
ttcttcatga ggagtaaaaa tccaaggctt tactgctgat agtgctaatt ggcattaacc 3540
acaaaatgag aattatattt gtcaaccttc tccttataaa taagttcaga catacattta 3600
ataacatagg gtgacttgtg tttttaggta tttaaataat aaaatttcaa gggatagttt 3660
ttattcaatg tatataagac aggtagtgcc tgatttacta ctttatataa aatagtacct 3720
ccttcagtta ctgtttctga tttaatgtac ggaactttat ttgttgttgt tgttgttgtt 3780
gttgttgttg ttttaaagca gtccaaattt ggaccttagc aatcatgtct tttgtatagg 3840
tacttaatgt taatacatat tacactacag tttacttttc agaatactaa agactttata 3900
actgcatgaa cttggatttt tttaatcact catatggtag aattttataa acacatacat 3960
gataccatcc aaattcttgc ttttaataac aaaggtacaa tattttgttt tagtatgaaa 4020
atctggtaga tcctattaca cttctgttta tattaaatcc acaatatttt attacatttt 4080
taacttgtat aaattttagg tcaaatcctt caagccaacc tatactaaaa attagttcca 4140
taatcacaaa tggctctttt gtgtaattgt ttaatttcac ctgaatatca taatgcttaa 4200
agccatatgg agttggaaat tatttccaaa gcatatttat tccattgttt tagtctggct 4260
atttacagta taaaaaaagc atttttatta aaatactgtg tagttctttg agatagttgc 4320
ttatgcatat agtaagtatt acattcttag agtagagcag agtttttagt tagtattaat 4380
ttattttcct ccattcatgt acttttcctt atatttccaa aactgttact gagaatgggt 4440
caagatcagt gagaaatctt tacagttgac aggaacctgg accccttacc ccaactttat 4500
gagtaatgct tggaataaaa actcttaagg caactcactg atttacttct agcaatagca 4560
tgatgttaca ggaatattac ctctgtttaa gcaaggtaat gtgtaaaatc agtctcggct 4620
gtcagaataa cttctaaaag gtatttttat aagcagttca agttactgaa aacctttttaa 4680
acctttctga agttcgttag tataaattac ttttctagga ttattaataa aagccacata 4740
ggtggcaagt tgtagtttta tatggctctg tagagtggtg aaccttctag aggaatatat 4800
gatttattca cagttcctca aggcctgggg atgatgatca gttataccta tttttgtgca 4860
attacatcat gttgtacatt agaaatggag agtttaatag ctctttaact gctgtcctca 4920
ttaggtaatg ataaatattt cccttaaata attgactatt ttgctgtgtt ttaaaaatga 4980
ttgaaattta tcttgccata tctcataatt tcatgcacaa gttgactgag ctaatcttga 5040
gaatatattc gtaaaatagg agcacattta gttgaggtat acaaggtagg actctagaca 5100
aaaccttcta ttttagcttt agtgaatttc aaaagtaatg ggtcttggag tatagatttt 5160
tattagtagc ttgaaagagc ttaatcatat gcagtaagta tttttattac caataaattt 5220
aaaatttttt aagaaaaata tttttatcct agggccaagt gttgcctgcc accaatcagt 5280
aagttagtct ataacaaatt ttaccctaac agttttacca cctagtaaca gtcatttctg 5340
aaaatatgtt ggatagaaag tcactctttg gcaaaagtgt tagaatttgc ttttgtgcca 5400
tctattcctt ttatggcatc tatcttgaaa gtaatcttgt attggagatt gaaagatgct 5460
gtaatttaga aattaacatg atatcttaaa ttacctttat gaaatatagt tttgtataat 5520
agcatagatt ttccttcaaa aaatgaacat ttatatatct acaaaaaatat ggagaagagt 5580
aatttgaaag cctactttct gaagaaaatg gtgggatttt tttttatcat gattaaatat 5640
caaaaaattg ccctatgaaa actttaaatc tctaaaacat ttgaaatact accatatttg 5700
tgatttattg agaataaaaa tccattttga aatgtaaaat ttttatgatc tgattcagtt 5760
ttaagaaaac atgaatgaac tagaagatat taaaaacatt tgacattggt aagaaatatt 5820
gatactgata ttgattttta tataggtatt tatttcagaa ttgatatttt gagaaaaata 5880
catgtgagtc attttttctg tttctctttt ctcttaacga ttatcactgt aattctgaat 5940
ctgaaaggta aaacaattag tcaaaatatt attgccatca ttctacctgt gttatgaaac 6000

-continued

```
tacttattca tagttaattc tcattaacac ttacatttcc ataaagaaaa ctcaagtatt   6060

aataaaagag actttactgg cttaagaggg ctgtgaaaga tttttgatag tgaatcatga   6120

ccctaaggga gagatttgtg tgataaaagt attgtatata atagatcagc gatttttgta   6180

aggcaaacag aatttgtaag ttggcagatc ttcctaagtt gcaaaatgta atgatgagct   6240

tggtggagaa gaatgagtcg ttcttggaat acctatgtgc agccactacc catctcaatg   6300

tcaccttgtt tgcattcttg gatagcttgt atatgtagta gtttgatgaa taatttaaag   6360

aaaaacacct aaaatttgaa aaatgattgt aggatcaaaa aaggcagatg aaattactta   6420

atactcagtg ttttggagag tattcctttt agtttgttgg ttggctggtt tgaacgatag   6480

aaatatgcag catgcaatat atgcttatat ttcattttaa tttctgatat ataatgaact   6540

tcttgggaga ggtactgaat ctttgatgtt ttttgtcatt gttctcaagt gcaatataac   6600

aatgtaacca aatctagata atttcaaagt tgtcattaat ttagtaagcc taatataaac   6660

aaatatttgt attatttttg ttagcaggaa agagtgatta agtgaggtta tttaccccta   6720

aatggtccat tctgcattgt atttcaggct ggaaatgaat tattctttac cagttttgaa   6780

acactttgaa atatcctaag gtaacttgga agctgtgtag tatatcaaat taatttgcta   6840

cctaataaca tagaaagtaa atatctttgt ggtcacccac attgggtgag acagaaaatg   6900

aatctgttct aaaatttgta atttgctaac ttgatttgag ttagtgaaaa ctggtacagt   6960

gttctgcttg atttacaaca tgtaacttgt gactgtacaa taaacataag catatggtac   7020

caaaaaaaaa aaaaaaa                                                  7037
```

```
<210> SEQ ID NO 11
<211> LENGTH: 1048
<212> TYPE: PRT
<213> ORGANISM: Homo sapiens

<400> SEQUENCE: 11

Met Ala Phe Pro Pro Arg Arg Arg Leu Arg Leu Gly Pro Arg Gly Leu
1               5                   10                  15

Pro Leu Leu Leu Ser Gly Leu Leu Leu Pro Leu Cys Arg Ala Phe Asn
            20                  25                  30

Leu Asp Val Asp Ser Pro Ala Glu Tyr Ser Gly Pro Glu Gly Ser Tyr
        35                  40                  45

Phe Gly Phe Ala Val Asp Phe Phe Val Pro Ser Ala Ser Ser Arg Met
    50                  55                  60

Phe Leu Leu Val Gly Ala Pro Lys Ala Asn Thr Thr Gln Pro Gly Ile
65                  70                  75                  80

Val Glu Gly Gly Gln Val Leu Lys Cys Asp Trp Ser Ser Thr Arg Arg
                85                  90                  95

Cys Gln Pro Ile Glu Phe Asp Ala Thr Gly Asn Arg Asp Tyr Ala Lys
            100                 105                 110

Asp Asp Pro Leu Glu Phe Lys Ser His Gln Trp Phe Gly Ala Ser Val
        115                 120                 125

Arg Ser Lys Gln Asp Lys Ile Leu Ala Cys Ala Pro Leu Tyr His Trp
    130                 135                 140

Arg Thr Glu Met Lys Gln Glu Arg Glu Pro Val Gly Thr Cys Phe Leu
145                 150                 155                 160

Gln Asp Gly Thr Lys Thr Val Glu Tyr Ala Pro Cys Arg Ser Gln Asp
                165                 170                 175

Ile Asp Ala Asp Gly Gln Gly Phe Cys Gln Gly Gly Phe Ser Ile Asp
            180                 185                 190
```

-continued

```
Phe Thr Lys Ala Asp Arg Val Leu Leu Gly Gly Pro Gly Ser Phe Tyr
        195                 200                 205

Trp Gln Gly Gln Leu Ile Ser Asp Gln Val Ala Glu Ile Val Ser Lys
    210                 215                 220

Tyr Asp Pro Asn Val Tyr Ser Ile Lys Tyr Asn Asn Gln Leu Ala Thr
225                 230                 235                 240

Arg Thr Ala Gln Ala Ile Phe Asp Asp Ser Tyr Leu Gly Tyr Ser Val
                245                 250                 255

Ala Val Gly Asp Phe Asn Gly Asp Gly Ile Asp Asp Phe Val Ser Gly
            260                 265                 270

Val Pro Arg Ala Ala Arg Thr Leu Gly Met Val Tyr Ile Tyr Asp Gly
        275                 280                 285

Lys Asn Met Ser Ser Leu Tyr Asn Phe Thr Gly Glu Gln Met Ala Ala
    290                 295                 300

Tyr Phe Gly Phe Ser Val Ala Ala Thr Asp Ile Asn Gly Asp Asp Tyr
305                 310                 315                 320

Ala Asp Val Phe Ile Gly Ala Pro Leu Phe Met Asp Arg Gly Ser Asp
                325                 330                 335

Gly Lys Leu Gln Glu Val Gly Gln Val Ser Val Ser Leu Gln Arg Ala
            340                 345                 350

Ser Gly Asp Phe Gln Thr Thr Lys Leu Asn Gly Phe Glu Val Phe Ala
        355                 360                 365

Arg Phe Gly Ser Ala Ile Ala Pro Leu Gly Asp Leu Asp Gln Asp Gly
    370                 375                 380

Phe Asn Asp Ile Ala Ile Ala Ala Pro Tyr Gly Gly Glu Asp Lys Lys
385                 390                 395                 400

Gly Ile Val Tyr Ile Phe Asn Gly Arg Ser Thr Gly Leu Asn Ala Val
                405                 410                 415

Pro Ser Gln Ile Leu Glu Gly Gln Trp Ala Ala Arg Ser Met Pro Pro
            420                 425                 430

Ser Phe Gly Tyr Ser Met Lys Gly Ala Thr Asp Ile Asp Lys Asn Gly
        435                 440                 445

Tyr Pro Asp Leu Ile Val Gly Ala Phe Gly Val Asp Arg Ala Ile Leu
    450                 455                 460

Tyr Arg Ala Arg Pro Val Ile Thr Val Asn Ala Gly Leu Glu Val Tyr
465                 470                 475                 480

Pro Ser Ile Leu Asn Gln Asp Asn Lys Thr Cys Ser Leu Pro Gly Thr
                485                 490                 495

Ala Leu Lys Val Ser Cys Phe Asn Val Arg Phe Cys Leu Lys Ala Asp
            500                 505                 510

Gly Lys Gly Val Leu Pro Arg Lys Leu Asn Phe Gln Val Glu Leu Leu
        515                 520                 525

Leu Asp Lys Leu Lys Gln Lys Gly Ala Ile Arg Arg Ala Leu Phe Leu
    530                 535                 540

Tyr Ser Arg Ser Pro Ser His Ser Lys Asn Met Thr Ile Ser Arg Gly
545                 550                 555                 560

Gly Leu Met Gln Cys Glu Glu Leu Ile Ala Tyr Leu Arg Asp Glu Ser
                565                 570                 575

Glu Phe Arg Asp Lys Leu Thr Pro Ile Thr Ile Phe Met Glu Tyr Arg
            580                 585                 590

Leu Asp Tyr Arg Thr Ala Ala Asp Thr Thr Gly Leu Gln Pro Ile Leu
        595                 600                 605

Asn Gln Phe Thr Pro Ala Asn Ile Ser Arg Gln Ala His Ile Leu Leu
    610                 615                 620
```

```
Asp Cys Gly Glu Asp Asn Val Cys Lys Pro Lys Leu Glu Val Ser Val
625                 630                 635                 640

Asp Ser Asp Gln Lys Lys Ile Tyr Ile Gly Asp Asp Asn Pro Leu Thr
                645                 650                 655

Leu Ile Val Lys Ala Gln Asn Gln Gly Glu Gly Ala Tyr Glu Ala Glu
            660                 665                 670

Leu Ile Val Ser Ile Pro Leu Gln Ala Asp Phe Ile Gly Val Val Arg
        675                 680                 685

Asn Asn Glu Ala Leu Ala Arg Leu Ser Cys Ala Phe Lys Thr Glu Asn
    690                 695                 700

Gln Thr Arg Gln Val Val Cys Asp Leu Gly Asn Pro Met Lys Ala Gly
705                 710                 715                 720

Thr Gln Leu Leu Ala Gly Leu Arg Phe Ser Val His Gln Gln Ser Glu
                725                 730                 735

Met Asp Thr Ser Val Lys Phe Asp Leu Gln Ile Gln Ser Ser Asn Leu
            740                 745                 750

Phe Asp Lys Val Ser Pro Val Val Ser His Lys Val Asp Leu Ala Val
        755                 760                 765

Leu Ala Ala Val Glu Ile Arg Gly Val Ser Ser Pro Asp His Ile Phe
    770                 775                 780

Leu Pro Ile Pro Asn Trp Glu His Lys Glu Asn Pro Glu Thr Glu Glu
785                 790                 795                 800

Asp Val Gly Pro Val Val Gln His Ile Tyr Glu Leu Arg Asn Asn Gly
                805                 810                 815

Pro Ser Ser Phe Ser Lys Ala Met Leu His Leu Gln Trp Pro Tyr Lys
            820                 825                 830

Tyr Asn Asn Asn Thr Leu Leu Tyr Ile Leu His Tyr Asp Ile Asp Gly
        835                 840                 845

Pro Met Asn Cys Thr Ser Asp Met Glu Ile Asn Pro Leu Arg Ile Lys
    850                 855                 860

Ile Ser Ser Leu Gln Thr Thr Glu Lys Asn Asp Thr Val Ala Gly Gln
865                 870                 875                 880

Gly Glu Arg Asp His Leu Ile Thr Lys Arg Asp Leu Ala Leu Ser Glu
                885                 890                 895

Gly Asp Ile His Thr Leu Gly Cys Gly Val Ala Gln Cys Leu Lys Ile
            900                 905                 910

Val Cys Gln Val Gly Arg Leu Asp Arg Gly Lys Ser Ala Ile Leu Tyr
        915                 920                 925

Val Lys Ser Leu Leu Trp Thr Glu Thr Phe Met Asn Lys Glu Asn Gln
    930                 935                 940

Asn His Ser Tyr Ser Leu Lys Ser Ser Ala Ser Phe Asn Val Ile Glu
945                 950                 955                 960

Phe Pro Tyr Lys Asn Leu Pro Ile Glu Asp Ile Thr Asn Ser Thr Leu
                965                 970                 975

Val Thr Thr Asn Val Thr Trp Gly Ile Gln Pro Ala Pro Met Pro Val
            980                 985                 990

Pro Val Trp Val Ile Ile Leu Ala  Val Leu Ala Gly Leu  Leu Leu Leu
        995                 1000                 1005

Ala Val  Leu Val Phe Val Met  Tyr Arg Met Gly Phe  Phe Lys Arg
    1010                 1015                 1020

Val Arg  Pro Pro Gln Glu Glu  Gln Glu Arg Glu Gln  Leu Gln Pro
    1025                 1030                 1035

His Glu  Asn Gly Glu Gly Asn  Ser Glu Thr
```

1040 1045

<210> SEQ ID NO 12
<211> LENGTH: 2374
<212> TYPE: DNA
<213> ORGANISM: Canis familiaris

<400> SEQUENCE: 12
atgcgggcgc ggccgctctg ggccgcggtg ctgctgctgg gggcgctggc gggcaccggc 60
gtcggagtgt ccaacatctg taccacacga ggtgtccact cctgccagca atgtctagct 120
gtgagtcctg tgtgtgcctg gtgctcagat gaggccctgc ctctgggctc tccccgctgt 180
aacctgaagg aaaatctgct gaaggataac tgtgccctgg aatccattga gttccccatc 240
agtgaggtcc gcatcctgga ggccaggccc cttagcaaca agggctctgg agacagctcc 300
cagattactc aagtcagccc tcagaggatt gcgctgcggc tccggccaga tgattcaaag 360
aatttctcca tccaagttcg gcaagtagag gattaccctg tggacatcta ctacttgatg 420
gacctgtctt attccatgaa ggatgatctg tcgagcatcc agaacctagg caccaggctg 480
gcctcccaga tgcacaagct caccagtaac ttgcggattg gcttcggggc ttttgtggac 540
aagcctgtgt ctccatacat gtacatctcc ccaccagagg ccctcaaaaa cccctgctat 600
gatatgaaga ccacctgttt gcctatgttt ggctacaaac atgtgctgac gctaactgac 660
caggtgaccc gcttcaatga ggaagtgaaa aagcagagtg tgtcacggaa ccgagatgcc 720
ccagagggcg gctttgatgc tatcatgcag gctacagtct gtgatgagaa gattggctgg 780
aggaatgatg catcccactt gctggtattt accactgatg ccaagaccca tatagcgctg 840
gatggaaggc tggcaggcat tgtccaacct aacgatgggc agtgtcacat tggcagtgac 900
aaccattatt ctgcctccac taccatggat tatccctctc tgggactgat gacagagaag 960
ctctcccaga aaaacatcaa tttgatcttt gcagtaacgg aaaatgtggt caatctctac 1020
cagaactaca gtgagctcat cccagggacc acagtgggga ttctgtctac ggattccagc 1080
aatgtccttc agctcattgt tgatgcttat ggaaaaatcc gctctaaagt ggagctggaa 1140
gtgcgtgacc tccctgagga gttgtctcta tcgttcaacg ccacctgtct caacaatgag 1200
gtcatcccgg gcctcaagtc ttgtgtcggc ctcaagattg gagacacggt gagcttcagc 1260
attgaggcca aagtgcgagg ctgcccccag gagaaggaga agtccttcac catcaagcct 1320
gtgggcttca aagacagcct caccatccag gtcacctttg actgtgactg tgcctgccag 1380
gcccaggctg agccttccag tcaccgctgc aacaatggca atgggacctt tgagtgtggg 1440
gtgtgcctct gtgggcctgg ctggctgggg tcccagtgtg aatgctcgga agaggactat 1500
catccctccc agcaggacga gtgcagcccc cgggagggcc agcccgcctg cagccagcgg 1560
ggcgagtgcc tgtgtggcca atgtgtctgc catagcagtg actttggcaa gatcacgggc 1620
aagtactgcg agtgtgatga cttctcctgt gtccgctaca agggggagat gtgctcaggc 1680
catggccagt gcagctgtgg ggactgcctg tgtgactccg actggaccgg ctactactgc 1740
aactgtacca cgcgcactga cacgtgcatg tccagcaacg ggctgctgtg cggcggtcgg 1800
ggcaagtgtg agtgtggcag ctgcgtgtgc atccaacctg gctcctacgg ggacacctgc 1860
gagaagtgcc ccacctgccc tgacgcctgc acctttaaga aggagtgtgt ggagtgtaag 1920
aaatttgacc gaggaactct ccatgatgat aatacctgca accgttactg tcgtgatgag 1980
attgagtctg tgaaggagct taaggatact ggcaaggatg cagtgaattg tacatacaag 2040
aatgaggatg actgtgttgt cagatttcag tactatgaag actccagtgg aaagtccatt 2100

-continued

```
ctctatgtgg tagaagagcc agagtgtccc aagggtcctg acatcctggt ggtcctgctt   2160

tcagtgatgg gggccatttt gctcattggc cttgctactc tgctcatctg gaagctcctc   2220

atcaccatcc atgatcggaa ggagtttgct aaatttgagg aagagcgagc cagagcaaaa   2280

tgggacacag ccaacaaccc actgtataaa gaggccacat ccacttttac caacatcacc   2340

taccggggca cttaacacca aggagccatc ctca                               2374


<210> SEQ ID NO 13
<211> LENGTH: 784
<212> TYPE: PRT
<213> ORGANISM: Canis familiaris

<400> SEQUENCE: 13

Met Arg Ala Arg Pro Leu Trp Ala Ala Val Leu Leu Leu Gly Ala Leu
1               5                   10                  15

Ala Gly Thr Gly Val Gly Val Ser Asn Ile Cys Thr Thr Arg Gly Val
            20                  25                  30

His Ser Cys Gln Gln Cys Leu Ala Val Ser Pro Val Cys Ala Trp Cys
        35                  40                  45

Ser Asp Glu Ala Leu Pro Leu Gly Ser Pro Arg Cys Asn Leu Lys Glu
    50                  55                  60

Asn Leu Leu Lys Asp Asn Cys Ala Leu Glu Ser Ile Glu Phe Pro Ile
65                  70                  75                  80

Ser Glu Val Arg Ile Leu Glu Ala Arg Pro Leu Ser Asn Lys Gly Ser
                85                  90                  95

Gly Asp Ser Ser Gln Ile Thr Gln Val Ser Pro Gln Arg Ile Ala Leu
            100                 105                 110

Arg Leu Arg Pro Asp Asp Ser Lys Asn Phe Ser Ile Gln Val Arg Gln
        115                 120                 125

Val Glu Asp Tyr Pro Val Asp Ile Tyr Tyr Leu Met Asp Leu Ser Tyr
    130                 135                 140

Ser Met Lys Asp Asp Leu Ser Ser Ile Gln Asn Leu Gly Thr Arg Leu
145                 150                 155                 160

Ala Ser Gln Met His Lys Leu Thr Ser Asn Leu Arg Ile Gly Phe Gly
                165                 170                 175

Ala Phe Val Asp Lys Pro Val Ser Pro Tyr Met Tyr Ile Ser Pro Pro
            180                 185                 190

Glu Ala Leu Lys Asn Pro Cys Tyr Asp Met Lys Thr Thr Cys Leu Pro
        195                 200                 205

Met Phe Gly Tyr Lys His Val Leu Thr Leu Thr Asp Gln Val Thr Arg
    210                 215                 220

Phe Asn Glu Glu Val Lys Lys Gln Ser Val Ser Arg Asn Arg Asp Ala
225                 230                 235                 240

Pro Glu Gly Gly Phe Asp Ala Ile Met Gln Ala Thr Val Cys Asp Glu
                245                 250                 255

Lys Ile Gly Trp Arg Asn Asp Ala Ser His Leu Leu Val Phe Thr Thr
            260                 265                 270

Asp Ala Lys Thr His Ile Ala Leu Asp Gly Arg Leu Ala Gly Ile Val
        275                 280                 285

Gln Pro Asn Asp Gly Gln Cys His Ile Gly Ser Asp Asn His Tyr Ser
    290                 295                 300

Ala Ser Thr Thr Met Asp Tyr Pro Ser Leu Gly Leu Met Thr Glu Lys
305                 310                 315                 320

Leu Ser Gln Lys Asn Ile Asn Leu Ile Phe Ala Val Thr Glu Asn Val
                325                 330                 335
```

-continued

```
Val Asn Leu Tyr Gln Asn Tyr Ser Glu Leu Ile Pro Gly Thr Thr Val
            340                 345                 350

Gly Ile Leu Ser Thr Asp Ser Ser Asn Val Leu Gln Leu Ile Val Asp
        355                 360                 365

Ala Tyr Gly Lys Ile Arg Ser Lys Val Glu Leu Glu Val Arg Asp Leu
    370                 375                 380

Pro Glu Glu Leu Ser Leu Ser Phe Asn Ala Thr Cys Leu Asn Asn Glu
385                 390                 395                 400

Val Ile Pro Gly Leu Lys Ser Cys Val Gly Leu Lys Ile Gly Asp Thr
                405                 410                 415

Val Ser Phe Ser Ile Glu Ala Lys Val Arg Gly Cys Pro Gln Glu Lys
            420                 425                 430

Glu Lys Ser Phe Thr Ile Lys Pro Val Gly Phe Lys Asp Ser Leu Thr
        435                 440                 445

Ile Gln Val Thr Phe Asp Cys Asp Cys Ala Cys Gln Ala Gln Ala Glu
    450                 455                 460

Pro Ser Ser His Arg Cys Asn Asn Gly Asn Gly Thr Phe Glu Cys Gly
465                 470                 475                 480

Val Cys Leu Cys Gly Pro Gly Trp Leu Gly Ser Gln Cys Glu Cys Ser
                485                 490                 495

Glu Glu Asp Tyr His Pro Ser Gln Gln Asp Glu Cys Ser Pro Arg Glu
            500                 505                 510

Gly Gln Pro Ala Cys Ser Gln Arg Gly Glu Cys Leu Cys Gly Gln Cys
        515                 520                 525

Val Cys His Ser Ser Asp Phe Gly Lys Ile Thr Gly Lys Tyr Cys Glu
    530                 535                 540

Cys Asp Asp Phe Ser Cys Val Arg Tyr Lys Gly Glu Met Cys Ser Gly
545                 550                 555                 560

His Gly Gln Cys Ser Cys Gly Asp Cys Leu Cys Asp Ser Asp Trp Thr
                565                 570                 575

Gly Tyr Tyr Cys Asn Cys Thr Thr Arg Thr Asp Thr Cys Met Ser Ser
            580                 585                 590

Asn Gly Leu Leu Cys Gly Gly Arg Gly Lys Cys Glu Cys Gly Ser Cys
        595                 600                 605

Val Cys Ile Gln Pro Gly Ser Tyr Gly Asp Thr Cys Glu Lys Cys Pro
    610                 615                 620

Thr Cys Pro Asp Ala Cys Thr Phe Lys Lys Glu Cys Val Glu Cys Lys
625                 630                 635                 640

Lys Phe Asp Arg Gly Thr Leu His Asp Asp Asn Thr Cys Asn Arg Tyr
                645                 650                 655

Cys Arg Asp Glu Ile Glu Ser Val Lys Glu Leu Lys Asp Thr Gly Lys
            660                 665                 670

Asp Ala Val Asn Cys Thr Tyr Lys Asn Glu Asp Asp Cys Val Val Arg
        675                 680                 685

Phe Gln Tyr Tyr Glu Asp Ser Ser Gly Lys Ser Ile Leu Tyr Val Val
    690                 695                 700

Glu Glu Pro Glu Cys Pro Lys Gly Pro Asp Ile Leu Val Val Leu Leu
705                 710                 715                 720

Ser Val Met Gly Ala Ile Leu Leu Ile Gly Leu Ala Thr Leu Leu Ile
                725                 730                 735

Trp Lys Leu Leu Ile Thr Ile His Asp Arg Lys Glu Phe Ala Lys Phe
            740                 745                 750

Glu Glu Glu Arg Ala Arg Ala Lys Trp Asp Thr Ala Asn Asn Pro Leu
```

-continued

```
        755                 760                 765

Tyr Lys Glu Ala Thr Ser Thr Phe Thr Asn Ile Thr Tyr Arg Gly Thr
    770                 775                 780


<210> SEQ ID NO 14
<211> LENGTH: 4894
<212> TYPE: DNA
<213> ORGANISM: Homo sapiens

<400> SEQUENCE: 14

cgccgcggga ggcggacgag atgcgagcgc ggccgcggcc ccggccgctc tgggcgactg     60

tgctggcgct gggggcgctg gcgggcgttg gcgtaggagg gcccaacatc tgtaccacgc    120

gaggtgtgag ctcctgccag cagtgcctgg ctgtgagccc catgtgtgcc tggtgctctg    180

atgaggccct gcctctgggc tcacctcgct gtgacctgaa ggagaatctg ctgaaggata    240

actgtgcccc agaatccatc gagttcccag tgagtgaggc ccgagtacta gaggacaggc    300

ccctcagcga caagggctct ggagacagct cccaggtcac tcaagtcagt ccccagagga    360

ttgcactccg gctccggcca gatgattcga agaatttctc catccaagtg cggcaggtgg    420

aggattaccc tgtggacatc tactacttga tggacctgtc ttactccatg aaggatgatc    480

tgtggagcat ccagaacctg ggtaccaagc tggccaccca gatgcgaaag ctcaccagta    540

acctgcggat tggcttcggg gcatttgtgg acaagcctgt gtcaccatac atgtatatct    600

ccccaccaga ggccctcgaa aacccctgct atgatatgaa gaccacctgc ttgcccatgt    660

ttggctacaa acacgtgctg acgctaactg accaggtgac ccgcttcaat gaggaagtga    720

agaagcagag tgtgtcacgg aaccgagatg ccccagaggg tggctttgat gccatcatgc    780

aggctacagt ctgtgatgaa aagattggct ggaggaatga tgcatcccac ttgctggtgt    840

ttaccactga tgccaagact catatagcat tggacggaag gctggcaggc attgtccagc    900

ctaatgacgg gcagtgtcat gttggtagtg acaatcatta ctctgcctcc actaccatgg    960

attatccctc tttggggctg atgactgaga agctatccca gaaaaacatc aatttgatct   1020

ttgcagtgac tgaaaatgta gtcaatctct atcagaacta tagtgagctc atcccaggga   1080

ccacagttgg ggttctgtcc atggattcca gcaatgtcct ccagctcatt gttgatgctt   1140

atgggaaaat ccgttctaaa gtagagctgg aagtgcgtga cctccctgaa gagttgtctc   1200

tatccttcaa tgccacctgc ctcaacaatg aggtcatccc tggcctcaag tcttgtatgg   1260

gactcaagat tggagacacg gtgagcttca gcattgaggc caaggtgcga ggctgtcccc   1320

aggagaagga gaagtccttt accataaagc ccgtgggctt caaggacagc ctgatcgtcc   1380

aggtcacctt tgattgtgac tgtgcctgcc aggcccaagc tgaacctaat agccatcgct   1440

gcaacaatgg caatgggacc tttgagtgtg gggtatgccg ttgtgggcct ggctggctgg   1500

gatcccagtg tgagtgctca gaggaggact atcgcccttc ccagcaggac gaatgcagcc   1560

cccgggaggg tcagcccgtc tgcagccagc ggggcgagtg cctctgtggt caatgtgtct   1620

gccacagcag tgactttggc aagatcacgg gcaagtactg cgagtgtgac gacttctcct   1680

gtgtccgcta caagggggag atgtgctcag gccatggcca gtgcagctgt ggggactgcc   1740

tgtgtgactc cgactggacc ggctactact gcaactgtac cacgcgtact gacacctgca   1800

tgtccagcaa tgggctgctg tgcagcggcc gcggcaagtg tgaatgtggc agctgtgtct   1860

gtatccagcc gggctcctat ggggacacct gtgagaagtg ccccacctgc ccagatgcct   1920

gcacctttaa gaaagaatgt gtggagtgta agaagtttga ccggggagcc ctacatgacg   1980

aaaatacctg caaccgttac tgccgtgacg agattgagtc agtgaaagag cttaaggaca   2040
```

-continued

```
ctggcaagga tgcagtgaat tgtacctata agaatgagga tgactgtgtc gtcagattcc   2100
agtactatga agattctagt ggaaagtcca tcctgtatgt ggtagaagag ccagagtgtc   2160
ccaagggccc tgacatcctg gtggtcctgc tctcagtgat gggggccatt ctgctcattg   2220
gccttgccgc cctgctcatc tggaaactcc tcatcaccat ccacgaccga aaagaattcg   2280
ctaaatttga ggaagaacgc gccagagcaa aatgggacac agccaacaac ccactgtata   2340
aagaggccac gtctaccttc accaatatca cgtaccgggg cacttaatga taagcagtca   2400
tcctcagatc attatcagcc tgtgccacga ttgcaggagt ccctgccatc atgtttacag   2460
aggacagtat ttgtggggag ggatttgggg ctcagagtgg ggtaggttgg gagaatgtca   2520
gtatgtggaa gtgtgggtct gtgtgtgtgt atgtgggggt ctgtgtgttt atgtgtgtgt   2580
gttgtgtgtg ggagtgtgta atttaaaatt gtgatgtgtc ctgataagct gagctcctta   2640
gcctttgtcc cagaatgcct cctgcaggga ttcttcctgc ttagcttgag ggtgactatg   2700
gagctgagca ggtgttcttc attacctcag tgagaagcca gctttcctca tcaggccatt   2760
gtccctgaag agaagggcag ggctgaggcc tctcattcca gaggaaggga caccaagcct   2820
tggctctacc ctgagttcat aaatttatgg ttctcaggcc tgactctcag cagctatggt   2880
aggaactgct gggcttggca gcccgggtca tctgtacctc tgcctccttt cccctccctc   2940
aggccgaagg aggagtcagg gagagctgaa ctattagagc tgcctgtgcc ttttgccatc   3000
ccctcaaccc agctatggtt ctctcgcaag ggaagtcctt gcaagctaat tctttgacct   3060
gttgggagtg aggatgtctg ggccactcag gggtcattca tggcctgggg gatgtaccag   3120
catctcccag ttcataatca caacccttca gatttgcctt attggcagct ctactctgga   3180
ggtttgttta gaagaagtgt gtcaccctta ggccagcacc atctctttac ctcctaattc   3240
cacaccctca ctgctgtaga catttgctat gagctgggga tgtctctcat gaccaaatgc   3300
ttttcctcaa agggagagag tgctattgta gagccagagg tctggcccta tgcttccggc   3360
ctcctgtccc tcatccatag cacctccaca tacctggccc tgtgccttgg tgtgctgtat   3420
ccatccatgg ggctgattgt atttaccttc tacctcttgg ctgccttgtg aaggaattat   3480
tcccatgagt tggctgggaa taagtgccag gatggaatga tgggtcagtt gtatcagcac   3540
gtgtggcctg ttcttctatg ggttggacaa cctcatttta actcagtctt taatctgaga   3600
ggccacagtg caattttatt ttatttttct catgatgagg ttttcttaac ttaaaagaac   3660
atgtatataa acatgcttgc attatatttg taaatttatg tgatggcaaa gaaggagagc   3720
ataggaaacc acacagactt gggcagggta cagacactcc cacttggcat cattcacagc   3780
aagtcactgg ccagtggctg gatctgtgag ggctctctc atgatagaag gctatgggga   3840
tagatgtgtg gacacattgg acctttcctg aggaagaggg actgttcttt tgtcccagaa   3900
aagcagtggc tccattggtg ttgacataca tccaacatta aaagccaccc ccaaatgccc   3960
aagaaaaaaa gaaagactta tcaacatttg ttccatgagc agaaaactgg agctctggcc   4020
tcagtgttac agctaaataa tctttaatta aggcaagtca ctttcttctt cttaaagctg   4080
ttttctagtt tgagaaatga tgggatttta gcagccagtc ttgaaggtct ctttcagtat   4140
caacattcta agatgctggg acttactgtg tcatcaaatg tgcggttaag attctctggg   4200
atattgatac tgtttgtgtt tttagttggg agatctgaga gacctggctt tggcaagagc   4260
agatgtcatt ccatatcacc tttctcaatg aaagtctcat tctatcctct ctccaaaccc   4320
gttttccaac atttgttaat agttacgtct ctcctgatgt agcacttaag cttcatttag   4380
ttattatttc tttcttcact ttgcacacat ttgcatccac atattaggga agaggaatcc   4440
```

```
ataagtagct gaaatatcta ttctgtatta ttgtgttaac attgagaata agccttggaa   4500

ttagatatgg ggcaatgact gagccctgtc tcacccatgg attactcctt actgtaggga   4560

atggcagtat ggtagaggga taaatagggg gcggggaggg atagtcatgg atccaagaag   4620

tccttagaaa tagtggcagg gaacaggtgt ggaagctcat gcctgtaatt ataaccttca   4680

gctactaaga caggtgtggt ggctcacgcc tgtgattata atcttcagtt actaagacag   4740

agtccatgag agtgttaatg ggacattttc tttagataag atgttttata tgaagaaact   4800

gtatcaaagg gggaagaaaa tgtatttaac aggtgaatca aatcaggaat cttgtctgag   4860

ctactggaat gaagttcaca ggtcttgaag acca                               4894


<210> SEQ ID NO 15
<211> LENGTH: 788
<212> TYPE: PRT
<213> ORGANISM: Homo sapiens

<400> SEQUENCE: 15

Met Arg Ala Arg Pro Arg Pro Arg Pro Leu Trp Ala Thr Val Leu Ala
1               5                   10                  15

Leu Gly Ala Leu Ala Gly Val Gly Val Gly Gly Pro Asn Ile Cys Thr
            20                  25                  30

Thr Arg Gly Val Ser Ser Cys Gln Gln Cys Leu Ala Val Ser Pro Met
        35                  40                  45

Cys Ala Trp Cys Ser Asp Glu Ala Leu Pro Leu Gly Ser Pro Arg Cys
    50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
    130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
                165                 170                 175

Ile Gly Phe Gly Ala Phe Val Asp Lys Pro Val Ser Pro Tyr Met Tyr
            180                 185                 190

Ile Ser Pro Pro Glu Ala Leu Glu Asn Pro Cys Tyr Asp Met Lys Thr
        195                 200                 205

Thr Cys Leu Pro Met Phe Gly Tyr Lys His Val Leu Thr Leu Thr Asp
    210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
                245                 250                 255

Val Cys Asp Glu Lys Ile Gly Trp Arg Asn Asp Ala Ser His Leu Leu
            260                 265                 270

Val Phe Thr Thr Asp Ala Lys Thr His Ile Ala Leu Asp Gly Arg Leu
        275                 280                 285

Ala Gly Ile Val Gln Pro Asn Asp Gly Gln Cys His Val Gly Ser Asp
```

-continued

```
    290                 295                 300

Asn His Tyr Ser Ala Ser Thr Thr Met Asp Tyr Pro Ser Leu Gly Leu
305                 310                 315                 320

Met Thr Glu Lys Leu Ser Gln Lys Asn Ile Asn Leu Ile Phe Ala Val
                325                 330                 335

Thr Glu Asn Val Val Asn Leu Tyr Gln Asn Tyr Ser Glu Leu Ile Pro
            340                 345                 350

Gly Thr Thr Val Gly Val Leu Ser Met Asp Ser Ser Asn Val Leu Gln
        355                 360                 365

Leu Ile Val Asp Ala Tyr Gly Lys Ile Arg Ser Lys Val Glu Leu Glu
    370                 375                 380

Val Arg Asp Leu Pro Glu Glu Leu Ser Leu Ser Phe Asn Ala Thr Cys
385                 390                 395                 400

Leu Asn Asn Glu Val Ile Pro Gly Leu Lys Ser Cys Met Gly Leu Lys
                405                 410                 415

Ile Gly Asp Thr Val Ser Phe Ser Ile Glu Ala Lys Val Arg Gly Cys
            420                 425                 430

Pro Gln Glu Lys Glu Lys Ser Phe Thr Ile Lys Pro Val Gly Phe Lys
        435                 440                 445

Asp Ser Leu Ile Val Gln Val Thr Phe Asp Cys Asp Cys Ala Cys Gln
    450                 455                 460

Ala Gln Ala Glu Pro Asn Ser His Arg Cys Asn Asn Gly Asn Gly Thr
465                 470                 475                 480

Phe Glu Cys Gly Val Cys Arg Cys Gly Pro Gly Trp Leu Gly Ser Gln
                485                 490                 495

Cys Glu Cys Ser Glu Glu Asp Tyr Arg Pro Ser Gln Gln Asp Glu Cys
            500                 505                 510

Ser Pro Arg Glu Gly Gln Pro Val Cys Ser Gln Arg Gly Glu Cys Leu
        515                 520                 525

Cys Gly Gln Cys Val Cys His Ser Ser Asp Phe Gly Lys Ile Thr Gly
    530                 535                 540

Lys Tyr Cys Glu Cys Asp Asp Phe Ser Cys Val Arg Tyr Lys Gly Glu
545                 550                 555                 560

Met Cys Ser Gly His Gly Gln Cys Ser Cys Gly Asp Cys Leu Cys Asp
                565                 570                 575

Ser Asp Trp Thr Gly Tyr Tyr Cys Asn Cys Thr Thr Arg Thr Asp Thr
            580                 585                 590

Cys Met Ser Ser Asn Gly Leu Leu Cys Ser Gly Arg Gly Lys Cys Glu
        595                 600                 605

Cys Gly Ser Cys Val Cys Ile Gln Pro Gly Ser Tyr Gly Asp Thr Cys
    610                 615                 620

Glu Lys Cys Pro Thr Cys Pro Asp Ala Cys Thr Phe Lys Lys Glu Cys
625                 630                 635                 640

Val Glu Cys Lys Lys Phe Asp Arg Gly Ala Leu His Asp Glu Asn Thr
                645                 650                 655

Cys Asn Arg Tyr Cys Arg Asp Glu Ile Glu Ser Val Lys Glu Leu Lys
            660                 665                 670

Asp Thr Gly Lys Asp Ala Val Asn Cys Thr Tyr Lys Asn Glu Asp Asp
        675                 680                 685

Cys Val Val Arg Phe Gln Tyr Tyr Glu Asp Ser Ser Gly Lys Ser Ile
    690                 695                 700

Leu Tyr Val Val Glu Glu Pro Glu Cys Pro Lys Gly Pro Asp Ile Leu
705                 710                 715                 720
```

```
Val Val Leu Leu Ser Val Met Gly Ala Ile Leu Leu Ile Gly Leu Ala
                725                 730                 735

Ala Leu Leu Ile Trp Lys Leu Leu Ile Thr Ile His Asp Arg Lys Glu
            740                 745                 750

Phe Ala Lys Phe Glu Glu Glu Arg Ala Arg Ala Lys Trp Asp Thr Ala
        755                 760                 765

Asn Asn Pro Leu Tyr Lys Glu Ala Thr Ser Thr Phe Thr Asn Ile Thr
    770                 775                 780

Tyr Arg Gly Thr
785


<210> SEQ ID NO 16
<211> LENGTH: 277
<212> TYPE: DNA
<213> ORGANISM: Artificial
<220> FEATURE:
<223> OTHER INFORMATION: Predicted nucleic acid sequence for dog CD31

<400> SEQUENCE: 16

gaatccttct ctaatcccaa attccacgtc agccccgaag gagtgatcac agaaggagat      60

cagctctaca ttaggtgcac cattcaagtg acacatctgg tccaagcatt tccagaaatc     120

ataatccaga aggacaaggc aattgtagca cacaagaggc atggtaacga agccacctac     180

tcagtgatgg ccatggcgga gcacaatggc aattacacat gcaaagtgga agccagccgg     240

atatccaagg tcagcagcat cgtggtcaac ataacag                              277


<210> SEQ ID NO 17
<211> LENGTH: 3189
<212> TYPE: DNA
<213> ORGANISM: Homo sapiens

<400> SEQUENCE: 17

tttccagcca tggctgccat tacctgacca gcgccacagc cggtctctct gcaggcgccg      60

ggagaagtga ccagagcaat ttctgctttt cacagggcgg gtttctcaac ggtgacttgt     120

gggcagtgcc ttctgctgag cgagtcatgg cccgaaggca gaactaactg tgcctgcagt     180

cttcactctc aggatgcagc cgaggtgggc ccaaggggcc acgatgtggc ttggagtcct     240

gctgaccctt ctgctctgtt caagccttga gggtcaagaa aactctttca caatcaacag     300

tgttgacatg aagagcctgc cggactggac ggtgcaaaat gggaagaacc tgaccctgca     360

gtgcttcgcg gatgtcagca ccacctctca cgtcaagcct cagcaccaga tgctgttcta     420

taaggatgac gtgctgtttt acaacatctc ctccatgaag agcacagaga gttattttat     480

tcctgaagtc cggatctatg actcagggac atataaatgt actgtgattg tgaacaacaa     540

agagaaaacc actgcagagt accaggtgtt ggtggaagga gtgcccagtc ccagggtgac     600

actggacaag aaagaggcca tccaaggtgg gatcgtgagg gtcaactgtt ctgtcccaga     660

ggaaaaggcc ccaatacact tcacaattga aaaacttgaa ctaaatgaaa aaatggtcaa     720

gctgaaaaga gagaagaatt ctcgagacca gaattttgtg atactggaat tccccgttga     780

ggaacaggac cgcgttttat ccttccgatg tcaagctagg atcatttctg ggatccatat     840

gcagacctca gaatctacca agagtgaact ggtcaccgtg acggaatcct tctctacacc     900

caagttccac atcagcccca ccggaatgat catggaagga gctcagctcc acattaagtg     960

caccattcaa gtgactcacc tggcccagga gtttccagaa atcataattc agaaggacaa    1020

ggcgattgtg gcccacaaca gacatggcaa caaggctgtg tactcagtca tggccatggt    1080

ggagcacagt ggcaactaca cgtgcaaagt ggagtccagc cgcatatcca aggtcagcag    1140
```

-continued catcgtggtc aacataacag aactattttc caagcccgaa ctggaatctt ccttcacaca 1200
tctggaccaa ggtgaaagac tgaacctgtc ctgctccatc ccaggagcac ctccagccaa 1260
cttcaccatc cagaaggaag atacgattgt gtcacagact caagatttca ccaagatagc 1320
ctcaaagtcg gacagtggga cgtatatctg cactgcaggt attgacaaag tggtcaagaa 1380
aagcaacaca gtccagatag tcgtatgtga aatgctctcc cagcccagga tttcttatga 1440
tgcccagttt gaggtcataa aaggacagac catcgaagtc cgttgcgaat cgatcagtgg 1500
aactttgcct atttcttacc aacttttaaa aacaagtaaa gttttggaga atagtaccaa 1560
gaactcaaat gatcctgcgg tattcaaaga caaccccact gaagacgtcg aataccagtg 1620
tgttgcagat aattgccatt cccacgccaa aatgttaagt gaggttctga gggtgaaggt 1680
gatagccccg gtggatgagg tccagatttc tatcctgtca agtaaggtgg tggagtctgg 1740
agaggacatt gtgctgcaat gtgctgtgaa tgaaggatct ggtcccatca cctataagtt 1800
ttacagagaa aaagagggca aacccttcta tcaaatgacc tcaaatgcca cccaggcatt 1860
ttggaccaag cagaaggcta acaaggaaca ggagggagag tattactgca cagccttcaa 1920
cagagccaac cacgcctcca gtgtccccag aagcaaaata ctgacagtca gagtcattct 1980
tgccccatgg aagaaaggac ttattgcagt ggttatcatc ggagtgatca ttgctctctt 2040
gatcattgcg gccaaatgtt attttctgag gaaagccaag gccaagcaga tgccagtgga 2100
aatgtccagg ccagcagtac cacttctgaa ctccaacaac gagaaaatgt cagatcccaa 2160
tatggaagct aacagtcatt acggtcacaa tgacgatgtc ggaaaccatg caatgaaacc 2220
aataaatgat aataaagagc ctctgaactc agacgtgcag tacacggaag ttcaagtgtc 2280
ctcagctgag tctcacaaag atctaggaaa gaaggacaca gagacagtgt acagtgaagt 2340
ccggaaagct gtccctgatg ccgtggaaag cagatactct agaacggaag gctcccttga 2400
tggaacttag acagcaaggc cagatgcaca tccctggaag gacatccatg ttccgagaag 2460
aacagatgat ccctgtattt caagacctct gtgcacttat ttatgaacct gccctgctcc 2520
cacagaacac agcaattcct caggctaagc tgccggttct taaatccatc ctgctaagtt 2580
aatgttgggt agaaagagat acagaggggc tgttgaattt cccacataca ctccttccac 2640
caagttggaa catccttgga aattggaaga gcacaagagg agatccaggg caaggccatt 2700
gggatattct gaaacttgaa tattttgttt tgtgcagaga taaagacctt ttccatgcac 2760
cctcatacac agaaaccaat ttcttttttt atactcaatc atttctagcg catggcctgg 2820
ttagaggctg gtttttctc ttttcctttg gtccttcaaa ggcttgtagt tttgggtagt 2880
ccttgttctt tggaaataca cagtgctgac cagacagcct ccccctgtcc cctctatgac 2940
ctcgccctcc acaaatggga aaaccagact acttgggagc accgcctgtg aaataccaac 3000
ctgaagacac ggttcattca ggcaacgcac aaaacagaaa atgaaggtgg aacaagcaca 3060
gatgttcttc aactgttttt gtctacactc tttctctttt cctctaccat gctgaaggct 3120
gaaagacagg aagatggtgc catcagcaaa tattattctt aattgaaaac ttgaaaaaaa 3180
aaaaaaaaa 3189

<210> SEQ ID NO 18
<211> LENGTH: 738
<212> TYPE: PRT
<213> ORGANISM: Homo sapiens

<400> SEQUENCE: 18

Met Gln Pro Arg Trp Ala Gln Gly Ala Thr Met Trp Leu Gly Val Leu

-continued

```
1               5                   10                  15

Leu Thr Leu Leu Leu Cys Ser Ser Leu Glu Gly Gln Glu Asn Ser Phe
            20                  25                  30

Thr Ile Asn Ser Val Asp Met Lys Ser Leu Pro Asp Trp Thr Val Gln
        35                  40                  45

Asn Gly Lys Asn Leu Thr Leu Gln Cys Phe Ala Asp Val Ser Thr Thr
    50                  55                  60

Ser His Val Lys Pro Gln His Gln Met Leu Phe Tyr Lys Asp Asp Val
65                  70                  75                  80

Leu Phe Tyr Asn Ile Ser Ser Met Lys Ser Thr Glu Ser Tyr Phe Ile
                85                  90                  95

Pro Glu Val Arg Ile Tyr Asp Ser Gly Thr Tyr Lys Cys Thr Val Ile
            100                 105                 110

Val Asn Asn Lys Glu Lys Thr Thr Ala Glu Tyr Gln Val Leu Val Glu
        115                 120                 125

Gly Val Pro Ser Pro Arg Val Thr Leu Asp Lys Lys Glu Ala Ile Gln
    130                 135                 140

Gly Gly Ile Val Arg Val Asn Cys Ser Val Pro Glu Glu Lys Ala Pro
145                 150                 155                 160

Ile His Phe Thr Ile Glu Lys Leu Glu Leu Asn Glu Lys Met Val Lys
                165                 170                 175

Leu Lys Arg Glu Lys Asn Ser Arg Asp Gln Asn Phe Val Ile Leu Glu
            180                 185                 190

Phe Pro Val Glu Glu Gln Asp Arg Val Leu Ser Phe Arg Cys Gln Ala
        195                 200                 205

Arg Ile Ile Ser Gly Ile His Met Gln Thr Ser Glu Ser Thr Lys Ser
    210                 215                 220

Glu Leu Val Thr Val Thr Glu Ser Phe Ser Thr Pro Lys Phe His Ile
225                 230                 235                 240

Ser Pro Thr Gly Met Ile Met Glu Gly Ala Gln Leu His Ile Lys Cys
                245                 250                 255

Thr Ile Gln Val Thr His Leu Ala Gln Glu Phe Pro Glu Ile Ile Ile
            260                 265                 270

Gln Lys Asp Lys Ala Ile Val Ala His Asn Arg His Gly Asn Lys Ala
        275                 280                 285

Val Tyr Ser Val Met Ala Met Val Glu His Ser Gly Asn Tyr Thr Cys
    290                 295                 300

Lys Val Glu Ser Ser Arg Ile Ser Lys Val Ser Ser Ile Val Val Asn
305                 310                 315                 320

Ile Thr Glu Leu Phe Ser Lys Pro Glu Leu Glu Ser Ser Phe Thr His
                325                 330                 335

Leu Asp Gln Gly Glu Arg Leu Asn Leu Ser Cys Ser Ile Pro Gly Ala
            340                 345                 350

Pro Pro Ala Asn Phe Thr Ile Gln Lys Glu Asp Thr Ile Val Ser Gln
        355                 360                 365

Thr Gln Asp Phe Thr Lys Ile Ala Ser Lys Ser Asp Ser Gly Thr Tyr
    370                 375                 380

Ile Cys Thr Ala Gly Ile Asp Lys Val Val Lys Lys Ser Asn Thr Val
385                 390                 395                 400

Gln Ile Val Val Cys Glu Met Leu Ser Gln Pro Arg Ile Ser Tyr Asp
                405                 410                 415

Ala Gln Phe Glu Val Ile Lys Gly Gln Thr Ile Glu Val Arg Cys Glu
            420                 425                 430
```

```
Ser Ile Ser Gly Thr Leu Pro Ile Ser Tyr Gln Leu Leu Lys Thr Ser
        435                 440                 445

Lys Val Leu Glu Asn Ser Thr Lys Asn Ser Asn Asp Pro Ala Val Phe
    450                 455                 460

Lys Asp Asn Pro Thr Glu Asp Val Glu Tyr Gln Cys Val Ala Asp Asn
465                 470                 475                 480

Cys His Ser His Ala Lys Met Leu Ser Glu Val Leu Arg Val Lys Val
                485                 490                 495

Ile Ala Pro Val Asp Glu Val Gln Ile Ser Ile Leu Ser Ser Lys Val
            500                 505                 510

Val Glu Ser Gly Glu Asp Ile Val Leu Gln Cys Ala Val Asn Glu Gly
        515                 520                 525

Ser Gly Pro Ile Thr Tyr Lys Phe Tyr Arg Glu Lys Glu Gly Lys Pro
    530                 535                 540

Phe Tyr Gln Met Thr Ser Asn Ala Thr Gln Ala Phe Trp Thr Lys Gln
545                 550                 555                 560

Lys Ala Asn Lys Glu Gln Glu Gly Glu Tyr Tyr Cys Thr Ala Phe Asn
                565                 570                 575

Arg Ala Asn His Ala Ser Ser Val Pro Arg Ser Lys Ile Leu Thr Val
            580                 585                 590

Arg Val Ile Leu Ala Pro Trp Lys Lys Gly Leu Ile Ala Val Val Ile
        595                 600                 605

Ile Gly Val Ile Ile Ala Leu Leu Ile Ile Ala Ala Lys Cys Tyr Phe
    610                 615                 620

Leu Arg Lys Ala Lys Ala Lys Gln Met Pro Val Glu Met Ser Arg Pro
625                 630                 635                 640

Ala Val Pro Leu Leu Asn Ser Asn Asn Glu Lys Met Ser Asp Pro Asn
                645                 650                 655

Met Glu Ala Asn Ser His Tyr Gly His Asn Asp Asp Val Gly Asn His
            660                 665                 670

Ala Met Lys Pro Ile Asn Asp Asn Lys Glu Pro Leu Asn Ser Asp Val
        675                 680                 685

Gln Tyr Thr Glu Val Gln Val Ser Ser Ala Glu Ser His Lys Asp Leu
    690                 695                 700

Gly Lys Lys Asp Thr Glu Thr Val Tyr Ser Glu Val Arg Lys Ala Val
705                 710                 715                 720

Pro Asp Ala Val Glu Ser Arg Tyr Ser Arg Thr Glu Gly Ser Leu Asp
                725                 730                 735

Gly Thr
```

```
<210> SEQ ID NO 19
<211> LENGTH: 157
<212> TYPE: DNA
<213> ORGANISM: Artificial
<220> FEATURE:
<223> OTHER INFORMATION: Predicited nucleic acid sequence for dog
      CD105

<400> SEQUENCE: 19

cctccagggg tggctgtgag gattcagagc tgataaggcc accgactgcc tagggtgggg      60

cctggggcac tggggtgttc ggcccctgag gccgggttaa ctgtccccca gggtacagac     120

cctgttcaga gggcctcggg gaaacctccc agccccc                              157


<210> SEQ ID NO 20
<211> LENGTH: 3142
<212> TYPE: DNA
```

-continued

<213> ORGANISM: Homo sapiens

<400> SEQUENCE: 20

```
cctgggccgg ccgggctgga tgagccggga gctccctgct gccggtcata ccacagcctt     60
catctgcgcc ctggggccag gactgctgct gtcactgcca tccattggag cccagcaccc    120
cctccccgcc catccttcgg acagcaactc cagcccagcc ccgcgtccct gtgtccactt    180
ctcctgaccc ctcggccgcc accccagaag gctggagcag ggacgccgtc gctccggccg    240
cctgctcccc tcgggtcccc gtgcgagccc acgccggccc cggtgcccgc ccgcagccct    300
gccactggac acaggataag gcccagcgca caggccccca cgtggacagc atggaccgcg    360
gcacgctccc tctggctgtt gccctgctgc tggccagctg cagcctcagc cccacaagtc    420
ttgcagaaac agtccattgt gaccttcagc ctgtgggccc cgagaggggc gaggtgacat    480
ataccactag ccaggtctcg aagggctgcg tggctcaggc ccccaatgcc atccttgaag    540
tccatgtcct cttcctggag ttcccaacgg gcccgtcaca gctggagctg actctccagg    600
catccaagca aaatggcacc tggccccgag aggtgcttct ggtcctcagt gtaaacagca    660
gtgtcttcct gcatctccag gccctgggaa tcccactgca cttggcctac aattccagcc    720
tggtcacctt ccaagagccc ccgggggtca acaccacaga gctgccatcc ttccccaaga    780
cccagatcct tgagtgggca gctgagaggg gccccatcac ctctgctgct gagctgaatg    840
acccccagag catcctcctc cgactgggcc aagcccaggg gtcactgtcc ttctgcatgc    900
tggaagccag ccaggacatg ggccgcacgc tcgagtggcg gccgcgtact ccagccttgg    960
tccggggctg ccacttggaa ggcgtggccg gccacaagga ggcgcacatc ctgagggtcc   1020
tgccgggcca ctcggccggg ccccggacgg tgacggtgaa ggtggaactg agctgcgcac   1080
ccggggatct cgatgccgtc ctcatcctgc agggtccccc ctacgtgtcc tggctcatcg   1140
acgccaacca caacatgcag atctggacca ctggagaata ctccttcaag atctttccag   1200
agaaaaacat tcgtggcttc aagctcccag acacacctca aggcctcctg gggggaggccc  1260
ggatgctcaa tgccagcatt gtggcatcct tcgtggagct accgctggcc agcattgtct   1320
cacttcatgc ctccagctgc ggtggtaggc tgcagacctc acccgcaccg atccagacca   1380
ctcctcccaa ggacacttgt agcccggagc tgctcatgtc cttgatccag acaaagtgtg   1440
ccgacgacgc catgaccctg gtactaaaga aagagcttgt tgcgcatttg aagtgcacca   1500
tcacgggcct gaccttctgg gaccccagct gtgaggcaga ggacaggggt gacaagtttg   1560
tcttgcgcag tgcttactcc agctgtggca tgcaggtgtc agcaagtatg atcagcaatg   1620
aggcggtggt caatatcctg tcgagctcat caccacagcg gaaaaaggtg cactgcctca   1680
acatggacag cctctctttc cagctgggcc tctacctcag cccacacttc ctccaggcct   1740
ccaacaccat cgagccgggg cagcagagct ttgtgcaggt cagagtgtcc ccatccgtct   1800
ccgagttcct gctccagtta gacagctgcc acctggactt ggggcctgag ggaggcaccg   1860
tggaactcat ccagggccgg gcggccaagg gcaactgtgt gagcctgctg tccccaagcc   1920
ccgagggtga cccgcgcttc agcttcctcc tccacttcta cacagtaccc atacccaaaa   1980
ccggcaccct cagctgcacg gtagccctgc gtcccaagac cgggtctcaa gaccaggaag   2040
tccataggac tgtcttcatg cgcttgaaca tcatcagccc tgacctgtct ggttgcacaa   2100
gcaaaggcct cgtcctgccc gccgtgctgg gcatcacctt tggtgccttc ctcatcgggg   2160
ccctgctcac tgctgcactc tggtacatct actcgcacac gcgtgagtac cccaggcccc   2220
cacagtgagc atgccgggcc cctccatcca cccgggggag cccagtgaag cctctgaggg   2280
```

-continued

```
attgaggggc cctggcagga ccctgacctc cgcccctgcc cccgctcccg ctcccaggtt   2340

cccccagcaa gcgggagccc gtggtggcgg tggctgcccc ggcctcctcg gagagcagca   2400

gcaccaacca cagcatcggg agcacccaga gcaccccctg ctccaccagc agcatggcat   2460

agccccggcc ccccgcgctc gcccagcagg agagactgag cagccgccag ctgggagcac   2520

tggtgtgaac tcaccctggg agccagtcct ccactcgacc cagaatggag cctgctctcc   2580

gcgcctaccc ttcccgcctc cctctcagag gcctgctgcc agtgcagcca ctggcttgga   2640

acaccttggg gtccctccac cccacagaac cttcaaccca gtgggtctgg gatatggctg   2700

cccaggagac agaccacttg ccacgctgtt gtaaaaaccc aagtccctgt catttgaacc   2760

tggatccagc actggtgaac tgagctgggc aggaagggag aacttgaaac agattcaggc   2820

cagcccagcc aggccaacag cacctccccg ctgggaagag aagagggccc agcccagagc   2880

cacctggatc tatccctgcg gcctccacac ctgaacttgc ctaactaact ggcaggggag   2940

acaggagcct agcggagccc agcctgggag cccagagggt ggcaagaaca gtgggcgttg   3000

ggagcctagc tcctgccaca tggagccccc tctgccggtc gggcagccag cagaggggga   3060

gtagccaagc tgcttgtcct gggcctgccc ctgtgtattc accaccaata aatcagacca   3120

tgaaacctga aaaaaaaaaa aa                                            3142


<210> SEQ ID NO 21
<211> LENGTH: 625
<212> TYPE: PRT
<213> ORGANISM: Homo sapiens

<400> SEQUENCE: 21

Met Asp Arg Gly Thr Leu Pro Leu Ala Val Ala Leu Leu Leu Ala Ser
1               5                   10                  15

Cys Ser Leu Ser Pro Thr Ser Leu Ala Glu Thr Val His Cys Asp Leu
            20                  25                  30

Gln Pro Val Gly Pro Glu Arg Gly Glu Val Thr Tyr Thr Thr Ser Gln
        35                  40                  45

Val Ser Lys Gly Cys Val Ala Gln Ala Pro Asn Ala Ile Leu Glu Val
    50                  55                  60

His Val Leu Phe Leu Glu Phe Pro Thr Gly Pro Ser Gln Leu Glu Leu
65                  70                  75                  80

Thr Leu Gln Ala Ser Lys Gln Asn Gly Thr Trp Pro Arg Glu Val Leu
                85                  90                  95

Leu Val Leu Ser Val Asn Ser Ser Val Phe Leu His Leu Gln Ala Leu
            100                 105                 110

Gly Ile Pro Leu His Leu Ala Tyr Asn Ser Ser Leu Val Thr Phe Gln
        115                 120                 125

Glu Pro Pro Gly Val Asn Thr Thr Glu Leu Pro Ser Phe Pro Lys Thr
    130                 135                 140

Gln Ile Leu Glu Trp Ala Ala Glu Arg Gly Pro Ile Thr Ser Ala Ala
145                 150                 155                 160

Glu Leu Asn Asp Pro Gln Ser Ile Leu Leu Arg Leu Gly Gln Ala Gln
                165                 170                 175

Gly Ser Leu Ser Phe Cys Met Leu Glu Ala Ser Gln Asp Met Gly Arg
            180                 185                 190

Thr Leu Glu Trp Arg Pro Arg Thr Pro Ala Leu Val Arg Gly Cys His
        195                 200                 205

Leu Glu Gly Val Ala Gly His Lys Glu Ala His Ile Leu Arg Val Leu
    210                 215                 220
```

```
Pro Gly His Ser Ala Gly Pro Arg Thr Val Thr Val Lys Val Glu Leu
225                 230                 235                 240

Ser Cys Ala Pro Gly Asp Leu Asp Ala Val Leu Ile Leu Gln Gly Pro
                245                 250                 255

Pro Tyr Val Ser Trp Leu Ile Asp Ala Asn His Asn Met Gln Ile Trp
            260                 265                 270

Thr Thr Gly Glu Tyr Ser Phe Lys Ile Phe Pro Glu Lys Asn Ile Arg
        275                 280                 285

Gly Phe Lys Leu Pro Asp Thr Pro Gln Gly Leu Leu Gly Glu Ala Arg
    290                 295                 300

Met Leu Asn Ala Ser Ile Val Ala Ser Phe Val Glu Leu Pro Leu Ala
305                 310                 315                 320

Ser Ile Val Ser Leu His Ala Ser Ser Cys Gly Gly Arg Leu Gln Thr
                325                 330                 335

Ser Pro Ala Pro Ile Gln Thr Thr Pro Pro Lys Asp Thr Cys Ser Pro
            340                 345                 350

Glu Leu Leu Met Ser Leu Ile Gln Thr Lys Cys Ala Asp Asp Ala Met
        355                 360                 365

Thr Leu Val Leu Lys Lys Glu Leu Val Ala His Leu Lys Cys Thr Ile
    370                 375                 380

Thr Gly Leu Thr Phe Trp Asp Pro Ser Cys Glu Ala Glu Asp Arg Gly
385                 390                 395                 400

Asp Lys Phe Val Leu Arg Ser Ala Tyr Ser Ser Cys Gly Met Gln Val
                405                 410                 415

Ser Ala Ser Met Ile Ser Asn Glu Ala Val Val Asn Ile Leu Ser Ser
            420                 425                 430

Ser Ser Pro Gln Arg Lys Lys Val His Cys Leu Asn Met Asp Ser Leu
        435                 440                 445

Ser Phe Gln Leu Gly Leu Tyr Leu Ser Pro His Phe Leu Gln Ala Ser
    450                 455                 460

Asn Thr Ile Glu Pro Gly Gln Gln Ser Phe Val Gln Val Arg Val Ser
465                 470                 475                 480

Pro Ser Val Ser Glu Phe Leu Leu Gln Leu Asp Ser Cys His Leu Asp
                485                 490                 495

Leu Gly Pro Glu Gly Gly Thr Val Glu Leu Ile Gln Gly Arg Ala Ala
            500                 505                 510

Lys Gly Asn Cys Val Ser Leu Leu Ser Pro Ser Pro Glu Gly Asp Pro
        515                 520                 525

Arg Phe Ser Phe Leu Leu His Phe Tyr Thr Val Pro Ile Pro Lys Thr
    530                 535                 540

Gly Thr Leu Ser Cys Thr Val Ala Leu Arg Pro Lys Thr Gly Ser Gln
545                 550                 555                 560

Asp Gln Glu Val His Arg Thr Val Phe Met Arg Leu Asn Ile Ile Ser
                565                 570                 575

Pro Asp Leu Ser Gly Cys Thr Ser Lys Gly Leu Val Leu Pro Ala Val
            580                 585                 590

Leu Gly Ile Thr Phe Gly Ala Phe Leu Ile Gly Ala Leu Leu Thr Ala
        595                 600                 605

Ala Leu Trp Tyr Ile Tyr Ser His Thr Arg Glu Tyr Pro Arg Pro Pro
    610                 615                 620

Gln
625
```

<210> SEQ ID NO 22

<211> LENGTH: 912
<212> TYPE: DNA
<213> ORGANISM: Artificial
<220> FEATURE:
<223> OTHER INFORMATION: Predicited nucleic acid sequence for dog CD106

<400> SEQUENCE: 22
ttccaggaag agaaaataac aaggactatt tttctccaga actactcgtg ctttattgtg 60
catcttcctt gataatacca gccattggga tgatcattta ctttgccaga agagccaaca 120
tgaaggggtc atacagtctt gtagaagcac agaaatcaaa agtgtagcta atgtttgcaa 180
tggtcaacta gagacactat ttatcagtcc aaattcttaa tactgctcat cattccatga 240
gggaaacaaa ctaagagtcc agacttccct gaatgtagtg aattcttgga aagaaatggc 300
ttcctgtgcc ccatgctgtg agcaagaggc taaaagaaaa ctttctgcct gaaactggag 360
tagctccttg atgtgtatat acaataacat gatctgtaca tatgtaaaat aaatttatgc 420
cataggagga tcacttggaa taacagcact ctatagttag atcttcaaaa tatttaaaca 480
gtgttgcctc ggttggtcgt aacggaatgc atcttaagaa aatttaacat gaatattgac 540
tggcagctaa cctatgtcat cttcttaata ttttgttttc tttaacaaaa ttttattttg 600
gtaaaattta tttcattgac aataatttca tgttttatga agataccaag gtttatcttt 660
ttatgggtaa atgataaacc aacaaggcac taggttcacc ttcaggtact aaatacttca 720
acccatggta taatggttga ctggatttct ctggatggta cttacatggt acgaagatgt 780
tttatgatgt tgtttatcag acttttgtgt aacttttcca atgtggtcta aaatgcaact 840
gcttttgatt ttcttttgta aatgtttagg ggttcttttt gtatagtaaa gtgataatat 900
ccagaattag aa 912

<210> SEQ ID NO 23
<211> LENGTH: 3119
<212> TYPE: DNA
<213> ORGANISM: Homo sapiens
<400> SEQUENCE: 23
cgcggtatct gcatcgggcc tcactggctt caggagctga ataccctccc aggcacacac 60
aggtgggaca caaataaggg ttttggaacc actattttct catcacgaca gcaacttaaa 120
atgcctggga agatggtcgt gatccttgga gcctcaaata tactttggat aatgtttgca 180
gcttctcaag cttttaaaat cgagaccacc ccagaatcta gatatcttgc tcagattggt 240
gactccgtct cattgacttg cagcaccaca ggctgtgagt ccccattttt ctcttggaga 300
acccagatag atagtccact gaatgggaag gtgacgaatg aggggaccac atctacgctg 360
acaatgaatc ctgttagttt tgggaacgaa cactcttacc tgtgcacagc aacttgtgaa 420
tctaggaaat tggaaaaagg aatccaggtg gagatctact cttttcctaa ggatccagag 480
attcatttga gtggccctct ggaggctggg aagccgatca cagtcaagtg ttcagttgct 540
gatgtatacc catttgacag gctggagata gacttactga aaggagatca tctcatgaag 600
agtcaggaat ttctggagga tgcagacagg aagtccctgg aaaccaagag tttggaagta 660
acctttactc ctgtcattga ggatattgga aaagttcttg tttgccgagc taaattacac 720
attgatgaaa tggattctgt gcccacagta aggcaggctg taaaagaatt gcaagtctac 780
atatcaccca agaatacagt tatttctgtg aatccatcca caaagctgca agaaggtggc 840
tctgtgacca tgacctgttc cagcgagggt ctaccagctc cagagatttt ctggagtaag 900
aaattagata atgggaatct acagcacctt tctggaaatg caactctcac cttaattgct 960
atgaggatgg aagattctgg aatttatgtg tgtgaaggag ttaatttgat tgggaaaaac 1020
agaaaagagg tggaattaat tgttcaagag aaaccattta ctgttgagat ctcccctgga 1080
ccccggattg ctgctcagat tggagactca gtcatgttga catgtagtgt catgggctgt 1140
gaatccccat ctttctcctg gagaacccag atagacagcc ctctgagcgg gaaggtgagg 1200
agtgagggga ccaattccac gctgaccctg agccctgtga gttttgagaa cgaacactct 1260
tatctgtgca cagtgacttg tggacataag aaactggaaa agggaatcca ggtggagctc 1320
tactcattcc ctagagatcc agaaatcgag atgagtggtg gcctcgtgaa tgggagctct 1380
gtcactgtaa gctgcaaggt tcctagcgtg taccccccttg accggctgga gattgaatta 1440
cttaaggggg agactattct ggagaatata gagtttttgg aggatacgga tatgaaatct 1500
ctagagaaca aaagtttgga aatgaccttc atccctacca ttgaagatac tggaaaagct 1560
cttgtttgtc aggctaagtt acatattgat gacatggaat tcgaacccaa acaaaggcag 1620
agtacgcaaa cactttatgt caatgttgcc cccagagata caaccgtctt ggtcagccct 1680
tcctccatcc tggaggaagg cagttctgtg aatatgacat gcttgagcca gggctttcct 1740
gctccgaaaa tcctgtggag caggcagctc cctaacgggg agctacagcc tctttctgag 1800
aatgcaactc tcaccttaat ttctacaaaa atggaagatt ctggggttta tttatgtgaa 1860
ggaattaacc aggctggaag aagcagaaag gaagtggaat taattatcca agttactcca 1920
aaagacataa aacttacagc ttttccttct gagagtgtca aagaaggaga cactgtcatc 1980
atctcttgta catgtggaaa tgttccagaa acatggataa tcctgaagaa aaaagcggag 2040
acaggagaca cagtactaaa atctatagat ggcgcctata ccatccgaaa ggcccagttg 2100
aaggatgcgg gagtatatga atgtgaatct aaaaacaaag ttggctcaca attaagaagt 2160
ttaacacttg atgttcaagg aagagaaaac aacaaagact atttttctcc tgagcttctc 2220
gtgctctatt ttgcatcctc cttaataata cctgccattg gaatgataat ttactttgca 2280
agaaaagcca acatgaaggg gtcatatagt cttgtagaag cacagaaatc aaaagtgtag 2340
ctaatgcttg atatgttcaa ctggagacac tatttatctg tgcaaatcct tgatactgct 2400
catcattcct tgagaaaaac aatgagctga gaggcagact tccctgaatg tattgaactt 2460
ggaaagaaat gcccatctat gtcccttgct gtgagcaaga agtcaaagta aaacttgctg 2520
cctgaagaac agtaactgcc atcaagatga gagaactgga ggagttcctt gatctgtata 2580
tacaataaca taatttgtac atatgtaaaa taaaattatg ccatagcaag attgcttaaa 2640
atagcaacac tctatattta gattgttaaa ataactagtg ttgcttggac tattataatt 2700
taatgcatgt taggaaaatt tcacattaat atttgctgac agctgacctt tgtcatcttt 2760
cttctatttt attccctttc acaaaatttt attcctatat agtttattga caataatttc 2820
aggttttgta aagatgccgg gttttatatt tttatagaca aataataagc aaagggagca 2880
ctgggttgac tttcaggtac taaatacctc aacctatggt ataatggttg actgggtttc 2940
tctgtatagt actggcatgg tacggagatg tttcacgaag tttgttcatc agactcctgt 3000
gcaactttcc caatgtggcc taaaaatgca acttcttttt attttctttt gtaaatgttt 3060
aggttttttt gtatagtaaa gtgataattt ctggaattag aaaaaaaaaa aaaaaaaaa 3119

<210> SEQ ID NO 24
<211> LENGTH: 739
<212> TYPE: PRT
<213> ORGANISM: Homo sapiens

<400> SEQUENCE: 24

-continued

```
Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
            20                  25                  30

Ser Arg Tyr Leu Ala Gln Ile Gly Asp Ser Val Ser Leu Thr Cys Ser
        35                  40                  45

Thr Thr Gly Cys Glu Ser Pro Phe Phe Ser Trp Arg Thr Gln Ile Asp
    50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
    130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
        275                 280                 285

Tyr Val Cys Glu Gly Val Asn Leu Ile Gly Lys Asn Arg Lys Glu Val
    290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
            340                 345                 350

Ser Pro Leu Ser Gly Lys Val Arg Ser Glu Gly Thr Asn Ser Thr Leu
        355                 360                 365

Thr Leu Ser Pro Val Ser Phe Glu Asn Glu His Ser Tyr Leu Cys Thr
    370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415

Asn Gly Ser Ser Val Thr Val Ser Cys Lys Val Pro Ser Val Tyr Pro
```

-continued

```
            420                 425                 430

Leu Asp Arg Leu Glu Ile Glu Leu Leu Lys Gly Glu Thr Ile Leu Glu
        435                 440                 445

Asn Ile Glu Phe Leu Glu Asp Thr Asp Met Lys Ser Leu Glu Asn Lys
    450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
            500                 505                 510

Asp Thr Thr Val Leu Val Ser Pro Ser Ser Ile Leu Glu Glu Gly Ser
        515                 520                 525

Ser Val Asn Met Thr Cys Leu Ser Gln Gly Phe Pro Ala Pro Lys Ile
    530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
            580                 585                 590

Glu Leu Ile Ile Gln Val Thr Pro Lys Asp Ile Lys Leu Thr Ala Phe
        595                 600                 605

Pro Ser Glu Ser Val Lys Glu Gly Asp Thr Val Ile Ile Ser Cys Thr
    610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
            660                 665                 670

Lys Val Gly Ser Gln Leu Arg Ser Leu Thr Leu Asp Val Gln Gly Arg
        675                 680                 685

Glu Asn Asn Lys Asp Tyr Phe Ser Pro Glu Leu Leu Val Leu Tyr Phe
    690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val


<210> SEQ ID NO 25
<211> LENGTH: 180
<212> TYPE: DNA
<213> ORGANISM: Artificial
<220> FEATURE:
<223> OTHER INFORMATION: Predicted nucleic acid sequence for dog
      CD146

<400> SEQUENCE: 25

gggttcacat tcagtcgtcc cagatcgtgg agtccagtgg tctgtacacc ttggagagcg      60

ttctgaaggc ccagctggcc aaagaggata aagatgccca gttttactgt gagctcaact     120

accggctgcc cagcgggaac cacatgaagg agtctcagga agtcactgtc caggttttct     180


<210> SEQ ID NO 26
```

<211> LENGTH: 3335
<212> TYPE: DNA
<213> ORGANISM: Homo sapiens

<400> SEQUENCE: 26

```
ggcacgagct ccggccggga agcatggggc ttcccaggct ggtctgcgcc ttcttgctcg     60
ccgcctgctg ctgctgtcct cgcgtcgcgg gtgtgcccgg agaggctgag cagcctgcgc    120
ctgagctggt ggaggtggaa gtgggcagca cagcccttct gaagtgcggc ctctcccagt    180
cccaaggcaa cctcagccat gtcgactggt tttctgtcca caaggagaag cggacgctca    240
tcttccgtgt gcgccagggc cagggccaga gcgaacctgg ggagtacgag cagcggctca    300
gcctccagga cagaggggct actctggccc tgactcaagt cacccccaa gacgagcgca     360
tcttcttgtg ccagggcaag cgccctcggt cccaggagta ccgcatccag ctccgcgtct    420
acaaagctcc ggaggagcca aacatccagg tcaacccct gggcatccct gtgaacagta     480
aggagcctga ggaggtcgct acctgtgtag ggaggaacgg gtaccccatt cctcaagtca    540
tctggtacaa gaatggccgg cctctgaagg aggagaagaa ccgggtccac attcagtcgt    600
cccagactgt ggagtcgagt ggtttgtaca ccttgcagag tattctgaag gcacagctgg    660
ttaaagaaga caaagatgcc cagtttttact gtgagctcaa ctaccggctg cccagtggga   720
accacatgaa ggagtccagg gaagtcaccg tccctgtttt ctacccgaca gaaaaagtgt    780
ggctggaagt ggagcccgtg ggaatgctga aggaagggga ccgcgtggaa atcaggtgtt    840
tggctgatgg caaccctcca ccacacttca gcatcagcaa gcagaacccc agcaccaggg    900
aggcagagga agagacaacc aacgacaacg ggtcctggt gctggagcct gcccggaagg     960
aacacagtgg gcgctatgaa tgtcagggcc tggacttgga caccatgata tcgctgctga   1020
gtgaaccaca ggaactactg gtgaactatg tgtctgacgt ccgagtgagt cccgcagccc   1080
ctgagagaca ggaaggcagc agcctcaccc tgacctgtga ggcagagagt agccaggacc   1140
tcgagttcca gtggctgaga gaagagacag accaggtgct ggaaaggggg cctgtgcttc   1200
agttgcatga cctgaaacgg gaggcaggag gcggctatcg ctgcgtggcg tctgtgccca   1260
gcatacccgg cctgaaccgc acacagctgg tcaacgtggc catttttggc ccccccttgga  1320
tggcattcaa ggagaggaag gtgtgggtga aagagaatat ggtgttgaat ctgtcttgtg   1380
aagcgtcagg gcacccccgg cccaccatct cctggaacgt caacggcacg gcaagtgaac   1440
aagaccaaga tccacagcga gtcctgagca ccctgaatgt cctcgtgacc ccggagctgt   1500
tggagacagg tgttgaatgc acggcctcca acgacctggg caaaaacacc agcatcctct   1560
tcctggagct ggtcaattta accaccctca caccagactc caacacaacc actggcctca   1620
gcacttccac tgccagtcct cataccagag ccaacagcac ctccacagag agaaagctgc   1680
cggagccgga gagccggggc gtggtcatcg tggctgtgat tgtgtgcatc ctggtcctgg   1740
cggtgctggg cgctgtcctc tatttcctct ataagaaggg caagctgccg tgcaggcgct   1800
cagggaagca ggagatcacg ctgcccccgt ctcgtaagag cgaacttgta gttgaagtta   1860
agtcagataa gctcccagaa gagatgggcc tcctgcaggg cagcagcggt gacaagaggg   1920
ctccgggaga ccagggagag aaatacatcg atctgaggca ttagccccga atcacttcag   1980
ctcccttccc tgcctggacc attcccagct ccctgctcac tcttctctca gccaaagcct   2040
ccaaagggac tagagagaag cctcctgctc ccctcgcctg cacacccccct ttcaaagggc  2100
cactgggtta ggacctgagg acctcacttg gccctgcaag gcccgctttt cagggaccag   2160
tccaccacca tctcctccac gttgagtgaa gctcatccca agcaaggagc cccagtctcc   2220
```

-continued

```
cgagcgggta ggagagtttc ttgcagaacg tgttttttct ttacacacat tatggctgta   2280

aatacctggc tcctgccagc agctgagctg ggtagcctct ctgagctggt ttcctgcccc   2340

aaaggctggc ttccaccatc caggtgcacc actgaagtga ggacacaccg gagccaggcg   2400

cctgctcatg ttgaagtgcg ctgttcacac ccgctccgga gagcacccca gcagcatcca   2460

gaagcagctg cagtgttgct gccaccaccc tcctgtctgc ctcttcaaag tctcctgtga   2520

catttttctt ttggtcagaa gccaggaact ggtgtcattc cttaaaagat acgtgccggg   2580

gccaggtgtg gtggctcacg cctgtaatcc cagcactttg ggaggccgag gcgggcggat   2640

cacaaagtca ggacgagacc atcctggcta acacggtgaa accctgtctc tactaaaaat   2700

acaaaaaaaa attagctagg cgtagtggtt ggcacctata gtcccagcta ctcggaaggc   2760

tgaagcagga gaatggtatg aatccaggag gtggagcttg cagtgagccg agaccgtgcc   2820

actgcactcc agcctgggca acacagcgag actccgtctc gaggaaaaaa aaagaaaaga   2880

cgcgtgcctg cggtgaggaa gctgggcgct gttttcgagt tcaggtgaat tagcctcaat   2940

cccccgtgtt cacttggctc ccatagccct cttgatggat cacgtaaaac tgaaaggcag   3000

cggggagcag acaaagatga ggtctacact gtccttcatg ggattaaag ctatggttat   3060

attagcacca aacttctaca aaccaagctc agggccccaa ccctagaagg gcccaaatga   3120

gagaatggta cttagggatg gaaaacgggc ctggctagag ctacgggtgt gtgtgtctgt   3180

ctatgtgtat gcatacatat gtgtgtatat atggttttgt caggtgtgta aatttgcaaa   3240

ttgtttcctt tatatatgta tgtatatata tatatgaaaa tatatatata tatgaaaaat   3300

aaagcttaat tgtcccagaa aaaaaaaaaa aaaaa                              3335
```

<210> SEQ ID NO 27
<211> LENGTH: 646
<212> TYPE: PRT
<213> ORGANISM: Homo sapiens

<400> SEQUENCE: 27

```
Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
        35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
```

-continued

```
            180                 185                 190

Ser Gln Thr Val Glu Ser Ser Gly Leu Tyr Thr Leu Gln Ser Ile Leu
        195                 200                 205

Lys Ala Gln Leu Val Lys Glu Asp Lys Asp Ala Gln Phe Tyr Cys Glu
    210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro Pro His Phe Ser Ile Ser Lys Gln Asn
        275                 280                 285

Pro Ser Thr Arg Glu Ala Glu Glu Glu Thr Thr Asn Asp Asn Gly Val
    290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
        355                 360                 365

Ser Ser Gln Asp Leu Glu Phe Gln Trp Leu Arg Glu Glu Thr Asp Gln
    370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
            420                 425                 430

Met Ala Phe Lys Glu Arg Lys Val Trp Val Lys Glu Asn Met Val Leu
        435                 440                 445

Asn Leu Ser Cys Glu Ala Ser Gly His Pro Arg Pro Thr Ile Ser Trp
    450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
        515                 520                 525

Thr Thr Gly Leu Ser Thr Ser Thr Ala Ser Pro His Thr Arg Ala Asn
    530                 535                 540

Ser Thr Ser Thr Glu Arg Lys Leu Pro Glu Pro Glu Ser Arg Gly Val
545                 550                 555                 560

Val Ile Val Ala Val Ile Val Cys Ile Leu Val Leu Ala Val Leu Gly
                565                 570                 575

Ala Val Leu Tyr Phe Leu Tyr Lys Lys Gly Lys Leu Pro Cys Arg Arg
            580                 585                 590

Ser Gly Lys Gln Glu Ile Thr Leu Pro Pro Ser Arg Lys Thr Glu Leu
        595                 600                 605
```

-continued

```
Val Val Glu Val Lys Ser Asp Lys Leu Pro Glu Glu Met Gly Leu Leu
    610                 615                 620

Gln Gly Ser Ser Gly Asp Lys Arg Ala Pro Gly Asp Gln Gly Glu Lys
625                 630                 635                 640

Tyr Ile Asp Leu Arg His
                645
```

<210> SEQ ID NO 28
<211> LENGTH: 8694
<212> TYPE: DNA
<213> ORGANISM: Canis familiaris

<400> SEQUENCE: 28

```
tcggcctcag ctgctgggag catggcctag gccggtggcg ctgtcgtgcg gccaccttcc     60

caacggacct tcgagatacc tgttggcccc gcttgcaggg aaagatgagt cctaccagac    120

ttgtgagggt gctgctggct ctggccctca tcttgccagg gaaactttgt acaaaaggga    180

ctgttggaag gtcatcgatg gcccgatgta gcctcttcgg aggtgacttc atcaacacct    240

ttgatgagag catgtacagc tttgcgggag attgcagtta cctcctggct ggggactgcc    300

aggaacactc cgtctcactt atcgggggtt tccaaaatgg caaaagagtg agcctctccg    360

tgtatctcgg agaatttttc gacattcatt tgtttgtcaa tggtaccatg ctgcagggga    420

cccaaagcat ctccatgccc tacgcctcca atgggctgta tctagaggcc gaggctggct    480

actacaagct gtccagtgag gcctacggct ttgtggccag aattgatggc aatggcaact    540

ttcaagtcct gctgtcagac agatacttca acaagacctg tgggctgtgt ggcaacttta    600

atatctttgc tgaggatgac ttcaggactc aagaagggac gttgacttcg gacccctatg    660

actttgccaa ctcctgggcc ctgagcagtg gggaacaacg gtgcaaacgg gtgtcccctc    720

ccagcagccc atgcaatgtc tcctctgatg aagtgcagca ggtcctgtgg gagcagtgcc    780

agctcctgaa gagtgcctcg gtgtttgccc gctgccaccc gctggtggac cctgagcctt    840

ttgtcgccct gtgtgaaagg actctgtgca cctgtgtcca ggggatggag tgcccttgtg    900

ggtcctcct ggagtacgcc cgggcctgtg cccagcaggg ggttgtcttg tacggctgga     960

ccgaccacag cgtctgccga ccagcatgcc ctgctggcat ggagtacaag gagtgcgtgt   1020

ccccttgcac cagaacttgc cagagccttc atgtcaaaga agtgtgtcag gagcaatgtg   1080

tagatggctg cagctgcccc gagggccagc tcctggatga aggccactgc gtgggaagtg   1140

ctgagtgttc ctgtgtgcat gctgggcaac ggtaccctcc gggcgcctcc ctcttacagg   1200

actgccacac ctgcatttgc cgaaatagcc tgtggatctg cagcaatgaa gaatgcccag   1260

gcgagtgtct ggtcacagga cagtcccact tcaagagctt cgacaacagg tacttcacct   1320

tcagtgggat ctgccagtac ctgctggccc aggactgcca ggaccacacc ttctctgttg   1380

tcatagagac tgtccagtgt gccgatgacc tggatgctgt ctgcacccgc tcggtcaccg   1440

tccgcctgcc tggacatcac aacagccttg tgaagctgaa gcatggggga ggagtctcca   1500

tggatggcca ggatatccag attcctctcc tgcaaggtga cctccgcatc cagcacaccg   1560

tgatggcctc cgtgcgcctc agctacgggg aggacctgca gatggattgg gacggccggg   1620

gcaggctgct ggtgacgctg tccccggcct acgcggggaa gacgtgcggc ctgtgcggga   1680

actacaacgg caaccggggg gacgacttcg tgacgcccgc aggcctggcg gagcccctgg   1740

tggaggactt cgggaacgcc tggaagctgc tcggggcctg cgagaacctg cagaagcagc   1800

accgcgatcc ctgcagcctc aacccgcgcc aggccaggtt tgcggaggag gcgtgcgcgc   1860

tgctgacgtc ctcgaagttc gagccctgcc accgagcggt gggtcctcag ccctacgtgc   1920
```

-continued

```
agaactgccg ctacgacgtc tgctcctgct ccgacggcag agactgtctt tgcagcgccg   1980
tggccaacta cgccgcagcc tgtgcccgga ggggcgtgca catcgcgtgg cgggagcccg   2040
gcttctgtgc gctgagctgc ccccagggcc aggtgtacct gcagtgtggg acccccctgca   2100
acatgacctg tcgctccctc tcttacccgg aggaggactg caatgaggtc tgcttggaag   2160
gctgcttctg cccccccaggg ctgtacctgg atgagagggg agattgtgtg cccaaggctc   2220
agtgtccctg ttactatgat ggtgagatct ttcagcccga agacatcttc tcagaccatc   2280
acaccatgtg ctactgtgag gatggcttca tgcactgtac cacaagtgga ggcctgggaa   2340
gcctgctgcc caacccggtg ctcagcagcc cccggtctca ccgcagcaaa aggagcctgt   2400
cctgtcggcc ccccatggtc aagttggtgt gtcccgctga taacccgagg gctgaaggac   2460
tggagtgtgc caaaacctgc cagaactatg acctgcagtg catgagcaca ggctgtgtct   2520
ccggctgcct ctgcccgcag ggcatggtcc ggcatgaaaa caggtgtgtg gcgctggaaa   2580
gatgtccctg cttccaccaa ggccaagagt acgccccagg agaaaccgtg aaaattgact   2640
gcaacacttg tgtctgtcgg gaccggaagt ggaactgcac agaccatgtg tgtgatgcca   2700
cttgctctgc catcggcatg gcgcactacc tcaccttcga cggactcaag tacctgttcc   2760
ctggggagtg ccagtatgtt ctggtgcagg attactgtgg cagtaaccct gggaccttcc   2820
ggatcctggt ggggaacgag ggtgcagct acccctcagt gaaatgcaag aagcgggtca   2880
ccatcctggt ggaaggagga gagattgaac tgtttgatgg ggaggtgaat gtgaagaaac   2940
ccatgaagga tgagactcac tttgaggtgg tagagtctgg tcagtacgtc attctgctgc   3000
tgggcaaggc actctctgtg gtctgggacc accgcctgag catctctgtg accctgaagc   3060
ggacatacca ggagcaggtg tgtggcctgt gtgggaattt tgatggcatc cagaacaatg   3120
atttcaccag cagcagcctc caaatagaag aagaccctgt ggaccttggg aattcctgga   3180
aagtgaaccc gcagtgtgcc gacaccaaga aagtaccact ggactcctct cctgccgtct   3240
gccacaacaa catcatgaag cagacgatgg tggattcctc ctgcaggatc ctcaccagtg   3300
atattttcca ggactgcaac aggctggtgg accctgagcc attcctggac atttgcatct   3360
acgacacttg ctcctgtgag tccattgggg actgcacctg cttctgtgac accattgctg   3420
cttacgccca tgtctgtgcc cagcatggca aggtggtagc ctggaggaca gccacattct   3480
gtccccagaa ttgcgaggag cggaatctcc acgagaatgg gtatgagtgt gagtggcgct   3540
ataacagctg tgcccctgcc tgtcccatca cgtgccagca ccccgagcca ctggcatgcc   3600
ctgtacagtg tgttgaaggt tgccatgcgc actgccctcc agggaaaatc ctggatgagc   3660
ttttgcagac ctgcatcgac cctgaagact gtcctgtgtg tgaggtggct ggtcgtcgct   3720
tggccccagg aaagaaaatc atcttgaacc ccagtgaccc tgagcactgc caaatttgtc   3780
attgtgatgg tgtcaacttc acctgtcagg cctgcagaga acccggaagt cttgtggtgc   3840
cccccacaga aggccccatt ggctctacca cctcgtatgt ggaggacacg ccggagccgc   3900
ccctccatga cttccactgc agcaggcttc tggacctggt tttcctgctg gatggctcct   3960
ccaagctgtc tgaggacgag tttgaagtgc tgaaggtctt tgtggtgggt atgatggagc   4020
atctgcacat ctcccagaag cggatccgcg tggctgtggt ggagtaccac gacggctccc   4080
acgcctacat cgagctcaag gaccggaagc gaccctcaga gctgcggcgc atcaccagcc   4140
aggtgaagta cgcgggcagc gaggtggcct ccaccagtga ggtcttaaag tacacgctgt   4200
tccagatctt tggcaagatc gaccgcccgg aagcgtctcg cattgccctg ctcctgatgg   4260
ccagccagga gccctcaagg ctggcccgga atttggtccg ctatgtgcag ggcctgaaga   4320
```

-continued

```
agaagaaagt cattgtcatc cctgtgggca tcgggcccca cgccagcctt aagcagatcc   4380
acctcataga gaagcaggcc cctgagaaca aggcctttgt gttcagtggt gtggatgagt   4440
tggagcagcg aagggatgag attatcaact acctctgtga ccttgccccc gaagcacctg   4500
cccctactca gcaccccccca atggcccagg tcacggtggg ttcggagctg ttgggggttt   4560
catctccagg acccaaaagg aactccatgg tcctggatgt ggtgtttgtc ctggaagggt   4620
cagacaaaat tggtgaggcc aactttaaca aaagcaggga gttcatggag gaggtgattc   4680
agcggatgga cgtgggccag gacaggatcc acgtcacagt gctgcagtac tcgtacatgg   4740
tgaccgtgga gtacaccttc agcgaggcgc agtccaaggg cgaggtccta cagcaggtgc   4800
gggatatccg ataccggggt ggcaacagga ccaacactgg actggccctg caatacctgt   4860
ccgaacacag cttctcggtc agccaggggg accgggagca ggtacctaac ctggtctaca   4920
tggtcacagg aaaccccgct tctgatgaga tcaagcggat gcctggagac atccaggtgg   4980
tgcccatcgg ggtgggtcca catgccaatg tgcaggagct ggagaagatt ggctggccca   5040
atgcccccat cctcatccat gactttgaga tgctccctcg agaggctcct gatctggtgc   5100
tacagaggtg ctgctctgga gaggggctgc agatccccac cctctccccc accccagatt   5160
gcagccagcc cctggatgtg gtcctcctcc tggatggctc ttccagcatt ccagcttctt   5220
actttgatga aatgaagagc ttcaccaagg ctttcatttc aagagctaat atagggcccc   5280
ggctcactca agtgtcggtg ctgcaatatg gaagcatcac cactatcgat gtgccttgga   5340
atgtagccta tgagaaagtc catttactga gccttgtgga cctcatgcag caggagggag   5400
gccccagcca aattggggat gctttgagct ttgccgtgcg atatgtcacc tcagaagtcc   5460
atggtgccag gcccggagcc tcgaaagcgg tggttatcct agtcacagat gtctccgtgg   5520
attcagtgga tgctgcagcc gaggccgcca gatccaaccg agtgacagtg ttccccattg   5580
gaatcgggga tcggtacagt gaggcccagc tgagcagctt ggcaggccca aaggctggct   5640
ccaatatggt aaggctccag cgaattgaag acctccccac cgtggccacc ctgggaaatt   5700
ccttcttcca caagctgtgc tctgggtttg atagagtttg cgtggatgag gatgggaatg   5760
agaagaggcc cggggatgtc tggaccttgc cagaccagtg ccacacagtg acttgcctgc   5820
cagatggcca gaccttgctg aagagtcatc gggtcaactg tgaccggggg ccaaggcctt   5880
cgtgccccaa tggccagccc cctctcaggg tagaggagac ctgtggctgc cgctggacct   5940
gtccctgtgt gtgcatgggc agctctaccc ggcacatcgt gacctttgat gggcagaatt   6000
tcaagctgac tggcagctgt tcgtatgtcc tatttcaaaa caaggagcag gacctggagg   6060
tgattctcca taatggtgcc tgcagccctg ggcgaaggga gacctgcatg aaatccattg   6120
aggtgaagca tgacggcctc tcagttgagc tccacagtga catgcagatg acagtgaatg   6180
ggagactagt ctccatccca tatgtgggtg gagacatgga agtcaatgtt tatgggacca   6240
tcatgtatga ggtcagattc aaccatcttg gccacatctt cacattcacc ccccaaaaca   6300
atgagttcca gctgcagctc agccccagga cctttgcttc gaagacatat ggtctctgtg   6360
ggatctgtga tgagaacgga gccaatgact tcattctgag ggatgggaca gtcaccacag   6420
actggaaggc actcatccag gaatggaccg tacagcagct tgggaagaca tgccagcctg   6480
tccctgagga gcagtgtcct gtctccagca gttcccactg ccaggtcctc ctctcagaat   6540
tgtttgccga gtgccacaag gtcctcgctc cagccacctt ttatgccatg tgccagcccg   6600
acagttgcca cccgaagaaa gtgtgtgagg cgattgcctt gtatgcccac ctctgtcgga   6660
ccaaaggggt ctgtgtggac tggaggaggg ccaatttctg tgctatgtca tgtccaccat   6720
```

-continued

```
ccctggtgta caaccactgt gagcatggct gccctcggct ctgtgaaggc aatacaagct   6780
cctgtgggga ccaaccctcg gaaggctgct tctgcccccc aaaccaagtc atgctggaag   6840
gtagctgtgt ccccgaggag gcctgtaccc agtgcatcag cgaggatgga gtccggcacc   6900
agttcctgga aacctgggtc ccagcccacc agccttgcca gatctgcacg tgcctcagtg   6960
ggcggaaggt caactgtacg ttgcagccct gccccacagc cagagctccc acctgtggcc   7020
cgtgtgaagt ggcccgcctc cgccagaacg cagagcagtg ctgcccggag tacgagtgtg   7080
tgtgtgacct ggtgagctgt gacctgcccc cggtgcctcc ctgcgaagat ggcctccaga   7140
tgaccctgac caatcctggc gagtgcagac ccaacttcac ctgtgcctgc aggaaggatg   7200
aatgcagacg ggagtccccg ccctcttgtc ccccgcaccg gacgccggcc cttcggaaga   7260
ctcagtgctg tgatgagtat gagtgtgcat gcaactgtgt caactccacg gtgagctgcc   7320
tgctggggta cctggcctcg gctgtcacca acgactgtgg ctgcaccaca acaacctgct   7380
tccctgacaa ggtgtgtgtc caccgaggca ccatctaccc tgtgggccag ttctgggagg   7440
aggcctgtga cgtgtgcacc tgcacggact tggaggactc tgtgatgggc ctgcgtgtgg   7500
cccagtgctc ccagaagccc tgtgaggaca actgcctgtc gggcttcact tatgtccttc   7560
atgaaggcga gtgctgtgga aggtgtctgc catctgcctg tgaggtggtc atcggttcac   7620
cacggggcga cgcccagtct cactggaaga atgttggctc tcactgggcc tcccctgaca   7680
acccctgcct catcaatgag tgtgtccgag tgaaggaaga ggtctttgtg caacagagga   7740
atgtctcctg cccccagctg aatgtcccca cctgccccac gggcttccag ctgagctgta   7800
agacctcaga gtgttgtccc acctgtcact gcgagcccct ggaggcctgc ttgctcaatg   7860
gtaccatcat tgggccgggg aaaagtctga tgattgatgt gtgtacaacc tgccgctgca   7920
ccgtccaggt gggagtcatc tctggattca agctggagtg caggaagacc acctgtgagg   7980
catgcccccct gggttataag gaagagaaga accaaggtga atgctgtggg agatgtctgc   8040
ctatagcttg caccattcag ctaagaggag gacagatcat gacactgaag cgtgatgaga   8100
ctatccagga tggctgtgac agtcacttct gcaaggtcaa tgaaagagga gagtacatct   8160
gggagaagag agtcacgggt tgcccacctt tcgatgaaca caagtgtctg gctgagggag   8220
ggaaaatcat gaaaattcca ggcacctgct gtgacacatg tgaggagcca gaatgcaagg   8280
atatcattgc caagctgcag cgtgtcaaag tgggagactg taagtctgaa gaggaagtgg   8340
acattcatta ctgtgagggt aaatgtgcca gcaaagccgt gtactccatc cacatggagg   8400
atgtgcagga ccagtgctcc tgctgctcgc ccacccagac ggagcccatg caggtgcccc   8460
tgcgctgcac caatggctcc ctcatctacc atgagatcct caatgccatg caatgcaggt   8520
gttcccccag gaagtgcagc aagtgaggcc actgccctgg atgctactgt cgcctgcctt   8580
acccgacctc actggactgg ccagagtgct gctcagtcct cctcagtcct cctcctgctc   8640
tgctcttgtg cttcctgatc ccacaataaa ggtcaatctt tcaccttgca aaaa         8694
```

<210> SEQ ID NO 29
<211> LENGTH: 2813
<212> TYPE: PRT
<213> ORGANISM: Canis familiaris

<400> SEQUENCE: 29

```
Met Ser Pro Thr Arg Leu Val Arg Val Leu Leu Ala Leu Ala Leu Ile
1               5                   10                  15

Leu Pro Gly Lys Leu Cys Thr Lys Gly Thr Val Gly Arg Ser Ser Met
            20                  25                  30
```

-continued

```
Ala Arg Cys Ser Leu Phe Gly Gly Asp Phe Ile Asn Thr Phe Asp Glu
        35                  40                  45

Ser Met Tyr Ser Phe Ala Gly Asp Cys Ser Tyr Leu Leu Ala Gly Asp
    50                  55                  60

Cys Gln Glu His Ser Val Ser Leu Ile Gly Gly Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Met Leu Gln Gly Thr Gln Ser Ile Ser Met Pro
            100                 105                 110

Tyr Ala Ser Asn Gly Leu Tyr Leu Glu Ala Glu Ala Gly Tyr Tyr Lys
        115                 120                 125

Leu Ser Ser Glu Ala Tyr Gly Phe Val Ala Arg Ile Asp Gly Asn Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Arg Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Arg Cys Lys Arg Val Ser Pro Pro Ser Ser
        195                 200                 205

Pro Cys Asn Val Ser Ser Asp Glu Val Gln Gln Val Leu Trp Glu Gln
    210                 215                 220

Cys Gln Leu Leu Lys Ser Ala Ser Val Phe Ala Arg Cys His Pro Leu
225                 230                 235                 240

Val Asp Pro Glu Pro Phe Val Ala Leu Cys Glu Arg Thr Leu Cys Thr
                245                 250                 255

Cys Val Gln Gly Met Glu Cys Pro Cys Gly Val Leu Leu Glu Tyr Ala
            260                 265                 270

Arg Ala Cys Ala Gln Gln Gly Val Val Leu Tyr Gly Trp Thr Asp His
        275                 280                 285

Ser Val Cys Arg Pro Ala Cys Pro Ala Gly Met Glu Tyr Lys Glu Cys
    290                 295                 300

Val Ser Pro Cys Thr Arg Thr Cys Gln Ser Leu His Val Lys Glu Val
305                 310                 315                 320

Cys Gln Glu Gln Cys Val Asp Gly Cys Ser Cys Pro Glu Gly Gln Leu
                325                 330                 335

Leu Asp Glu Gly His Cys Val Gly Ser Ala Glu Cys Ser Cys Val His
            340                 345                 350

Ala Gly Gln Arg Tyr Pro Pro Gly Ala Ser Leu Leu Gln Asp Cys His
        355                 360                 365

Thr Cys Ile Cys Arg Asn Ser Leu Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Gln
                405                 410                 415

Asp Cys Gln Asp His Thr Phe Ser Val Val Ile Glu Thr Val Gln Cys
            420                 425                 430

Ala Asp Asp Leu Asp Ala Val Cys Thr Arg Ser Val Thr Val Arg Leu
        435                 440                 445

Pro Gly His His Asn Ser Leu Val Lys Leu Lys His Gly Gly Gly Val
```

-continued

```
    450                 455                 460

Ser Met Asp Gly Gln Asp Ile Gln Ile Pro Leu Leu Gln Gly Asp Leu
465                 470                 475                 480

Arg Ile Gln His Thr Val Met Ala Ser Val Arg Leu Ser Tyr Gly Glu
                485                 490                 495

Asp Leu Gln Met Asp Trp Asp Gly Arg Gly Arg Leu Leu Val Thr Leu
            500                 505                 510

Ser Pro Ala Tyr Ala Gly Lys Thr Cys Gly Leu Cys Gly Asn Tyr Asn
        515                 520                 525

Gly Asn Arg Gly Asp Asp Phe Val Thr Pro Ala Gly Leu Ala Glu Pro
    530                 535                 540

Leu Val Glu Asp Phe Gly Asn Ala Trp Lys Leu Leu Gly Ala Cys Glu
545                 550                 555                 560

Asn Leu Gln Lys Gln His Arg Asp Pro Cys Ser Leu Asn Pro Arg Gln
                565                 570                 575

Ala Arg Phe Ala Glu Glu Ala Cys Ala Leu Leu Thr Ser Ser Lys Phe
            580                 585                 590

Glu Pro Cys His Arg Ala Val Gly Pro Gln Pro Tyr Val Gln Asn Cys
        595                 600                 605

Arg Tyr Asp Val Cys Ser Cys Ser Asp Gly Arg Asp Cys Leu Cys Ser
    610                 615                 620

Ala Val Ala Asn Tyr Ala Ala Ala Cys Ala Arg Arg Gly Val His Ile
625                 630                 635                 640

Ala Trp Arg Glu Pro Gly Phe Cys Ala Leu Ser Cys Pro Gln Gly Gln
                645                 650                 655

Val Tyr Leu Gln Cys Gly Thr Pro Cys Asn Met Thr Cys Arg Ser Leu
            660                 665                 670

Ser Tyr Pro Glu Glu Asp Cys Asn Glu Val Cys Leu Glu Gly Cys Phe
        675                 680                 685

Cys Pro Pro Gly Leu Tyr Leu Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Thr Ser Gly Gly Leu Gly Ser Leu Leu Pro Asn Pro Val
            740                 745                 750

Leu Ser Ser Pro Arg Ser His Arg Ser Lys Arg Ser Leu Ser Cys Arg
        755                 760                 765

Pro Pro Met Val Lys Leu Val Cys Pro Ala Asp Asn Pro Arg Ala Glu
    770                 775                 780

Gly Leu Glu Cys Ala Lys Thr Cys Gln Asn Tyr Asp Leu Gln Cys Met
785                 790                 795                 800

Ser Thr Gly Cys Val Ser Gly Cys Leu Cys Pro Gln Gly Met Val Arg
                805                 810                 815

His Glu Asn Arg Cys Val Ala Leu Glu Arg Cys Pro Cys Phe His Gln
            820                 825                 830

Gly Gln Glu Tyr Ala Pro Gly Glu Thr Val Lys Ile Asp Cys Asn Thr
        835                 840                 845

Cys Val Cys Arg Asp Arg Lys Trp Asn Cys Thr Asp His Val Cys Asp
    850                 855                 860

Ala Thr Cys Ser Ala Ile Gly Met Ala His Tyr Leu Thr Phe Asp Gly
865                 870                 875                 880
```

-continued

```
Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Glu
            900                 905                 910

Gly Cys Ser Tyr Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Lys Pro Met Lys Asp Glu Thr His Phe Glu Val Val Glu Ser Gly Gln
945                 950                 955                 960

Tyr Val Ile Leu Leu Leu Gly Lys Ala Leu Ser Val Val Trp Asp His
                965                 970                 975

Arg Leu Ser Ile Ser Val Thr Leu Lys Arg Thr Tyr Gln Glu Gln Val
            980                 985                 990

Cys Gly Leu Cys Gly Asn Phe Asp  Gly Ile Gln Asn Asn  Asp Phe Thr
        995                 1000                1005

Ser Ser  Ser Leu Gln Ile Glu  Glu Asp Pro Val Asp  Leu Gly Asn
    1010                1015                1020

Ser Trp  Lys Val Asn Pro Gln  Cys Ala Asp Thr Lys  Lys Val Pro
    1025                1030                1035

Leu Asp  Ser Ser Pro Ala Val  Cys His Asn Asn Ile  Met Lys Gln
    1040                1045                1050

Thr Met  Val Asp Ser Ser Cys  Arg Ile Leu Thr Ser  Asp Ile Phe
    1055                1060                1065

Gln Asp  Cys Asn Arg Leu Val  Asp Pro Glu Pro Phe  Leu Asp Ile
    1070                1075                1080

Cys Ile  Tyr Asp Thr Cys Ser  Cys Glu Ser Ile Gly  Asp Cys Thr
    1085                1090                1095

Cys Phe  Cys Asp Thr Ile Ala  Ala Tyr Ala His Val  Cys Ala Gln
    1100                1105                1110

His Gly  Lys Val Val Ala Trp  Arg Thr Ala Thr Phe  Cys Pro Gln
    1115                1120                1125

Asn Cys  Glu Glu Arg Asn Leu  His Glu Asn Gly Tyr  Glu Cys Glu
    1130                1135                1140

Trp Arg  Tyr Asn Ser Cys Ala  Pro Ala Cys Pro Ile  Thr Cys Gln
    1145                1150                1155

His Pro  Glu Pro Leu Ala Cys  Pro Val Gln Cys Val  Glu Gly Cys
    1160                1165                1170

His Ala  His Cys Pro Pro Gly  Lys Ile Leu Asp Glu  Leu Leu Gln
    1175                1180                1185

Thr Cys  Ile Asp Pro Glu Asp  Cys Pro Val Cys Glu  Val Ala Gly
    1190                1195                1200

Arg Arg  Leu Ala Pro Gly Lys  Lys Ile Ile Leu Asn  Pro Ser Asp
    1205                1210                1215

Pro Glu  His Cys Gln Ile Cys  His Cys Asp Gly Val  Asn Phe Thr
    1220                1225                1230

Cys Gln  Ala Cys Arg Glu Pro  Gly Ser Leu Val Val  Pro Pro Thr
    1235                1240                1245

Glu Gly  Pro Ile Gly Ser Thr  Thr Ser Tyr Val Glu  Asp Thr Pro
    1250                1255                1260

Glu Pro  Pro Leu His Asp Phe  His Cys Ser Arg Leu  Leu Asp Leu
    1265                1270                1275

Val Phe  Leu Leu Asp Gly Ser  Ser Lys Leu Ser Glu  Asp Glu Phe
    1280                1285                1290
```

```
Glu Val  Leu Lys Val Phe Val  Val Gly Met Met Glu  His Leu His
    1295                 1300                 1305

Ile Ser  Gln Lys Arg Ile Arg  Val Ala Val Val Glu  Tyr His Asp
    1310                 1315                 1320

Gly Ser  His Ala Tyr Ile Glu  Leu Lys Asp Arg Lys  Arg Pro Ser
    1325                 1330                 1335

Glu Leu  Arg Arg Ile Thr Ser  Gln Val Lys Tyr Ala  Gly Ser Glu
    1340                 1345                 1350

Val Ala  Ser Thr Ser Glu Val  Leu Lys Tyr Thr Leu  Phe Gln Ile
    1355                 1360                 1365

Phe Gly  Lys Ile Asp Arg Pro  Glu Ala Ser Arg Ile  Ala Leu Leu
    1370                 1375                 1380

Leu Met  Ala Ser Gln Glu Pro  Ser Arg Leu Ala Arg  Asn Leu Val
    1385                 1390                 1395

Arg Tyr  Val Gln Gly Leu Lys  Lys Lys Lys Val Ile  Val Ile Pro
    1400                 1405                 1410

Val Gly  Ile Gly Pro His Ala  Ser Leu Lys Gln Ile  His Leu Ile
    1415                 1420                 1425

Glu Lys  Gln Ala Pro Glu Asn  Lys Ala Phe Val Phe  Ser Gly Val
    1430                 1435                 1440

Asp Glu  Leu Glu Gln Arg Arg  Asp Glu Ile Ile Asn  Tyr Leu Cys
    1445                 1450                 1455

Asp Leu  Ala Pro Glu Ala Pro  Ala Pro Thr Gln His  Pro Pro Met
    1460                 1465                 1470

Ala Gln  Val Thr Val Gly Ser  Glu Leu Leu Gly Val  Ser Ser Pro
    1475                 1480                 1485

Gly Pro  Lys Arg Asn Ser Met  Val Leu Asp Val Val  Phe Val Leu
    1490                 1495                 1500

Glu Gly  Ser Asp Lys Ile Gly  Glu Ala Asn Phe Asn  Lys Ser Arg
    1505                 1510                 1515

Glu Phe  Met Glu Glu Val Ile  Gln Arg Met Asp Val  Gly Gln Asp
    1520                 1525                 1530

Arg Ile  His Val Thr Val Leu  Gln Tyr Ser Tyr Met  Val Thr Val
    1535                 1540                 1545

Glu Tyr  Thr Phe Ser Glu Ala  Gln Ser Lys Gly Glu  Val Leu Gln
    1550                 1555                 1560

Gln Val  Arg Asp Ile Arg Tyr  Arg Gly Gly Asn Arg  Thr Asn Thr
    1565                 1570                 1575

Gly Leu  Ala Leu Gln Tyr Leu  Ser Glu His Ser Phe  Ser Val Ser
    1580                 1585                 1590

Gln Gly  Asp Arg Glu Gln Val  Pro Asn Leu Val Tyr  Met Val Thr
    1595                 1600                 1605

Gly Asn  Pro Ala Ser Asp Glu  Ile Lys Arg Met Pro  Gly Asp Ile
    1610                 1615                 1620

Gln Val  Val Pro Ile Gly Val  Gly Pro His Ala Asn  Val Gln Glu
    1625                 1630                 1635

Leu Glu  Lys Ile Gly Trp Pro  Asn Ala Pro Ile Leu  Ile His Asp
    1640                 1645                 1650

Phe Glu  Met Leu Pro Arg Glu  Ala Pro Asp Leu Val  Leu Gln Arg
    1655                 1660                 1665

Cys Cys  Ser Gly Glu Gly Leu  Gln Ile Pro Thr Leu  Ser Pro Thr
    1670                 1675                 1680

Pro Asp  Cys Ser Gln Pro Leu  Asp Val Val Leu Leu  Leu Asp Gly
```

-continued

```
    1685                1690                1695

Ser Ser  Ser Ile Pro Ala Ser  Tyr Phe Asp Glu Met  Lys Ser Phe
    1700                1705                1710

Thr Lys  Ala Phe Ile Ser Arg  Ala Asn Ile Gly Pro  Arg Leu Thr
    1715                1720                1725

Gln Val  Ser Val Leu Gln Tyr  Gly Ser Ile Thr Thr  Ile Asp Val
    1730                1735                1740

Pro Trp  Asn Val Ala Tyr Glu  Lys Val His Leu Leu  Ser Leu Val
    1745                1750                1755

Asp Leu  Met Gln Gln Glu Gly  Gly Pro Ser Gln Ile  Gly Asp Ala
    1760                1765                1770

Leu Ser  Phe Ala Val Arg Tyr  Val Thr Ser Glu Val  His Gly Ala
    1775                1780                1785

Arg Pro  Gly Ala Ser Lys Ala  Val Val Ile Leu Val  Thr Asp Val
    1790                1795                1800

Ser Val  Asp Ser Val Asp Ala  Ala Ala Glu Ala Ala  Arg Ser Asn
    1805                1810                1815

Arg Val  Thr Val Phe Pro Ile  Gly Ile Gly Asp Arg  Tyr Ser Glu
    1820                1825                1830

Ala Gln  Leu Ser Ser Leu Ala  Gly Pro Lys Ala Gly  Ser Asn Met
    1835                1840                1845

Val Arg  Leu Gln Arg Ile Glu  Asp Leu Pro Thr Val  Ala Thr Leu
    1850                1855                1860

Gly Asn  Ser Phe Phe His Lys  Leu Cys Ser Gly Phe  Asp Arg Val
    1865                1870                1875

Cys Val  Asp Glu Asp Gly Asn  Glu Lys Arg Pro Gly  Asp Val Trp
    1880                1885                1890

Thr Leu  Pro Asp Gln Cys His  Thr Val Thr Cys Leu  Pro Asp Gly
    1895                1900                1905

Gln Thr  Leu Leu Lys Ser His  Arg Val Asn Cys Asp  Arg Gly Pro
    1910                1915                1920

Arg Pro  Ser Cys Pro Asn Gly  Gln Pro Pro Leu Arg  Val Glu Glu
    1925                1930                1935

Thr Cys  Gly Cys Arg Trp Thr  Cys Pro Cys Val Cys  Met Gly Ser
    1940                1945                1950

Ser Thr  Arg His Ile Val Thr  Phe Asp Gly Gln Asn  Phe Lys Leu
    1955                1960                1965

Thr Gly  Ser Cys Ser Tyr Val  Leu Phe Gln Asn Lys  Glu Gln Asp
    1970                1975                1980

Leu Glu  Val Ile Leu His Asn  Gly Ala Cys Ser Pro  Gly Ala Lys
    1985                1990                1995

Glu Thr  Cys Met Lys Ser Ile  Glu Val Lys His Asp  Gly Leu Ser
    2000                2005                2010

Val Glu  Leu His Ser Asp Met  Gln Met Thr Val Asn  Gly Arg Leu
    2015                2020                2025

Val Ser  Ile Pro Tyr Val Gly  Gly Asp Met Glu Val  Asn Val Tyr
    2030                2035                2040

Gly Thr  Ile Met Tyr Glu Val  Arg Phe Asn His Leu  Gly His Ile
    2045                2050                2055

Phe Thr  Phe Thr Pro Gln Asn  Asn Glu Phe Gln Leu  Gln Leu Ser
    2060                2065                2070

Pro Arg  Thr Phe Ala Ser Lys  Thr Tyr Gly Leu Cys  Gly Ile Cys
    2075                2080                2085
```

-continued

```
Asp Glu  Asn Gly Ala Asn Asp  Phe Ile Leu Arg Asp  Gly Thr Val
    2090                 2095                 2100

Thr Thr  Asp Trp Lys Ala Leu  Ile Gln Glu Trp Thr  Val Gln Gln
    2105                 2110                 2115

Leu Gly  Lys Thr Cys Gln Pro  Val Pro Glu Glu Gln  Cys Pro Val
    2120                 2125                 2130

Ser Ser  Ser Ser His Cys Gln  Val Leu Leu Ser Glu  Leu Phe Ala
    2135                 2140                 2145

Glu Cys  His Lys Val Leu Ala  Pro Ala Thr Phe Tyr  Ala Met Cys
    2150                 2155                 2160

Gln Pro  Asp Ser Cys His Pro  Lys Lys Val Cys Glu  Ala Ile Ala
    2165                 2170                 2175

Leu Tyr  Ala His Leu Cys Arg  Thr Lys Gly Val Cys  Val Asp Trp
    2180                 2185                 2190

Arg Arg  Ala Asn Phe Cys Ala  Met Ser Cys Pro Pro  Ser Leu Val
    2195                 2200                 2205

Tyr Asn  His Cys Glu His Gly  Cys Pro Arg Leu Cys  Glu Gly Asn
    2210                 2215                 2220

Thr Ser  Ser Cys Gly Asp Gln  Pro Ser Glu Gly Cys  Phe Cys Pro
    2225                 2230                 2235

Pro Asn  Gln Val Met Leu Glu  Gly Ser Cys Val Pro  Glu Glu Ala
    2240                 2245                 2250

Cys Thr  Gln Cys Ile Ser Glu  Asp Gly Val Arg His  Gln Phe Leu
    2255                 2260                 2265

Glu Thr  Trp Val Pro Ala His  Gln Pro Cys Gln Ile  Cys Thr Cys
    2270                 2275                 2280

Leu Ser  Gly Arg Lys Val Asn  Cys Thr Leu Gln Pro  Cys Pro Thr
    2285                 2290                 2295

Ala Arg  Ala Pro Thr Cys Gly  Pro Cys Glu Val Ala  Arg Leu Arg
    2300                 2305                 2310

Gln Asn  Ala Glu Gln Cys Cys  Pro Glu Tyr Glu Cys  Val Cys Asp
    2315                 2320                 2325

Leu Val  Ser Cys Asp Leu Pro  Pro Val Pro Pro Cys  Glu Asp Gly
    2330                 2335                 2340

Leu Gln  Met Thr Leu Thr Asn  Pro Gly Glu Cys Arg  Pro Asn Phe
    2345                 2350                 2355

Thr Cys  Ala Cys Arg Lys Asp  Glu Cys Arg Arg Glu  Ser Pro Pro
    2360                 2365                 2370

Ser Cys  Pro Pro His Arg Thr  Pro Ala Leu Arg Lys  Thr Gln Cys
    2375                 2380                 2385

Cys Asp  Glu Tyr Glu Cys Ala  Cys Asn Cys Val Asn  Ser Thr Val
    2390                 2395                 2400

Ser Cys  Leu Leu Gly Tyr Leu  Ala Ser Ala Val Thr  Asn Asp Cys
    2405                 2410                 2415

Gly Cys  Thr Thr Thr Thr Cys  Phe Pro Asp Lys Val  Cys Val His
    2420                 2425                 2430

Arg Gly  Thr Ile Tyr Pro Val  Gly Gln Phe Trp Glu  Glu Ala Cys
    2435                 2440                 2445

Asp Val  Cys Thr Cys Thr Asp  Leu Glu Asp Ser Val  Met Gly Leu
    2450                 2455                 2460

Arg Val  Ala Gln Cys Ser Gln  Lys Pro Cys Glu Asp  Asn Cys Leu
    2465                 2470                 2475

Ser Gly  Phe Thr Tyr Val Leu  His Glu Gly Glu Cys  Cys Gly Arg
    2480                 2485                 2490
```

```
Cys Leu  Pro Ser Ala Cys Glu  Val Val Ile Gly Ser  Pro Arg Gly
    2495                 2500                 2505

Asp Ala  Gln Ser His Trp Lys  Asn Val Gly Ser His  Trp Ala Ser
    2510                 2515                 2520

Pro Asp  Asn Pro Cys Leu Ile  Asn Glu Cys Val Arg  Val Lys Glu
    2525                 2530                 2535

Glu Val  Phe Val Gln Gln Arg  Asn Val Ser Cys Pro  Gln Leu Asn
    2540                 2545                 2550

Val Pro  Thr Cys Pro Thr Gly  Phe Gln Leu Ser Cys  Lys Thr Ser
    2555                 2560                 2565

Glu Cys  Cys Pro Thr Cys His  Cys Glu Pro Leu Glu  Ala Cys Leu
    2570                 2575                 2580

Leu Asn  Gly Thr Ile Ile Gly  Pro Gly Lys Ser Leu  Met Ile Asp
    2585                 2590                 2595

Val Cys  Thr Thr Cys Arg Cys  Thr Val Gln Val Gly  Val Ile Ser
    2600                 2605                 2610

Gly Phe  Lys Leu Glu Cys Arg  Lys Thr Thr Cys Glu  Ala Cys Pro
    2615                 2620                 2625

Leu Gly  Tyr Lys Glu Glu Lys  Asn Gln Gly Glu Cys  Cys Gly Arg
    2630                 2635                 2640

Cys Leu  Pro Ile Ala Cys Thr  Ile Gln Leu Arg Gly  Gly Gln Ile
    2645                 2650                 2655

Met Thr  Leu Lys Arg Asp Glu  Thr Ile Gln Asp Gly  Cys Asp Ser
    2660                 2665                 2670

His Phe  Cys Lys Val Asn Glu  Arg Gly Glu Tyr Ile  Trp Glu Lys
    2675                 2680                 2685

Arg Val  Thr Gly Cys Pro Pro  Phe Asp Glu His Lys  Cys Leu Ala
    2690                 2695                 2700

Glu Gly  Gly Lys Ile Met Lys  Ile Pro Gly Thr Cys  Cys Asp Thr
    2705                 2710                 2715

Cys Glu  Glu Pro Glu Cys Lys  Asp Ile Ile Ala Lys  Leu Gln Arg
    2720                 2725                 2730

Val Lys  Val Gly Asp Cys Lys  Ser Glu Glu Glu Val  Asp Ile His
    2735                 2740                 2745

Tyr Cys  Glu Gly Lys Cys Ala  Ser Lys Ala Val Tyr  Ser Ile His
    2750                 2755                 2760

Met Glu  Asp Val Gln Asp Gln  Cys Ser Cys Cys Ser  Pro Thr Gln
    2765                 2770                 2775

Thr Glu  Pro Met Gln Val Pro  Leu Arg Cys Thr Asn  Gly Ser Leu
    2780                 2785                 2790

Ile Tyr  His Glu Ile Leu Asn  Ala Met Gln Cys Arg  Cys Ser Pro
    2795                 2800                 2805

Arg Lys  Cys Ser Lys
    2810
```

<210> SEQ ID NO 30
<211> LENGTH: 33834
<212> TYPE: DNA
<213> ORGANISM: Homo sapiens

<400> SEQUENCE: 30

```
gaattcatcg tcaagagagc tttatttgca tgagtgcaaa ggatgaaaat tctagactgg     60

gcgtggtggc tcacgcctgt aatcccagca ctttgggaga ccgaggtggg cagatcacga    120

ggtcaggagt ttgagaccag cctggctaac atagtggaac cccatctcta ctaaaaatac    180
```

-continued

```
aaaaaattag ctgggtgtag tggtgtgtgc atgtaatccc agctacttgg gaggctgagg    240
caggagaatt gcttgaagcc gggaggcaga ggttgcagtg agccatgatt gcatcactgc    300
actccagccc agcggacagt gcgagactcc atctcaaaaa aaaaaaaaga aagaaaagaa    360
tattctaaaa aaagacttaa ttccccccgc caccccaccc caaaacaagt ggagacaggc    420
aaacttcctt atcttctagg ttgggggatg gatttttttc ctggtccact gtttggaaga    480
tgtttccctt caaactttca gcttttgcag ggatctccgt tctagttctc cctctgggtc    540
aggcccgtag ctgcactgcc cattcttgta atgtgcggcc tccagtctgg agggttccca    600
gactggccta cgctaggcca cccatgggcc taccctgcct catgctcatt taggctcctc    660
ttcctcattg accctttaag atattcctta ctttcctccc agatcaactg tggatttaaa    720
gaacatttgt tgtatttagc acagcattta aagatatttt gtaatgaaag ggttttcaga    780
ttagttattt agttttttta aataagagct ggaagtggaa atcccgatgg ccttttcttt    840
tcttttcttt tttttcttga gacggagtct tgctctgtca cccaggctgg agtgcagtgg    900
ctcgatctca gctcactgca agctccgcct cccgggttca cgccattctc ctgcctcagc    960
ctcccgagta gctgggacta caggcgcccc gccaccacgc ctggctaatt ttttgtgttt   1020
ttagtagaga cggggtttca ctatgttagc caggatggtc ttgatccctt gacctcgtga   1080
tccgcccacc tcggcctccc aaagtgctgg gattacaggc gtgaaccacc gtgcccggcc   1140
ccccaatggc cttttctact gtctcatgct gattctgcct ctggtgccat ttttcttcct   1200
tgggagtgtg catcttcctc tcctggggcg gtaaagggag tagcagagtg cgaggtatgt   1260
gggaagggag gaggttggaa cctagtggtt tctcaaagtc ttagggcagg aggtatcatg   1320
gagaagcagt gaggaggtct tccataccca gacatgcctc agggtgcttg tctcagtgcc   1380
tggaatccca gcacgagagt catcttcccc ccaccgctgc ccattgcatc agttacttat   1440
tttagtagga attagtttag cagatggtgt tgagaattag gcttttggga atgggaggct   1500
gggaagaaga attgtgtgtg tgtgtgtgtg tgtgtgtgtg tgtgtgtgtg taagatcagg   1560
gtaccagaag tgggtggaaa tgtccttgag aattagaatt attagaatgt agcaacagta   1620
gaagtattag actcaaacca tcactcccca ccttcaccat tttacaaagg cttaggcttg   1680
tggccaagac cttcatcttt agccgatcca ttcaaccctg gccaggatcc aaatggactg   1740
tttttgtcag ggccaggacc ggatccttca tacctggggt gcataggaag tgttagtact   1800
ccccttcctc caaacacagc agcaaaattg gctcaggttg aggtgttttt ctcaacttcc   1860
ctggagtcca gccctggaag ctggatcagg aagctgtgtt gttctactgt gattccccct   1920
ggcctgtatc agcttgccct gaaacaacca gcattcctgg ttatcccaca caggtggggc   1980
actctaggaa gaccagggat caagtgtggg ggtgtaggga tagggggtgt ttggggaggg   2040
caaggcagtt aattaaggca gctgccagga ggtctccctc caaactctac aaagctttat   2100
cagcttggag gtacttctaa taccatttcc tttcattgtt tccttttggt aattaaaagg   2160
aggccaatcc cctgttgtgg cagctcacag ctattgtggt gggaaaggga gggtggttgg   2220
tggatgtcac agcttgggct ttatctcccc cagcagtggg gactccacag cccctgggct   2280
acataacagc aagacagtcc ggagctgtag cagacctgat tgagcctttg cagcagctga   2340
gagcatggcc tagggtgggc ggcaccattg tccagcagct gagtttccca gggaccttgg   2400
agatagccgc agccctcatt tgcaggggaa ggtatggcct ttggaaggag agctggctca   2460
gttgtgggag gaagatgcag gactgactga tccctgctcc tggggagctg gagttctctg   2520
tcgctggact agaagggctt tgtttggagg ggcaattcaa ttcagccagg gatgatccta   2580
```

-continued

```
atactccctc ctccacttgc ctctgagggt cctggggctg cttttcttca tgcagtgggt   2640
tttactgttt gatagtactt cactcaaatg agttggaatg aagtttgccc tcacctctga   2700
gaacctggga gcagctgaat gtacctgcgt gttaggactg ggaggggaca cctgcttgga   2760
gaccgagacc tggcagtatc tgacatctca gtgttccttc cacagatgta tcacagattg   2820
gcttgatttc acctttggct ggatgggacc ttaggtagga agggagtcac ccccagtgaa   2880
tctcaggcag cagattctgc acttcattta acaacttttc ccgaggagag gggctacagc   2940
aggggctcta agtgacttgg ggtacgctct gccagccagg atgaattgtc cctctcttgg   3000
gggtcacaca gtggggaagt ctgcctgcat ccagggccgc tggactcctg tccatttttt   3060
cagatgaact cagcaaacat ttgctgggca tctcctgggt gctaagcatc ttgccaggtg   3120
ctggggttgg aggcaaggga gacagccttt gctcttgtga aggcacttgt ggtacagagt   3180
caggggccaa caagcaaacc gtcaagttgg tggttcctga gcattctcta tgtctgggct   3240
gctgtggtgg gcacacaagt gtaagacggt tcctactcgc cagtttggat gcagaggcag   3300
gaaggaatga ggtgtgtgtt agctcccagc tgcttcagga ggcagggatg tgaggcccag   3360
cgggcctgga gggaaggcag cgttttcctc ctgtcttggg cctgggactg ctgtctgtgg   3420
aaaggtgccc acaggtccca gctcacagcg attgttaccc ttgggcctgg cactggccag   3480
gggtttttc gggggccaga agtccatgtt caaaggggaa aagggggtca cgaggatcaa   3540
tcttttctcc tgctttaaag aaatgttttt gctactgcat gccctgatag tcgccacacc   3600
agcagccgcc tacctgggca gcaatgacca gctcacgtct cttgcttctt tgcagatgat   3660
tcctgccaga tttgccgggg tgctgcttgc tctggccctc attttgccag gtaggtacaa   3720
aagggcctcc atttctcatt cctgccccag ggccatctgg agtgacacct ttccgggaat   3780
cagcaggtgt gtctggagct cacctgtgtg cccagcccta acttaggctg ttggttgcct   3840
cctgtgaagg ttctgcggag ttcccaccct tgacttgtat tccagagacc aggtgcctgc   3900
aaatgccatc tcctgttggg gaattaagaa gcataaaggt ggcacagaac tgtcctatat   3960
tatgggggca caggatgagg aggaaggaat ccaagacttg gatggattat tagttttcga   4020
taagattgtg gaggtcacct tgttgaacct cccatggtac aatgaagaga ctgagggtca   4080
gagaggagaa atgactgctc caaagtctcc tagagccaaa atcagaggtc agtcttcctg   4140
ggttccaggc caacaccctt tccactgcac tgcatcatac tgctgccctt cccttgctaa   4200
gattctgggt ctgcaaatgg cgggagggga cttttgacct tgggcgcttt ccacttagat   4260
ctctcaggtc agcagcatcc agctactgcc cacaggtgag tctgggaaaa aaaatacaca   4320
tttgtcacac tctctgcatc ttcctactag gtgggtcttt tgccggggaa cccagaacac   4380
ttagagattt actgctgtat ttccccacct gccgacacac acacacccat agtcagtgaa   4440
ggagttagcc tgtgacgccg gaggagttca cacttcagag agtctatgtg tcaggcacac   4500
agtctgatct gtttaaaatt taacatgccc aagacatgct agtagattta tgtacaaaga   4560
tgctcactgc aatctatcta taatattaaa acatggaaaa atgctagaaa cctaacaata   4620
gagggctata ctatagacat tcagatgcaa aatataatgc agccactaaa aaccgcatat   4680
tggaagtata tacactagca cgacaaattg tttacaatct attgagaaat aaacagaggt   4740
tataggtagt ttgcacaagt tggtcaccaa tttataaaaa acccacagct gtatatatgc   4800
tatacaacaa aatggaaaga tgaacattga aatgttaact ctaatcatcg ctgaatgttg   4860
ggttacagat ggttttaact tctttgtctt ttcttttctt tttctttttc ttttttttt    4920
cgagacagag tctcactctg tcgcccagtc tagagtgcag tggtatgatg ttggctccct   4980
```

-continued

```
gcaacctctg cctcctgggc tcaagtgatt ctcctgcctc agcctcacca gtagctggga   5040
ttacaggcgc ccaccactac acccggctag tttttgtatt tttagtagag acagggtttc   5100
gccatgttgg gcaggctggt cttgaattcc tgacctcagg tgatctgccc acctcggcct   5160
cccaaagtgc tgggattata ggcgtgagcc actgtgcccg gccagcttct ttgttttctt   5220
ctgtatgccc caaattttta ataatggaca tgatgacatt ttaaatcagt aagtaaatgt   5280
cattgaaact aatggatttc ctgaaaaact gttccttagt tattgctgtg agtctggggt   5340
catatctggg agctgaaagc aacagcttta gtctcattta ggatggaaaa tacctcccca   5400
cagcccagtt tctatcagag gcagtctaat ttctacgagg ccagagaggt ttgagctgat   5460
ggtcccagtt gtgccctgag atcaccagcc caacctgtgg cctctccctc cagggaccct   5520
ttgtgcagaa ggaactcgcg gcaggtcatc cacggcccga tgcagccttt tcggaagtga   5580
cttcgtcaac acctttgatg ggagcatgta cagctttgcg ggatactgca gttacctcct   5640
ggcagggggc tgccagaaac gctccttctc gattattggt gagttctggg cactgcaggg   5700
aggacttcag agggagggct ggctgagctc agccctggtg tgggggagga ttcctgctct   5760
caggacagtg tctgagtgga aaggtcactg ctgagaacaa ggagaggaac agcctttctg   5820
tgacacgtag cccctcttgg ctttccccgg gtctctcccc acgggagccg ggtgggatgg   5880
atgaagagag tcttcatctt tggtagtcca ctgtgtccgt tgctctgggg cccggcgatg   5940
ccctgggaac tccacagcat caaggcaaat gatgaactag agaaggtgct ttggaacgtg   6000
taaaactcct tgccagagag aagactcgtt gttgttttct tggtggcctg tggatcagaa   6060
catcagctta tgctgaggac ttcctgtatt cctgcagaag ggctggtact gtccctgcca   6120
tgtccctgca tccccacaac agccctggga tgtagctgta gtcatcccag ttttaccaat   6180
ggagaaccaa ggctcatgaa ggttgcatga tccttccaag gcctgacaga caataaaagg   6240
tggagctgag gccgggcacg gtggctcatg cctgtaatcc cagtactttg ggaggccaag   6300
gtgggtggat cacctgaggt caagagtttg agaccagcct ggccaacatg gtgaaacccc   6360
atctctacta aaaatacaaa aattagccgg gtgtggtggt gtgtgtctat aatcccagct   6420
acttgggagg ctgaggcagg agaatcgctt gaacctggtt gcaataagct gagatacact   6480
ccagcctggg caacagagcg agactccatc tcaaaaaaaa aaacaaccca caaaaaaacaa  6540
aaaaactgga ctaagcaggc caaggacaga gcccaaggcc aaggcttaat ctagaagagg   6600
gctcagaagt gccccactca agtttggtca aggagggagt ctttggcaac acctggacac   6660
ttacctgaga tctgggctgt agggctcctg gggtcattgc tccatcagtc agcggggact   6720
gacacagggt cctccatgtg cccagcactg ggctaggctc tgtctagcac ctggctatag   6780
ctatgagctc ctttttgggg cgttttctgc tgagaaaagg ttacgtagat aatgattctt   6840
aatcaatgta ttcatttttt gagaggagta ataatcacta ctattgactt ttttctcttt   6900
caggggactt ccagaatggc aagagagtga gcctctccgt gtatcttggg gaatttttttg  6960
acatccattt gtttgtcaat ggtaccgtga cacaggggga ccaaaggtaa gccaacaatg   7020
tctgagttag aaaggaccct agggatcccc tgacacaacc ccctcatttt tagatgagga   7080
agctggggcc cagagaatgg aagcaaatgt tccaaggaag tgagtagcag ggctgggtga   7140
gagccagctc tcccgattgc tgatctaggt cctcagccac tttgcaccat gttctgaacc   7200
ctacaacatg ggttggggt tagaaggtgg gagagacatc cagaaaatgc acaagaagcc    7260
cacttctgaa cttagccttt gccctccaga gtctccatgc cctatgcctc caaagggctg   7320
tatctagaaa ctgaggctgg gtactacaag ctgtccggtg aggcctatgg ctttgtggcc   7380
```

aggatcgatg gcagcggcaa ctttcaagtc ctgctgtcag acagatactt caacaagacc 7440
tgcgggctgt gtggcaactt taacatcttt gctgaagatg actttatgac ccaagaaggt 7500
aagatgttct gggataccat ttccctaaag tgtggccatg ctttttattt ccttgctcat 7560
aaaccttcac taacatgcct tccctggcat tcaagcctca ctgtgacctc acctcaattt 7620
atgttgccaa ccttatctct ttgcattcca ttccaatgcc tagacctcta gtgaaaccag 7680
gtcttagagc tcctcaaagc tgacttcgtt caactttgaa ttcacaactg ggttgcctga 7740
ggaggggtga accagccaag ccagagatgg gtcaagtcaa aactcctgtg ctgctcagta 7800
gtgggattgc acttgtgaat agccgcgcac tccagcctgg gaaacatagc cagaccctgt 7860
ctctttataa aaaattaaaa caaaacacac aaaaccacca gcagacctag aattttcacc 7920
cagaagttct gggacaggca taactgaagc attactttcc tgaaactttc ctccacaggg 7980
accttgacct cggaccctta tgactttgcc aactcatggg ctctgagcag tggagaacag 8040
tggtgtgaac gggcatctcc tcccagcagc tcatgcaaca tctcctctgg ggaaatgcag 8100
aaggtgggtg tggactggcc tgggtgcacc tggatggtgt gtgatttctg gatctaaaag 8160
acagaaggac tcagtctcat atccttccat ctgggggagg aatggactta cgcagggcca 8220
tttcctccaa aactaactgt ggctagagtc taattctaat acatctcgag cctgaagctc 8280
taaaaatgag tctgggctaa tgacttcagg tgctgaggga gctgccttgg tttccctagc 8340
agggctaagt ctcagtgcca cactcaggga gacactaacg gagcataccg ctgaggcggc 8400
ccctcttcct gcagggcctg tgggagcagt gccagcttct gaagagcacc tcggtgtttg 8460
cccgctgcca ccctctggtg gaccccgagc cttttgtggc cctgtgtgag aagactttgt 8520
gtgagtgtgc tgggggggctg gagtgcgcct gccctgccct cctggagtac gcccggacct 8580
gtgcccagga gggaatggtg ctgtacggct ggaccgacca cagcgcgtgc agtaagtcgg 8640
ccccctgccc cgtcctgccc tgccggggat gaacggtctg tcctgggtgg tgtcccttag 8700
ggtgcttcgg ggctgtgtca cgtatgtgcg gctttaccac acccagccag ccagtgacta 8760
caaagccacg tgtcccggac ccatttcctg aatggctcct gccctctgtc aaacgggctt 8820
cccaaagccc cgtgtcctgc ccctgcctcc gtcccgcccc cacgcctccc ctggcgcccc 8880
ctgacttccc tcaggaaatc cgacccctgc actcacacag tgttctctgc ttcccaccaa 8940
gatcttggca gttgcggttt tggtttttgt cttcaccgcc tgcccgcccg aattgatgag 9000
gagcaggacg ctgacctggc tgtccgtgtg tggtgatctt ggggaagggt gggggtcctg 9060
ggtgccccga tgggtcttgg taagggcctc acaagatgga agatgttcat ctaagggagg 9120
ggtggcctca ggggggcacg tggctcactg gggtgagaa ggacctggaa gcctgaagac 9180
agaggggagc agtcagagtg ggcacgagag gctcaggctg tggcatggct ggtgagatga 9240
tgcaccggtg ggacctgccc tgggtagacc cctttgatgt tccttttcag gcccagtgtg 9300
ccctgctggt atggagtata ggcagtgtgt gtccccttgc gccaggacct gccagagcct 9360
gcacatcaat gaaatgtgtc aggagcgatg cgtggatggc tgcagctgcc ctggtaatga 9420
acttcccact ttatttacag atcagagacc ttgccagcac ttcccttcct tatattgcat 9480
tatgtgaaag ataaacacca cagaacaagt tctttgagct tcctggaaga aacccaacca 9540
ttgtccctgg ggattctata gttgtgggat gagtgacgca atgacaatgt tgaggtcttt 9600
gtcttgatgc ccttgacccc agagggacag ctcctggatg aaggcctctg cgtggagagc 9660
accgagtgtc cctgcgtgca ttccggaaag cgctaccctc ccggcacctc cctctctcga 9720
gactgcaaca cctggtaatg gggctgcgc agcgtgctct gggagacctg cctgggggac 9780

-continued

```
tggggaggga agaattttaa ccctatgaag attctgctag caccagctct tttcttttcc   9840
cacatccctt cgtttgggga ctgtgataac taccaagagc tctaaatcca tttgcatacc   9900
cttgtgtttg cagaaccacc aatgacctgt gctttttccc tccaacagca tttgccgaaa   9960
cagccagtgg atctgcagca atgaagaatg tccaggtagg cgacctgccg ctcattctct  10020
tcctccttcc ctgaatcggg gaggcgtctc ctcctatttt ctcgtagaac ttgtttttag  10080
actggtttgg gcaaaggacg tccatgcagt tttggggaag ggcaccctgc ttgcatatgc  10140
attccacctt ggccacccca ggggaagtgc cctcacctcc cattcttctc ccttcctctg  10200
tgtctctcca ggggagtgcc ttgtcactgg tcaatcccac ttcaagagct ttgacaacag  10260
atacttcacc ttcagtggga tctgccagta cctgctggcc cgggattgcc aggaccactc  10320
cttctccatt gtcattgaga ctgtccaggt gagctttgcc agcccggctg ctggtcgggt  10380
ggtgggttga ggcctttctc tgattaagag ggtcctgggc tggggagctg gataggcagg  10440
gggtgcagca aagtcaccct gtgttccctc ttggcagtgt gctgatgacc gcgacgctgt  10500
gtgcacccgc tccgtcaccg tccggctgcc tggcctgcac aacagccttg tgaaactgaa  10560
gcatggggca ggagttgcca tggatggcca ggacatccag ctccccctcc tgaaaggtat  10620
gcttcgtcct gctccatcag gcctggggct ggcacagccc atcccttagc accctccttc  10680
tcaaccctgg cctaagtcat tgctcttcag tgctaccatc cttttgagac accccatttc  10740
ctcccaaata catctgcctg ccaccaccct gtcctctccc cacctctgcc tgagtcctgt  10800
cctgctgggt tccaggtgac ctccgcatcc agcatacagt gacggcctcc gtgcgcctca  10860
gctacgggga ggacctgcag atggactggg atggccgcgg gaggctgctg gtgaaggtag  10920
gtgccctcac ggggtactgg ctccctgcgg cccgaccctt acaaagtacc ccttgtgctc  10980
tgggtagaat ggctttgtgt ggtgggagaa gaattcccag agtggcctgg tctctcctgc  11040
agctgtcccc cgtctacgcc gggaagacct gcggcctgtg tgggaattac aatggcaacc  11100
agggcgacga cttccttacc ccctctgggc tggcagagcc ccgggtggag gacttcggga  11160
acgcctggaa gctgcacggg gactgccagg acctgcagaa gcagcacagc gatccctgcg  11220
ccctcaaccc gcgcatgagt atgtgaaccc gggggcaagg caggagggga gtgttgaccg  11280
ggaggcgtgg cccccactcc tccccaccac atcccaggct cgctcctctc gccccacagc  11340
caggttctcc gaggaggcgt gcgcggtcct gacgtccccc acattcgagg cctgccatcg  11400
tgccgtcagc ccgctgccct acctgcggaa ctgccgctac gacgtgtgct cctgctcgga  11460
cggccgcgag tgcctgtgcg gcgccctggc cagctatgcc gcggcctgcg cggggagagg  11520
cgtgcgcgtc gcgtggcgcg agccaggccg ctgtggtgcg tgccctccct gcccgcagcc  11580
ctccgggccg ccccccaaat ccgtccacgt gtgcttttcg aagccctttc tctgcgttgt  11640
ttcctgtgga aattgggggt cacagctaca aggggtggca agtcctagaa ccacagtcct  11700
tgctgtccaa cattcccgct gaggccttac ttcttctcct ctctcttcta gagctgaact  11760
gcccgaaagg ccaggtgtac ctgcagtgcg ggaccccctg caacctgacc tgccgctctc  11820
tctcttaccc ggatgaggaa tgcaatgagg cctgcctgga gggctgcttc tgccccccag  11880
ggctctacat ggatgagagg ggggactgcg tgcccaaggc ccagtgcccc tgttactatg  11940
acggtgagat cttccagcca gaagacatct tctcagacca tcacaccatg tggtaagtgc  12000
aggcagcagt gtcagggacc tctaaaacag cagagctggg gaggaaaacg ggatcaatta  12060
agcaaataac tgaaaaaagt cccatgggat ttagtgacgt ggggatcatc cattggtaac  12120
gttagcaagc tgtgcttcag gaggggttat gggactggga cctggttgga aggggcagag  12180
```

-continued

```
agtgagtggg aggtgaagat gtggaggcag cgagtataga cgagtctcgt gaagctcggc  12240
tatgatttc ttctctgcag ctactgtgag gatggcttca tgcactgtac catgagtgga  12300
gtccccggaa gcttgctgcc tgacgctgtc ctcagcagtc ccctgtctca tcgcagtgag  12360
tactgtcccc ctggaaggcc cattgactcc atcctgccca gattcctcac gtgtggaatg  12420
gcgggagaga gctgggtatg taagccagag gtcagaagcc caggtgagaa gatgccctcc  12480
cagtcccaca cagggaccct ggctcaggca gccgctggtc cccgtgagtg ggcaactctg  12540
agtctcttga atttagtcac agactctagg ggaccaaagg acagtgtgga aggtaggtcc  12600
attatctcct tcactaatca tctctttgct tttcctacct tcgaggcaaa aggagcctat  12660
cctgtcggcc ccccatggtc aagctggtgt gtcccgctga caacctgcgg gctgaagggc  12720
tcgagtgtac caaaacgtgc cagaactatg acctggagtg catgagcatg ggctgtgtct  12780
ctggctgcct ctgcccccg ggcatggtga gtcaccaggc acagagctgg tgcctgccct  12840
tcagttttct tgtaggcagg aggagggctt tagatcagtc actgtggccc tgaggacttt  12900
tggattcttt tctcttaggt ccggcatgag aacagatgtg tggccctgga aaggtgtccc  12960
tgcttccatc agggcaagga gtatgcccct ggagaaacag tgaagattgg ctgcaacact  13020
tggtgaggct cagtgagggg ctgcgccggg gacccaggcc ctgcgggtgg agtgagggtg  13080
cacgcggcca caggaccttc cgcacttgga caacccttc ccttctttgc ctcagtttcc  13140
cccttttagg gacagccact aggcttccct gtctcctgct gggccccatg ctgggcctat  13200
gaagtccaca ctccacgcta caggtcctca acttccttgg gcttcctgga gggttgggag  13260
gcacccagag tattctgtgt tccttcattg cctccatggc ccagatgggc ccctcaaacc  13320
caaggtgccc aacttgtcat ctctgccatg actgctccta gtgtctgtcg ggaccggaag  13380
tggaactgca cagaccatgt gtgtgatgcc acgtgctcca cgatcggcat ggcccactac  13440
ctcaccttcg acgggctcaa atacctgttc cccggggagt gccagtacgt tctggtgcag  13500
gtgagaggtg gggagatggg gagagggtgc tgtttctttc taggaggggt gggaggtgtg  13560
gcctcaggtt gggttctgtg gatctgtctg cagaaacaac tctggggtct ggtttctact  13620
ggagtacttc ccagtccttc acagaagtgc ctgaagcggt aggggatttg aagctcaaag  13680
tggttgtcca ttttccctct gctcacctgg ggacttataa aaagggcatt cacctgggca  13740
tatcccccgt cccccagaca cacacagagg cacatatgcg cagccatgga cgtggcaaga  13800
tcctgtgaca cgtactcaaa ggcctgtgat gaagagatgc caatcttctg gtctggtgag  13860
agccagtggg gataatggtc ttctcctggc actcctcttt ccccaggatt actgcggcag  13920
taaccctggg acctttcgga tcctagtggg gaataaggga tgcagccacc cctcagtgaa  13980
atgcaagaaa cgggtcacca tcctggtgga gggaggagag attgagctgt ttgacgggga  14040
ggtaagtgca gcctcatctc caccctcatg tcccgctttg tgcttctgcc acttaatagg  14100
aacatttcca agcattcatt tagagctcgt gtgaatggaa taacgcacag ccattaaaga  14160
ggatgaggtg agatggtcac agacatgtcc tggcgtgggg ctggcctgca ggggtgcagt  14220
ggcaggtggg gtcctggagg ggtggcagtg cctgcactcg tgggcactga agacagatgg  14280
gcaggtgtag agtggaggga ggatctggct gtcgagcctg cccttcatcc tcctggattt  14340
cttgctttgt cttcctccag gtgaatgtga agaggcccat gaaggatgag actcactttg  14400
aggtggtgga gtctggccgg tacatcattc tgctgctggg caaagccctc tccgtggtct  14460
gggaccgcca cctgagcatc tccgtggtcc tgaagcagac ataccaggtc agtggctttc  14520
ttgcttcatc ttgttgggga cttggccttt ggagtgtttt ctgctccctg atcgtaggtc  14580
```

-continued

```
tctaaggact tgctttatga atccaggtgc tcctgtgttg ggtgcatata tatttaggat  14640
agttagggac agtgatagtt cccaccagtg atctcagggc caaggctgcc tgattcccac  14700
ctctgccctt ggctgactat gtgacatggg catgttgcct ctctgtttcc atagctttaa  14760
ataaaatggg gccagcaagg aagctcagga atgggtcttg gcaatggcaa ggctttgctg  14820
ctcacctcgg gcctcctctg agtctctgtc ccgctcctcc tcctcttcct cgaatgccct  14880
ctgcctccat tgccgccagg aatgttcccc tttcccctga gccggagagc atgctcctgg  14940
gcttgacggt gctcatccct caacttgtct ctcaaggaga aagtgtgtgg cctgtgtggg  15000
aattttgatg gcatccagaa caatgacctc accagcagca acctccaagt ggaggaagac  15060
cctgtggact ttgggaactc ctggaaagtg agctcgcagt gtgctgacac cagaaaagta  15120
cgtctgggtc tctgtgtgga cagagcccta gagcttgctt cctggaatgt ccctctgtcc  15180
ccattgtcat gggggctgga agggggggttg tgggtggtat gacctccagg tggctgcagg  15240
gtgggaagga gggtctcttg gatccttctg ggctgaataa ccccagtttg accagctgac  15300
ggctggccta tctcttgcct ggttcccagg tgcctctgga ctcatcccct gccacctgcc  15360
ataacaacat catgaagcag acgatggtgg attcctcctg tagaatcctt accagtgacg  15420
tcttccagga ctgcaacaag ctggtgagga ccttgagggt agtgggaagc agacggtccc  15480
aaggcttggc ctggtggtat ggacacagag tgtgaccttc taacgtggac actaccctcg  15540
tgtcttgaca tgatctgcac caagacacca cttcggcttt ttttcttggc tttcaatctg  15600
ggaaacaaaa agtaaaatca acagtttcta ggggaagcaa tgcctggcaa aacatttcct  15660
tctgcatgag aagtaactcc ccttggcatg tgccaatgct tctctttcag ccccagtctt  15720
aggatttgtt ctcttattga agtatcttgt tttcaacacc agagccagag atttcctttt  15780
cctgtcactg ctgcatttgt ccagaccaaa agaccttcct ctcccacccc ctaaaacccc  15840
ttggtgccca tttcttgtct cacagaaatt cttttctggc cttaattttg gtgattttga  15900
gtcctcgtat tatgacttat ttttgtgtct tcatctctaa tgacaaggag gaattcgttc  15960
ttctggaaaa tcctcaggct cattgtgttc tgcagaaggc cagcagcact gcattattca  16020
actcttcttg ctggaatgca gattagaaac taagaatctt gccttcccac tcattccctc  16080
tttgagacca ttgagctgca tttctccttc tacctggacc cccttatcct taaattgacc  16140
atcagaacat ttgcacccag actaagagcc agagttcctg acacctggcc ataggcctgg  16200
gccacctgag gctgcctttg caggtggacc ccgagccata tctggatgtc tgcatttacg  16260
acacctgctc ctgtgagtcc attggggact gcgcctgctt ctgcgacacc attgctgcct  16320
atgcccacgt gtgtgcccag catggcaagg tggtgacctg gaggacggcc acattgtgcc  16380
gtgagtactg acgccctcat gttctcagat gccctccctt cttcccatgt gtctatgctt  16440
gaagaccttg tgagtgcagg gggatatctt catgggcgag aggaattcag aaccaataga  16500
ttctggttta ggtgcttcaa caatccagaa gtctctaata ttggtgacgc ccatagtccc  16560
ctagttcccc aacattatct ccagatggcg caggccatca ccacatgggt ctgcagtcct  16620
ggaggctttg cctgttgtgg ccacagcctt gtctcctgtc tacacagccc agagctgcga  16680
ggagaggaat ctccgggaga acgggtatga gtgtgagtgg cgctataaca gctgtgcacc  16740
tgcctgtcaa gtcacgtgtc agcaccctga gccactggcc tgccctgtgc agtgtgtgga  16800
gggctgccat gcccactgcc ctccaggtga ggcctctatc cctgggggtc aggctggtgg  16860
gatgggatag ggatggatgg aaaggtgctt ctaggtcttg cttcatctca gcctccacct  16920
gccacgtcct atctctgacc tgcaaggctg ctgcaggttc cgtgggttct ttcatcagag  16980
```

-continued

```
tcaggacagt cgtgattttt ctcaagtcga gctcctccaa aatgcttttc tgtgcctatt  17040
tatgggattc tcacctaaag cagcccctgc cgatagaact ttctgcagtg ggggaatgtt  17100
gtattgaatg caggcaggag gagttggctt ctagggcagg aggaggagtt ggctcctccc  17160
ttttagttaa aaatgaggct tcctcgtggg aaaggggagc gttttggttc ctaatgagag  17220
ctttcttttg cagggaaaat cctggatgag cttttgcaga cctgcgttga ccctgaagac  17280
tgtccagtgt gtgaggtggc tggccggcgt tttgcctcag gaaagaaagt caccttgaat  17340
cccagtgacc ctgagcactg ccagatttgg taaaacagat tcctgggttg tttgaagtga  17400
tgaatcttat tgcttctcca tgttttgaag gtggggggca tgctatttgg ggacagatgt  17460
taaacaatga catctcactt ggatgtggaa tggtccatgg gatctcaagt tcaggtggaa  17520
cagaggagat tctgtgggaa tatggaagtc attgtacact gtagggctca gaagtgtcca  17580
caggttcttc ctgaaccatt ttaatttctt cgctcttttc tgcagccact gtgatgttgt  17640
caacctcacc tgtgaagcct gccaggagcc gggaggcctg gtggtgcctc ccacagatgc  17700
cccggtgagc cccaccactc tgtatgtgga ggacatctcg gaaccgccgt tgcacgattt  17760
ctactgcagc aggctactgg acctggtctt cctgctggat ggctcctcca ggctgtccga  17820
ggctgagttt gaagtgctga aggcctttgt ggtggacatg atggagcggc tgcgcatctc  17880
ccagaagtgg gtccgcgtgg ccgtggtgga gtaccacgac ggctcccacg cctacatcgg  17940
gctcaaggac cggaagcgac cgtcagagct gcggcgcatt gccagccagg tgaagtatgc  18000
gggcagccag gtggcctcca ccagcgaggt cttgaaatac acactgttcc aaatcttcag  18060
caagatcgac cgccctgaag cctcccgcat cgccctgctc ctgatggcca gccaggagcc  18120
ccaacggatg tcccggaact ttgtccgcta cgtccagggc ctgaagaaga agaaggtcat  18180
tgtgatcccg gtgggcattg ggccccatgc caacctcaag cagatccgcc tcatcgagaa  18240
gcaggcccct gagaacaagg ccttcgtgct gagcagtgtg gatgagctgg agcagcaaag  18300
ggacgagatc gttagctacc tctgtgacct tgcccctgaa gcccctcctc ctactctgcc  18360
cccccacatg gcacaagtca ctgtgggccc ggggctcttg gggggtttcga ccctggggcc  18420
caagaggaac tccatggttc tggatgtggc gttcgtcctg gaaggatcgg acaaaattgg  18480
tgaagccgac ttcaacagga gcaaggagtt catggaggag gtgattcagc ggatggatgt  18540
gggccaggac agcatccacg tcacggtgct gcagtactcc tacatggtga ccgtggagta  18600
ccccttcagc gaggcacagt ccaaagggga catcctgcag cgggtgcgag agatccgcta  18660
ccagggcggc aacaggacca acactgggct ggccctgcgg tacctctctg accacagctt  18720
cttggtcagc cagggtgacc gggagcaggc gcccaacctg gtctacatgg tcaccggaaa  18780
tcctgcctct gatgagatca agaggctgcc tggagacatc caggtggtgc ccattggagt  18840
gggccctaat gccaacgtgc aggagctgga gaggattggc tggcccaatg cccctatcct  18900
catccaggac tttgagacgc tcccccgaga ggctcctgac ctggtgctgc agaggtgctg  18960
ctccggagag ggcctgcaga tccccaccct ctcccctgca cctggtatgc tggcaccttg  19020
tgtgcaggtg ggagggctgg gcgagggctg gcatggcctt ggtgctacat gcatctgcca  19080
agatacgact cgggttctaa tcctggcttc cctggtctgt gtggccttgg ttgaaacttg  19140
ccttcaaagg gcctgtgttt cctcacctcc ctggcaggga gacaaactgt gatccttttt  19200
cggggcctgc tggcacctgt gtgctcacct tcctggttgt ctttgcagac tgcagccagc  19260
ccctggacgt gatccttctc ctggatggct cctccagttt cccagcttct tattttgatg  19320
aaatgaagag tttcgccaag gctttcattt caaaagccaa tataggtggg tgagcgaggc  19380
```

acctgaagca gcaggtgacg aagaggctct ttttgtggct ctacttgatt caaaataatc 19440
cgcattttct cgttccgttt agggcctcgt ctcactcagg tgtcagtgct gcagtatgga 19500
agcatcacca ccattgacgt gccatggaac gtggtcccgg agaaagccca tttgctgagc 19560
cttgtggacg tcatgcagcg ggagggaggc cccagccaaa tcggtaacgt tggtgccaca 19620
ggctggatgc agaagctgca ttctggttct tatttttggc ataagtgact gtgtgacctc 19680
ggccagtcac tttgctcctt ggccttagtt tcttctcctg gaaagtgagg ggctagatgc 19740
tcttccacgt ctctccagat ctcaactggg tgttccttgg agtttctgaa tcattcagct 19800
tttaagtgac ttaaggatcc accgttaaga cagggtgtcg agccgcagtc agtactgact 19860
tggcgtgatc tgttctccat cctcagggga tgccttgggc tttgctgtgc gatacttgac 19920
ttcagaaatg catggtgcca ggccgggagc ctcaaaggcg gtggtcatcc tggtcacgga 19980
cgtctctgtg gattcagtgg atgcagcagc tgatgccgcc aggtccaaca gtaagaatct 20040
ggtgtacagt cctcaattca ggagagcgat gtttgttgtc tatctctcca tgaggacggg 20100
ggacagggag ggactttatg tgcttggttc actgctgtac ccctattgct tacaatagta 20160
cctgacacag agtagcagct cattaatatc tgttgactga acatcttcct catagggctg 20220
atgtatgtga ccagcctgga aaacatgagg ctgtattcag atgctggata taacgtcagg 20280
ccagtccatt ttgagccttc ttgcccacag atcctttctt gtctctttgc taactctagg 20340
agtgacagtg ttccctattg gaattggaga tcgctacgat gcagcccagc tacggatctt 20400
ggcaggccca gcaggcgact ccaacgtggt gaagctccag cgaatcgaag acctccctac 20460
catggtcacc ttgggcaatt ccttcctcca caaactgtgc tctggtgagt cttataatac 20520
ctttcttact tccctcaaaa tcatgtccct atgtctccac tgttaacctt gttcagattc 20580
ttttcagagt tgagttgact tcaaaaacta gaccaggttg cttaagcaga cattgtgaat 20640
ggttcagaat ttctgggtga aagatgggaa ctaaggtctt atttgtgtct gttgcaggat 20700
ttgttaggat ttgcatggat gaggatggga atgagaagag ggtaagttcc tttctgttga 20760
ctttgaaaga aaggttagag atgtgtttgg ggctcttgtt cccactggtt aatttttcct 20820
cctttggtct tagtccagtg cttcctttta ctattatctt gtttttgcgg gtccatctgt 20880
acatcttgtg ttttgcttcc tgtctcatgt acagggggcc tccttgctgt gtaggcctgt 20940
gttcaattct aggggtcagt tgtctggcag atgggcttag agttggagta cctcatctta 21000
ttccctgcct gaatctgctg ttttcttctg cagcccgggg acgtctggac cttgccagac 21060
cagtgccaca ccgtgacttg ccagccagat ggccagacct tgctgaagag tcatcgggtc 21120
aactgtgacc gggggctgag gccttcgtgc cctaacagcc agtcccctgt taaagtggaa 21180
gagacctgtg gctgccgctg gacctgcccc tgtgagtcct ttgcttctcc agccagggca 21240
gcgtcagaag tgtggttcta taatttgcca cattttatgt aacaggaaaa tatttaatgg 21300
ccaagtgtta cttacctaaa cctctctacc tctcagagcc ccagtttcct aatctgtaaa 21360
aaaaggagga aattgttcta tatgacctca aagggcctgt tccgttctct actgtattta 21420
tctgtgtgca acttggtcac acctgcctgt ctgcatgtag taggcatggg ggtttggata 21480
acgtcgcatc catcctctgc ttctctctgt ccaggcgtgt gcacaggcag ctccactcgg 21540
cacatcgtga cctttgatgg gcagaatttc aagctgactg gcagctgttc ttatgtccta 21600
tttcaaaaca aggagcagga cctggaggtg attctccata atggtgcctg cagccctgga 21660
gcaaggcagg gctgcatgaa atccatcgag gtgaagcaca gtgccctctc cgtcgagctg 21720
cacagtgaca tggaggtgag aagtactttc tgtggatccg tggtaaggca atagaatgtc 21780
aggaaaacca cctggacctg gtggcagttg cttttagttg atgctcttgt taggagctct 21840
gccttctgct taagtggagg agaggagtac cactttctta gaggggttta ttgccatccc 21900
cttgtcttgg cgtgatttca tgttgttccg ggctcagatt tgcaagatgg aatcactttt 21960
agatagcata aaattgtgaa tttagtgcca gtttctggca ctggtggaga attgggattg 22020
gcatcaggat tgtttactcg gaaggtatta tgagtccaat gcctaaaccc tgtaagcttt 22080
ccaaagggaa acatttatgg cctaaattag gtcttttgaa aatatttaag gcctacataa 22140
aacgtcaggc tccaaaattt gaaaagaaaa ctgcaaaact gatatatata tatataaatg 22200
attgattaaa tgcttacaaa aggttacact atgccaactt ctttacttgt tcgtgtagaa 22260
atcataaaaa cctaggattc ctcattgcta ggactacgga tgagctcttt cttctttgtg 22320
caggtgacgg tgaatgggag actggtctct gttccttacg tgggtgggaa catggaagtc 22380
aacgtttatg gtgccatcat gcatgaggtc agattcaatc accttggtca catcttcaca 22440
ttcactccac aaaacaatga gttccaactg cagctcagcc ccaagacttt tgcttcaaag 22500
acgtatggtc tgtgtggtaa gaacattttc tcaactcctc ttctccccct gctatacatt 22560
tataaacctt acttgctcta ctctgaggct cttggatgct tatatttcag ggtctagtag 22620
cgagggtcag attctggtga ggatcaagaa tggcctgtct ctggcatcaa tgtttttgta 22680
cccagggcca ctcagtttat cttttttttg tttgtttgtt tctctaggga tctgtgatga 22740
gaacggagcc aatgacttca tgctgaggga tggcacagtc accacagact ggaaaacact 22800
tgttcaggaa tggactgtgc agcggccagg gcagacgtgc cagcccatcc tggaggagca 22860
gtgtcttgtc cccgacagct cccactgcca ggtcctcctc ttaccactgt ttgctgaatg 22920
ccacaaggtc ctggctccag ccacattcta tgccatctgc cagcaggaca gttgccacca 22980
ggagcaagtg tgtgaggtga tcgcctctta tgcccacctc tgtcggacca acggggtctg 23040
cgttgactgg aggacacctg atttctgtgg tgagtctcca agttacctct gaaaatcctg 23100
gagaccagct aactgggctt gctcagcctc tctgtgcccc agattcttta tttagctgca 23160
agaaaggttg ggaaatatag tcctcattct ggtggtcata tgcccagcct aaagttctgt 23220
ttctatggaa ggtggggagg atgaagattg gtggaaaata gccgtctctg ccctggcaag 23280
tttgtctgat gattaaccat gttgaatcag ctgtgcccat ttcactctgg ctggtgtggg 23340
cctttgcaag tgacctcctt ctctgtctac agctatgtca tgcccaccat ctctggtcta 23400
caaccactgt gagcatggct gtccccggca ctgtgatggc aacgtgagct cctgtgggga 23460
ccatccctcc gaaggctgtt tctgccctcc agataaagtc atgttggaag gcagctgtgt 23520
ccctgaagag gcctgcactc agtgcattgg tgaggatgga gtccagcacc aggtaggagc 23580
ctgggccttt cacttcccat ggggctgcga attctgggct tcgtacctag aatgtcctgt 23640
gccctttctg aaccttgctt tgccctcagt tcctggaagc ctgggtcccg gaccaccagc 23700
cctgtcagat ctgcacatgc ctcagcgggc ggaaggtcaa ctgcacaacg cagccctgcc 23760
ccacggccaa aggtgagagt cctcccctcc ctggtgcctt catggaggaa caagggcccc 23820
tgcaaggccc cccagccacc catcttcacc tctggcagag cagactcaaa cactggcacc 23880
tagagtccta gagtgggtgg gcttccttgc ccagcctgca tttcccatca ctgggcctgg 23940
gagccccatt ctgcacctgg ggtcgacatt ctcagattaa ccctcgcctc tggtccccag 24000
caacggtcag acttaagagt cccctggagg gtaaatgtga gggtgtcaac aggaacatgg 24060
ggacactcat ctgtcagagg tcccgtggcc tggatccttg tgggatgacc gtacagaact 24120
cctactagtt ttcagtgagc aagaacattt caaatccctc tgaggctgtc ccaccactaa 24180

```
tttctctgac ttttgtggcc gttcctctcc tctagctccc acgtgtggcc tgtgtgaagt  24240
agcccgcctc cgccagaatg cagaccagtg ctgccccgag tatgagtgtg gtatgtgtcc  24300
caccaggggg atgtctccag ggcccaaccc tagccccagg gggcaccacg ttgaaggtgc  24360
tgaaaggtgt ctctgttctc aggcacaggg tgtgtgaaag gaggtgggta aggaccgatt  24420
ggatactcca aaaaagtgga aagggttacc tctggagaat aggatttgct tcctagaaga  24480
atctactgta aattactaaa cacaggtttg acaggattaa tacaagaatg gggtgattac  24540
tggggactat ggagatatac tgaagaaaag gtcatgccaa agcaacccat tttcattttc  24600
aataagattt tgaggctgct agatatagag aagaccacac actgggcacc ttgagttcag  24660
caggttgttt gctagaggtt ttcatgctag ccttgcaggc tgctctgtga atagtgggct  24720
gaataatggt ataagtccgt gaattcagag ctgatggaat tacggttagc atggcaggaa  24780
atcattagtg cctttgtccc agtcctgtcc agtgtgttta ttgcttgtac agatgaagac  24840
ctaaagcaca ggcttgtaca atttgcagtg atgcagatat tgaagggaga gcagatagat  24900
caggggacag tccaaggaac taaaagaaaa tcatataatc ggagaaactt atttgtactc  24960
gtgaaattga tcagaaataa atagaagtcc tgtaggggag ggagatgtgg cttgagaaca  25020
attaatgtaa aggaggtctt agaatgttag cagtagagag aactagaggg atcatttact  25080
tcaagcccct cattttatag acattactag tctcctacaa tgtgccgggc actttgccct  25140
tattattttg tgaactcctc agactgatcc tataaggtag agttcccacc ttccagaaga  25200
agaaacaggt ctagaggatc caagttgact tggctgagat gtgaaagccc tagtggatga  25260
taagaataat cagtatgtga cttggattga tctatctgtc tgtctgtctg tctatctatc  25320
tatctatcta tctatctatc tatctatcta tctatctatc tatccatcta tccatccatc  25380
ctatgtattt atcatctgtc ctatctctat ctaacctatg tatctattta tcatctatcc  25440
tgtctctatc tatcctttgt atctatcatc tatcctatct ctatctaagc tatatatcta  25500
tttatcatct atcctctatc atctatctat ctatctatct atctatctct attgtatcta  25560
gttatctatc ctatatctat gtatgtatct atctgtctgt ctaatctatc taacctgtgt  25620
atctatttat aatctatcct atctctatct aacctatgta tctatcatct atcctatctc  25680
tgtctaacat atgtatctat catctattct atatctatct gtctatctac cctatgtttt  25740
atcatctatc ctatctctct ctaagctgtg tatctatcat ctatcctcta tctatcatcc  25800
atctatctat ctatctatct aatgtaccta gttatctatc ctgtatgtat gtatgtatgt  25860
atgtatctat ctatcaaatc tatctcatgt atctagttat cattctatct atctatctat  25920
ctatctatct atctatctat ctatctatct atcctaaccc atgtaatctc tgtctccatc  25980
atcatcactt acctaaaaca gtagaagtct gcatgaatag gaatgtagca tcccactcac  26040
aggtaataaa agagtaacct ttctgaactc tgcatggacg tctctctttc tggccctcag  26100
tgtgtgaccc agtgagctgt gacctgcccc cagtgcctca ctgtgaacgt ggcctccagc  26160
ccacactgac caaccctggc gagtgcagac ccaacttcac ctgcggtaag gcctctgtgg  26220
atgaggaggg gtggtgtggc ctctctctgc tggtgtgagg gaggccatcc tcctcaggga  26280
cctcttccaa gatcacgtca tttcctgttt tctacctagc tgaatctggg ttgggagtac  26340
atctggaaca gaggggttag ggtcacacct gcacggaatc cttccggctg cacgctgctg  26400
aaggatacca ggtgtgggca cagcacaggc acctccgtct tgggtttatg aagaagcagc  26460
tggggctgag atgaggaggc ctccgaatct aatctttatt tctgcccatc ctcctgtatg  26520
tcatcaaggg gagggaatgt ttccttgact tcccctcatc attggatctt attcccaaac  26580
```

-continued

```
aaatttatag tttttcgcct ctgaaggtgt atatatgtaa tcactatata ctgtaactta  26640
aacatagcga tggactaaaa taagacacga caagaaacca aattctgtat ttacctcccg  26700
agaatcccca ctctaactcc gttggcgttc ttgtcctgct gatgtggaca ctcacccgac  26760
ttcctagatg tgagacttca aggtgggagg agagcacatt gtgtttgaag ggagctggaa  26820
acaggcaaag gacacaggga caggatttgg tcttttaaaa gtgacattgt ggctttgaca  26880
agattgctgg caatctttca ttccacactg attgctggcg gacctaaagt gtagggtatt  26940
gttctaggta ctgaggtggg gataggatca cagaagctcc tggcatagaa cagtgcttag  27000
cagggcgtgg tgtacccaga cctactggac ttagagattc tacatctgac acctctgaga  27060
atgaaggaac ccgccccttc cagatgtatg tgggaaagtg atagagcagg gattgagcag  27120
ccttcacttc tcctccatta gagttcctag cttcacattt cccttttga ttaatgttca  27180
tatttttctg cagatggact gcttttggta acattgaata actcccagcc cgtgagcttg  27240
gccctcacac atttctgact taatcttctg agtctaaagc tccctggcac cctatagcat  27300
agctgaatac ttacgagccc tggctgggcg cagtgctcag tgtggccttg tcctatcctc  27360
agcctgcagg aaggaggagt gcaaaagagt gtccccaccc tcctgccccc cgcaccgttt  27420
gcccaccctt cggaagaccc agtgctgtga tgagtatgag tgtgcctgca actgtgtcaa  27480
ctccacagtg agctgtcccc ttgggtactt ggcctcaacc gccaccaatg actgtggctg  27540
taccacaacc acctgccttc ccgacaaggt aaggactgct tggctattaa ctatcagtta  27600
atagtttact catttattta ttgctgtcag tttatccttc tatccaccca tccattcatc  27660
catccaccta cccatccaat atttgctaag caacatgtgc tcctcatgga agatttgcat  27720
cctacccagc attcccttct tgcccaaacc aagtgctaca aggcttggtt ggggggcagt  27780
cagcattcca gctcagcctg agtggaaatt tagttaactc aggaggcatt tcttgtgagc  27840
ctactatgta ctaagcatgg ctaggtgctg aggttacaaa taatgtgcag gacatggtct  27900
ttacctttat aagcttattt taggttagct aaggaaataa catgattgca tggattattt  27960
agagatcagt taatagttat acatacatgt tgagatgagg tcttgctatg ttgcctaggc  28020
tggtcttgga ctcctgggct caagtgatcc tcccacctct gcctcacgag taggtgagat  28080
tacaagtgca caccaccaca cctggctacg agcagttaat agtttactca tttatttatt  28140
gctgtcagtt tatccatcta tccacccatc cattcatcca tccatctgcc catccaatat  28200
ttactaagca actactgtgt tctaacagaa ttggcactgt gctaggtgct atgggagaaa  28260
tgttaagatg aagttcctat gtatgccctt gttagtatat atgacaatag tctataaact  28320
gaatataata aagtgtcaac gaatggtaca gattttcatt acaaacagca gtcttatagg  28380
tgaaagagcc accaagatta gctatcatta aagatttaat tgatggagtg ggaaagtgaa  28440
gggcgcgaaa gtggcggagt gagaactgaa atgagccaga actgcagcag gaagacctga  28500
gcatagttat agctgctgca ttgaggggag tcctgacatg aatgacagac aagctgcagt  28560
catctctcct tggagcctgt tagggctgga acagatcttt atttgtctgg aatgcttaag  28620
acctctcttc ccctctggac gctcttccag ctcagggatt ctaagcacgc agttttggag  28680
aagcgggaac aagtctagga ggctacagtt gctgctgctg ctttcttata tctctgttct  28740
ccttctcgtc ttcctgccca cccctcctgc cttgctgttt ttctattaat gtttcttgtg  28800
tgtctttaat ctatagtaat gccactcccc atttttatgc ctttgatttg ttggggaagc  28860
tgggtcattt gtcctgtaga atgtcatgaa ttcccacatt ctcagcacct agagcggctt  28920
ctgtgtagta ggtgctaact caccgcttgt ttcaatgaaa caaatgagtt cactcacgaa  28980
```

```
aacttatgtc tacaggtgtg tgtccaccga agcaccatct accctgtggg ccagttctgg  29040
gaggagggct gcgatgtgtg cacctgcacc gacatggagg atgccgtgat gggcctccgc  29100
gtggcccagt gctcccagaa gccctgtgag gacagctgtc ggtcggtgag tggggcaggg  29160
gctgggcatg cctgcagcta tcagagcggg aaagtagagg agggcatctt aggaagggta  29220
agaaaggttc tttttttttt tgaaatggag actcgctctg tcgcccaggt ctttcagggg  29280
gcagaattat atctctgcag ctgatgtaag acttcgttta gtgacctggt ggttgctgct  29340
tcttggcatg gccctgaggc tggttgacaa caaagatgaa aatgcccaga ccagtgatca  29400
cttggcacaa ccccagggct cagtacgcag gaggcgtagg taagagcccc tgtgtctttg  29460
ctgctggcct gtccttactc tgtttttttct gcttttccag ggcttcactt acgttctgca  29520
tgaaggcgag tgctgtggaa ggtgcctgcc atctgcctgt gaggtggtga ctggctcacc  29580
gcggggggac tcccagtctt cctggaagag tgtaggtcca ggcccccggg acggggagga  29640
gggcagattg gggccactcc agggaccagc gttgaccttg gtttcatcta gtcccctggc  29700
ttctccaagg tgcttgcctg ggtgcctcag tcaggtgatt ttgacccaaa ctgtttgagt  29760
ggtgctcact gagacgagcc ccactcatcc cctccgtggg ccctaccctg tggtgggact  29820
tacatgttaa gccaggcttc acgtctagaa accaccttcc tgagagaaga gcacattccc  29880
actgggaccc tgggctccag ccctgcccca gcttgttgga ctaactctgg tgccctgcag  29940
gtcggctccc agtgggcctc cccggagaac ccctgcctca tcaatgagtg tgtccgagtg  30000
aaggaggagg tctttataca acaaaggaac gtctcctgcc cccagctgga ggtccctgtc  30060
tgcccctcgg gctttcagct gagctgtaag acctcagcgt gctgcccaag ctgtcgctgt  30120
ggtaaggcat gcaggctggg gctgggctgg accgggcacc acctttaagc ctctctttcc  30180
acttttggct cctgaattcg aattcttgaa actgaaattt tcaagagtag cgtttcattg  30240
tttcataaac ccaaacatcc tcccattcat cccatctctt aaatgtaaat tcacataagc  30300
aagcgctgtc acttggagaa cgtacggggc tcttctcatt gtgggctgca tggggaaggg  30360
aggccgctgt gggctccagc agtaggaccc ccagcgctgg gttgtggggt gggggggaaag  30420
ggccgaccga tacaggaggg aggcccagac acggaggagg agccccaaag agagcagcct  30480
gctcgccggt ctcaccaggg tgtgttttgc ccactctcac tctgcacttt tctctccccc  30540
agagcgcatg gaggcctgca tgctcaatgg cactgtcatt ggggtgagcc gctgtcctct  30600
tctccagagc aagtggtggg gacagggaag ggggtactgt gggaagggga gcaggcaagt  30660
cattgtaaag cagaaatgaa ggaaaccaga gagacccaac cccagctttc cactgcctgt  30720
gggacgtgcc tggcatcatg gagcccaggc taggaccatc ttcctgactc tccgggcctg  30780
tctcacactc acttcctggc ccccacctca ggcacctgtg catttcttct gtgtgcagag  30840
aagcactctg aagtcattgt gcacgtttta gtttgtcccc tctgccacta cctgggctgc  30900
ctctttggca tgaaagttct cactcttacc atctcgatac tggaggtggg aggacgggaa  30960
ggcagtgggc cataggagac aggaggagca gcagagcgat ggctcatggg agctatgggt  31020
gggtgggcag gagacagggt atgagagtga ggtgagtggg gggttggggg atgctggggg  31080
gcctgaccct ggtgcctctg cttccagccc gggaagactg tgatgatcga tgtgtgcacg  31140
acctgccgct gcatggtgca ggtgggggtc atctctggat tcaagctgga gtgcaggaag  31200
accacctgca acccctgccc cctggtaaga gaggctcaat ggggaccgag ggcatggact  31260
ggacgcgtgt gggacccagg cagtgggacc tcactgcggt ctttaaataa atgaattcta  31320
ggtgaaacta ctggataaga gagatgagag gccagcaaaa tcagcctact tacaattggg  31380
```

-continued atgttttaag gaggttaact atggctgctt tttccccctc tggatgcagg gttacaagga 31440
agaaaataac acaggtgaat gttgtgggag atgtttgcct acggcttgca ccattcagct 31500
aagaggagga cagatcatga cactgaaggt aggagcaagc tgaatgcagg gctccctcac 31560
atatcaccat cttgcttcct tttttggaaa tgcatttaac tggtcggaag agtctacata 31620
gcagccctgt tcataggata caagctgtaa aactgggact ccacttctgg tctgtgttct 31680
gggtgtgggg gctttattat acactgtctt cttgtttcat ggttctgcag attgtttcgt 31740
catctccatg gagtcaagct catggtttga agtggctttg tgaaccaaac actgtctctg 31800
actttaccca ctcctctttc cttccagcgt gatgagacgc tccaggatgg ctgtgatact 31860
cacttctgca aggtcaatga gagaggagag tacttctggg agaagagggt cacaggctgc 31920
ccaccctttg atgaacacaa gtgtctggct gagggagtga gtactcattc tgctttcctc 31980
tttactgtct caatctctaa gaacaagatt cttctgaata gtgtgcatcc cagctccggc 32040
ataatttctc agtgtctgag gcacatctct ggcctagttg aagaatcagt gagattacga 32100
aatcaaagcc tacggagaga taaaattctc tgcaatatag gatgttttaa aaaaatattt 32160
tccttaaggg aggctgagtg tgtgattctt gaataaaatg tgagatcaaa ctgattttta 32220
gtctccctgg gaatgaagat cctgatgact caactggaag agaattcaga atcatcaaaa 32280
ttgtttcagc ctggtcaggt agggtggtca agctgctcac atttatgata ggaaagcata 32340
gtttacatct gggcacttaa gcacagggct gtgagttcgg agctaaaaat tggcccggag 32400
tgacctgaaa gctgtctact ctgtactttt tgtgcctaac ctgaaatttt gctgttttct 32460
tagggtaaaa ttatgaaaat tccaggcacc tgctgtgaca catgtgagtg cgttactaat 32520
atcttgtccc ttgaaaccca tcagagcaag tccaggggct ctttgcagct tgctccttga 32580
aacccattag caagccgaaa gggacctatt tccagcccag tgagggcact ggggctgaag 32640
agtgttctct agaaccccag ccagtcctca agtttcatct ctcacctgtc ctgtaggtga 32700
ggagcctgag tgcaacgaca tcactgccag gctgcagtat gtcaaggtgg gaagctgtaa 32760
gtctgaagta gaggtggata tccactactg ccaggtaagg gctctgcttc aataagggct 32820
gggtgcggag ggttgagcct ccgtgttcgg atacctatcc ttagttacat tctagaagga 32880
tctggaaaat tcgcagggaa gagaagggaa ataaactgga agcatttttt tttaagcaaa 32940
tgttttattg aagtaactgg aaatttttga ctccaggaaa aaaacaaaaa tggaggaaag 33000
actcagcaaa tcctttacag aaaatggaga gttatttatg caagatgggg gccacaattc 33060
ttgaagatca gtcaaacata tataaaattt tcctgcataa aacatgcata atcaggcata 33120
aaacatttta tgcattaaca tgcataaaaa ttgcagctag aggggtgtgg gtatgatatt 33180
attaccatag agaagaggac atgtcagacc tatgatcttc ctttacaaat tgcctagctg 33240
tcctgggtgc ttctgggtga gatcagacct gccttgcttg gagggggtca gggagaaagc 33300
aggctgcccc agagccctgc ctaagccagg acttcccacc attgtgaagc tcccatcttc 33360
ctctgctttc ttgcagggca aatgtgccag caaagccatg tactccattg acatcaacga 33420
tgtgcaggac cagtgctcct gctgctctcc gacacggacg gagcccatgc aggtggccct 33480
gcactgcacc aatggctctg ttgtgtacca tgaggttctc aatgccatgg agtgcaaatg 33540
ctcccccagg aagtgcagca agtgaggctg ctgcagctgc atgggtgcct gctgctgcct 33600
gccttggcct gatggccagg ccagagtgct gccagtcctc tgcatgttct gctcttgtgc 33660
ccttctgagc ccacaataaa ggctgagctc ttatcttgca aaaggctgct ggtgcactgt 33720
gtcgtagggc tgagatggca acggtgggca ggggctgagt tctgagaccg gttctgagga 33780
aggaagcaca ggccccatct gcaagcctca gtgtcagtgt gagatactgc caac 33834

<210> SEQ ID NO 31
<211> LENGTH: 2813
<212> TYPE: PRT
<213> ORGANISM: Homo sapiens

<400> SEQUENCE: 31

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365
```

```
Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800
```

-continued

```
Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                 1005

Ser Ser  Asn Leu Gln Val Glu  Glu Asp Pro Val Asp  Phe Gly Asn
    1010                 1015                 1020

Ser Trp  Lys Val Ser Ser Gln  Cys Ala Asp Thr Arg  Lys Val Pro
    1025                 1030                 1035

Leu Asp  Ser Ser Pro Ala Thr  Cys His Asn Asn Ile  Met Lys Gln
    1040                 1045                 1050

Thr Met  Val Asp Ser Ser Cys  Arg Ile Leu Thr Ser  Asp Val Phe
    1055                 1060                 1065

Gln Asp  Cys Asn Lys Leu Val  Asp Pro Glu Pro Tyr  Leu Asp Val
    1070                 1075                 1080

Cys Ile  Tyr Asp Thr Cys Ser  Cys Glu Ser Ile Gly  Asp Cys Ala
    1085                 1090                 1095

Cys Phe  Cys Asp Thr Ile Ala  Ala Tyr Ala His Val  Cys Ala Gln
    1100                 1105                 1110

His Gly  Lys Val Val Thr Trp  Arg Thr Ala Thr Leu  Cys Pro Gln
    1115                 1120                 1125

Ser Cys  Glu Glu Arg Asn Leu  Arg Glu Asn Gly Tyr  Glu Cys Glu
    1130                 1135                 1140

Trp Arg  Tyr Asn Ser Cys Ala  Pro Ala Cys Gln Val  Thr Cys Gln
    1145                 1150                 1155

His Pro  Glu Pro Leu Ala Cys  Pro Val Gln Cys Val  Glu Gly Cys
    1160                 1165                 1170

His Ala  His Cys Pro Pro Gly  Lys Ile Leu Asp Glu  Leu Leu Gln
    1175                 1180                 1185

Thr Cys  Val Asp Pro Glu Asp  Cys Pro Val Cys Glu  Val Ala Gly
    1190                 1195                 1200

Arg Arg  Phe Ala Ser Gly Lys  Lys Val Thr Leu Asn  Pro Ser Asp
```

-continued

```
        1205                1210                1215

Pro Glu  His Cys Gln Ile Cys  His Cys Asp Val Val  Asn Leu Thr
    1220                1225                1230

Cys Glu  Ala Cys Gln Glu Pro  Gly Gly Leu Val Val  Pro Pro Thr
    1235                1240                1245

Asp Ala  Pro Val Ser Pro Thr  Thr Leu Tyr Val Glu  Asp Ile Ser
    1250                1255                1260

Glu Pro  Pro Leu His Asp Phe  Tyr Cys Ser Arg Leu  Leu Asp Leu
    1265                1270                1275

Val Phe  Leu Leu Asp Gly Ser  Ser Arg Leu Ser Glu  Ala Glu Phe
    1280                1285                1290

Glu Val  Leu Lys Ala Phe Val  Val Asp Met Met Glu  Arg Leu Arg
    1295                1300                1305

Ile Ser  Gln Lys Trp Val Arg  Val Ala Val Val Glu  Tyr His Asp
    1310                1315                1320

Gly Ser  His Ala Tyr Ile Gly  Leu Lys Asp Arg Lys  Arg Pro Ser
    1325                1330                1335

Glu Leu  Arg Arg Ile Ala Ser  Gln Val Lys Tyr Ala  Gly Ser Gln
    1340                1345                1350

Val Ala  Ser Thr Ser Glu Val  Leu Lys Tyr Thr Leu  Phe Gln Ile
    1355                1360                1365

Phe Ser  Lys Ile Asp Arg Pro  Glu Ala Ser Arg Ile  Ala Leu Leu
    1370                1375                1380

Leu Met  Ala Ser Gln Glu Pro  Gln Arg Met Ser Arg  Asn Phe Val
    1385                1390                1395

Arg Tyr  Val Gln Gly Leu Lys  Lys Lys Lys Val Ile  Val Ile Pro
    1400                1405                1410

Val Gly  Ile Gly Pro His Ala  Asn Leu Lys Gln Ile  Arg Leu Ile
    1415                1420                1425

Glu Lys  Gln Ala Pro Glu Asn  Lys Ala Phe Val Leu  Ser Ser Val
    1430                1435                1440

Asp Glu  Leu Glu Gln Gln Arg  Asp Glu Ile Val Ser  Tyr Leu Cys
    1445                1450                1455

Asp Leu  Ala Pro Glu Ala Pro  Pro Pro Thr Leu Pro  Pro His Met
    1460                1465                1470

Ala Gln  Val Thr Val Gly Pro  Gly Leu Leu Gly Val  Ser Thr Leu
    1475                1480                1485

Gly Pro  Lys Arg Asn Ser Met  Val Leu Asp Val Ala  Phe Val Leu
    1490                1495                1500

Glu Gly  Ser Asp Lys Ile Gly  Glu Ala Asp Phe Asn  Arg Ser Lys
    1505                1510                1515

Glu Phe  Met Glu Glu Val Ile  Gln Arg Met Asp Val  Gly Gln Asp
    1520                1525                1530

Ser Ile  His Val Thr Val Leu  Gln Tyr Ser Tyr Met  Val Thr Val
    1535                1540                1545

Glu Tyr  Pro Phe Ser Glu Ala  Gln Ser Lys Gly Asp  Ile Leu Gln
    1550                1555                1560

Arg Val  Arg Glu Ile Arg Tyr  Gln Gly Gly Asn Arg  Thr Asn Thr
    1565                1570                1575

Gly Leu  Ala Leu Arg Tyr Leu  Ser Asp His Ser Phe  Leu Val Ser
    1580                1585                1590

Gln Gly  Asp Arg Glu Gln Ala  Pro Asn Leu Val Tyr  Met Val Thr
    1595                1600                1605
```

-continued

```
Gly Asn  Pro Ala Ser Asp Glu  Ile Lys Arg Leu Pro  Gly Asp Ile
    1610                 1615                 1620

Gln Val  Val Pro Ile Gly Val  Gly Pro Asn Ala Asn  Val Gln Glu
    1625                 1630                 1635

Leu Glu  Arg Ile Gly Trp Pro  Asn Ala Pro Ile Leu  Ile Gln Asp
    1640                 1645                 1650

Phe Glu  Thr Leu Pro Arg Glu  Ala Pro Asp Leu Val  Leu Gln Arg
    1655                 1660                 1665

Cys Cys  Ser Gly Glu Gly Leu  Gln Ile Pro Thr Leu  Ser Pro Ala
    1670                 1675                 1680

Pro Asp  Cys Ser Gln Pro Leu  Asp Val Ile Leu Leu  Leu Asp Gly
    1685                 1690                 1695

Ser Ser  Ser Phe Pro Ala Ser  Tyr Phe Asp Glu Met  Lys Ser Phe
    1700                 1705                 1710

Ala Lys  Ala Phe Ile Ser Lys  Ala Asn Ile Gly Pro  Arg Leu Thr
    1715                 1720                 1725

Gln Val  Ser Val Leu Gln Tyr  Gly Ser Ile Thr Thr  Ile Asp Val
    1730                 1735                 1740

Pro Trp  Asn Val Val Pro Glu  Lys Ala His Leu Leu  Ser Leu Val
    1745                 1750                 1755

Asp Val  Met Gln Arg Glu Gly  Gly Pro Ser Gln Ile  Gly Asp Ala
    1760                 1765                 1770

Leu Gly  Phe Ala Val Arg Tyr  Leu Thr Ser Glu Met  His Gly Ala
    1775                 1780                 1785

Arg Pro  Gly Ala Ser Lys Ala  Val Val Ile Leu Val  Thr Asp Val
    1790                 1795                 1800

Ser Val  Asp Ser Val Asp Ala  Ala Ala Asp Ala Ala  Arg Ser Asn
    1805                 1810                 1815

Arg Val  Thr Val Phe Pro Ile  Gly Ile Gly Asp Arg  Tyr Asp Ala
    1820                 1825                 1830

Ala Gln  Leu Arg Ile Leu Ala  Gly Pro Ala Gly Asp  Ser Asn Val
    1835                 1840                 1845

Val Lys  Leu Gln Arg Ile Glu  Asp Leu Pro Thr Met  Val Thr Leu
    1850                 1855                 1860

Gly Asn  Ser Phe Leu His Lys  Leu Cys Ser Gly Phe  Val Arg Ile
    1865                 1870                 1875

Cys Met  Asp Glu Asp Gly Asn  Glu Lys Arg Pro Gly  Asp Val Trp
    1880                 1885                 1890

Thr Leu  Pro Asp Gln Cys His  Thr Val Thr Cys Gln  Pro Asp Gly
    1895                 1900                 1905

Gln Thr  Leu Leu Lys Ser His  Arg Val Asn Cys Asp  Arg Gly Leu
    1910                 1915                 1920

Arg Pro  Ser Cys Pro Asn Ser  Gln Ser Pro Val Lys  Val Glu Glu
    1925                 1930                 1935

Thr Cys  Gly Cys Arg Trp Thr  Cys Pro Cys Val Cys  Thr Gly Ser
    1940                 1945                 1950

Ser Thr  Arg His Ile Val Thr  Phe Asp Gly Gln Asn  Phe Lys Leu
    1955                 1960                 1965

Thr Gly  Ser Cys Ser Tyr Val  Leu Phe Gln Asn Lys  Glu Gln Asp
    1970                 1975                 1980

Leu Glu  Val Ile Leu His Asn  Gly Ala Cys Ser Pro  Gly Ala Arg
    1985                 1990                 1995

Gln Gly  Cys Met Lys Ser Ile  Glu Val Lys His Ser  Ala Leu Ser
    2000                 2005                 2010
```

-continued

```
Val Glu  Leu His Ser Asp Met  Glu Val Thr Val Asn  Gly Arg Leu
    2015                 2020                 2025

Val Ser  Val Pro Tyr Val Gly  Gly Asn Met Glu Val  Asn Val Tyr
    2030                 2035                 2040

Gly Ala  Ile Met His Glu Val  Arg Phe Asn His Leu  Gly His Ile
    2045                 2050                 2055

Phe Thr  Phe Thr Pro Gln Asn  Asn Glu Phe Gln Leu  Gln Leu Ser
    2060                 2065                 2070

Pro Lys  Thr Phe Ala Ser Lys  Thr Tyr Gly Leu Cys  Gly Ile Cys
    2075                 2080                 2085

Asp Glu  Asn Gly Ala Asn Asp  Phe Met Leu Arg Asp  Gly Thr Val
    2090                 2095                 2100

Thr Thr  Asp Trp Lys Thr Leu  Val Gln Glu Trp Thr  Val Gln Arg
    2105                 2110                 2115

Pro Gly  Gln Thr Cys Gln Pro  Ile Leu Glu Glu Gln  Cys Leu Val
    2120                 2125                 2130

Pro Asp  Ser Ser His Cys Gln  Val Leu Leu Leu Pro  Leu Phe Ala
    2135                 2140                 2145

Glu Cys  His Lys Val Leu Ala  Pro Ala Thr Phe Tyr  Ala Ile Cys
    2150                 2155                 2160

Gln Gln  Asp Ser Cys His Gln  Glu Gln Val Cys Glu  Val Ile Ala
    2165                 2170                 2175

Ser Tyr  Ala His Leu Cys Arg  Thr Asn Gly Val Cys  Val Asp Trp
    2180                 2185                 2190

Arg Thr  Pro Asp Phe Cys Ala  Met Ser Cys Pro Pro  Ser Leu Val
    2195                 2200                 2205

Tyr Asn  His Cys Glu His Gly  Cys Pro Arg His Cys  Asp Gly Asn
    2210                 2215                 2220

Val Ser  Ser Cys Gly Asp His  Pro Ser Glu Gly Cys  Phe Cys Pro
    2225                 2230                 2235

Pro Asp  Lys Val Met Leu Glu  Gly Ser Cys Val Pro  Glu Glu Ala
    2240                 2245                 2250

Cys Thr  Gln Cys Ile Gly Glu  Asp Gly Val Gln His  Gln Phe Leu
    2255                 2260                 2265

Glu Ala  Trp Val Pro Asp His  Gln Pro Cys Gln Ile  Cys Thr Cys
    2270                 2275                 2280

Leu Ser  Gly Arg Lys Val Asn  Cys Thr Thr Gln Pro  Cys Pro Thr
    2285                 2290                 2295

Ala Lys  Ala Pro Thr Cys Gly  Leu Cys Glu Val Ala  Arg Leu Arg
    2300                 2305                 2310

Gln Asn  Ala Asp Gln Cys Cys  Pro Glu Tyr Glu Cys  Val Cys Asp
    2315                 2320                 2325

Pro Val  Ser Cys Asp Leu Pro  Pro Val Pro His Cys  Glu Arg Gly
    2330                 2335                 2340

Leu Gln  Pro Thr Leu Thr Asn  Pro Gly Glu Cys Arg  Pro Asn Phe
    2345                 2350                 2355

Thr Cys  Ala Cys Arg Lys Glu  Glu Cys Lys Arg Val  Ser Pro Pro
    2360                 2365                 2370

Ser Cys  Pro Pro His Arg Leu  Pro Thr Leu Arg Lys  Thr Gln Cys
    2375                 2380                 2385

Cys Asp  Glu Tyr Glu Cys Ala  Cys Asn Cys Val Asn  Ser Thr Val
    2390                 2395                 2400

Ser Cys  Pro Leu Gly Tyr Leu  Ala Ser Thr Ala Thr  Asn Asp Cys
```

```
    2405                2410                2415

Gly Cys  Thr Thr Thr Thr Cys  Leu Pro Asp Lys Val  Cys Val His
    2420                2425                2430

Arg Ser  Thr Ile Tyr Pro Val  Gly Gln Phe Trp Glu  Glu Gly Cys
    2435                2440                2445

Asp Val  Cys Thr Cys Thr Asp  Met Glu Asp Ala Val  Met Gly Leu
    2450                2455                2460

Arg Val  Ala Gln Cys Ser Gln  Lys Pro Cys Glu Asp  Ser Cys Arg
    2465                2470                2475

Ser Gly  Phe Thr Tyr Val Leu  His Glu Gly Glu Cys  Cys Gly Arg
    2480                2485                2490

Cys Leu  Pro Ser Ala Cys Glu  Val Val Thr Gly Ser  Pro Arg Gly
    2495                2500                2505

Asp Ser  Gln Ser Ser Trp Lys  Ser Val Gly Ser Gln  Trp Ala Ser
    2510                2515                2520

Pro Glu  Asn Pro Cys Leu Ile  Asn Glu Cys Val Arg  Val Lys Glu
    2525                2530                2535

Glu Val  Phe Ile Gln Gln Arg  Asn Val Ser Cys Pro  Gln Leu Glu
    2540                2545                2550

Val Pro  Val Cys Pro Ser Gly  Phe Gln Leu Ser Cys  Lys Thr Ser
    2555                2560                2565

Ala Cys  Cys Pro Ser Cys Arg  Cys Glu Arg Met Glu  Ala Cys Met
    2570                2575                2580

Leu Asn  Gly Thr Val Ile Gly  Pro Gly Lys Thr Val  Met Ile Asp
    2585                2590                2595

Val Cys  Thr Thr Cys Arg Cys  Met Val Gln Val Gly  Val Ile Ser
    2600                2605                2610

Gly Phe  Lys Leu Glu Cys Arg  Lys Thr Thr Cys Asn  Pro Cys Pro
    2615                2620                2625

Leu Gly  Tyr Lys Glu Glu Asn  Asn Thr Gly Glu Cys  Cys Gly Arg
    2630                2635                2640

Cys Leu  Pro Thr Ala Cys Thr  Ile Gln Leu Arg Gly  Gly Gln Ile
    2645                2650                2655

Met Thr  Leu Lys Arg Asp Glu  Thr Leu Gln Asp Gly  Cys Asp Thr
    2660                2665                2670

His Phe  Cys Lys Val Asn Glu  Arg Gly Glu Tyr Phe  Trp Glu Lys
    2675                2680                2685

Arg Val  Thr Gly Cys Pro Pro  Phe Asp Glu His Lys  Cys Leu Ala
    2690                2695                2700

Glu Gly  Gly Lys Ile Met Lys  Ile Pro Gly Thr Cys  Cys Asp Thr
    2705                2710                2715

Cys Glu  Glu Pro Glu Cys Asn  Asp Ile Thr Ala Arg  Leu Gln Tyr
    2720                2725                2730

Val Lys  Val Gly Ser Cys Lys  Ser Glu Val Glu Val  Asp Ile His
    2735                2740                2745

Tyr Cys  Gln Gly Lys Cys Ala  Ser Lys Ala Met Tyr  Ser Ile Asp
    2750                2755                2760

Ile Asn  Asp Val Gln Asp Gln  Cys Ser Cys Cys Ser  Pro Thr Arg
    2765                2770                2775

Thr Glu  Pro Met Gln Val Ala  Leu His Cys Thr Asn  Gly Ser Val
    2780                2785                2790

Val Tyr  His Glu Val Leu Asn  Ala Met Glu Cys Lys  Cys Ser Pro
    2795                2800                2805
```

Arg Lys Cys Ser Lys
2810

<210> SEQ ID NO 32
<211> LENGTH: 2326
<212> TYPE: DNA
<213> ORGANISM: Canis familiaris

<400> SEQUENCE: 32
cctgctgctc accctggagg gtctgctctt tctctgggcc gcgtcctgcc aggagtgcac 60
caagtacaaa gtgagcacgt gccgggactg tgtggagtcg gggcccggct gcgcctggtg 120
ccagaagctg aacttcactg ggctagggga gcccgactcc gttcgctgtg acacccgaga 180
gcagctgctg ctgaaaggat gtgcggctga cgacatcatg gaccctcaga gcctggccga 240
gatccaggag gacaagaagg gcggccggca gcagctgtcc ccgcagaaag tgacgctcta 300
cctgagacca ggtcaggcgg ctgccttcaa tgtgaccttc cggcgggcca agggctaccc 360
catcgacctg tactacctga tggatctgtc ctactccatg ctggacgacc tcatcaacgt 420
caagaagctg gggggcgacc tgctgcgggc gctcaacgaa atcaccgagt ccggccgcat 480
cggcttcggg tctttcgtgg acaagacggt gctccccttc gtcaacacgc accccgagaa 540
gctgaagaac ccgtgcccca acaaggagaa ggagtgccag gcgccgttcg ccttcagaca 600
cgtgctgaag ctcacgaaca actccaacaa gttccagacg gaggtcggga agcagctgat 660
ttcggggaac ctggacgcgc ccgagggcgg gctggatgcc atgatgcagg tcgccgcgtg 720
cccggagcaa atcggctggc gcaacgtcac tcggctgctg gtgttcgcca cggacgacgg 780
cttccacttt gcgggcgacg ggaagctggg tgccatcctg acccccaatg acggccgctg 840
ccacctggag gacaacatgt acaagaggag caatgaattt gactacccgt cggtgggcca 900
gctggcacac aaactggccg aaagcaacat ccagcccatc ttcgcggtga ccaagagaat 960
ggtgacgacc tatgagaagc tcaccgaggt catccccaag tcagcggtcg gggagctgtc 1020
ggacgattcc agcaacgtgg tccagctcat caagaacgcc tacaacaaac tgtcctccag 1080
ggtcttcctg gaccacagcc tggcccccag caccctcaag gtcacctatg actccttctg 1140
cagtaacggg gtgtcgcagg tggaccagcc cagaggggac tgcgacggcg tccagatcaa 1200
cgtcccgatc accttccagg tgaaggtcac ggccacggag tgcatccagg agcagtcgtt 1260
tataatccgg gcactgggct tcacggacac ggtgaccgtg cacgtcatcc cccagtgcga 1320
gtgccagtgc cgggacgtgg gccaggacca cggcctctgc agyggcaagg gctccctgga 1380
gtgtggcatc tgcaggtgtg aggctggcta catcgggaag aactgcgagt gcctgacgca 1440
cggccgcagc agccaggagc tggagggcag ctgtcggagg gacaacagct ctctcatctg 1500
ctcggggctg ggggactgcc tctgcgggca gtgcgtgtgc cacaggagcg acgttcccaa 1560
caagaacatc ttcgggcgct actgcgagtg tgacaatgtc aactgcgagc gctatgacgg 1620
gcaggtgtgc gggggtaaag ttcggggctc ctgcaactgc ggcaagtgcc agtgcgagca 1680
gaactacgag ggctcggcgt gccagtgcgt gaagtccacc cagggctgcc tgagcacgga 1740
gggcatcgag tgcaacgggc gcggccgctg tcgctgtaac gtgtgcgagt gcgacggggg 1800
ctaccagccg ccgctgtgcg gggactgcct gggctgcccg tcgccctgtg gccggtacat 1860
cacctgtgcc cagtgcctga agttcaagca gggcccctcg gggaggaact gcagcgtgga 1920
gtgtgggaac gtgggcctgc tgagcaaacc cccggagaag gggcgcaggt gcaaggagcg 1980
ggatctggag ggctgctgga tcacctacac gctgcggcag cgggccggct gggacagcta 2040
tgaaatccac gtggacgaca gccgggagtg tgtgggggc ccccaaatcg cccccatcgt 2100
gggcggcacc gtgtcgggag tcgtgctcat cggcatcctc ctgctggcca tctggaaggc 2160
tctgacccac ctgagtgacc tccgcgagtt caagcgattc gagaaggaga agctcaggtc 2220
ccagtggaac aacgacaacc cccttttcaa gagcgccacc accacagtca tgaaccccag 2280
gtttgctgag agttagggcg ctcggcggag acggcgctgg ctgagc 2326

<210> SEQ ID NO 33
<211> LENGTH: 764
<212> TYPE: PRT
<213> ORGANISM: Canis familiaris

<400> SEQUENCE: 33

Leu Leu Leu Thr Leu Glu Gly Leu Leu Phe Leu Trp Ala Ala Ser Cys
1 5 10 15

Gln Glu Cys Thr Lys Tyr Lys Val Ser Thr Cys Arg Asp Cys Val Glu
20 25 30

Ser Gly Pro Gly Cys Ala Trp Cys Gln Lys Leu Asn Phe Thr Gly Leu
35 40 45

Gly Glu Pro Asp Ser Val Arg Cys Asp Thr Arg Glu Gln Leu Leu Leu
50 55 60

Lys Gly Cys Ala Ala Asp Asp Ile Met Asp Pro Gln Ser Leu Ala Glu
65 70 75 80

Ile Gln Glu Asp Lys Lys Gly Gly Arg Gln Gln Leu Ser Pro Gln Lys
85 90 95

Val Thr Leu Tyr Leu Arg Pro Gly Gln Ala Ala Ala Phe Asn Val Thr
100 105 110

Phe Arg Arg Ala Lys Gly Tyr Pro Ile Asp Leu Tyr Tyr Leu Met Asp
115 120 125

Leu Ser Tyr Ser Met Leu Asp Asp Leu Ile Asn Val Lys Lys Leu Gly
130 135 140

Gly Asp Leu Leu Arg Ala Leu Asn Glu Ile Thr Glu Ser Gly Arg Ile
145 150 155 160

Gly Phe Gly Ser Phe Val Asp Lys Thr Val Leu Pro Phe Val Asn Thr
165 170 175

His Pro Glu Lys Leu Lys Asn Pro Cys Pro Asn Lys Glu Lys Glu Cys
180 185 190

Gln Ala Pro Phe Ala Phe Arg His Val Leu Lys Leu Thr Asn Asn Ser
195 200 205

Asn Lys Phe Gln Thr Glu Val Gly Lys Gln Leu Ile Ser Gly Asn Leu
210 215 220

Asp Ala Pro Glu Gly Gly Leu Asp Ala Met Met Gln Val Ala Ala Cys
225 230 235 240

Pro Glu Gln Ile Gly Trp Arg Asn Val Thr Arg Leu Leu Val Phe Ala
245 250 255

Thr Asp Asp Gly Phe His Phe Ala Gly Asp Gly Lys Leu Gly Ala Ile
260 265 270

Leu Thr Pro Asn Asp Gly Arg Cys His Leu Glu Asp Asn Met Tyr Lys
275 280 285

Arg Ser Asn Glu Phe Asp Tyr Pro Ser Val Gly Gln Leu Ala His Lys
290 295 300

Leu Ala Glu Ser Asn Ile Gln Pro Ile Phe Ala Val Thr Lys Arg Met
305 310 315 320

Val Thr Thr Tyr Glu Lys Leu Thr Glu Val Ile Pro Lys Ser Ala Val
325 330 335

-continued

```
Gly Glu Leu Ser Asp Asp Ser Ser Asn Val Val Gln Leu Ile Lys Asn
            340                 345                 350

Ala Tyr Asn Lys Leu Ser Ser Arg Val Phe Leu Asp His Ser Leu Ala
        355                 360                 365

Pro Ser Thr Leu Lys Val Thr Tyr Asp Ser Phe Cys Ser Asn Gly Val
    370                 375                 380

Ser Gln Val Asp Gln Pro Arg Gly Asp Cys Asp Gly Val Gln Ile Asn
385                 390                 395                 400

Val Pro Ile Thr Phe Gln Val Lys Val Thr Ala Thr Glu Cys Ile Gln
                405                 410                 415

Glu Gln Ser Phe Ile Ile Arg Ala Leu Gly Phe Thr Asp Thr Val Thr
            420                 425                 430

Val His Val Ile Pro Gln Cys Glu Cys Gln Cys Arg Asp Val Gly Gln
        435                 440                 445

Asp His Gly Leu Cys Ser Gly Lys Gly Ser Leu Glu Cys Gly Ile Cys
    450                 455                 460

Arg Cys Glu Ala Gly Tyr Ile Gly Lys Asn Cys Glu Cys Leu Thr His
465                 470                 475                 480

Gly Arg Ser Ser Gln Glu Leu Glu Gly Ser Cys Arg Arg Asp Asn Ser
                485                 490                 495

Ser Leu Ile Cys Ser Gly Leu Gly Asp Cys Leu Cys Gly Gln Cys Val
            500                 505                 510

Cys His Arg Ser Asp Val Pro Asn Lys Asn Ile Phe Gly Arg Tyr Cys
        515                 520                 525

Glu Cys Asp Asn Val Asn Cys Glu Arg Tyr Asp Gly Gln Val Cys Gly
    530                 535                 540

Gly Lys Val Arg Gly Ser Cys Asn Cys Gly Lys Cys Gln Cys Glu Gln
545                 550                 555                 560

Asn Tyr Glu Gly Ser Ala Cys Gln Cys Val Lys Ser Thr Gln Gly Cys
                565                 570                 575

Leu Ser Thr Glu Gly Ile Glu Cys Asn Gly Arg Gly Arg Cys Arg Cys
            580                 585                 590

Asn Val Cys Glu Cys Asp Gly Gly Tyr Gln Pro Pro Leu Cys Gly Asp
        595                 600                 605

Cys Leu Gly Cys Pro Ser Pro Cys Gly Arg Tyr Ile Thr Cys Ala Gln
    610                 615                 620

Cys Leu Lys Phe Lys Gln Gly Pro Ser Gly Arg Asn Cys Ser Val Glu
625                 630                 635                 640

Cys Gly Asn Val Gly Leu Leu Ser Lys Pro Pro Glu Lys Gly Arg Arg
                645                 650                 655

Cys Lys Glu Arg Asp Leu Glu Gly Cys Trp Ile Thr Tyr Thr Leu Arg
            660                 665                 670

Gln Arg Ala Gly Trp Asp Ser Tyr Glu Ile His Val Asp Asp Ser Arg
        675                 680                 685

Glu Cys Val Gly Gly Pro Gln Ile Ala Pro Ile Val Gly Gly Thr Val
    690                 695                 700

Ser Gly Val Val Leu Ile Gly Ile Leu Leu Leu Ala Ile Trp Lys Ala
705                 710                 715                 720

Leu Thr His Leu Ser Asp Leu Arg Glu Phe Lys Arg Phe Glu Lys Glu
                725                 730                 735

Lys Leu Arg Ser Gln Trp Asn Asn Asp Asn Pro Leu Phe Lys Ser Ala
            740                 745                 750

Thr Thr Thr Val Met Asn Pro Arg Phe Ala Glu Ser
        755                 760
```

<210> SEQ ID NO 34
<211> LENGTH: 2788
<212> TYPE: DNA
<213> ORGANISM: Homo sapiens

<400> SEQUENCE: 34
gttgggcctg agaccgtcac caagacccct tccctccaca ggacatgctg ggcctgcgcc 60
ccccacttct cgccctggtg gggctgctct ccctcgggtg cgtcctctct caggagtgca 120
cgaagttcaa ggtcagcagc tgccgggaat gcatcgagtc ggggcccggc tgcacctggt 180
gccagaagct gaacttcaca gggccggggg atcctgactc cattcgctgc gacacccggc 240
cacagctgct catgaggggc tgtgcggctg acgacatcat ggaccccaca agcctcgctg 300
aaacccagga agaccacaat gggggccaga agcagctgtc cccacaaaaa gtgacgcttt 360
acctgcgacc aggccaggca gcagcgttca acgtgacctt ccggcgggcc aagggctacc 420
ccatcgacct gtactatctg atggacctct cctactccat gcttgatgac ctcaggaatg 480
tcaagaagct aggtggcgac ctgctccggg ccctcaacga gatcaccgag tccggccgca 540
ttggcttcgg gtccttcgtg gacaagaccg tgctgccgtt cgtgaacacg caccctgata 600
agctgcgaaa cccatgcccc aacaaggaga aagagtgcca gcccccgttt gccttcaggc 660
acgtgctgaa gctgaccaac aactccaacc agtttcagac cgaggtcggg aagcagctga 720
tttccggaaa cctggatgca cccgagggtg ggctggacgc catgatgcag gtcgccgcct 780
gcccggagga aatcggctgg cgcaacgtca cgcggctgct ggtgtttgcc actgatgacg 840
gcttccattt cgcgggcgac gggaagctgg gcgccatcct gacccccaac gacggccgct 900
gtcacctgga ggacaacttg tacaagagga gcaacgaatt cgactaccca tcggtgggcc 960
agctggcgca caagctggct gaaaacaaca tccagcccat cttcgcggtg accagtagga 1020
tggtgaagac ctacgagaaa ctcaccgaga tcatccccaa gtcagccgtg gggggagctgt 1080 ctgaggactc cagcaatgtg gtccatctca ttaagaatgc ttacaataaa ctctcctcca 1140
gggtattcct ggatcacaac gccctccccg acaccctgaa agtcacctac gactccttct 1200
gcagcaatgg agtgacgcac aggaaccagc ccagaggtga ctgtgatggc gtgcagatca 1260
atgtcccgat caccttccag gtgaaggtca cggccacaga gtgcatccag gagcagtcgt 1320
ttgtcatccg ggcgctgggc ttcacggaca tagtgaccgt gcaggtcctt ccccagtgtg 1380
agtgccggtg ccgggaccag agcagagacc gcagcctctg ccatggcaag ggcttcttgg 1440
agtgcggcat ctgcaggtgt gacactggct acattgggaa aaactgtgag tgccagacac 1500
agggccggag cagccaggag ctggaaggaa gctgccggaa ggacaacaac tccatcatct 1560
gctcagggct gggggactgt gtctgcgggc agtgcctgtg ccacaccagc gacgtccccg 1620
gcaagctgat atacgggcag tactgcgagt gtgacaccat caactgtgag cgctacaacg 1680
gccaggtctg cggcggcccg gggagggggc tctgcttctg cgggaagtgc cgctgccacc 1740
cgggctttga gggctcagcg tgccagtgcg agaggaccac tgagggctgc ctgaacccgc 1800
ggcgtgttga gtgtagtggt cgtggccggt gccgctgcaa cgtatgcgag tgccattcag 1860
gctaccagct gcctctgtgc caggagtgcc ccggctgccc ctcaccctgt ggcaagtaca 1920
tctcctgcgc cgagtgcctg aagttcgaaa agggcccctt tgggaagaac tgcagcgcgg 1980
cgtgtccggg cctgcagctg tcgaacaacc ccgtgaaggg caggacctgc aaggagaggg 2040
actcagaggg ctgctgggtg gcctacacgc tggagcagca ggacgggatg gaccgctacc 2100
tcatctatgt ggatgagagc cgagagtgtg tggcaggccc caacatcgcc gccatcgtcg 2160

```
ggggcaccgt ggcaggcatc gtgctgatcg gcattctcct gctggtcatc tggaaggctc   2220

tgatccacct gagcgacctc cgggagtaca ggcgctttga gaaggagaag ctcaagtccc   2280

agtggaacaa tgataatccc cttttcaaga gcgccaccac gacggtcatg aaccccaagt   2340

ttgctgagag ttaggagcac ttggtgaaga caaggccgtc aggacccacc atgtctgccc   2400

catcacgcgg ccgagacatg gcttgccaca gctcttgagg atgtcaccaa ttaaccagaa   2460

atccagttat tttccaccct caaaatgaca gccatggccg gccgggtgct tctgggggct   2520

cgtcgggggg acagctccac tctgactggc acagtctttg catggagact tgaggaggga   2580

gggcttgagg ttggtgaggt taggtgcgtg tttcctgtgc aagtcaggac atcagtctga   2640

ttaaaggtgg tgccaattta tttacattta aacttgtcag ggtataaaat gacatcccat   2700

taattatatt gttaatcaat cacgtgtata gaaaaaaaat aaaacttcaa tacaggctgt   2760

ccatggaaaa aaaaaaaaaa aaaaaaaa                                      2788


<210> SEQ ID NO 35
<211> LENGTH: 769
<212> TYPE: PRT
<213> ORGANISM: Homo sapiens

<400> SEQUENCE: 35

Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
            20                  25                  30

Cys Arg Glu Cys Ile Glu Ser Gly Pro Gly Cys Thr Trp Cys Gln Lys
        35                  40                  45

Leu Asn Phe Thr Gly Pro Gly Asp Pro Asp Ser Ile Arg Cys Asp Thr
    50                  55                  60

Arg Pro Gln Leu Leu Met Arg Gly Cys Ala Ala Asp Asp Ile Met Asp
65                  70                  75                  80

Pro Thr Ser Leu Ala Glu Thr Gln Glu Asp His Asn Gly Gly Gln Lys
                85                  90                  95

Gln Leu Ser Pro Gln Lys Val Thr Leu Tyr Leu Arg Pro Gly Gln Ala
            100                 105                 110

Ala Ala Phe Asn Val Thr Phe Arg Arg Ala Lys Gly Tyr Pro Ile Asp
        115                 120                 125

Leu Tyr Tyr Leu Met Asp Leu Ser Tyr Ser Met Leu Asp Asp Leu Arg
    130                 135                 140

Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
            180                 185                 190

Asn Lys Glu Lys Glu Cys Gln Pro Pro Phe Ala Phe Arg His Val Leu
        195                 200                 205

Lys Leu Thr Asn Asn Ser Asn Gln Phe Gln Thr Glu Val Gly Lys Gln
    210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
```

```
            260                 265                 270

Gly Lys Leu Gly Ala Ile Leu Thr Pro Asn Asp Gly Arg Cys His Leu
        275                 280                 285

Glu Asp Asn Leu Tyr Lys Arg Ser Asn Glu Phe Asp Tyr Pro Ser Val
    290                 295                 300

Gly Gln Leu Ala His Lys Leu Ala Glu Asn Asn Ile Gln Pro Ile Phe
305                 310                 315                 320

Ala Val Thr Ser Arg Met Val Lys Thr Tyr Glu Lys Leu Thr Glu Ile
                325                 330                 335

Ile Pro Lys Ser Ala Val Gly Glu Leu Ser Glu Asp Ser Ser Asn Val
            340                 345                 350

Val His Leu Ile Lys Asn Ala Tyr Asn Lys Leu Ser Ser Arg Val Phe
        355                 360                 365

Leu Asp His Asn Ala Leu Pro Asp Thr Leu Lys Val Thr Tyr Asp Ser
    370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Val Ile Arg Ala Leu Gly
            420                 425                 430

Phe Thr Asp Ile Val Thr Val Gln Val Leu Pro Gln Cys Glu Cys Arg
        435                 440                 445

Cys Arg Asp Gln Ser Arg Asp Arg Ser Leu Cys His Gly Lys Gly Phe
    450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Asn Ser Ile Ile Cys Ser Gly Leu Gly Asp Cys
            500                 505                 510

Val Cys Gly Gln Cys Leu Cys His Thr Ser Asp Val Pro Gly Lys Leu
        515                 520                 525

Ile Tyr Gly Gln Tyr Cys Glu Cys Asp Thr Ile Asn Cys Glu Arg Tyr
    530                 535                 540

Asn Gly Gln Val Cys Gly Gly Pro Gly Arg Gly Leu Cys Phe Cys Gly
545                 550                 555                 560

Lys Cys Arg Cys His Pro Gly Phe Glu Gly Ser Ala Cys Gln Cys Glu
                565                 570                 575

Arg Thr Thr Glu Gly Cys Leu Asn Pro Arg Arg Val Glu Cys Ser Gly
            580                 585                 590

Arg Gly Arg Cys Arg Cys Asn Val Cys Glu Cys His Ser Gly Tyr Gln
        595                 600                 605

Leu Pro Leu Cys Gln Glu Cys Pro Gly Cys Pro Ser Pro Cys Gly Lys
    610                 615                 620

Tyr Ile Ser Cys Ala Glu Cys Leu Lys Phe Glu Lys Gly Pro Phe Gly
625                 630                 635                 640

Lys Asn Cys Ser Ala Ala Cys Pro Gly Leu Gln Leu Ser Asn Asn Pro
                645                 650                 655

Val Lys Gly Arg Thr Cys Lys Glu Arg Asp Ser Glu Gly Cys Trp Val
            660                 665                 670

Ala Tyr Thr Leu Glu Gln Gln Asp Gly Met Asp Arg Tyr Leu Ile Tyr
        675                 680                 685
```

```
Val Asp Glu Ser Arg Glu Cys Val Ala Gly Pro Asn Ile Ala Ala Ile
    690                 695                 700

Val Gly Gly Thr Val Ala Gly Ile Val Leu Ile Gly Ile Leu Leu Leu
705                 710                 715                 720

Val Ile Trp Lys Ala Leu Ile His Leu Ser Asp Leu Arg Glu Tyr Arg
                725                 730                 735

Arg Phe Glu Lys Glu Lys Leu Lys Ser Gln Trp Asn Asn Asp Asn Pro
            740                 745                 750

Leu Phe Lys Ser Ala Thr Thr Thr Val Met Asn Pro Lys Phe Ala Glu
        755                 760                 765

Ser


<210> SEQ ID NO 36
<211> LENGTH: 119
<212> TYPE: DNA
<213> ORGANISM: Artificial
<220> FEATURE:
<223> OTHER INFORMATION: Predicted nucleic acid sequence for dog CD45,
      partial sequence within chromosome 7, positions 18132 to 17986

<400> SEQUENCE: 36

tctttttaaa gagttactgg aaacctgaag tgatgattgc tgctcaggga cccctaaaag     60

agaccattgg tgacttttgg cagatgatat tccaaagaaa agtcaaagtc attgttatg     119


<210> SEQ ID NO 37
<211> LENGTH: 128
<212> TYPE: DNA
<213> ORGANISM: Artificial
<220> FEATURE:
<223> OTHER INFORMATION: Predicted nucleic acid sequence for dog CD45,
      partial sequence within chromosome 7, positions 19420 to 19293

<400> SEQUENCE: 37

atgactttaa cagagtgcca ctaaaacatg aactggagat gagcaaagag agtgagcatg     60

attcagatga atcttctgat gatgacagtg actcagagga aacaagtaga tacatcaatg    120

cgtctttt                                                             128


<210> SEQ ID NO 38
<211> LENGTH: 158
<212> TYPE: DNA
<213> ORGANISM: Artificial
<220> FEATURE:
<223> OTHER INFORMATION: Predicted nucleic acid sequence for dog CD45,
      partial sequence within chromosome 7, positions 27292 to 27135

<400> SEQUENCE: 38

aaaaaagaga aggccaccgg aagagaggtg actcacattc agttcaccag ctggccagac     60

catggggtgc ctgaagatcc tcacctgctt ctgaagctgc ggaggagagt gaacgctttc    120

agcaacttct tcagtggccc cattgtggtg cactgcag                            158


<210> SEQ ID NO 39
<211> LENGTH: 140
<212> TYPE: DNA
<213> ORGANISM: Artificial
<220> FEATURE:
<223> OTHER INFORMATION: Predicted nucleic acid sequence for dog CD45,
      partial sequence within chromosome 7, positions 26930 to 26791

<400> SEQUENCE: 39

cagtgctggt gtgggacgca caggcaccta tattggaatt gatgccatgc tagaaggcct     60

ggaagcggaa aacaaagtag atgtttatgg ttatgttgtc aagctaaggc gacagagatg    120
```

```
cttgatggtc caagtggagg                                            140


<210> SEQ ID NO 40
<211> LENGTH: 111
<212> TYPE: DNA
<213> ORGANISM: Artificial
<220> FEATURE:
<223> OTHER INFORMATION: Predicted nucleic acid sequence for dog CD45,
      partial sequence within chromosome 7, positions 35370 to 35260

<400> SEQUENCE: 40

gatgatgaaa aacaactgat gactgtggag ccaatccatg cagatatttt gttggaaact     60

tataagagga agatcgctga tgaaggaaga ctgtttctgg ctgaatttca g             111


<210> SEQ ID NO 41
<211> LENGTH: 4315
<212> TYPE: DNA
<213> ORGANISM: Homo sapiens

<400> SEQUENCE: 41

ggaaattgtt cctcgtctga taagacaaca gtggagaaag gacgcatgct gtttcttagg     60

gacacggctg gcttccagat atgaccatgt atttgtggct taaactcttg gcatttggct    120

ttgcctttct ggacacagaa gtatttgtga cagggcaaag cccaacacct tcccccactg    180

gattgactac agcaaagatg cccagtgttc cactttcaag tgacccctta cctactcaca    240

ccactgcatt ctcacccgca agcacctttg aaagagaaaa tgacttctca gagaccacaa    300

cttctcttag tccagacaat acttccaccc aagtatcccc ggactctttg gataatgcta    360

gtgcttttaa taccacaggt gtttcatcag tacagacgcc tcaccttccc acgcacgcag    420

actcgcagac gccctctgct ggaactgaca cgcagacatt cagcggctcc gccgccaatg    480

caaaactcaa ccctacccca ggcagcaatg ctatctcaga tgtcccagga gagaggagta    540

cagccagcac ctttcctaca gacccagttt ccccattgac aaccaccctc agccttgcac    600

accacagctc tgctgcctta cctgcacgca cctccaacac caccatcaca gcgaacacct    660

cagatgccta ccttaatgcc tctgaaacaa ccactctgag cccttctgga agcgctgtca    720

tttcaaccac aacaatagct actactccat ctaagccaac atgtgatgaa aaatatgcaa    780

acatcactgt ggattactta tataacaagg aaactaaatt atttacagca aagctaaatg    840

ttaatgagaa tgtggaatgt ggaaacaata cttgcacaaa caatgaggtg cataacctta    900

cagaatgtaa aaatgcgtct gtttccatat ctcataattc atgtactgct cctgataaga    960

cattaatatt agatgtgcca ccaggggttg aaaagtttca gttacatgat tgtacacaag   1020

ttgaaaaagc agatactact atttgtttaa aatggaaaaa tattgaaacc tttacttgtg   1080

atacacagaa tattacctac agatttcagt gtggtaatat gatatttgat aataaagaaa   1140

ttaaattaga aaaccttgaa cccgaacatg agtataagtg tgactcagaa atactctata   1200

ataaccacaa gtttactaac gcaagtaaaa ttattaaaac agattttggg agtccaggag   1260

agcctcagat tattttttgt agaagtgaag ctgcacatca aggagtaatt acctggaatc   1320

cccctcaaag atcatttcat aattttaccc tctgttatat aaaagagaca gaaaaagatt   1380

gcctcaatct ggataaaaac ctgatcaaat atgatttgca aaatttaaaa ccttatacga   1440

aatatgtttt atcattacat gcctacatca ttgcaaaagt gcaacgtaat ggaagtgctg   1500

caatgtgtca tttcacaact aaaagtgctc ctccaagcca ggtctggaac atgactgtct   1560

ccatgacatc agataatagt atgcatgtca agtgtaggcc tcccagggac cgtaatggcc   1620
```

-continued

```
cccatgaacg ttaccatttg gaagttgaag ctggaaatac tctggttaga aatgagtcgc   1680
ataagaattg cgatttccgt gtaaaagatc ttcaatattc aacagactac acttttaagg   1740
cctattttca caatggagac tatcctggag aaccctttat tttacatcat tcaacatctt   1800
ataattctaa ggcactgata gcatttctgg catttctgat tattgtgaca tcaatagccc   1860
tgcttgttgt tctctacaaa atctatgatc tacataagaa aagatcctgc aatttagatg   1920
aacagcagga gcttgttgaa agggatgatg aaaaacaact gatgaatgtg gagccaatcc   1980
atgcagatat tttgttggaa acttataaga ggaagattgc tgatgaagga agaccttttc   2040
tggctgaatt tcagagcatc ccgcgggtgt tcagcaagtt tcctataaag gaagctcgaa   2100
agccctttaa ccagaataaa aaccgttatg ttgacattct tccttatgat tataaccgtg   2160
ttgaactctc tgagataaac ggagatgcag ggtcaaacta cataaatgcc agctatattg   2220
atggtttcaa agaacccagg aaatacattg ctgcacaagg tcccagggat gaaactgttg   2280
atgatttctg gaggatgatt tggaacaga aagccacagt tattgtcatg gtcactcgat   2340
gtgaagaagg aaacaggaac aagtgtgcag aatactggcc gtcaatggaa gagggcactc   2400
gggcttttgg agatgttgtt gtaaagatca accagcacaa aagatgtcca gattacatca   2460
ttcagaaatt gaacattgta aataaaaaag aaaaagcaac tggaagagag gtgactcaca   2520
ttcagttcac cagctggcca gaccacgggg tgcctgagga tcctcacttg ctcctcaaac   2580
tgagaaggag agtgaatgcc ttcagcaatt tcttcagtgg tcccattgtg gtgcactgca   2640
gtgctggtgt tgggcgcaca ggaacctata tcggaattga tgccatgcta gaaggcttgg   2700
aagccgagaa caaagtggat gtttatggtt atgttgtcaa gctaaggcga cagagatgcc   2760
tgatggttca agtagaggcc cagtacatct tgatccatca ggctttggtg gaatacaatc   2820
agtttggaga aacagaagtg aatttgtctg aattacatcc atatctacat aacatgaaga   2880
aaagggatcc acccagtgag ccgtctccac tagaggctga attccagaga cttccttcat   2940
ataggagctg gaggacacag cacattggaa atcaagaaga aaataaaagt aaaaacagga   3000
attctaatgt catcccatat gactataaca gagtgccact taaacatgag ctggaaatga   3060
gtaaagagag tgagcatgat tcagatgaat cctctgatga tgacagtgat tcagaggaac   3120
caagcaaata catcaatgca tcttttataa tgagctactg gaaacctgaa gtgatgattg   3180
ctgctcaggg accactgaag gagaccattg gtgacttttg gcagatgatc ttccaaagaa   3240
aagtcaaagt tattgttatg ctgacagaac tgaaacatgg agaccaggaa atctgtgctc   3300
agtactgggg agaaggaaag caaacatatg gagatattga agttgacctg aaagacacag   3360
acaaatcttc aacttatacc cttcgtgtct ttgaactgag acattccaag aggaaagact   3420
ctcgaactgt gtaccagtac caatatacaa actggagtgt ggagcagctt cctgcagaac   3480
ccaaggaatt aatctctatg attcaggtcg tcaaacaaaa acttccccag aagaattcct   3540
ctgaagggaa caagcatcac aagagtacac ctctactcat tcactgcagg gatggatctc   3600
agcaaacggg aatattttgt gctttgttaa atctcttaga aagtgcggaa acagaagagg   3660
tagtggatat ttttcaagtg gtaaaagctc tacgcaaagc taggctaggc atggtttcca   3720
cattcgagca atatcaattc ctatatgacg tcattgccag cacctaccct gctcagaatg   3780
gacaagtaaa gaaaaacaac catcaagaag ataaaattga atttgataat gaagtggaca   3840
aagtaaagca ggatgctaat tgtgttaatc cacttggtgc cccagaaaag ctccctgaag   3900
caaaggaaca ggctgaaggt tctgaaccca cgagtggcac tgaggggcca gaacattctg   3960
tcaatggtcc tgcaagtcca gctttaaatc aaggttcata ggaaaagaca taaatgagga   4020
```

-continued aactccaaac ctcctgttag ctgttatttc tatttttgta gaagtaggaa gtgaaaatag 4080
gtatacagtg gattaattaa atgcagcgaa ccaatatttg tagaagggtt atattttact 4140
actgtggaaa aatatttaag atagttttgc cagaacagtt tgtacagacg tatgcttatt 4200
ttaaaatttt atctcttatt cagtaaaaaa caacttcttt gtaatcgtta tgagtgtata 4260
tgtatgtgtg tatgggtgtg tgtttgtgtg agagacagag aaagagagag aattc 4315

<210> SEQ ID NO 42
<211> LENGTH: 1304
<212> TYPE: PRT
<213> ORGANISM: Homo sapiens

<400> SEQUENCE: 42

Met Tyr Leu Trp Leu Lys Leu Leu Ala Phe Gly Phe Ala Phe Leu Asp
1 5 10 15

Thr Glu Val Phe Val Thr Gly Gln Ser Pro Thr Pro Ser Pro Thr Gly
20 25 30

Leu Thr Thr Ala Lys Met Pro Ser Val Pro Leu Ser Ser Asp Pro Leu
35 40 45

Pro Thr His Thr Thr Ala Phe Ser Pro Ala Ser Thr Phe Glu Arg Glu
50 55 60

Asn Asp Phe Ser Glu Thr Thr Thr Ser Leu Ser Pro Asp Asn Thr Ser
65 70 75 80

Thr Gln Val Ser Pro Asp Ser Leu Asp Asn Ala Ser Ala Phe Asn Thr
85 90 95

Thr Gly Val Ser Ser Val Gln Thr Pro His Leu Pro Thr His Ala Asp
100 105 110

Ser Gln Thr Pro Ser Ala Gly Thr Asp Thr Gln Thr Phe Ser Gly Ser
115 120 125

Ala Ala Asn Ala Lys Leu Asn Pro Thr Pro Gly Ser Asn Ala Ile Ser
130 135 140

Asp Val Pro Gly Glu Arg Ser Thr Ala Ser Thr Phe Pro Thr Asp Pro
145 150 155 160

Val Ser Pro Leu Thr Thr Thr Leu Ser Leu Ala His His Ser Ser Ala
165 170 175

Ala Leu Pro Ala Arg Thr Ser Asn Thr Thr Ile Thr Ala Asn Thr Ser
180 185 190

Asp Ala Tyr Leu Asn Ala Ser Glu Thr Thr Thr Leu Ser Pro Ser Gly
195 200 205

Ser Ala Val Ile Ser Thr Thr Thr Ile Ala Thr Thr Pro Ser Lys Pro
210 215 220

Thr Cys Asp Glu Lys Tyr Ala Asn Ile Thr Val Asp Tyr Leu Tyr Asn
225 230 235 240

Lys Glu Thr Lys Leu Phe Thr Ala Lys Leu Asn Val Asn Glu Asn Val
245 250 255

Glu Cys Gly Asn Asn Thr Cys Thr Asn Asn Glu Val His Asn Leu Thr
260 265 270

Glu Cys Lys Asn Ala Ser Val Ser Ile Ser His Asn Ser Cys Thr Ala
275 280 285

Pro Asp Lys Thr Leu Ile Leu Asp Val Pro Pro Gly Val Glu Lys Phe
290 295 300

Gln Leu His Asp Cys Thr Gln Val Glu Lys Ala Asp Thr Thr Ile Cys
305 310 315 320

Leu Lys Trp Lys Asn Ile Glu Thr Phe Thr Cys Asp Thr Gln Asn Ile
325 330 335

```
Thr Tyr Arg Phe Gln Cys Gly Asn Met Ile Phe Asp Asn Lys Glu Ile
            340                 345                 350

Lys Leu Glu Asn Leu Glu Pro Glu His Glu Tyr Lys Cys Asp Ser Glu
        355                 360                 365

Ile Leu Tyr Asn Asn His Lys Phe Thr Asn Ala Ser Lys Ile Ile Lys
    370                 375                 380

Thr Asp Phe Gly Ser Pro Gly Glu Pro Gln Ile Ile Phe Cys Arg Ser
385                 390                 395                 400

Glu Ala Ala His Gln Gly Val Ile Thr Trp Asn Pro Pro Gln Arg Ser
                405                 410                 415

Phe His Asn Phe Thr Leu Cys Tyr Ile Lys Glu Thr Glu Lys Asp Cys
            420                 425                 430

Leu Asn Leu Asp Lys Asn Leu Ile Lys Tyr Asp Leu Gln Asn Leu Lys
        435                 440                 445

Pro Tyr Thr Lys Tyr Val Leu Ser Leu His Ala Tyr Ile Ile Ala Lys
    450                 455                 460

Val Gln Arg Asn Gly Ser Ala Ala Met Cys His Phe Thr Thr Lys Ser
465                 470                 475                 480

Ala Pro Pro Ser Gln Val Trp Asn Met Thr Val Ser Met Thr Ser Asp
                485                 490                 495

Asn Ser Met His Val Lys Cys Arg Pro Pro Arg Asp Arg Asn Gly Pro
            500                 505                 510

His Glu Arg Tyr His Leu Glu Val Glu Ala Gly Asn Thr Leu Val Arg
        515                 520                 525

Asn Glu Ser His Lys Asn Cys Asp Phe Arg Val Lys Asp Leu Gln Tyr
    530                 535                 540

Ser Thr Asp Tyr Thr Phe Lys Ala Tyr Phe His Asn Gly Asp Tyr Pro
545                 550                 555                 560

Gly Glu Pro Phe Ile Leu His His Ser Thr Ser Tyr Asn Ser Lys Ala
                565                 570                 575

Leu Ile Ala Phe Leu Ala Phe Leu Ile Ile Val Thr Ser Ile Ala Leu
            580                 585                 590

Leu Val Val Leu Tyr Lys Ile Tyr Asp Leu His Lys Lys Arg Ser Cys
        595                 600                 605

Asn Leu Asp Glu Gln Gln Glu Leu Val Glu Arg Asp Asp Glu Lys Gln
    610                 615                 620

Leu Met Asn Val Glu Pro Ile His Ala Asp Ile Leu Leu Glu Thr Tyr
625                 630                 635                 640

Lys Arg Lys Ile Ala Asp Glu Gly Arg Leu Phe Leu Ala Glu Phe Gln
                645                 650                 655

Ser Ile Pro Arg Val Phe Ser Lys Phe Pro Ile Lys Glu Ala Arg Lys
            660                 665                 670

Pro Phe Asn Gln Asn Lys Asn Arg Tyr Val Asp Ile Leu Pro Tyr Asp
        675                 680                 685

Tyr Asn Arg Val Glu Leu Ser Glu Ile Asn Gly Asp Ala Gly Ser Asn
    690                 695                 700

Tyr Ile Asn Ala Ser Tyr Ile Asp Gly Phe Lys Glu Pro Arg Lys Tyr
705                 710                 715                 720

Ile Ala Ala Gln Gly Pro Arg Asp Glu Thr Val Asp Asp Phe Trp Arg
                725                 730                 735

Met Ile Trp Glu Gln Lys Ala Thr Val Ile Val Met Val Thr Arg Cys
            740                 745                 750

Glu Glu Gly Asn Arg Asn Lys Cys Ala Glu Tyr Trp Pro Ser Met Glu
```

-continued

```
        755                 760                 765

Glu Gly Thr Arg Ala Phe Gly Asp Val Val Val Lys Ile Asn Gln His
    770                 775                 780

Lys Arg Cys Pro Asp Tyr Ile Ile Gln Lys Leu Asn Ile Val Asn Lys
785                 790                 795                 800

Lys Glu Lys Ala Thr Gly Arg Glu Val Thr His Ile Gln Phe Thr Ser
                805                 810                 815

Trp Pro Asp His Gly Val Pro Glu Asp Pro His Leu Leu Leu Lys Leu
            820                 825                 830

Arg Arg Arg Val Asn Ala Phe Ser Asn Phe Phe Ser Gly Pro Ile Val
        835                 840                 845

Val His Cys Ser Ala Gly Val Gly Arg Thr Gly Thr Tyr Ile Gly Ile
    850                 855                 860

Asp Ala Met Leu Glu Gly Leu Glu Ala Glu Asn Lys Val Asp Val Tyr
865                 870                 875                 880

Gly Tyr Val Val Lys Leu Arg Arg Gln Arg Cys Leu Met Val Gln Val
                885                 890                 895

Glu Ala Gln Tyr Ile Leu Ile His Gln Ala Leu Val Glu Tyr Asn Gln
            900                 905                 910

Phe Gly Glu Thr Glu Val Asn Leu Ser Glu Leu His Pro Tyr Leu His
        915                 920                 925

Asn Met Lys Lys Arg Asp Pro Pro Ser Glu Pro Ser Pro Leu Glu Ala
    930                 935                 940

Glu Phe Gln Arg Leu Pro Ser Tyr Arg Ser Trp Arg Thr Gln His Ile
945                 950                 955                 960

Gly Asn Gln Glu Glu Asn Lys Ser Lys Asn Arg Asn Ser Asn Val Ile
                965                 970                 975

Pro Tyr Asp Tyr Asn Arg Val Pro Leu Lys His Glu Leu Glu Met Ser
            980                 985                 990

Lys Glu Ser Glu His Asp Ser Asp  Glu Ser Ser Asp Asp  Asp Ser Asp
        995                 1000                1005

Ser Glu  Glu Pro Ser Lys Tyr  Ile Asn Ala Ser Phe  Ile Met Ser
    1010                1015                1020

Tyr Trp  Lys Pro Glu Val Met  Ile Ala Ala Gln Gly  Pro Leu Lys
    1025                1030                1035

Glu Thr  Ile Gly Asp Phe Trp  Gln Met Ile Phe Gln  Arg Lys Val
    1040                1045                1050

Lys Val  Ile Val Met Leu Thr  Glu Leu Lys His Gly  Asp Gln Glu
    1055                1060                1065

Ile Cys  Ala Gln Tyr Trp Gly  Glu Gly Lys Gln Thr  Tyr Gly Asp
    1070                1075                1080

Ile Glu  Val Asp Leu Lys Asp  Thr Asp Lys Ser Ser  Thr Tyr Thr
    1085                1090                1095

Leu Arg  Val Phe Glu Leu Arg  His Ser Lys Arg Lys  Asp Ser Arg
    1100                1105                1110

Thr Val  Tyr Gln Tyr Gln Tyr  Thr Asn Trp Ser Val  Glu Gln Leu
    1115                1120                1125

Pro Ala  Glu Pro Lys Glu Leu  Ile Ser Met Ile Gln  Val Val Lys
    1130                1135                1140

Gln Lys  Leu Pro Gln Lys Asn  Ser Ser Glu Gly Asn  Lys His His
    1145                1150                1155

Lys Ser  Thr Pro Leu Leu Ile  His Cys Arg Asp Gly  Ser Gln Gln
    1160                1165                1170
```

```
Thr Gly  Ile Phe Cys Ala Leu  Leu Asn Leu Leu Glu  Ser Ala Glu
    1175                 1180                 1185

Thr Glu  Glu Val Val Asp Ile  Phe Gln Val Val Lys  Ala Leu Arg
    1190                 1195                 1200

Lys Ala  Arg Pro Gly Met Val  Ser Thr Phe Glu Gln  Tyr Gln Phe
    1205                 1210                 1215

Leu Tyr  Asp Val Ile Ala Ser  Thr Tyr Pro Ala Gln  Asn Gly Gln
    1220                 1225                 1230

Val Lys  Lys Asn Asn His Gln  Glu Asp Lys Ile Glu  Phe Asp Asn
    1235                 1240                 1245

Glu Val  Asp Lys Val Lys Gln  Asp Ala Asn Cys Val  Asn Pro Leu
    1250                 1255                 1260

Gly Ala  Pro Glu Lys Leu Pro  Glu Ala Lys Glu Gln  Ala Glu Gly
    1265                 1270                 1275

Ser Glu  Pro Thr Ser Gly Thr  Glu Gly Pro Glu His  Ser Val Asn
    1280                 1285                 1290

Gly Pro  Ala Ser Pro Ala Leu  Asn Gln Gly Ser
    1295                 1300


<210> SEQ ID NO 43
<211> LENGTH: 208
<212> TYPE: DNA
<213> ORGANISM: Artificial
<220> FEATURE:
<223> OTHER INFORMATION: Predicted nucleic acid sequence for dog CD133,
      partial sequence within position 50894 to 51101

<400> SEQUENCE: 43

agattatcta ctatgaaatc gggattatta tttgtgctgt cctggggctg ctctttgtga     60

ttctgatgcc gctggtggga ttttgctttg gtctgtgtcg ttgctgtaac aaatgtggtg    120

gagaaatgca tcagcgacag aagaaaaatg ggccttcct gaggaaatac tttacagtct    180

ccctcctggt gatttgtata ttcataag                                       208


<210> SEQ ID NO 44
<211> LENGTH: 3794
<212> TYPE: DNA
<213> ORGANISM: Homo sapiens

<400> SEQUENCE: 44

ccaagttcta cctcatgttt ggaggatctt gctagctatg gccctcgtac tcggctccct     60

gttgctgctg ggctgtgcg ggaactcctt ttcaggaggg cagccttcat ccacagatgc    120

tcctaaggct tggaattatg aattgcctgc aacaaattat gagacccaag actcccataa    180

agctggaccc attggcattc tctttgaact agtgcatatc tttctctatg tggtacagcc    240

gcgtgatttc ccagaagata ctttgagaaa attcttacag aaggcatatg aatccaaaat    300

tgattatgac aagccagaaa ctgtaatctt aggtctaaag attgtctact atgaagcagg    360

gattattcta tgctgtgtcc tggggctgct gtttattatt ctgatgcctc tggtggggta    420

tttcttttgt atgtgtcgtt gctgtaacaa atgtggtgga gaaatgcacc agcgacagaa    480

ggaaaatggg cccttcctga ggaaatgctt tgcaatctcc ctgttggtga tttgtataat    540

aataagcatt ggcatcttct atggttttgt ggcaaatcac caggtaagaa cccggatcaa    600

aaggagtcgg aaactggcag atagcaattt caaggacttg cgaactctct tgaatgaaac    660

tccagagcaa atcaaatata tattggccca gtacaacact accaaggaca aggcgttcac    720

agatctgaac agtatcaatt cagtgctagg aggcggaatt cttgaccgac tgagacccaa    780
```

-continued

```
catcatccct gttcttgatg agattaagtc catggcaaca gcgatcaagg agaccaaaga    840
ggcgttggag aacatgaaca gcaccttgaa gagcttgcac caacaaagta cacagcttag    900
cagcagtctg accagcgtga aaactagcct gcggtcatct ctcaatgacc ctctgtgctt    960
ggtgcatcca tcaagtgaaa cctgcaacag catcagattg tctctaagcc agctgaatag   1020
caaccctgaa ctgaggcagc ttccacccgt ggatgcagaa cttgacaacg ttaataacgt   1080
tcttaggaca gatttggatg gcctggtcca acagggctat caatccctta atgatatacc   1140
tgacagagta caacgccaaa ccacgactgt cgtagcaggt atcaaaaggg tcttgaattc   1200
cattggttca gatatcgaca atgtaactca gcgtcttcct attcaggata tactctcagc   1260
attctctgtt tatgttaata acactgaaag ttacatccac agaaatttac ctacattgga   1320
agagtatgat tcatactggt ggctgggtgg cctggtcatc tgctctctgc tgaccctcat   1380
cgtgattttt tactacctgg gcttactgtg tggcgtgtgc ggctatgaca ggcatgccac   1440
cccgaccacc cgaggctgtg tctccaacac cggaggcgtc ttcctcatgg ttggagttgg   1500
attaagtttc ctcttttgct ggatattgat gatcattgtg gttcttacct ttgtctttgg   1560
tgcaaatgtg gaaaaactga tctgtgaacc ttacacgagc aaggaattat tccgggtttt   1620
ggatacaccc tacttactaa atgaagactg ggaatactat ctctctggga agctatttaa   1680
taaatcaaaa atgaagctca cttttgaaca agtttacagt gactgcaaaa aaaatagagg   1740
cacttacggc actcttcacc tgcagaacag cttcaatatc agtgaacatc tcaacattaa   1800
tgagcatact ggaagcataa gcagtgaatt ggaaagtctg aaggtaaatc ttaatatctt   1860
tctgttgggt gcagcaggaa gaaaaaacct tcaggatttt gctgcttgtg gaatagacag   1920
aatgaattat gacagctact tggctcagac tggtaaatcc cccgcaggag tgaatctttt   1980
atcatttgca tatgatctag aagcaaaagc aaacagtttg cccccaggaa atttgaggaa   2040
ctccctgaaa agagatgcac aaactattaa aacaattcac cagcaacgag tccttcctat   2100
agaacaatca ctgagcactc tataccaaag cgtcaagata cttcaacgca cagggaatgg   2160
attgttggag agagtaacta ggattctagc ttctctggat tttgctcaga acttcatcac   2220
aaacaatact tcctctgtta ttattgagga aactaagaag tatgggagaa caataatagg   2280
atattttgaa cattatctgc agtggatcga gttctctatc agtgagaaag tggcatcgtg   2340
caaacctgtg gccaccgctc tagatactgc tgttgatgtc tttctgtgta gctacattat   2400
cgaccccttg aatttgtttt ggtttggcat aggaaaagct actgtatttt tacttccggc   2460
tctaattttt gcggtaaaac tggctaagta ctatcgtcga atggattcgg aggacgtgta   2520
cgatgatgtt gaaactatac ccatgaaaaa tatggaaaat ggtaataatg gttatcataa   2580
agatcatgta tatggtattc acaatcctgt tatgacaagc ccatcacaac attgatagct   2640
gatgttgaaa ctgcttgagc atcaggatac tcaaagtgga aaggatcaca gatttttggt   2700
agtttctggg tctacaagga ctttccaaat ccaggagcaa cgccagtggc aacgtagtga   2760
ctcaggcggg caccaaggca acggcaccat tggtctctgg gtagtgcttt aagaatgaac   2820
acaatcacgt tatagtccat ggtccatcac tattcaagga tgactccctc ccttcctgtc   2880
tatttttgtt ttttactttt ttacactgag tttctattta gacactacaa catatggggt   2940
gtttgttccc attggatgca tttctatcaa aactctatca aatgtgatgg ctagattcta   3000
acatattgcc atgtgtggag tgtgctgaac acacaccagt ttacaggaaa gatgcatttt   3060
gtgtacagta aacggtgtat atacctttttg ttaccacaga gtttttttaaa caaatgagta   3120
ttataggact ttcttctaaa tgagctaaat aagtcaccat tgacttcttg gtgctgttga   3180
```

-continued

```
aaataatcca ttttcactaa aagtgtgtga aacctacagc atattcttca cgcagagatt   3240

ttcatctatt atactttatc aaagattggc catgttccac ttggaaatgg catgcaaaag   3300

ccatcataga gaaacctgcg taactccatc tgacaaattc aaaagagaga gagagatctt   3360

gagagagaaa tgctgttcgt tcaaaagtgg agttgtttta acagatgcca attacggtgt   3420

acagtttaac agagttttct gttgcattag gataaacatt aattggagtg cagctaacat   3480

gagtatcatc agactagtat caagtgttct aaaatgaaat atgagaagat cctgtcacaa   3540

ttcttagatc tggtgtccag catggatgaa acctttgagt ttggtcccta aatttgcatg   3600

aaagcacaag gtaaatattc atttgcttca ggagtttcat gttggatctg tcattatcaa   3660

aagtgatcag caatgaagaa ctggtcggac aaaatttaac gttgatgtaa tggaattcca   3720

gatgtaggca ttccccccag gtcttttcat gtgcagattg cagttctgat tcatttgaat   3780

aaaaaggaac ttgg                                                     3794
```

<210> SEQ ID NO 45
<211> LENGTH: 865
<212> TYPE: PRT
<213> ORGANISM: Homo sapiens

<400> SEQUENCE: 45

```
Met Ala Leu Val Leu Gly Ser Leu Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
        195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
            260                 265                 270
```

-continued

```
Met Asn Ser Thr Leu Lys Ser Leu His Gln Gln Ser Thr Gln Leu Ser
        275                 280                 285

Ser Ser Leu Thr Ser Val Lys Thr Ser Leu Arg Ser Ser Leu Asn Asp
    290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
        355                 360                 365

Asp Arg Val Gln Arg Gln Thr Thr Thr Val Val Ala Gly Ile Lys Arg
    370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Glu Tyr Asp Ser
            420                 425                 430

Tyr Trp Trp Leu Gly Gly Leu Val Ile Cys Ser Leu Leu Thr Leu Ile
        435                 440                 445

Val Ile Phe Tyr Tyr Leu Gly Leu Leu Cys Gly Val Cys Gly Tyr Asp
    450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
            500                 505                 510

Lys Leu Ile Cys Glu Pro Tyr Thr Ser Lys Glu Leu Phe Arg Val Leu
        515                 520                 525

Asp Thr Pro Tyr Leu Leu Asn Glu Asp Trp Glu Tyr Tyr Leu Ser Gly
    530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
        595                 600                 605

Leu Leu Gly Ala Ala Gly Arg Lys Asn Leu Gln Asp Phe Ala Ala Cys
    610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
            660                 665                 670

Asp Ala Gln Thr Ile Lys Thr Ile His Gln Gln Arg Val Leu Pro Ile
        675                 680                 685

Glu Gln Ser Leu Ser Thr Leu Tyr Gln Ser Val Lys Ile Leu Gln Arg
```

-continued

```
    690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
                725                 730                 735

Glu Glu Thr Lys Lys Tyr Gly Arg Thr Ile Ile Gly Tyr Phe Glu His
            740                 745                 750

Tyr Leu Gln Trp Ile Glu Phe Ser Ile Ser Glu Lys Val Ala Ser Cys
        755                 760                 765

Lys Pro Val Ala Thr Ala Leu Asp Thr Ala Val Asp Val Phe Leu Cys
    770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
                805                 810                 815

Lys Tyr Tyr Arg Arg Met Asp Ser Glu Asp Val Tyr Asp Asp Val Glu
            820                 825                 830

Thr Ile Pro Met Lys Asn Met Glu Asn Gly Asn Asn Gly Tyr His Lys
        835                 840                 845

Asp His Val Tyr Gly Ile His Asn Pro Val Met Thr Ser Pro Ser Gln
    850                 855                 860

His
865
```

EARLY DETECTION OF HEMANGIOSARCOMA AND ANGIOSARCOMA

CROSS-REFERENCE TO RELATED APPLICATIONS

The present application is a nonprovisional and claims the benefit of U.S. Ser. No. 60/608,745, filed Sep. 10, 2004, which is incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant Nos. CA46934 and CA86264 awarded by the National Institutes of Health. The Government has certain rights in this invention.

BACKGROUND

Canine hemangiosarcoma (HSA) is an incurable tumor of cells that line blood vessels in dogs. Of the approximately 65 million owned dogs in the United States in 2004, between 1.5 and 2.5 million will get this disease and die from it. The disease accounts for about 7% of all canine cancers. Because the disease is extremely indolent, treatment is largely ineffective and microscopic metastases are often present at the time of diagnosis. The tumors at this stage are largely resistant to chemotherapy, and thus standard-of-care (surgery and intensive chemotherapy) provides a median survival of little more than six months (Clifford, C. A., et al. (2000) J. Vet. Intern. Med. 14:479-485; Sorenmo, K., et al. (2000), J. Vet. Intern. Med. 14:395-398; and Sorenmo, K. U., et al. (1993) J. Vet. Intern. Med. 7:370-376). Common primary sites for HSA are spleen and right atrium (visceral), and subcutis. Local infiltration and systemic metastases are the common growth patterns and metastatic sites are wide spread, with lung and liver being the most frequently affected organs (Oksanen, A. (1978) J. Comp. Pathol. 88:585-595; and Brown, N. O., et al., (1985) J. Am. Vet. Med. Assoc. 186:56-58). Morbidity and mortality are usually due to acute internal hemorrhage secondary to tumor rupture. Many dogs die from severe abdominal or thoracic hemorrhage before any treatment can be instituted. Although dogs of any age and breed are susceptible to HSA, it occurs more commonly in dogs beyond middle age, and in breeds such as Golden Retrievers, German Shepherd Dogs, Portuguese Water Dogs, and Skye Terriers, among others. The estimated lifetime risk of HSA in Golden Retrievers is 1 in 5, illustrating the magnitude of this problem.

There is presently no effective technology for early diagnosis of HSA. The only means available to diagnose the disease (for cavitary tumors such as those that occur in the spleen or heart) are imaging methods such as ultrasound and radiographs. Ultrasound, however, although moderately specific is not sensitive. Radiographs are neither specific nor sensitive. Careful examination of blood smears may suggest the presence of chronic hemorrhage (anemia and thrombocytopenia) and vascular abnormalities (red blood cell fragmentation) that are consistent with HSA; however, the method is neither sensitive or specific to confirm the diagnosis. A biopsy is required for confirmation of imaging results, and even then, distinction between hemangiosarcoma and benign proliferative lesions (hemangioma, hematoma) can be difficult. Skin biopsies where there is no lesion would be of little use to provide early diagnosis for cutaneous hemangiosarcoma. The same is true for splenic, hepatic (liver), or cardiac (heart) tumors, with the added issue that the risk of these procedures in the absence of a visible tumor (on radiographs or ultrasound) is unacceptable.

Human angiosarcomas are similar to canine HSA (see, e.g., Fosmire, S. P., et al (2004) Laboratory Investigation 84:562-572). These tumors are uncommon soft tissue sarcomas that can arise in a variety of locations, such as the liver, spleen, skin breast and endocrine organs (see, e.g., Fedok, F. G., et al. (1999) Am J. Otolaryngol. 20:223-231; Hai, S. A., et al., (2000) J. Natl. Med. Assoc. 92:143-146; and Budd, G. T. (2002) Curr. Oncol. Rep. 4:515-519). Like canine HSA, treatment of human angiosarcomas can be challenging and often is not successful.

Given the severity of canine HSA and human angiosarcomas coupled with the lack of effective treatment options once the tumor has metastasized, it would be useful to have a method for early detection of these two diseases. Early detection would allow for treatment options having a higher chance of successfully treating the tumor.

SUMMARY OF THE CLAIMED INVENTION

The invention provides methods for early detection of hemangiosarcoma or angiosarcoma in a subject. The method comprises providing a population of cells from the subject and determining the level at which cells within the cell population concurrently express a plurality of cell markers, and the plurality of cell markers comprising at least one primitive hematopoietic cell marker and at least one endothelial cell marker. Such methods determine whether or not cells within the cell population express at least one leukemia cell marker or leukocyte-specific cell marker. In such methods, at least one primitive hematopoietic cell marker is selected from the group consisting of CD117, CD34, and CD133. At least one endothelial cell marker is selected from the group consisting of CD51/CD61, CD31, CD105, CD106 CD146 and von Willebrand Factor (vWF). At least one leukemia cell marker or leukocyte-specific cell marker is selected from the group consisting of CD18, CD3, CD5, CD21 and CD11b. The level at which cells in the cell population concurrently express the plurality of cell markers is compared with a control level of concurrent expression of the markers. In such methods an increase in the expression level of the plurality of cell markers relative to the control expression level, and the absence of expression of CD18, CD3, CD5, CD21 and/or CD11b collectively are an indication of hemangiosarcoma or angiosarcoma.

In some methods the determining step comprises incubating the population of cells with labeled antibodies that specifically bind the at least one primitive hematopoietic cell marker, the at least one endothelial cell marker and the at least one leukemia cell marker or leukocyte-specific cell marker under conditions such that cells expressing the markers become labeled. The antibodies that bind different markers are differentially labeled. Multiparameter flow cytometry is used to detect the labeled cells.

In some methods the subject is a dog and the method detects hemangiosarcoma. Dog breeds that may be subjects of the invention are selected from the group consisting of a Golden Retriever, a German Shepherd, a Portuguese Water Dog, or a Skye Terrier.

In some methods the subject is a human and the method detects angiosarcoma.

Humans screened using the methods of the invention include individuals having a risk factor for angiosarcoma, the risk factor being prior exposure to vinyl chloride, prior exposure to ionizing radiation, mutation in the Von Hippel-Lindau gene or infection with human immunodeficiency virus (HIV).

Populations of cells used in methods of the invention can be obtained from a blood samples.

Some methods of the invention comprise determining the level at which cells in the population of cells concurrently express at least one primitive hematopoietic cell marker selected from the group consisting of CD117, CD133 and CD34.

Some methods of the invention comprise determining the level at which cells in the population concurrently express at least one leukemia cell marker or leukocyte-specific cell marker selected from the group consisting of CD18, CD3, CD5, CD21 and CD11b.

Some methods of the invention comprise determining the level at which cells in the population concurrently express CD117, CD34, CD51/CD61, and CD18, and/or CD3, CD5, CD21 or CD11b.

Some methods of the invention further comprise determining the fraction of cells in the cell population that concurrently express the plurality of cell markers. The control is a threshold level representative of the fraction of cells that currently express the plurality of cell markers in a control population. The comparing step comprises comparing the fraction of cells in the cell population that concurrently express the plurality of cell markers with the threshold level.

In some methods of the invention, the expression level of the plurality of cell markers is determined at the mRNA level or at the protein level.

Some methods of invention detect hemangiosarcoma in dogs. A population of cells is obtained from a blood sample. The determining step further comprises incubating the population of cells with differentially labeled antibodies that specifically bind to CD117, CD34, CD51/61, and CD 18 and/or CD3, CD5, CD21 or CD11b under conditions such that cells expressing CD117, CD34, CD51/61, and CD 18 and/or CD3, CD5, CD21 or CD11b become labeled. The labeled cells are detected by multiparameter flow cytometry.

The invention provides methods for early detection of hemangiosarcoma or angiosarcoma. A population of cells is obtained from the subject and the level at which cells within the cell population concurrently express at least one primitive hematopoietic cell marker, at least one endothelial cell marker and at least one leukemia cell marker or leukocyte-specific cell marker are determined. The at least one primitive hematopoietic cell marker is selected from the group consisting of CD117, CD34 and CD133. The at least one endothelial cell marker is selected from the group consisting of CD51/CD61, CD31, CD105, CD106, CD146 and von Willebrand Factor (vWF). The at least one leukemia cell marker or leukocyte-specific cell marker is selected from the group consisting of CD18, CD3, CD5, CD21 and CD11b. The lower the expression of the at least one leukemia marker or leukocyte-specific cell marker and the greater the concurrent expression of the at least one primitive hematopoietic cell marker and the at least one endothelial cell marker, the greater the likelihood of hemangiosarcoma or angiosarcoma. Some methods provide early detection of hemangiosarcoma in dogs; other methods provide early detection of angiosarcoma in humans.

In some methods of the invention, the determining step comprises incubating the population of cells with labeled antibodies that specifically bind the at least one primitive hematopoietic cell marker, the at least one endothelial cell marker and the at least one leukemia cell marker or leukocyte-specific cell marker. The incubations are done under conditions such that cells expressing the markers become labeled. Antibodies that bind different markers are differentially labeled. Labeled cells are detected by multiparameter flow cytometry.

The invention provides methods for distinguishing between hemangiosarcoma and leukemia. Such methods comprise providing a cell population from a subject suspected of having hemangiosarcoma or leukemia and determining whether cells in the cell population concurrently express a plurality of markers associated with a proliferative primitive hematopoietic cell. The plurality of markers comprise at least one primitive hematopoietic cell marker and at least one endothelial cell marker. Whether the cells in the cell population also express also at least one leukemia marker or leukocyte-specific cell marker is also determined. The at least one primitive hematopoietic cell marker is selected from the group consisting of CD117, CD34 and CD133. The at least one endothelial cell marker is selected from the group consisting of CD51/CD61, CD31, CD105, CD146 and von Willebrand Factor (vWF). The at least one leukemia marker or leukocyte-specific cell marker is selected from the group consisting of CD18, CD3, CD5, CD21 and CD11b. The concurrent expression of the plurality of cell makers and the expression of the at least one leukemia marker or leukocyte-specific cell marker is an indication that the cell sample contains leukemia cells, whereas the concurrent expression of the plurality of cell markers but not expression of the at least one leukemia marker or leukocyte-specific cell marker is an indication that the cell population contains cells from a hemangiosarcoma.

The invention provides methods of treating a dog having or suspected of having hemangiosarcoma. The method comprises administering an antibody to the dog, wherein the antibody specifically binds CD51/CD61, CD31, or CD105. In some methods, the antibody is linked to a cytotoxic agent.

Some methods of the invention are directed to treating a dog having or suspected of having hemangiosarcoma, the method comprising administering an antibody to the dog. The antibody is a bispecific antibody that can specifically bind a pair of antigens. The pair of antigens is selected from the group consisting of 1) CD34 AND CD51/CD61, 2) CD117 AND CD51/CD61, 3) CD34 AND CD31, 4) CD117 AND CD31, 5) CD34 AND CD105, and 6) CD117 AND CD105.

The invention provides methods of collecting cells from a hemangiosarcoma or an angiosarcoma. The methods comprise providing a cell population suspected of containing cells from a hemangiosarcoma or angiosarcoma, and labeling cells in the cell population that concurrently express at least one primitive hematopoietic cell marker and at least one endothelial cell marker. The at least one primitive hematopoietic cell marker is selected from the group consisting of CD117, CD34 and CD133. The at least one endothelial cell marker is selected from the group consisting of CD51/CD61, CD31, CD105, CD106, CD146 and von Willebrand Factor (vWF). The methods further determine whether or not the cells in the cell population express at least one leukemia cell marker or leukocyte-specific cell marker. The at least one leukemia cell marker or leukocyte-specific cell marker is selected from the group consisting of CD18, CD3, CD5, CD21 and CD11b. The labeled cells are separated from the unlabeled cells if the labeled cells do not express the at least one leukemia cell marker or leukocyte-specific cell marker, thereby collecting cells that are from a hemangiosarcoma or an angiosarcoma.

The invention provides populations of cells comprising early proliferative endothelial cells that are bound to a plurality of labeled antibodies. The plurality of antibodies comprise an antibody that specifically binds a primitive hematopoietic cell marker, selected from the group consisting of CD117, CD34 and CD133, and an antibody that specifically binds an endothelial cell marker, selected from the group consisting of CD51/CD61, CD31, CD105, CD106 and CD146.

The invention provides methods to detect residual disease in a subject undergoing treatment for hemangiosarcoma or angiosarcoma. The methods comprise providing a population of cells from the subject, and determining (i) the level at which cells within the cell population concurrently express a plurality of cell markers, the plurality of cell markers comprising at least one primitive hematopoietic cell marker and at least one endothelial cell marker, and (ii) whether cells within the cell population express at least one leukemia cell marker or leukocyte-specific cell marker. The at least one primitive hematopoietic cell marker is selected from the group consisting of CD117, CD34, CD133. The at least one endothelial cell marker is selected from the group consisting of CD51/CD61, CD31, CD105, CD106 CD146 and von Willebrand Factor (vWF). The at least one leukemia cell marker or leukocyte-specific cell marker is selected from the group consisting of CD18, CD3, CD5, CD21 and CD11b. The methods compare the level at which cells in the cell population concurrently express the plurality of cell markers with the level of concurrent expression of the markers in a control cell population. An increase in the expression level of the plurality of cell markers relative to the expression level of the markers in the control cell population and an absence of expression of CD18, CD3, CD5, CD21 or CD11b are collectively an indication of residual disease in the subject being treated for hemangiosarcoma or angiosarcoma.

In some methods to detect residual disease in a subject undergoing treatment for hemangiosarcoma or angiosarcoma the subject is a dog and the residual disease is hemangiosarcoma. In other methods, the subject is a human and the residual disease is hemangiosarcoma. Some methods comprise incubating the population of cells with first, second and third antibodies that specifically bind the at least one primitive hematopoietic cell marker, the at least one endothelial cell marker, and the at least one leukemia cell marker or leukocyte-specific cell marker respectively under conditions such that antibodies bind to the markers. The first, second and third antibodies bound to the markers are differentially labeled. Cells bound with labeled antibodies are detected by multiparameter flow cytometry.

Antibodies used in the methods of the invention can be labeled using a secondary detection scheme to increase sensitivity of the methods.

The invention provides kits for use in distinguishing between hemangiosarcoma and leukemia. The kits comprise a plurality of antibodies. The antibodies comprise: an antibody that specifically binds a primitive hematopoietic cell marker that is selected from the group consisting of CD117, CD34 and CD133; an antibody that specifically binds an endothelial cell marker that is selected from the group consisting of CD51/CD61, CD31, CD105, CD106, and CD146; and an antibody that specifically binds to a leukemia cell marker or leukocyte-specific cell marker that is selected from the group consisting of CD18, CD3, CD5, CD21 and CD11b.

In some kits of the invention, the antibodies are labeled such that antibodies that bind different markers bear different labels.

Some kits of the invention comprise an antibody that specifically binds CD117, an antibody that specifically binds CD34, an antibody that specifically binds CD51/61, and an antibody that specifically binds CD18, and an antibody that specifically binds CD3, CD5, CD21 or CD11b. Other kits of the invention comprise an antibody that specifically binds CD117, an antibody that specifically binds CD34, an antibody that specifically binds CD51/61, an antibody that specifically binds CD18, or an antibody that specifically binds CD3, CD5, CD21 or CD11b.

Some kits of the invention further comprise instructions on how to use the plurality of antibodies to distinguish between a hemangiosarcoma and leukemia.

BRIEF DESCRIPTION OF THE DRAWINGS

FIG. 1A shows the light scatter profile for nucleated cells (white blood cells, tumor cells) in the peripheral blood from a dog with a thoracic hemangiosarcoma. The gate drawn around the cells is used to exclude red blood cells, platelets, and cellular debris, while including all white blood cells (granulocytes, lymphocytes, monocytes) and other nucleated cells that may be present in the circulation (e.g., tumor cells). FIG. 1B depicts the fluorescence emission for the same cells "stained" with isotype control (irrelevant) antibodies conjugated to phycoerythrin (PE control) and fluorescein (FITC control). FIG. 1C also shows the light scatter profile for cells (white blood cells, tumor cells) in the peripheral blood from the same dog. FIG. 1D shows the fluorescence emission for the same cells "stained" with an antibody against CD51/CD61 conjugated to FITC (x-axis) and an antibody against CD117 conjugated to PE (y-axis). FIG. 1E shows the light scatter profile for nucleated cells where a gate is drawn around the area that should contain the leukocytes and FIG. 1F shows the fluorescence emission for this leukocyte population specifically (CD117 vs. CD51/61). FIG. 1G shows the light scatter profile for where a gate is drawn around the area that would contain large abnormal cells (such as tumor cells) and FIG. 1H depicts the fluorescence emission for this population specifically (CD117 vs. CD51/61).

FIGS. 5A-5F show multiparameter flow cytometry data from a dog with splenic hematoma (FIGS. 5A-5C) in comparison with a dog with hemangiosarcoma (FIGS. 5D-5F). Cells positive for CD133 and $\alpha_v\beta_3$ integrin were back-gated to two-dimensional light scatter histograms, and the percentage of positive cells that partitioned to regions encompassing the defined gate for HSA cells was determined.

DETAILED DESCRIPTION

I. Definitions

Figure 1B:
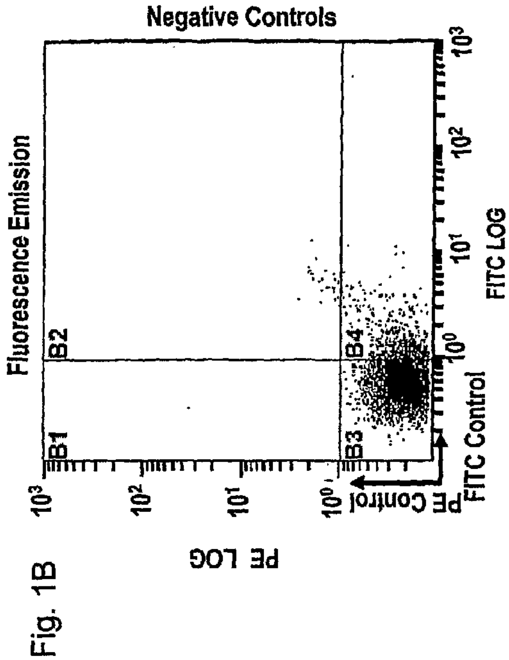
FIGS. 1A-1H illustrate that the light scatter (FIGS. 1A, 1C, 1E and 1G) and fluorescence emission (FIGS. 1B, 1D, 1F and 1H) characteristics of leukocytes and hemangiosarcoma cells are distinct and can be used to distinguish between the two sets of cells. The light scatter plots show forward scatter on the x-axis and side scatter on the y-axis. The fluorescence emission results are for the markers CD51/61 (x-axis) and CD117 (y-axis).
Figure 1D:
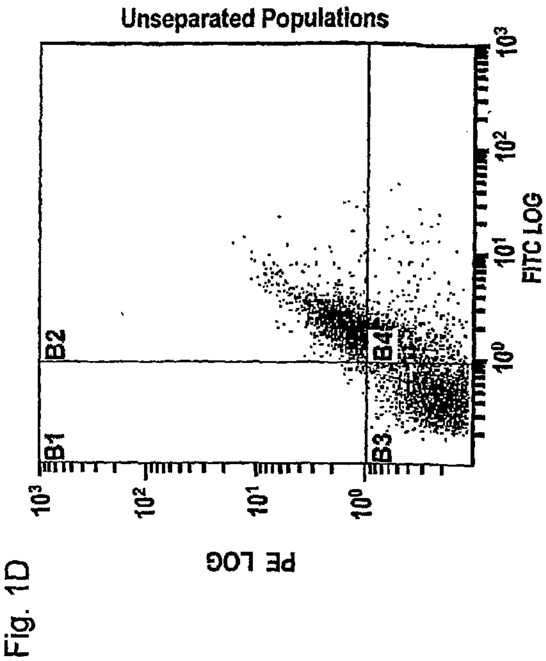
Figure 1A:
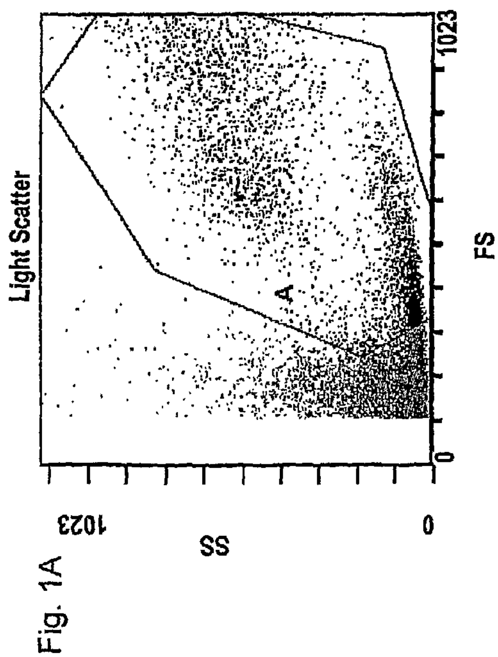
Figure 1C:
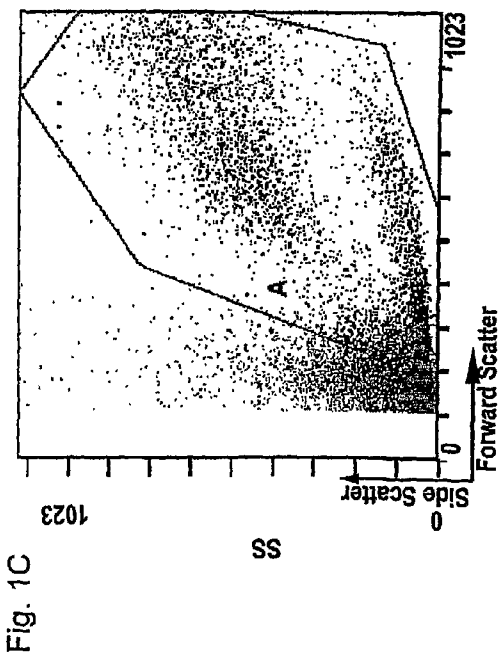
Figures 1E, 1F, 1G, 1H:
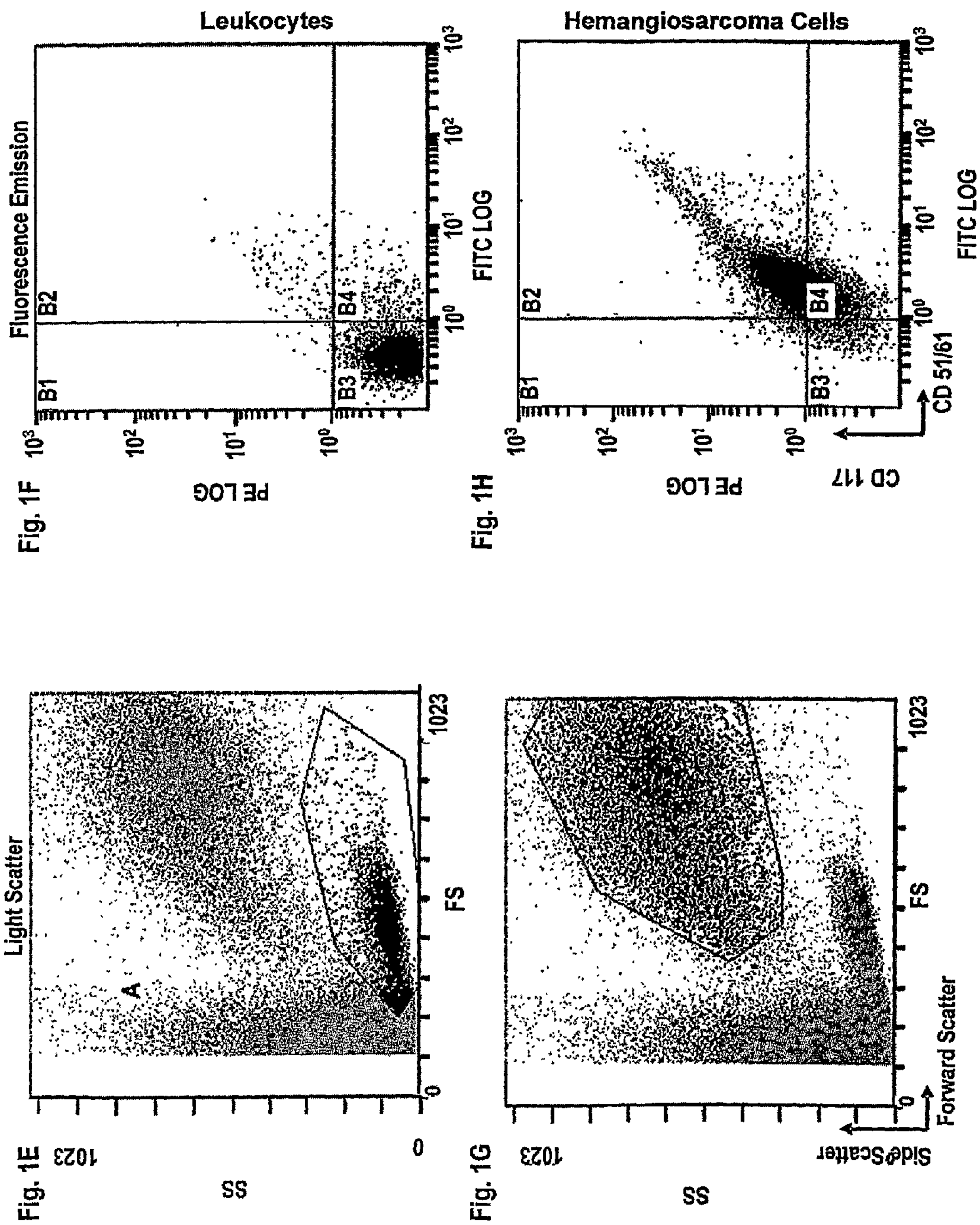
Figures 2A, 2B, 2C, 2D:
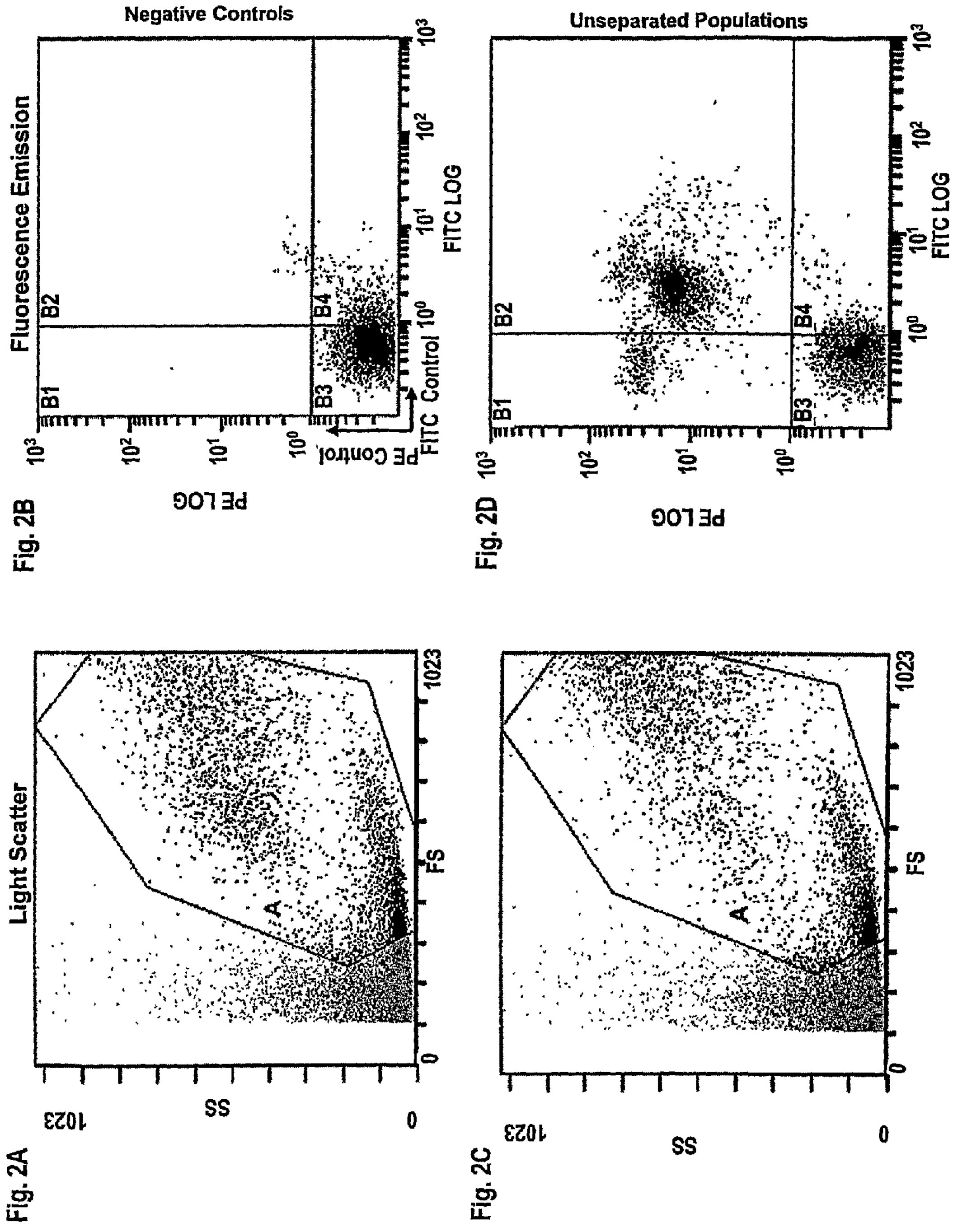
FIGS. 2A-2H shows the difference in CD45 expression in conjunction with expression of CD51/CD61 in the same populations (from the same patient) as in FIGS. 2A-2H.
Figure 2F:
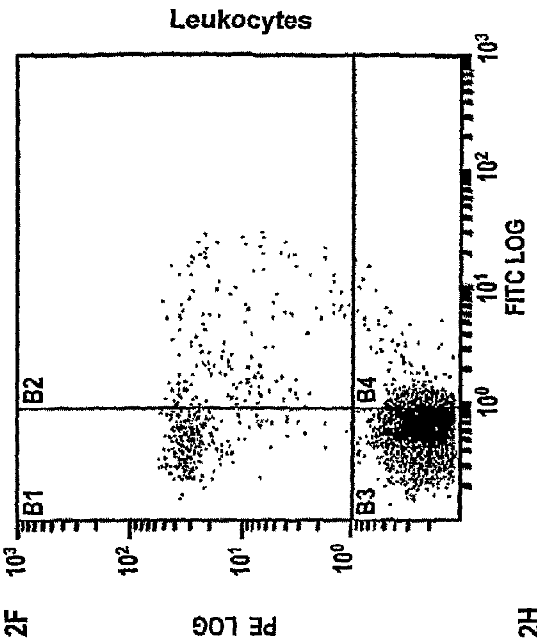
Figure 2H:
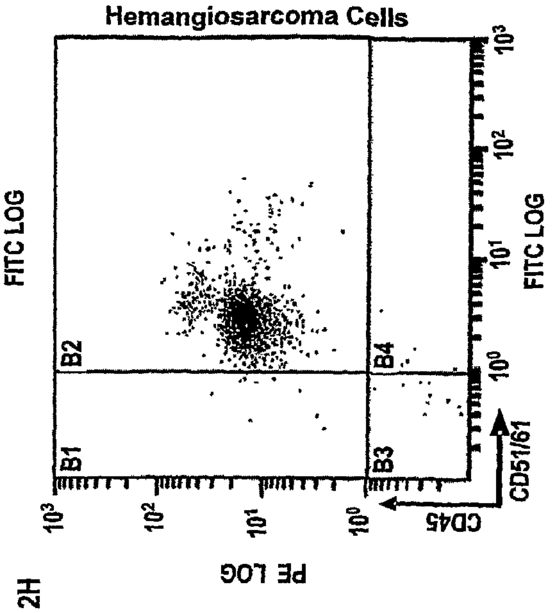
Figure 2E:
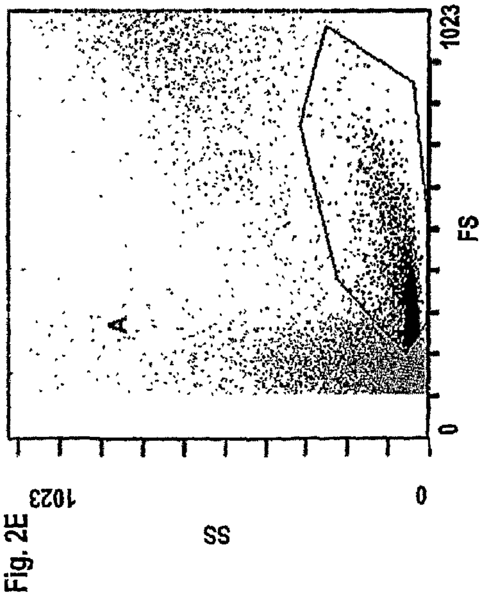
Figure 2G:
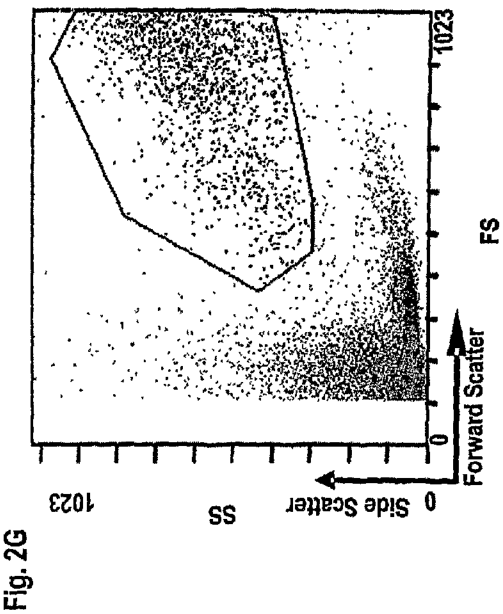
Figure 3A:
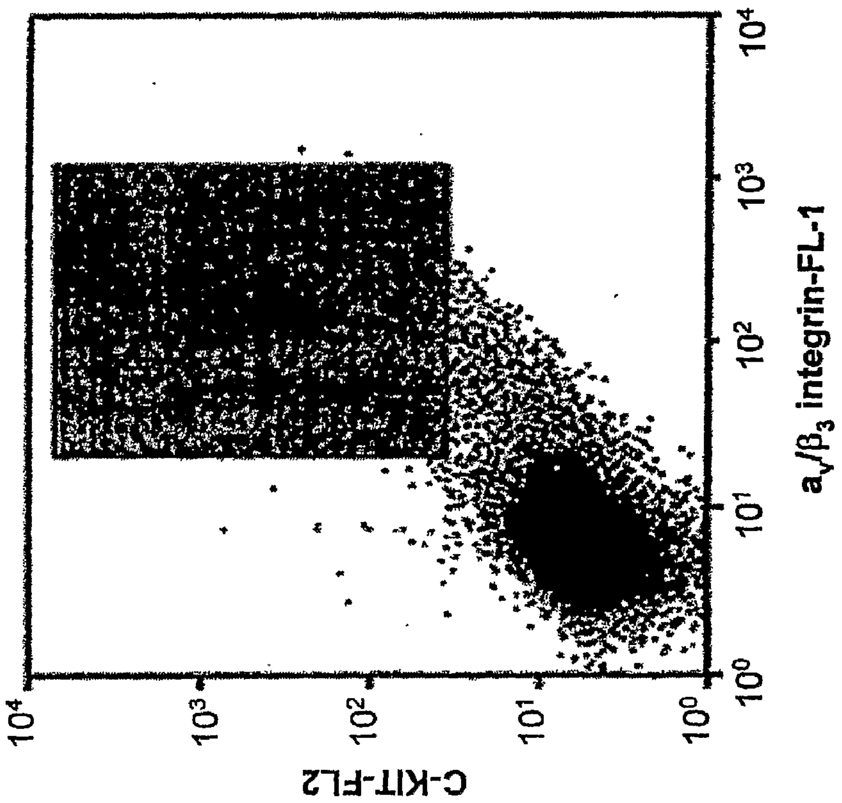
FIGS. 3A and 3B show 2-dimensional flow histograms from a multiparameter flow cytometry assay of anticoagulated peripheral blood from a canine patient using multiple fluorochromes. One fluorochrome is bound to antibodies recognizing c-KIT and $\alpha_v/\beta_3$ integrin to detect HSA cells in the sample, (FIG. 3A), a second flurochrome is bound to antibodies recognizing CD11b on granulocytes in the sample (FIG. 3B).
Figure 3B:
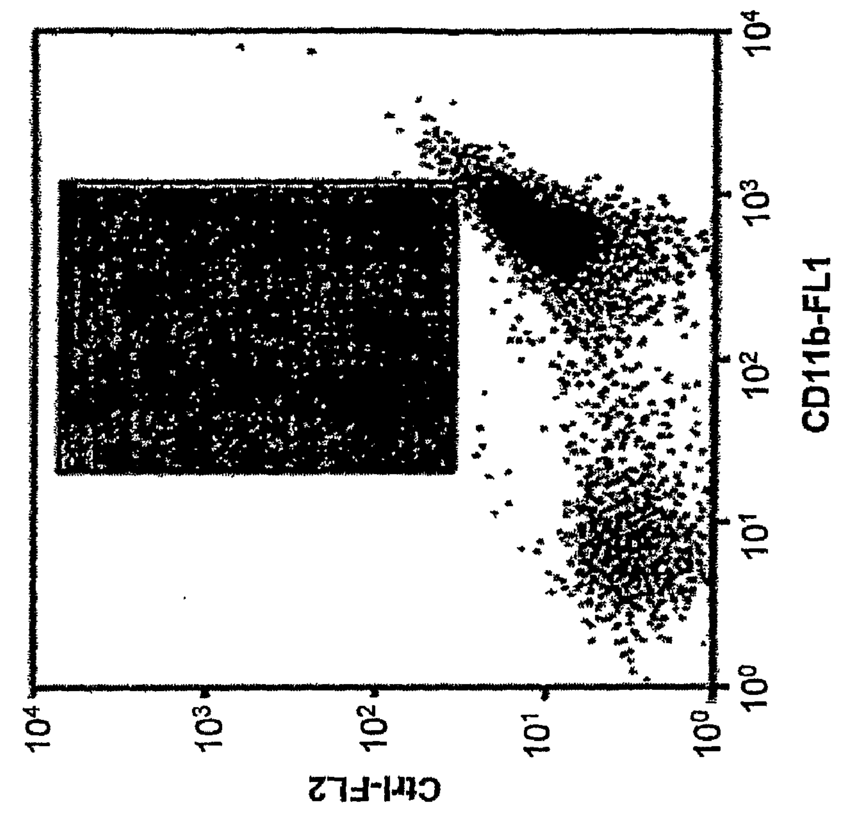

As used in this specification and the appended claims, the singular forms "a," "an" and "the" include plural references unless the content clearly dictates otherwise.

Unless defined otherwise, all technical and scientific terms used herein have the meaning commonly understood by a person skilled in the art to which this invention belongs. The following references provide one of skill with a general definition of many of the terms used in this invention: Stedman, T. L., STEDMAN'S MEDICAL DICTIONARY (26th ed., 1995); Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991).

The term "hemangiosarcoma" has its normal meaning in the art and refers generally to malignant neoplasms that are characterized by rapidly proliferating, extensively infiltrating, anaplastic cells derived from blood vessels and lining irregular blood-filled or lumpy spaces. Canine hemangiosarcoma (HSA), for example, arises from transformed vascular endothelial cells, most commonly in the spleen, right atrium or subcutis. Growth patterns are characterized by local infiltration and systemic metastases, with metastatic sites tending to be widespread. The lung and liver are the most frequently affected organs.

"Angiosarcoma" as used herein has its normal meaning in the art and refers generally to malignant neoplasms occurring most often in the liver, spleen, skin, breast and endocrine organs. These soft tissue sarcomas are believed to originate from the endothelial cells of blood vessels. Microscopically, the tumors are characterized by closely packed round or spindle-shaped cells, some of which line small spaces resembling vascular clefts.

The term "leukemia" has its normal meaning in the art and generally refers to a disease involving the progressive proliferation of abnormal leukocytes found in hematopoietic tissues, other organs, and usually in the blood in increased numbers. Symptoms of the disease typically include severe anemia, hemorrhages, and enlargement of lymph nodes or the spleen.

Lymphoma" as used herein refers generally to cancers that develop in the lymphatic system. In humans, one specific type of lymphoma is called Hodgkin's disease, which can be endemic (caused by Epstein Barr virus-dependent transformation of B lymphocytes) or sporadic (not associated with Epstein Barr virus infection), and is characterized by the presence of Reed Sternberg cells. All other lymphomas are grouped together and are called non-Hodgkin's lymphomas.

A "marker" as used herein refers generally to a protein or its corresponding transcript whose expression, or lack thereof, is characteristic of a particular type of cell or group of cells (e.g., endothelial cells) and/or cellular state (e.g., proliferating or non-proliferating). Some markers are cell-surface proteins whose expression can be detected using antibodies that specifically bind to the cell-surface protein. Specific examples of markers referred to herein include, but are not limited to CD117, CD34, CD51/61, CD18, CD45, CD31, CD105, CD106 and CD146. The "markers" referred to herein can include markers from various species (e.g., human and dog).

An "expression profile," as used herein, refers to a pattern of gene (e.g., marker) expression (e.g., pattern of expression of markers) that is associated with a particular type of cell and/or cellular state. The pattern can include genes (e.g., markers) that are expressed and/or that are not expressed. For instance, an expression profile may include the pattern of genes (e.g., markers) that are expressed and/or not expressed by primitive hematopoietic cells, primitive hematopoietic cells that are malignant (e.g., hemangiosarcoma, angiosarcoma or leukemia), or primitive hematopoietic cells that are malignant, but are distinct from leukemia (e.g., hemangiosarcoma, angiosarcoma). A profile can include the expression of as few as a single gene (marker), but more typically includes the concurrent expression of multiple genes (markers). The expression profile obtained for a particular cell or cellular state can be useful for a variety of applications, including diagnosis of a particular disease or condition and evaluation of various treatment regimes. Expression of genes (markers) that make up the expression profile can be determined at the transcript or protein level.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include post-translational modifications of the polypeptide, for example, glycosylations, acetylations, phosphorylations and the like.

As used herein, references to specific polypeptides (e.g., cell markers such as CD117, CD34, CD51/61, CD18, CD45, CD31, CD105 and CD146) refer to a polypeptide having a native amino acid sequence, as well naturally occurring variant forms (e.g., alternatively spliced forms), naturally occurring allelic variants and forms including postranslational modifications. As noted above, the specific protein markers referred to herein include the protein as expressed in various mammals, including humans and dogs.

"CD117" is the receptor for stem cell factor (SCF) and is thus sometimes referred to as the stem cell factor receptor (SCFR). It is also sometimes referred to in the literature as (c-Kit). An exemplary amino acid sequence from dog is provided in GenBank Accession No. NP_001003181 (SEQ ID NO: 2), which is encoded by the nucleic acid having the sequence of SEQ ID NO:1 (GenBank Accession No. AF044249). An exemplary amino acid sequence from human is provided in GenBank Accession No. AAC50968 (SEQ ID NO:4), which is encoded by the nucleic acid having the sequence of SEQ ID NO:3 (GenBank Accession No. NM_00022).

"CD34" is sometimes referred to as the ligand for CD62 or the ligand for L-selectin. CD34 is a protein expressed on early lymphohematopoietic stem and progenitor cells, small-vessel endothelial cells, embryonic fibroblasts, and some cells in fetal and adult nervous tissue. It is also expressed on hematopoietic progenitors derived from fetal yolk sac, embryonic liver, and extra-hepatic embryonic tissues. An exemplary amino acid sequence from dog is provided in GenBank Accession No. AAB41055 (SEQ ID NO:6), which is encoded by the nucleic acid having the sequence of SEQ ID NO:5 (GenBank Accession No. U49457). An exemplary amino acid sequence from human is provided in GenBank Accession No. NP_001764.1 (SEQ ID NO:8), which is encoded by the nucleic acid having the sequence of SEQ ID NO:7 (GenBank Accession No. NM_001773).

"CD133" is also sometimes referred to in the art as prominin 1, hProminin, and hematopoietic stem cell antigen. CD133 antigen is a 120 kDa five transmembrane domain glycoprotein (5-TM) expressed on primitive cell populations, such as CD34 bright hematopoietic stem and progenitor cells, neural and endothelial stem cells, and other primitive cells such as retina and retinoblastoma and developing epithelium. The CD133 gene codes for a pentaspan transmembrane glycoprotein and appears to belong to a molecular family of 5-TM proteins. This "family" includes members from several different species (which may be homologs) including human, mouse, rat, fly, and worm. The 5-transmembrane domain structure includes an extracellular N-terminus, two short intracellular loops, two large extracellular loops and an intracellular C-terminus. CD133 is expressed on primitive hematopoietic stem and progenitor cells and retinoblastoma, as well as on hemangioblasts, neural stem cells, and developing epithelium. Many leukemias express CD133 as well as CD34, but some leukemic blasts are CD133+ and CD34 negative. A predicted partial nucleic acid sequence for dog CD133 corresponds to position 50894 to position 51101 of GenBank Accession No. AAEX01026434.1 (SEQ ID NO:43). An exemplary amino acid sequence from human is provided in GenBank Accession No. NP_006008 (SEQ ID NO:45), which is encoded by the nucleic acid having the sequence of SEQ ID NO:44 (GenBank Accession No. NM_006017).

"CD51/CD61" is also sometimes referred to in the art as alpha$_v$beta$_3$ ($\alpha_v\beta_3$) integrin, the vitronectin receptor, or glycoprotein IIIa. A predicted partial nucleic acid sequence for dog CD51 corresponds to position 65528 to position 67792 from GenBank AAEX01022275.1, (SEQ ID NO:9). An exemplary amino acid sequence for dog CD61 is provided in GenBank Accession No. AAD49737.1 (CD61, beta-3, GP IIIa) (SEQ ID NO:13), which is encoded by the nucleic acid having the sequence of SEQ ID NO:12 (GenBank Accession No. AF170525 (beta-3)).

An exemplary amino acid sequence for human CD51 is provided in GenBank Accession No. NP_002201.1 (alpha-v) (SEQ ID NO:11), which is encoded by the nucleic acid having the sequence of SEQ ID NO:10 (GenBank Accession No. NM_002210). An exemplary amino acid sequence for human CD61 is provided by GenBank Accession No. NP_000203.2 (beta-3) (SEQ ID NO:15), which is encoded by the nucleic having the sequence of SEQ ID NO:14 (GenBank Accession No. NM_000212 (beta-3, GP IIIa)).

"CD31", also known as glycoprotein IIa (GPIIa), endocam, or platelet endothelial cell adhesion molecule (PECAM-1), refers to a cell adhesion protein that is highly expressed on endothelial cells and often concentrated at the junctions between them. CD31 also is present on virtually all monocytes, platelets, and granulocytes. A predicted partial nucleic acid sequence for dog CD31 corresponds to position 77862 to position 77586 of the minus strand of sequence from chromosome 9 (GenBank AAEX01022173.1) (SEQ ID NO:16). An exemplary amino acid sequence from human is provided in GenBank Accession No. AAH22512 (SEQ ID NO:18), which is encoded by the nucleic acid having the sequence of SEQ ID NO:17 (GenBank Accession No. BC022512).

"CD105," also sometimes referred to in the art as "endoglin," is a cell-surface glycoprotein that is over-expressed on vascular endothelium, particularly in angiogenic tissues. A predicted partial nucleic acid sequence for dog CD105 corresponds to positions 17214 to position 17370 of GenBank AAEX01025446.1 (SEQ ID NO:19). An exemplary amino acid sequence from human is provided in GenBank Accession No. NP_000109.1 (SEQ ID NO:21), which is encoded by the nucleic acid having the sequence of SEQ ID NO:20 (GenBank Accession No. NM_000118).

"CD106" is also referred to in the art as VCAM-1 because it is a vascular cell adhesion molecule. It is a member of the immunoglobulin superfamily, C2 subset. This protein is thought to be induced on human endothelial cells by TNF-alpha, IL-1, IFN-gamma or endotoxins. A predicted partial nucleic acid sequence for dog CD106 corresponds to position 134174 to position 135113 of AAEX01044853.1 (SEQ ID NO:22). An exemplary amino acid sequence from human is provided in GenBank Accession No. NP_001069 (SEQ ID NO:24), which is encoded by the nucleic acid having the sequence of SEQ ID NO:23 (GenBank Accession No. NM_001078).

"CD146," sometimes also referred to as A32, MCAM, Mel-CAM, MUC18, and S-Endo-1) is a cell-cell adhesion receptor that mediates calcium-independent homotypica endothelial cell adhesion. It is a cell-surface glycoprotein that belongs to the immunoglobulin super-gene family. A predicted partial nucleic acid sequence for dog CD146 corresponds to position 3260 to position 3439 of the sequence from chromosome 5 (GenBank AAEX01009397.1) (SEQ ID NO:25). An exemplary amino acid sequence from human is provided in GenBank Accession No. CAA48332.1 (SEQ ID NO:27), which is encoded by the nucleic acid having the sequence of SEQ ID NO:26 (GenBank Accession No. AF089868).

"CD3" is a 20 kD non-glycosylated transmembrane protein expressed by T cells.

"CD5" is a leukocyte-specific cell marker found on B1 and T cells.

"CD11b" (GenBank Accession No. NM000362) is also referred to as Mac 1$\alpha$ and integrin $\alpha_M$ chain, a member of the alpha integrin family. Canine CD11b is expressed by granulocytes, monocytes and some macrophages.

"CD21" is a component of the B-cell Receptor complex. It is a B cell specific marker.

"CD14" is part of the LPS receptor complex that further comprises TLR4 and MD-2. CD-14 is expressed mainly on monocytes and tissue macrophages in peripheral blood.

"CD18" is also referred to as $\beta$-2 integrin. CD18 is a cell-surface glycoprotein containing beta-chains that can be non-covalently linked to specific alpha-chains of the CD11 family of leukocyte-adhesion molecules (receptors, leukocyte-adhesion). An exemplary amino acid sequence from dog is provided in GenBank Accession No. AAD56947 (SEQ ID NO:33), which is encoded by the nucleic acid having the sequence of SEQ ID NO:32 (GenBank Accession No. AF181965). An exemplary amino acid sequence from human is provided in GenBank Accession No. AAH05861.1 (SEQ ID NO:35), which is encoded by the nucleic acid having the sequence of SEQ ID NO:34 (GenBank Accession No. BC005861).

"CD45" is a common leukocyte antigen and is a high-molecular weight glycoprotein expressed on the surface of all leukocytes and their hemopoietic progenitors. The CD45 family consists of multiple members that are all products of a single gene. Predicted partial nucleic acid sequences for dog CD45 are provided in SEQ ID NOS:36-40 (partial sequences from AAEX01013304.1. An exemplary amino acid sequence from human is provided in GenBank Accession No. NP_002829 (SEQ ID NO:42), which is encoded by the nucleic acid having the sequence of SEQ ID NO:41 (GenBank Accession No. Y00638).

"vWF" is an abbreviation for von Willebrand factor, also called Factor VIII-related antigen (F VIII-ra). vWF is a clotting protein present in the blood that is produced in the cells that line blood vessels and then is released into the blood stream. vWF has two functions: 1) bind and stabilize factor VIII, and 2) bind to platelets and enable them to function normally in making a platelet plug and clot. An exemplary amino acid sequence from dog is provided in GenBank Accession No. AAB93766.2 (SEQ ID NO:29), which is encoded by the nucleic acid having the sequence of SEQ ID NO:28 (GenBank Accession No. U66246). An exemplary amino acid sequence from human is provided in GenBank Accession No. NP_000543 (SEQ ID NO:31), which is encoded by the nucleic acid having the sequence of SEQ ID NO:30 (GenBank Accession No. AH005287).

The term "antibody" as used herein includes, but is not limited to, antibodies obtained from both polyclonal and monoclonal preparations, as well as the following: (i) chimeric antibody molecules (see, for example, Winter et al. (1991) *Nature* 349:293-299; and U.S. Pat. No. 4,816,567); (ii) F(ab')2 and F(ab) fragments; (iii) Fv molecules (noncovalent heterodimers, see, for example, Inbar et al. (1972) Proc. Natl. Acad. Sci. USA 69:2659-2662; and Ehrlich et al. (1980) Biochem 19:4091-4096); (iv) single-chain Fv molecules (sFv) (see, for example, Huston et al. (1988) Proc. Natl. Acad. Sci. USA 85:5879-5883); (v) dimeric and trimeric antibody fragment constructs; (vi) humanized antibody molecules (see, for example, Riechmann et al. (1988) Nature 332:323-327; Verhoeyan et al. (1988) Science 239:1534-1536; and U.K. Patent Publication No. GB 2,276,169, published 21 Sep. 1994); (vii) Mini-antibodies or minibodies (i.e., sFv polypeptide chains that include oligomerization domains at their C-termini, separated from the sFv by a hinge region; see, e.g., Pack et al. (1992) Biochem 31:1579-1584; Cumber et al. (1992) J. Immunology 149B:120-126); and, (vii) any functional fragments obtained from such molecules, wherein such fragments retain specific-binding properties of the parent antibody molecule.

The phrases "specifically binds" when referring to a protein, "specifically immunologically cross reactive with," or simply "specifically immunoreactive with" when referring to an antibody, refers to a binding reaction which is determinative of the presence of the protein in the presence of a heterogeneous population of proteins and other biologics. Thus, under designated conditions, a specified ligand binds preferentially to a particular protein and does not bind in a significant amount to other proteins present in the sample. A molecule or ligand (e.g., an antibody) that specifically binds to a protein has an association constant of at least $10^3$ $M^{-1}$ or $10^4$ $M^{-1}$, sometimes $10^5$ $M^{-1}$ or $10^6$ $M^{-1}$, in other instances $10^6$ $M^{-1}$ or $10^7$ $M^{-1}$, preferably $10^8$ $M^{-1}$ to $10^9$ $M^{-1}$, and more preferably, about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and conditions that can be used to determine specific immunoreactivity.

The term "label" refers generally to an agent that can be detected by some means (e.g., chemical, physical, electromagnetic or other analytical means). Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

A "subject" can be a mammal, including primates, non-human primates (e.g., monkey, ape, chimpanzee) and mammals other than primates (e.g., cat, dog, rat, mouse). Most typically the subject is a human or a dog.

A difference is typically considered to be "statistically significant" in general terms if an observed value differs by more than the level of experimental error. A difference, for example, can be "statistically significant" if the probability of the observed difference occurring by chance (the p-value) is less than some predetermined level. As used herein a "statistically significant difference" refers to a p-value that is <0.05, preferably <0.01 and most preferably <0.001.

A "control value" or simply "control" generally refers to a value (or range of values), such as expression levels, against which an experimental or determined value is compared. As used herein, the term typically refers to a measure of expression of one or more markers in a sample from a particular individual or population of individuals. For instance, the term can refer to the concentration of cells expressing one or more markers (e.g., the concentration of cells having a particular expression profile) in a sample. In the case of methods in which the risk of hemangiosarcoma or angiosarcoma is being evaluated, the control is typically the concentration or frequency of cells from the same tissue or body fluid as those under test having a particular expression profile as determined for an individual or population of individuals at low-risk for the disease and/or that has no discernible evidence of the disease (e.g., no detectable clinical manifestations). The control can also be the test sample analyzed with an irrelevant antibody or probe or primer instead of an antibody, probe or primer to a desired marker. If the signal from the antibody, probe or primer to the desired marker is not higher than that of the irrelevant control (and a margin of experimental error) expression is considered to be absent. Conversely, if the signal from the antibody, primer or probe to the desired marker is higher than that from an irrelevant control and an appropriate margin of experimental error, the marker is expressed. For comparison of leukemia cell marker levels, test samples can be compared with samples from the same tissue or body source either with individuals at low risk of disease (hemangiosarcoma or leukemia) or individuals known to have leukemia. Examples of suitable controls for dogs include those at low risk for hemangiosarcoma, i.e., dogs other than those at high risk (e.g., dogs beyond middle age, Golden Retrievers, German Shepherd Dog, Portuguese Water Dogs, Skye Terriers, or mixed breed dogs containing predominant derivation from such breeds). Absence of clinical manifestation of hemangiosarcoma or angiosarcoma can be evaluated by imaging techniques such as ultrasound, radiographs and/or magnetic imaging techniques (e.g., MRI), for instance. The control can be based upon a single individual, but more typically is a statistical value (e.g., an average or mean) determined from a population. The control can be determined contemporaneously with the test or experimental value or can be performed prior to the test assay. Thus, the control can be based upon contemporaneous or historical data.

In some methods, the control is a "threshold level." A "threshold level" as used herein generally refers to a threshold value for the expression level of one or more markers that are associated with hemangiosarcoma and/or angiosarcoma. In some instances, the threshold level is expressed as the concentration of cells that concurrently express the one or more markers of interest. If a measured value for the expression level of the markers in a test sample is above the threshold level, this is a statistically-significant indication that the test sample is from a subject that has hemangiosarcoma or angiosarcoma. If, however, the measured value of the test sample is below the threshold level, this is a statistically significant indication that the test sample is from a subject that does not have hemangiosarcoma or angiosarcoma. As with control values, a threshold level can be based upon a single individual, but more commonly represents a value determined from a population of samples to provide the desired level of statistical certainty. Thus, the threshold value is often a statistical value (e.g., an average or mean) established for a population of individuals.

The terms "nucleic acid," "polynucleotide," and "oligonucleotide" are used herein to include a polymeric form of nucleotides of any length, including, but not limited to, ribonucleotides or deoxyribonucleotides. There is no intended distinction in length between these terms. Further, these terms refer only to the primary structure of the molecule. Thus, in certain embodiments these terms can include triple-, double- and single-stranded DNA, as well as triple-, double- and single-stranded RNA. They also include modifications, such as by methylation and/or by capping, and unmodified forms of the polynucleotide. More particularly, these terms include polymers containing nonnucleotidic backbones, for example, polyamide (e.g., peptide nucleic acids (PNAs)) and polymorpholino polymers, and other synthetic sequence-specific nucleic acid polymers, providing that the polymers contain nucleobases in a configuration which allows for base pairing and base stacking, such as is found in DNA and RNA.

The term "expression" or "express" refers to the conversion of sequence information, contained in a gene, into a gene product. The gene product can be the direct transcriptional product of a gene (e.g., a mRNA) or a protein produced by translation of a mRNA. Gene products also include RNAs that are modified, by processes such as capping, polyadenylation, methylation, and editing, and proteins modified by, for example, methylation, acetylation, phosphorylation, ubiquitination, ADP-ribosylation, and glycosylation.

A "probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. The label attached to the probe can include any of a variety of different labels known in the art that can be detected by chemical or physical means, for example. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. Probes can vary significantly in size. Some probes are relatively short. Generally, probes are at least 7 to 15 nucleotides in length. Other probes are at least 20, 30 or 40 nucleotides long. Still other probes are somewhat longer, being at least 50, 60, 70, 80, 90 nucleotides long. Yet other probes are longer still, and are at least 100, 150, 200 or more nucleotides long. Probes can be of any specific length that falls within the foregoing ranges as well.

A "primer" is a single-stranded polynucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically is at least 7 nucleotides long and, more typically range from 10 to 30 nucleotides in length. Other primers can be somewhat longer such as 30 to 50 nucleotides long. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target DNA to which a primer hybridizes. The term "primer pair" means a set of primers including a 5' "upstream primer" that hybridizes with the complement of the 5' end of the DNA sequence to be amplified and a 3' "downstream primer" that hybridizes with the 3' end of the sequence to be amplified.

The term "target nucleic acid" refers to a nucleic acid (often derived from a biological sample), to which the probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid can refer to the specific subsequence of a larger nucleic acid to which the probe is directed or to the overall sequence (e.g., gene or mRNA) whose expression level it is desired to detect.

The term "complementary" means that one nucleic acid is identical to, or hybridizes selectively to, another nucleic acid molecule. Selectivity of hybridization exists when hybridization occurs that is more selective than total lack of specificity. Typically, selective hybridization will occur when there is at least about 55% identity over a stretch of at least 14-25 nucleotides, preferably at least 65%, more preferably at least 75%, and most preferably at least 90%. Preferably, one nucleic acid hybridizes specifically to the other nucleic acid. See M. Kanehisa, *Nucleic Acids Res.* 12:203 (1984).

The term "substantially complementary" means that a primer or probe need not be exactly complementary to its target sequence; instead, the primer or probe need be only sufficiently complementary to selectively hybridize to its respective strand at the desired annealing site. A non-complementary base or multiple bases can be included within the primer or probe, so long as the primer or probe retains sufficient complementarity with its polynucleotide binding site to form a stable duplex therewith.

A "perfectly matched probe" has a sequence perfectly complementary to a particular target sequence. The probe is typically perfectly complementary to a portion (subsequence) of a target sequence. The term "mismatch probe" refer to probes whose sequence is deliberately selected not to be perfectly complementary to a particular target sequence.

II. Overview

A variety of methods and kits are provided for detecting the presence of primitive proliferative endothelial cells. This detection capability allows the methods and kits to be used to diagnose and detect the early formation of hemangiosarcoma in dogs or angiosarcoma in humans since these malignant tumors arise from primitive proliferating endothelial cells. The methods can be used to detect or diagnose hemangiosarcoma or angiosarcoma asymptomatic subjects that do not present with typical symptoms associated with the diseases. The methods and kits are based, in part, on the finding that certain primitive proliferating endothelial proteins associated with hemangiosarcomas and angiosarcomas express characteristic markers, including characteristic cell-surface proteins. Cells expressing these characteristic proteins can be distinguished from hematopoietic cells associated with leukemias and lymphomas, which can express some of the same proteins, because hematopoietic cells associated with leukemias and lymphomas express other characteristic proteins that are not expressed by endothelial cells arising from hemangiosarcomas or angiosarcomas.

The methods and kits that are provided can be used to detect the existence of hemangiosarcomas and angiosarcomas at earlier stages than existing methods and can be conducted using non-invasive methods. This simplifies detection and means that therapies can be initiated sooner, thereby improving the chances for successfully treating the tumors. The ability to distinguish between hemangiosarcomas/angiosarcomas and leukemia/lymphomas also means that treatments can be tailored to the particular disease, thereby improving the efficacy of treatment. The methods and kits provided can also be used to monitor minimal residual disease in an individual undergoing treatment.

Antibodies that can be used to treat hemangiosarcoma in dogs and angiosarcomas in humans are also disclosed. Some of the antibodies are conjugated antibodies, which include (1) an antibody that specifically recognizes one or more of the characteristic proteins (i.e., antigens) expressed by the proliferating primitive endothelial cells, and (2) a cytotoxic agent (e.g., a chemotherapeutic) linked to the antibody. These antibodies can optionally be formulated as pharmaceutical compositions for use in the treatment of hemangiosarcoma and angiosarcomas.

III. Methods of Analyzing Primitive Endothelial Cells

A. Detecting Presence of Proliferative Primitive Endothelial Cell

It has been found that hemangiosarcoma is a tumor of “primitive” endothelial cells, i.e., cells that have not differentiated, that are committed to the endothelial lineage, and whose progeny carry characteristic defects that will similarly prevent or arrest their differentiation. These primitive (undifferentiated) endothelial cells can be distinguished from “benign” differentiated endothelial cells because the primitive endothelial cells express the markers CD117, CD133, and/or CD34. Primitive endothelial cells may also express other antigens, such as a Sca-1 homolog (as is seen in the mouse). Differentiated, normal or benign endothelial cells, in contrast, do not express CD117, CD34 or CD133 (or Sca-1 homolog). Primitive endothelial cells lack expression of proteins normally found in hematopoietic cells committed to leukocyte lineages, including CD18, CD11b, CD3, and CD21. Thus, certain methods that are provided herein involve detecting the presence or absence of primitive endothelial cells by detecting the presence or absence of expression of one or more cell markers that define primitive hematopoietic cells such as CD117, CD34, CD133 and/or a Sca-1 homolog that distinguish a primitive endothelial cell from a differentiated endothelial cell and/or cells committed to leukocyte lineages. Although detection of primitive hematopoietic cell markers provides some indication of risk of hemangiosarcoma or angiosarcoma, detection of these markers is typically coupled with the detection of expression of other characteristic markers to distinguish primitive endothelial cells per se from other hematopoietic stem cells and to further classify and/or confirm the type of cell as described in the following sections.

Variable expression of some cell markers, including CD14 and CD45, indicate HSA cells can attain different stages of differentiation. The difference in differentiation can affect response to therapy. Expression of these markers can be determined to identify prognosis or optimal treatment methods for an individual affected with HSA.

B. Assessment of Elevated Risk for Hemangiosarcoma or Angiosarcoma

Because the cells from a hemangiosarcoma or angiosarcoma are primitive endothelial cells, some methods are designed to detect the concurrent expression of (1) one or more primitive hematopoietic cell markers such as described supra, and (2) one or more endothelial cell markers in a population of cells from a test sample taken from a patient. These methods can be utilized as a diagnostic for hemangiosarcoma or angiosarcoma and/or to evaluate the efficacy of a treatment regime.

Examples of primitive hematopoietic cell markers include, but are not limited to, CD117, CD34, CD133 and/or a Sca-1 homolog. Examples of suitable endothelial cell markers that can be detected include, but are not limited to, CD51/CD61, CD31, CD105, CD106, CD146 and/or von Willebrand Factor (vWF). The endothelial cell marker can be a marker that is expressed by endothelial cells generally (e.g., CD31, CD105, CD106, CD146), and/or a proliferative endothelial cell marker that is associated with proliferative endothelial cells (e.g., CD51/CD61). Detection of concurrent expression of one or more primitive hematopoietic cell markers in combination with one or more endothelial cell markers thus provides strong evidence for hematopoietic ontogeny with endothelial commitment.

Some methods can be conducted such that one, some or all of the foregoing primitive hematopoietic cell markers are detected. Likewise, certain methods can be conducted such that one, some or all of the foregoing endothelial cell markers are detected (e.g., 1, 2, 3, 4, 5 or all 6 of the foregoing markers). Thus, the methods can detect any combination of one or more primitive hematopoietic cell markers and one or more endothelial (committed) cell markers, provided at least one each of a primitive hematopoietic cell marker and an endothelial cell marker are detected. The particular grouping of markers that are detected can be considered an expression profile that is characteristic of a primitive endothelial cell. Thus, the methods can be considered to involve detecting an expression profile that is characteristic of a primitive endothelial cell.

As one specific example, some methods that are provided involve detecting the concurrent expression of the primitive hematopoietic cell markers CD117 and CD34. These two primitive hematopoietic cell markers are detected in this particular method rather than just one to provide increased confidence that the cell is in fact a primitive hematopoietic cell. These methods also detect one, some or all of the endothelial cell markers listed above. But in certain methods, the cells are also examined for concurrent expression of CD51/61 in combination with CD117 and CD34. It can be useful to detect CD51/61 because its expression indicates not only that the cell is an endothelial cell, but more specifically that the cell is a proliferative endothelial cell. This is helpful because tumor cells from tumors such as hemangiosarcoma and angiosarcomas are proliferative.

Because bone marrow (hematopoietic) stein cells and precursor endothelial cells are also present in the circulation and concurrently express primitive hematopoietic and endothelial cell markers such as those just described, methods for evaluating the risk of hemangiosarcoma or angiosarcoma also typically involves comparing the concentration, frequency or fraction of cells concurrently expressing the markers in the test sample with respect to a control. This can involve determining, for instance, if there is a statistically significant difference between the frequency or concentration in the test sample as compared to the control. In some instances, this involves determining whether the concentration of cells concurrently expressing the markers in the test sample is above or below a threshold level. If the concentration is above the threshold level, then there is a statistical basis for concluding that the subject from which the test sample was obtained has hemangiosarcoma or angiosarcoma. If, on the other hand, the concentration is below the threshold level, there is a statistical basis for concluding that the subject from which the sample was obtained does not have hemangiosarcoma or angiosarcoma.

The concentration of cells that concurrently express the primitive hematopoietic cell and the endothelial cell markers is increased if a hemangiosarcoma or angiosarcoma is present because hemangiosarcomas and angiosarcomas by definition are in constant contact with the blood and thus shed cells into the circulation. This mechanism is also responsible, at least in part, for the high metastatic potential and hematogenous (through the blood) spread of these tumors. Thus, normal circulating precursor endothelial cells and malignant hemangiosarcoma or angiosarcoma cells can be distinguished based upon the quantity of cells that are concurrently expressing the primitive hematopoietic cell markers and the endothelial cell markers. The continuous release of HSA tumor cells into the circulation provides the opportunity to detect these cells in routine blood samples.

Some diagnostic methods and methods for assessing whether a subject is at elevated risk of hemangiosarcoma or angiosarcoma also involve distinguishing among the primitive hematopoietic cells to determine whether those cells that express the primitive hematopoietic cell marker(s) also express marker(s) that are characteristic of endothelial cells or marker(s) that are characteristic of leukemia or lymphoma. This determination can be done qualitatively or quantitatively. As described in greater detail below, the presence of the leukemia marker, in combination with the primitive hematopoietic cell markers, but not the endothelial cell markers, is an indication that the cells are associated with leukemia or lymphoma. The absence of expression of the leukemia marker, concurrent with the presence of an endothelial marker in contrast, is an indication that cells expressing the primitive hematopoietic cell markers are from a hemangiosarcoma or angiosarcoma rather than being leukemia cells.

C. Methods for Distinguishing Between Hemangiosarcoma or Angiosarcoma and Leukemia Hemangiosarcoma/angiosarcoma, leukemia, and lymphoma are all diseases that involve excessive proliferation of cells that originate from bone marrow (hematopoietic) precursors. Thus, the characteristic markers for hemangiosarcoma and angiosarcoma that have been identified can be utilized in combination with specific markers for hematopoietic progenitors committed to leukocyte, erythroid, or thrombopoietic lineages that give rise to leukemias and lymphomas to distinguish between hemangiosarcoma (or angiosarcoma) and leukemia or lymphoma. As indicated above (see also Table 1), the cells from hemangiosarcomas or angiosarcomas, as well as leukemia or lymphoma cells, all can express certain common markers (e.g., primitive hematopoietic cell markers such as CD117, CD34 and CD133). Hemangiosarcoma/angiosarcoma also express markers that identify them as committed to the endothelial lineage, such as CD51/61, CD31, CD105, CD106, CD146 and vWF.

In contrast, leukemia and lymphoma cells express markers that are unique to cells committed to traditional blood cell forming lineages (leukocytes, red blood cells, platelets) that include, but are not limited to, CD18 and CD45, which are referred to herein as "leukemia markers." Other leukocyte-specific markers, including CD3, CD21, CD5, and CD11b, are also not expressed by hemangiosarcoma cells. The differential expression of one or more of these leukemia-specific or leukocyte-specific markers can be used to distinguish hemangiosarcoma or angiosarcoma from leukemia or lymphoma. Specifically, detection of expression of leukemia or leukocyte-specific cell markers CD18, CD45, CD3, CD21, CD5 or CD11b in a cell population is an indication of leukemia or lymphoma. Conversely, elevated levels of cells expressing a primitive hematopoietic cell marker such as CD117, CD34 and/or CD133, in combination with an endothelial cell marker such as CD51/61, CD31, CD105, CD106, and/or CD146, in combination with a lack of expression of leukemia or leukocyte-specific cell markers, such as CD18, CD45, CD3, CD21, CD5 and/or CD11b are collectively indicative of hemangiosarcoma or angiosarcoma in a cell population.

The unique properties of laser light scatter, can also be used independently or in combination with detection of the leukemia markers or leukocyte-specific cell markers to make this distinction. Canine hemangiosarcoma cells are large (they segregate to higher channels than leukocytes based on forward angle (or 0°) light scatter) and they are granular or have complex cytoplasm, resulting in right angle (or 90°) side scatter that is comparable to or higher than granulocytes (neutrophils, eosinophils, basophils). The clear differences between the light scatter patterns of canine hemangiosarcoma cells and canine leukocytes can be seen in FIGS. 1A-1H and FIGS. 2A-2H. Further details regarding differences in the patterns are described in the example below.

Accordingly, certain cell classification and cell diagnostic methods involve determining whether cells in a test sample from a subject concurrently express at least one primitive hematopoietic cell marker, at least one endothelial cell marker, and at least one leukemia cell marker or leukocyte-specific cell marker. As described above, the primitive hematopoietic cell marker(s) and the endothelial cell marker(s) that are analyzed can include one, some or all of those listed supra. Likewise, the expression of one or multiple leukemia cell or leukocyte-specific cell markers can be analyzed. The markers from these three classes can be combined in any combination, so long as expression of at least one marker from each class is analyzed.

Thus, the most thorough assessment or diagnosis of a subject thought to be at increased risk for hemangiosarcoma or angiosarcoma involves (1) assessing whether the subject is at elevated risk for hemangiosarcoma or angiosarcoma as described above by determining if cells in the test sample obtained from the subject concurrently express at least one primitive hematopoietic cell marker and at least one endothelial cell marker at levels that are above that of a control (e.g., a threshold level), and (2) determining if the same cells also concurrently express one or more leukemia or leukocyte-specific cell markers. The expression of the one or more leukemia or leukocyte-specific cell markers can be done qualitatively (e.g., determining whether the marker is expressed by the cells or not) or quantitatively (e.g., with respect to a control such as a threshold level). In some methods, expression of the primitive hematopoietic cell marker(s), the endothelial cell marker(s) and the leukemia or leukocyte-specific cell marker(s) are conducted contemporaneously. As described in greater detail below, this may be accomplished, for example, by incubating cells from a test sample with differentially labeled antibodies that specifically bind markers from the three different classes and then detecting cells that are labeled with the antibodies using multiparameter flow cytometry. Alternatively, concurrent expression of the three classes of markers can be detected at the transcript level using probes that specifically hybridize to a segment of each of the marker transcripts in a hybridization assay and/or primers that specifically amplify the marker transcripts.

As a specific example of this general approach, some methods for diagnosing hemangiosarcoma in a dog involve testing a population of cells from a dog at risk for hemangiosarcoma for concurrent expression of CD117 and CD34 (examples of primitive hematopoietic cell markers) and CD51/CD61 (an example of a endothelial cell marker), and lack of expression of CD18 (an example of a committed leukocyte cell marker). If the cell population concurrently expresses CD117, CD34 and CD51/61 but not CD18 (i.e., the cells are $CD117^+$, $CD34^+$, $CD51/61^+$, $CD18^-$), then the differential diagnosis is that the dog has a hemangiosarcoma. If, however, the cell population concurrently expresses CD117, CD34, and CD18 (i.e., the cells are $CD117^+$, $CD34^+$, $CD18^+$), then the differential diagnosis is that the dog has leukemia or lymphoma. Absence of expression of these markers (e.g., expression below a threshold level), indicates that the dog is unlikely to be at immediate risk to develop, or to have hemangiosarcoma, leukemia or a lymphoma.

The same type of analysis would apply to humans, except that $CD117^+$, $CD34^+$, $CD51/61^+$, $CD18^-$ cells indicate that the human has angiosarcoma (rather than hemangiosarcoma which is specific to dogs rather than humans).

Although the foregoing methods have emphasized the ability to detect or diagnose hemangiosarcoma in dogs or angiosarcoma in humans, it should be clear that the capacity of the methods to distinguish between hemangiosarcoma/angiosarcoma from leukemia/lymphoma means that the methods can be used equally well to detect or diagnose leukemia or lymphoma in dogs or humans. The main difference between methods for diagnosing angiosarcoma and methods for diagnosing leukemia being that in methods for diagnosing angiosarcoma one looks for presence of expression of endothelial cell marker(s) and absence of expression of the leukemia cell marker(s) which rules out leukemia and lymphoma, whereas in methods for diagnosing leukemia one instead looks for presence of expression of the leukemia cell marker(s) and absence of expression of the endothelial cell marker(s). If the leukemia cell marker(s) are found to be expressed concurrently with at least one primitive hematopoietic cell marker and at least one endothelial cell marker, then this indicates that cells are from a subject with leukemia or lymphoma.

The following table summarizes which markers are associated with hemangiosarcomas, angiosarcomas, leukocyte-specific cells, leukemia and lymphoma, and thus indicates which combination of markers can be used to detect these diseases and distinguish between them.

TABLE I

| Markers | Primitive Endothelial Cells (Hemangiosarcoma and Angiosarcoma) | Benign Endothelial Cells | Leukemia and Lymphoma |
|---|---|---|---|
| Primitive Hematopoietic Cell Markers | | | |
| CD117 | Yes | No | Variable |
| CD34 | Yes (low to intermediate) | No | Variable |
| CD133 | Yes | No | Variable |
| Endothelial Cell Markers | | | |
| CD51/CD61 | Yes | Variable | No |
| CD31 | Yes | Yes | No |
| CD105 | Yes | Yes | No |
| CD106 | Yes | Yes | No |
| CD146 | Yes | Yes | No |
| Markers to Exclude HSA Cells | | | |
| CD18, CD11b, CD3, CD5, and CD21 | No | No | Yes |
| Leukemia Cell Markers | | | |
| CD18 | No | No | Yes |
| CD45 | Variable (when yes, low to intermediate) | Variable (usually No) | Yes (intermediate to high, except for B cell-chronic lymphocytic leukemia (CLL), which is No) |
| CD14 | Variable (when yes, low to intermediate) | Variable (usually No) | Yes (absent to high, depending on the type of leukemia; highest in monoblastic and monocytic leukemias, low to intermediate in |

TABLE I-continued

| Markers | Primitive Endothelial Cells (Hemangiosarcoma and Angiosarcoma) | Benign Endothelial Cells | Leukemia and Lymphoma |
|---|---|---|---|
| | | | other myeloid leukemias and some B cell leukemias) |

IV. Options for Detecting Markers

Expression of the various markers described above can be detected at the protein level by detecting the expressed proteins themselves, or at the transcript (i.e., mRNA) level by detecting transcript that encodes the corresponding proteins of interest. Conversely, proteins not expressed cannot be detected at the protein level or transcript level by the assays described below. Additional details regarding these various detection options follows.

A. Detecting Expressed Proteins

1. Multiparameter Flow Cytometry

Flow cytometry is one detection method that can be used to determine the level at which cells in a sample concurrently express the primitive hematopoietic cell markers, endothelial cell markers and/or leukemia or leukocyte specific cell markers (markers), in addition to the peculiar light scatter patterns, which are different between leukocytes (associated with leukemia and lymphoma) and primitive endothelial cells (associated with hemangiosarcoma and angiosarcoma). These differences are described in greater detail in the example below. Flow cytometry involves the quantitative multiparameter measurement of chemical or physical characteristics of cells in suspension. A flow cytometer can measure, for instance, the cell's light scatter and the electronic cell volume as a cell passes through detectors in the device. The flow cytometer can also measure a cell's axial (at a right angle) light loss and morphological information (derived from the cell shape or time duration of light scatter signals) as it passes through a fluorescent excitation beam. Thus, a flow cytometer can categorize cells on the basis of size, granularity, and fluorophore intensity.

The methods provided herein that use flow cytometry to detect the level of expression of the markers usually involve a process referred to in the art as "immunophenotyping." In this process, antigens expressed by a cell (e.g., the markers disclosed herein) can be identified by incubating cells with labeled antibodies that recognize different antigens/markers on the cell. The antibodies are generally differentially labeled such that different antigens/markers on the cell surface become labeled with antibodies bearing different labels. After a suitable incubation period, any unbound antibodies are subsequently removed by washing. The resulting labeled cells are then introduced into a flow cytometer where the fluorescent labels can be excited by the excitation beam and the resulting fluorescence emissions detected. Since different antigens/markers are associated with different fluorescent labels, each having a characteristic emission spectrum, the identity of the antigens/markers on the cell can be determined from the fluorescence signals that are detected. In some methods, the cells can also be incubated with a fluorescent dye which intercalates into the DNA, thereby allowing the DNA composition (ploidy) to be determined.

Additional details regarding the use of flow cytometry to detect cells that concurrently express the different markers disclosed herein are provided in the examples below. Further discussion on flow cytometry sufficient to guide the skilled practitioner is provided by De Rosa, S. C., et al. (2003) Nature Medicine 9:112-117, and Baumgarth, N. and Roederer, M. (2000) J. Immunological Methods 243:77-97.

2. Other Immunological Techniques

A variety of other immunological techniques can also be used to determine whether cells concurrently express the primitive hematopoietic cell markers, endothelial cell markers and/or leukemia or leukocyte-specific cell markers described herein. Antibodies that specifically bind these markers, for instance, can be used to detect such these markers in various diagnostic assays, including but not limited to, competitive binding assays, direct or indirect sandwich assays, enzyme-linked immunospecific assays (ELISA), and immunoprecipitation assays (see, e.g., *Monoclonal Antibodies: A Manual of Techniques*, CRC Press, Inc. (1987) pp. 147-158). Further guidance regarding the methodology and steps of a variety of antibody assays is provided, for example, in U.S. Pat. No. 4,376,110 to Greene; "Immunometric Assays Using Monoclonal Antibodies," in *Antibodies: A Laboratory Manual*, Cold Spring Harbor Laboratory, Chap. 14 (1988); Bolton and Hunter, "Radioimmunoassay and Related Methods," in *Handbook of Experimental Immunology* (D. M. Weir, ed.), Vol. 1, chap. 26, Blackwell Scientific Publications, 1986; Nakamura, et al., "Enzyme Immunoassays: Heterogeneous and Homogenous Systems," in *Handbook of Experimental Immunology* (D. M. Weir, ed.), Vol. 1, chap. 27, Blackwell Scientific Publications, 1986; and Current Protocols in Immunology, (John E. Coligan, et al., eds), chap. 2, section I, (1991).

3. Antibodies for Use in Flow Cytometry and Other Immunological Methods

Antibodies that recognize a number of the foregoing markers as expressed in canines are commercially available, including:

(1) canine CD117 (clone ACK45, BD Biosciences, pycoerythrin (PE) conjugate);

(2) canine CD34 (clone 2E9, BD Biosciences, biotin conjugate);

(3) canine CD51/CD61 (mAb 1976, Chemicon, APC or FITC conjugate);

(4) canine CD18 (clone YK1X490.6.4, Serotec, fluorescein isothiocyanate (FITC) conjugate and clone YFCI18.3, Serotec, FITC or biotin conjugate);

(5) canine CD45 (clone YK1X716.13, Serotec, PE conjugate);

(6) canine CD105 (cross reactive) (clone 8E11, Southern Biotechnology Associates, Birmingham, Ala., FITC conjugate);

(7) canine CD133 (clone 13A4, BD Biosciences);

(8)) canine CD11b antibody (clone CA16.3E10, Serotec);

9) canine anti-CD146 (MUC18, S-endo, clone P1H12 conjugated to biotin, catalog #MAB16985B, Chemicon Intl., Temecula, Calif.);

(10) canine CD CD3 (clone CA17.2A12, Serotec, Inc., FITC conjugate);

(11) canine CD5 antibody (clone YKIX322.3, Serotec, Inc.); and

(12) canine anti-B cell (CD21) antibody (clone Ca2.1D6, Serotec, Inc.).

Antibodies that recognize a number of the foregoing markers as expressed in humans are also commercially available, including:

(1) human CD117 (clone YB5.B8, BD Biosciences, pycoerythrin (PE), or APC, or PE-Cy5 conjugate);

(2) human CD34 (clone 581, BD Biosciences, allophycocyanin (APC) or PE conjugate);

(3) human CD51/CD61 (mAb 1976, Chemicon, biotin or FITC or PE conjugate);

(4) human CD18 (clone 6.7, BD Biosciences, FITC or PE, or APC, or PE-Cy5, or APC conjugate and clone L130, BD Biosciences, FITC conjugate);

(5) human CD45 (clone 2D1, BD Biosciences, APC, FITC, APC-Cy7, PerCP, PerCp-Cy5.5 conjugate and clone H130, BD Biosciences, FITC, PE, APC, biotin, PE-Cy7, PE-Cy5 conjugate);

(6) human CD105 (clone 8E11, Southern Biotechnology Associates, Birmingham, Ala., conjugated to FITC);

(7) human anti-CD146 (MUC18, S-endo, clone P1H12 conjugated to biotin, catalog #MAB16985B, Chemicon Intl., Temecula, Calif.);

(8) human CD106 (clone 1.G11b1, Southern Biotechnology Associates, Birmingham, Ala., conjugated to biotin, FITC, or PE);

(9) human CD133 (prominin, human promin-1, antibody AC133 PE, APC, biotin conjugate and antibody 293C3 PE, APC, biotin conjugate, Miltenyi Biotech, Auburn, Calif.); and

(10) murine CD133 (clone 13A4, eBioscience, San Diego, Calif.).

Additional antibodies to any of the markers described herein can be prepared according to routine methods that are known in the art (see, e.g., discussion below in the section on antibodies). Each antibody can also be obtained in purified form without a fluorochrome or biotin label, and labeled to any available fluorochrome in vitro using the AlexaFluor Zenon antibody labeling technology from Invitrogen/Molecular Probes, Eugene, Oreg. (emitting at 16 different wavelengths between 350 and 750 nm) or other equivalent technologies (e.g., Zymed and others). The resulting antibodies can be conjugated to any of a number of different labels, including for example, radioisotopes (e.g., $^{3}H$, $^{14}C$, $^{32}P$, $^{35}S$, $^{125}I$), fluorophores (e.g., pycoerythrin, fluorescein and rhodamine dyes and derivatives thereof), chromophores, chemiluminescent molecules, and enzyme substrates (e.g., the enzymes luciferase, alkaline phosphatase, beta-galactosidase and horse radish peroxidase).

Secondary detection systems employing an unlabelled antibody to bind to a cell marker and another labeled antibody to bind to the Fc region of the first antibody can be used in the immunoassays of the invention to increase the sensitivity of the assays.

Other markers that can optionally be detected in combination with those above include vascular endothelial growth factor (VEGF), which is constitutively elevated in HSA tumors, and is found at increased levels in blood samples from affected dogs. c-KIT, and vascular endothelial growth factor receptor-2 (VEGFR-2) are expressed by canine HSA cells in culture. These markers can be monitored in detection and diagnosis of HSA. The VEGF-2 tumor suppressor genes, include PTEN and VHL, are sometimes inactivated in canine HSA as well, providing cells a growth advantage within their microenvironment. Lack of PTEN, and VHL is therefore also an indicator of HSA.

A series of iterative steps can be used to identify circulating endothelial precursor cells (EPC) or HSA cells in peripheral blood. First, single color staining can be used to define background levels for each antibody and to verify that the relative number of leukocytes ($CD21^{+}$B cells, $CD3^{+}$ and $CD5^{+}$ T cells, $CD14^{+}$ monocytes, and $CD11b^{+}$ granulocytes) in samples are within previously reported reference ranges. Next, antibody combinations can be used for two-color staining. Color compensation can be adjusted using, e.g., BD Biosciences CompBeads. Populations staining positively for one or more of three markers associated with bone marrow progenitor cells (c-KIT, CD34, CD133) and for a marker associated with proliferating endothelial cells ($\alpha_v\beta_3$-integrin) can be "back-gated" to two-dimensional light scatter histograms to define the flow cytometric light scatter parameters of HSA cells versus normal leukocytes. Some protocols can be modified to exclude leukocytes using antibodies against CD5, CD11b, and CD21 labeled with FITC (and/or Alexa Fluor-488) to establish a "dump gate", and EPC can be detected in the remaining cell population by dual staining with antibodies against c-KIT, CD34, or CD133 (conjugated to PE) along with antibodies against $\alpha_v\beta_3$-integrin or CD146 (labeled with Alexa Fluor-647). Preferably at least 100,000 cells can be analyzed for each antibody pair to ensure statistical validity for rare-event determination.

B. Detecting Transcript that Encodes Markers

1. General Considerations

The level of gene expression and expression of the primitive hematopoietic cell markers, endothelial cell markers and leukemia or leukocyte-specific cell markers can also be detected qualitatively or quantitatively using a number of established techniques including, but not limited to, multiplex PCR, nucleic acid probe arrays, dot blot assays, in-situ hybridization, Northern-blots, and RNase protection assays (RPA). These are described further in the sections that follow.

Primers and/or probes having sequences that are appropriate for use in such detection schemes can be designed based upon the sequences for the different markers that are provided herein (e.g., SEQ ID NOS:1-45). See, e.g., Mitsuhashi, M. (1996) J. Clin. Lab. Anal. 10:285-93, which is incorporated herein by reference in its entirety for all purposes.

For the following methods that utilize probes to detect marker expression, the hybridization probes utilized in these methods are of sufficient length to specifically hybridize to a particular marker nucleic acid. Hybridization probes are typically at least 15 nucleotides in length, in some instances 20 to 30 nucleotides in length, in other instances 30 to 50 nucleotides in length, and in still other instances up to the full length of a marker nucleic acid. The probes are labeled with a detectable label, such as a radiolabel, fluorophore, chromophore or enzyme to facilitate detection. Methods for synthesizing the necessary probes include the phosphotriester method described by Narang et al. (1979) Methods of Enzymology 68:90, and the phosphodiester method disclosed by Brown et al. (1979) Methods of Enzymology 68:109.

2. Multiplex PCR

Various types of multiplex PCR can be utilized to detect expression of the cell markers described herein. Multiplex PCR in general refers to PCR methods in which more than one pair of primers is used, thus allowing the amplification of multiple DNA targets in a single run. If this approach is utilized, typically the methods are conducted as quantitative multiplex PCR so the level of expression can be more readily determined.

The quantitative multiplex PCR assays that are utilized with the current methods can be conventional quantitative PCR or "real time PCR" methods. Real-time PCR usually monitors the fluorescence emitted during an amplification reaction as an indicator of amplicon production during each PCR cycle (i.e., in real time) as opposed to the endpoint detection by conventional quantitative PCR methods. By recording the amount of fluorescence emission at each cycle, it is possible to monitor the PCR reaction during exponential phase where the first significant increase in the amount of PCR product correlates to the initial amount of target template.

There are several real-time strategies that can be used to detect the expression of the marker transcripts disclosed herein (i.e., the targets). A requirement that is common to each strategy is a probe bearing fluorescent moieties that is complementary to a section in the amplified target. One example of real-time analysis method that can be utilized with the current methods is the "Taqman" PCR approach. Reagents and equipment for performing such analyses are marketed by Applied Biosystems, Foster City, Calif. In this method, the probe used in such assays is typically a short (ca. 20-25 bases) polynucleotide that is labeled with two different fluorescent dyes. The 5' terminus of the probe is typically attached to a reporter dye and the 3' terminus is attached to a quenching dye, although the dyes can be attached at other locations on the probe as well. For each marker transcript, a probe is designed to have at least substantial sequence complementarity with a probe binding site on the marker transcript. Upstream and downstream PCR primers that bind to regions that flank the region encoding each marker are also added to the reaction mixture for use in amplifying the markers of interest.

When the probe is intact, energy transfer between the two fluorophors occurs and the quencher quenches emission from the reporter. During the extension phase of PCR, the probe is cleaved by the 5' nuclease activity of a nucleic acid polymerase such as Taq polymerase, thereby releasing the reporter dye from the polynucleotide-quencher complex and resulting in an increase of reporter emission intensity that can be measured by an appropriate detection system.

One detector which is specifically adapted for measuring fluorescence emissions during quantitative PCR reactions is the ABI 7700 manufactured by Applied Biosystems, Inc. in Foster City, Calif. Computer software provided with the instrument is capable of recording the fluorescence intensity of reporter and quencher over the course of the amplification. These recorded values can then be used to calculate the increase in normalized reporter emission intensity on a continuous basis and ultimately quantify the amount of the mRNA being amplified.

Information specific to the "TaqMan" type assays are is described, for example, in U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995), each of which is incorporated by reference in its entirety for all purposes.

Another real-time strategy that can be used to detect expression of the markers provided herein utilizes labeled probes called "Molecular Beacons," which are marketed by various entities including Proligo LLC, Boulder, Colo. and Synthegen LLC, Houston, Tex., under a license from Public Health Research Institute. In methods using this approach, the fluorophore and the quencher, attached to opposite ends of the probe, are held together by a base paired stem that becomes disrupted on hybridization of the loop to a target nucleic acid. Further details regarding the use of molecular beacons are provided by Tyagi, S., and F. R. Kramer (1996) Nature Biotechnology 14: 303-8; and Tyagi S., et al. (2000) Nature Biotechnology 18: 1191-96, each of which is incorporated by reference in its entirety for all purposes.

Additional details regarding the theory and operation of multiplex PCR assays are described, for example, by Wittwer, C. T., et al. (2001) Methods 25:430-42; Markoulatos, P., et al. (2002) J. Clin. Lab. Anal. 16:47-51; Elnifro, E. M., et al. (2000) J. Clin. Microbiol. Rev. 13:559-570; and Edwards, M. C. and Gibbs, R. A. (1994) PCR Methods Appl. 3:S65-75, each of which is incorporated herein by reference in its entirety for all purposes.

3. Nucleic Acid Probe Arrays

Marker transcripts can also be detected using a variety of hybridization methods. One example, is the use of nucleic acid probe arrays to detect and quantitate marker transcript. A variety of different types of arrays can be used to detect expression of the markers of interest depending upon the nature of the probes on the arrays. The array probes, can include, for example, synthesized probes of relatively short length (e.g., a 20-mer or a 25-mer), cDNA (full length or fragments of gene), amplified DNA, fragments of DNA (generated by restriction enzymes, for example) and reverse transcribed DNA (see, e.g., Southern et al. (1999) Nature Genetics Supplement 21:5-9 (1999).

Both custom and generic arrays can be utilized in detecting marker expression levels. Custom arrays can be prepared using probes that hybridize to particular preselected subsequences of mRNA gene sequences of the markers or amplification products prepared from them. Generic arrays are not specially prepared to bind to the marker sequences, but instead are designed to analyze mRNAs irrespective of sequence. Nonetheless, such arrays can still be utilized because marker transcripts only hybridize to those locations that include complementary probes. Thus, the different marker transcript levels can still be determined based upon the extent of binding at those locations bearing probes of complementary sequence.

In probe array methods, once nucleic acids have been obtained from a test sample, they typically are reversed transcribed into labeled cDNA, although labeled mRNA can be used directly. By differentially labeling the mRNA or cDNA, the expression levels of multiple markers can be determined simultaneously. The test sample containing the labeled nucleic acids is then contacted with the probes of the array. After allowing a period sufficient for any labeled marker nucleic acids present in the sample to hybridize to the probes, the array is typically subjected to one or more high stringency washes to remove unbound nucleic acids and to minimize nonspecific binding to the nucleic acid probes of the arrays. Binding of labeled nucleic acids corresponding to the markers is detected using any of a variety of commercially available scanners and accompanying software programs.

For example, if the nucleic acids from the sample are labeled with fluorescent labels, hybridization intensity can be determined by, for example, a scanning confocal microscope in photon counting mode. Appropriate scanning devices are described by e.g., U.S. Pat. No. 5,578,832 to Trulson et al., and U.S. Pat. No. 5,631,734 to Stem et al. and are available from Affymetrix, Inc., under the GeneChip™ label.

Those locations on the probe array that are hybridized to labeled nucleic acid are detected using a reader, such as described by U.S. Pat. No. 5,143,854, WO 90/15070, and U.S. Pat. No. 5,578,832. For customized arrays, the hybridization pattern can then be analyzed to determine the presence and/or relative amounts or absolute amounts of known mRNA species in samples being analyzed as described in e.g., WO 97/10365.

Further guidance regarding the use of probe arrays sufficient to guide one of skill in the art is provided in WO 97/10365, PCT/US/96/143839 and WO 97/27317.

4. Dot Blots and In-Situ Hybridization

Dot blots are another example of a hybridization assay approach that can be utilized to determine the amount of each of the marker transcripts that are present in a sample obtained from a subject being tested. In some assays, for instance, a sample from a subject being tested is spotted on a support (e.g., a filter) and then probed with labeled nucleic acid probes that specifically hybridize with the marker transcript sequences of interest. After the probes have been allowed to hybridize to the immobilized nucleic acids on the filter, unbound nucleic acids are rinsed away and the presence of hybridization complexes detected and quantitated on the basis of the amount of labeled probe bound to the filter. By using differentially labeled probes, transcripts from multiple markers can be detected at the same time.

In-situ hybridization methods are hybridization methods in which the cells are not lysed prior to hybridization. Because the method is performed in situ, it has the advantage that it is not necessary to prepare RNA from the cells. The method usually involves initially fixing test cells to a support (e.g., the walls of a microtiter well) and then permeabilizing the cells with an appropriate permeabilizing solution. A solution containing labeled probes for the markers of interest is then contacted with the cells and the probes allowed to hybridize with the labeled nucleic acids. Excess probe is digested, washed away and the amount of hybridized probe measured. This approach is described in greater detail by Harris, D. W. (1996) Anal. Biochem. 243:249-256; Singer, et al. (1986) Biotechniques 4:230-250; Haase et al. (1984) Methods in Virology, vol. VII, pp. 189-226; and Nucleic Acid Hybridization: A Practical Approach (Hames, et al., eds., 1987).

5. Northern Blots

Northern blots can also be used to detect and quantitate marker transcript. Such methods typically involve initially isolating total cellular or poly(A) RNA and separating the RNA on an agarose gel by electrophoresis. The gel is then overlaid with a sheet of nitrocellulose, activated cellulose, or glass or nylon membranes and the separated RNA transferred to the sheet or membrane by passing buffer through the gel and onto the sheet or membrane. The presence and amount of marker transcript present on the sheet or membrane can then be determined by probing with a labeled probe complementary to the marker transcripts to form labeled hybridization complexes that can be detected and optionally quantitated (see, e.g., Sambrook, et al. (1989) Molecular Cloning—A Laboratory Manual (2nd ed) Vols. 1-3, Cold Spring Harbor Laboratory, Cold Spring Harbor Press, NY).

6. RNAase Protection Assays

Ribonuclease protection assays (RPA) involve preparing a labeled antisense RNA probe for each of the markers of interest. These probes are subsequently allowed to hybridize in solution with marker transcript contained in a biological sample to form RNA:RNA hybrids. Unhybridized RNA is then removed by digestion with an RNAase, while the RNA:RNA hybrid is protected from degradation. The labeled RNA:RNA hybrid is separated by gel electrophoresis and the band corresponding to the markers detected and quantitated. Usually the labeled RNA probe is radiolabeled and the bands corresponding to the different markers detected and quantitated by autoradiography. RPA is discussed further by (Lynn et al. (1983) Proc. Natl. Acad. Sci. 80:2656; Zinn, et al. (1983) Cell 34:865; and Sambrook, et al. (1989) Molecular Cloning—A Laboratory Manual (2nd ed) Vols. 1-3, Cold Spring Harbor Laboratory, Cold Spring Harbor Press, NY).

V. Samples

A. General Considerations

Although the methods that are provided can generally be used to detect early formation of hemangiosarcoma in any breed of dog (or mix of breeds), the methods are often used in the early diagnosis of hemangiosarcoma in dogs that are at increased risk for hemangiosarcoma. As indicated in the background section, some dogs are inherently at higher risk than other dogs. These dogs include those of any breed that are beyond middle age and purebred dogs where the prevalence of hemangiosarcoma is high including, but not limited to, Golden Retrievers, German Shepherds, Portuguese Water Dogs, or Skye Terriers. Mix breed dogs are also at higher risk if their predominant derivation is from one of the foregoing breeds.

In the case of angiosarcoma, the methods can also be performed, for example, with samples from any human deemed to potentially have an angiosarcoma. The methods, however, have particular utility with the humans that are at increased risk for angiosarcoma because they have a risk factor that is correlated with angiosarcoma. Examples of such risk factors include, but are not limited to, occupational exposure to vinyl chloride for hepatic angiosarcoma, radiation therapy for mammary angiosarcoma, HIV-1 infection for Kaposi sarcoma, and heritable defects in the Von Hippel-Lindau gene in human infantile angiosarcomas.

B. Samples for Flow Cytometry

Blood samples are the type of sample most typically utilized in flow cytometry analyses. A typical sample size for flow cytometry is about 10 μl to about 1.0 ml, which includes about 100,000 ($10^5$) to 2,500,000 ($2.5\times10^6$) cells. One useful sample collection method is to collect blood by venipuncture into evacuated tubes containing an appropriate anticoagulant. The blood is then mixed well with the anticoagulant in the tube to prevent clotting. Various anticoagulants can be used. If the specimens will be processed within thirty hours of collection, then examples of suitable anticoagulants include potassium EDTA, acid citrate dextrose (ACD), or heparin. If, however, the samples will not be processed within 30 hours, of these three anticoagulants, either ACD or heparin should be used.

Typically, specimens for flow cytometry are maintained and transported (if necessary) under refrigerated temperatures (2-8° C.). This maintains the viability of the cells and their expression of antigens. Tubes are usually incubated in the dark to maximize fluorescence capability.

Once the sample has been combined with the labeled antibodies that specifically bind the markers of interest, the samples are typically vortexed to mix up the antibodies with the cells and break up cell aggregates. A source of protein may be included in the wash buffer to reduce cell clumps and autofluorescence. Before analysis, samples are generally fixed with a fixation solution (e.g., 1-2% buffered paraformaldehyde or formaldehyde).

Flow cytometry can include processes to distinguish primitive cells from normal cells. Normal leukocytes in a sample can be labeled using antibodies with one fluorochrome (in one color, e.g. FITC). A dump gate can be established to ignore the FITC color associated with the normal leukocytes, and to focus only on cells labeled with fluorochromes of other colors, such as red (PE) and blue (APC). Markers that can be used for the “dump gate” include CD3, CD5, CD11c, CD21, and optionally, CD18. CD45 and/or CD14 are not suitable as “dumpgate” markers, because hemangiosarcoma cells may express these markers at some stage differentiation. CD45 and/or CD14 can be used to distinguish monocytes and monocyte precursor cells from hemangiosarcoma cells based upon expression level, because these markers are expressed at higher levels in monocytes than in hemangiosarcoma cells.

Samples for analysis can be enriched for hemangiosarcoma cells by separation from erythrocytes and granulocytes by lysis or discontinuous gradients using conventional separation agents such as Ficoll-Hypaque.

As cultured cells can lose markers of interest after several passages (4-6 weeks), early passage cultured cells or other suitable cells, such as cells stably transfected to express desired markers, are optimal controls.

C. Samples for Transcript Detection

If marker expression is determined by measuring transcript levels, blood samples are typically used because they can be obtained in a relatively non-invasive manner. The methods can also be conducted with tissue biopsies from the tumor if available, but this is not typical because the methods are usually conducted to detect early onset of disease and because obtaining biopsies is more invasive. Many of the methods involving transcript detection are very sensitive and can be conducted with minimal sample volume (e.g., fractions of a milliliter of a blood sample). A variety of different sample types can be utilized in methods that involve detecting transcript levels including, but not limited to, blood and various samples taken from the tumor such as different types of effusion fluids (e.g., thoracic effusion, peritoneal effusion, pericardial effusion, or cystic fluid within a mass). Effusion fluids are collected from the site of the tumor. Effusion samples are usually treated with anticoagulants as described above for blood samples.

To measure the transcription level (and thereby the expression level) of the markers, a nucleic acid sample comprising mRNA transcripts of the markers, fragments, or nucleic acids derived from the mRNA transcripts is obtained. A nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, are all derived from the mRNA transcript and detection of such derived products is indicative of the presence and/or abundance of the original transcript in a sample. Thus, suitable samples include, but are not limited to, mRNA transcripts of the markers, cDNA reverse transcribed from the mRNA, cRNA transcribed from the cDNA, DNA amplified from the genes, and RNA transcribed from amplified DNA.

In some methods, a nucleic acid sample is the total mRNA isolated from a biological sample; in other instances, the nucleic acid sample is the total RNA from a biological sample. Any RNA isolation technique that does not select against the isolation of mRNA can be utilized for the purification of such RNA samples. For example, methods of isolation and purification of nucleic acids are described in detail in WO 97/10365, WO 97/27317, Chapter 3 of Laboratory Techniques in *Biochemistry and Molecular Biology: Hybridization With Nucleic Acid Probes*, Part I. *Theory and Nucleic Acid Preparation*, (P. Tijssen, ed.) Elsevier, N.Y. (1993); Chapter 3 of Laboratory Techniques in *Biochemistry and Molecular Biology: Hybridization With Nucleic Acid Probes*, Part 1. Theory and Nucleic Acid Preparation, (P. Tijssen, ed.) Elsevier, N.Y. (1993); and Sambrook et al., *Molecular Cloning: A Laboratory Manual*, Cold Spring Harbor Press, N.Y., (1989); *Current Protocols in Molecular Biology*, (Ausubel, F. M. et al., eds.) John Wiley & Sons, Inc., New York (1987-1993).

VI. Antibodies

A. General Considerations

Antibodies that specifically bind to the markers expressed by cells from hemangiosarcomas, angiosarcomas and/or leukemia cells are also provided. These antibodies can be of a variety of different types including, but not limited to, (i) monoclonal antibodies, (ii) chimeric antibody molecules; (iii) F(ab')2 and F(ab) fragments; (iv) Fv molecules; (v) single-chain Fv molecules (sFv); (vi) dimeric and trimeric antibody fragment constructs (e.g., diabodies and triabodies); (vii) humanized antibody molecules or canonized antibody molecules; (viii) Mini-antibodies or minibodies (i.e., sFv polypeptide chains that include oligomerization domains at their C-termini, separated from the sFv by a hinge region; and, (ix) any functional fragments obtained from such molecules, wherein such fragments retain specific-binding properties of the parent antibody molecule. The antibodies may be of any isotype, e.g., IgM, IgD, IgG, IgA, and IgE, with IgG, IgA and IgM often preferred. Humanized and caninized antibodies (see infra) may comprise sequences from more than one class or isotype.

The antibodies can be used with or without modification. Frequently, the antibodies are labeled by conjugating, either covalently or non-covalently, a detectable label. As labeled binding entities, the antibodies are particularly useful in diagnostic applications. The label can be any molecule capable of producing, either directly or indirectly, a detectable signal. Suitable labels include, but are not limited to, radioisotopes (e.g., $^{3}H$, $^{14}C$, $^{32}P$, $^{35}S$, $^{125}I$), fluorophores (e.g., fluorescein and rhodamine dyes and derivatives thereof), chromophores, chemiluminescent molecules, an enzyme substrate (including the enzymes luciferase, alkaline phosphatase, beta-galactosidase and horseradish peroxidase, for example).

The antibodies can be prepared, for example, using intact polypeptide or fragments containing antigenic determinants from proteins encoded by the markers that are disclosed herein. The polypeptide used to immunize an animal can be from natural sources, derived from translated cDNA, or prepared by chemical synthesis and can be conjugated with a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). Various adjuvants can be utilized to increase the immunological response, depending on the host species and include, but are not limited to, Freund's (complete and incomplete), mineral gels such as aluminum hydroxide, surface actives substances such as lysolecithin, pluronic polyols, polyanions, peptides, oil emulsions, dinitrophenol and carrier proteins, as well as human adjuvants such as BCG (bacille Calmette-Guerin) and *Corynebacterium parvum*.

Cultured hemangiosarcoma cell lines that express the markers can be prepared as described by Fosmire, S. P. et al. (2004) Laboratory Investigation 84:562-572, which is incorporated herein by reference in its entirety for all purposes.

B. Monoclonal Antibodies

Monoclonal antibodies that specifically recognize the markers described herein can be made from antigen containing fragments of the protein marker by the hybridoma technique, for example, of Kohler and Milstein (Nature, 256:495-

497, (1975); and U.S. Pat. No. 4,376,110). See also, Harlow & Lane, *Antibodies, A Laboratory Manual* (C.S.H.P., NY, 1988); and Goding et al., Monoclonal Antibodies: Principles and Practice (2d ed.) Acad. Press, N.Y. Human monoclonal antibodies that recognize the markers can be generated using, for example, the human B-cell hybridoma technique (Kosbor et al., *Immunology Today* 4:72 (1983); for a review, see also, Larrick et al., U.S. Pat. No. 5,001,065). The EBV-hybridoma technique is another approach to prepare monoclonal antibodies to the markers (see, e.g., Monoclonal Antibodies and Cancer Therapy, (1985) Alan R. Liss Inc., New York, N.Y., pp. 77-96).

C. Human Antibodies

Human monoclonal antibodies against a known antigen such as the markers disclosed herein can also be made using transgenic animals having elements of a human immune system (see, e.g., U.S. Pat. Nos. 5,569,825 and 5,545,806) or using human peripheral blood cells (Casali et al., 1986, Science 234:476). Human antibodies to the protein markers can be produced by screening a DNA library from human B cells according to the general protocol outlined by Huse et al., 1989, Science 246:1275. Antibodies binding to the protein markers are selected. Sequences encoding such antibodies (or binding fragments) are then cloned and amplified. The protocol described by Huse is often used with phage-display technology (see infra).

D. Humanized/Caninized and Chimeric Antibodies

Humanized or chimeric antibodies designed to reduce their potential antigenicity, without reducing their affinity for their target, are also provided. Preparation of chimeric, human-like and humanized antibodies have been described in the art (see, e.g., U.S. Pat. Nos. 5,585,089 and 5,530,101; Queen, et al., 1989, Proc. Nat'l Acad. Sci. USA 86:10029; and Verhoeyan et al., 1988, Science 239:1534). Humanized immunoglobulins have variable framework regions substantially from a human immunoglobulin (termed an acceptor immunoglobulin) and complementarity determining regions substantially from a non-human (e.g., mouse) immunoglobulin (referred to as the donor immunoglobulin). The constant region(s), if present, are also substantially from a human immunoglobulin.

The same approach taken in preparing humanized antibodies can also be used to incorporate the canine framework or constant region from dog immunoglobulins with the complementarity determining or variable region from another animal such as mouse, rat, rabbit or hamster, for instance.

E. Antibodies Prepared by Phage Display

Antibodies produced by the phage display methods that have specific binding affinity for the markers described herein are also included. Antibodies of this type can be produced using established methods (see, e.g., Dower et al., WO 91/17271, WO 92/01047; and Vaughan et al., 1996, Nature Biotechnology, 14: 309). In these methods, libraries of phage are produced in which members display different antibodies on their outer surfaces. Antibodies are usually displayed as Fv or Fab fragments. Phage displaying antibodies with a desired specificity are selected by affinity enrichment to a desired marker.

F. Bispecific and Hybrid Antibodies

Hybrid antibodies that can bind to a plurality of the markers disclosed herein are also provided. In such hybrid antibodies, one heavy and light chain pair is usually from an antibody against one marker and the other pair from an antibody raised against another marker. This results in the property of multi-functional valency, i.e., the ability to bind at least two different epitopes simultaneously, where at least one epitope is the epitope to which the anti-complex antibody binds. Such hybrids can be formed by fusion of hybridomas producing the respective component antibodies, or by recombinant techniques.

A hybrid antibody can bind any combination of two or more markers described herein (e.g., any two markers selected from the group consisting of CD117, CD34, CD133, CD51/61, CD31, CD105, CD106, CD146, vWF, CD18 and CD45). Examples of particular pairs that can be recognized by the hybrid antibody include, but are not limited to: 1) CD34 and CD51/61; 2) CD117 and CD51/61; 3) CD34 and CD31; 4) CD117 and CD31; and 5) CD34 and CD105; and 6) CD117 and CD105.

G. Antibodies Conjugated to a Cytotoxic Agent

The various antibodies that are provided can be used in the preparation of immunotoxins designed to kill cells that express one or more markers disclosed herein that are associated with a hemangiosarcoma or angiosarcoma (e.g., cells from hemangiosarcomas, angiosarcomas and/or or leukocyte or leukemia or lymphoma cells). These immunotoxins typically include two components and can be used to kill selected cells expressing the desired marker(s) in vitro or in vivo. One component is the "delivery vehicle," which is capable of delivering the toxic agent to a particular cell type, such as cells expressing the desired marker(s). The delivery vehicle in this instance is an antibody that specifically recognizes one or more of the markers described herein. To improve the selectivity in delivery, the antibody can be a hybrid antibody that binds at least two of the markers. The second component is a cytotoxic agent that usually is fatal to a cell when attached or adsorbed to the cell. The two components are chemically bonded to one another by any of a variety of well-known chemical procedures. For example, when the cytotoxic agent is a protein and the second component is an intact immunoglobulin, the linkage may be by way of heterobifunctional cross-linkers, e.g., SPDP, carbodiimide, glutaraldehyde, or the like. Further guidance regarding the production of various immunotoxins can be found, for example, in "Monoclonal Antibody—Toxin Conjugates: Aiming the Magic Bullet," Thorpe et al., Monoclonal Antibodies in Clinical Medicine, Academic Press, pp. 168-190 (1982), which is incorporated herein by reference in its entirety for all purposes. The components may also be linked genetically (see Chaudhary et al., Nature 339:394 (1989), incorporated herein by reference in its entirety for all purposes).

A variety of cytotoxic agents are suitable for use in immunotoxins. Cytotoxic agents can include radionuclides, such as Iodine-131 or other isotopes of iodine, Yttrium-90, Rhenium-188, and Bismuth-212 or other alpha emitters; a number of chemotherapeutic drugs, such as vindesine, methotrexate, adriamycin, and cisplatin; and cytotoxic proteins such as ribosomal inhibiting proteins like pokeweed antiviral protein, *Pseudomonas* exotoxin A, ricin, diphtheria toxin, ricin A chain, or an agent active at the cell surface, such as the phospholipase enzymes (e.g., phospholipase C).

VII. Pharmaceutical Compositions

The antibodies that are described herein, either in unconjugated form or conjugated to a cytotoxic agent, can serve as the active ingredient in pharmaceutical compositions formulated for use in the various applications disclosed herein. These pharmaceutical compositions may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., Remington's Pharmaceutical Sciences, 17th ed. 1985)).

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, topically, intravenously, intraperitoneally, subcutaneously, intrathecally (for intracranial angiosarcoma, e.g.) or intratumorally when the tumor is in the subcutaneous space. The formulations of compounds can be presented in unit-dose or multi-dose sealed containers, such as ampoules and vials. Solutions and suspensions can be prepared from sterile powders, granules, and tablets of the kind previously described.

The composition can be administered by means of an infusion pump, for example, of the type used for delivering chemotherapy to specific organs or tumors. Compositions of the inventions can be injected using a syringe or catheter directly into a tumor or at the site of a primary tumor prior to or after excision; or systemically following excision of the primary tumor. The compositions of the invention can be administered topically or locally as needed. For prolonged local administration, the enzymes may be administered in a controlled release implant injected at the site of a tumor. For topical treatment of a skin condition, the formulation may be administered to the skin in an ointment or gel.

The antibodies and pharmaceutical compositions thereof are particularly useful for parenteral administration, i.e., subcutaneously, intramuscularly or intravenously. The compositions for parenteral administration will commonly comprise a solution of the antibody or antibody conjugate or a cocktail thereof dissolved in an acceptable carrier, preferably an aqueous carrier. A variety of aqueous carriers can be used, e.g., water, buffered water, phosphate buffered saline (PBS), 0.4% saline, 0.3% glycine, human albumin solution and the like. These solutions are sterile and generally free of particulate matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride and sodium lactate. The concentration of antibody in these formulations can vary widely, i.e., from less than about 0.005%, usually at least about 1% to as much as 15 or 20% by weight and will be selected primarily based on fluid volumes, viscosities, etc., in accordance with the particular mode of administration selected.

The dose administered to a subject should be sufficient to effect a beneficial response in the subject over time (e.g., to reduce tumor size or tumor load). Early detection may allow for prolonged remission/survival since the tumor would not yet be clinically evident and would be more amenable to control or elimination using the aforementioned treatments. The optimal dose level for any patient will depend on a variety of factors including the efficacy of the specific modulator employed, the age, body weight, physical activity, and diet of the patient, and on the severity of a particular disease. The size of the dose also will be determined by the existence, nature, and extent of any adverse side-effects that accompany the administration of a particular compound or vector in a particular subject.

VIII. Treatment Methods

Once a subject has been diagnosed using the methods provided herein as having an elevated risk of hemangiosarcoma or angiosarcoma, various treatment options can be implemented. One option is to conduct surgery to try to excise the tumor (if a tumor mass is grossly detectable) using standard surgical procedures in the art. Another option is to begin chemotherapy to try to eradicate the tumor. Of course combined treatment regimes using both surgery and chemotherapy can be implemented.

The antibodies and methods disclosed herein can in a sense be used "prophylactically" in that they can be used to detect "tumor cells" before the tumor is clinically detectable using existing state-of-the-art techniques. This means that treatment (e.g., administration of antibodies such as described herein) need not be administered blindly simply to ward off the disease. Rather treatments can be tailored to the subject's particular needs when the disease is still at a microscopic stage, thereby increasing the ability to prevent the tumor from progressing to clinically evident disease. Antibodies of the invention can be combined with antibodies against other molecules expressed in hemangiosarcomas. These include VEGF, c-KIT, and VEGFR-2.

In therapeutic applications, compositions (e.g., the antibodies and pharmaceutical compositions provided herein or to other molecules present on hemangiosarcomas as described above) are administered to a subject that already has been diagnosed as having a hemangiosarcoma or an angiosarcoma (e.g., using the methods provided herein). The composition is administered in an amount sufficient to cure or at least partially arrest the disease and its complications (e.g., to reduce the tumor size or arrest its spread). An amount adequate to accomplish this is defined as a "therapeutically effective dose." Amounts effective for this use will depend upon the severity of the disease, the extent to which the tumor has metastasized, the age and weight of the subject, and other factors known to those of skill in the art, but generally range from about 1 to about 200 mg of antibody per dose, with dosages of from 5 to 70 mg per patient being more commonly used. Dosing schedules will vary with the disease state and status of the patient, and will typically range from a single bolus dosage or continuous infusion to multiple administrations per day (e.g., every 4-6 hours), or as indicated by the treating physician and the patient's condition.

It must be kept in mind that the materials of this invention may generally be employed in serious disease states, that is life-threatening or potentially life-threatening situations. In such cases, in view of the minimization of extraneous substances and the lower probability of "foreign substance" rejections which are achieved using certain antibodies described herein (e.g., chimeric or humanized antibodies), it is possible, and may be felt desirable by the treating clinician, to administer substantial excesses of these antibodies

IX. Other Applications

A. Monitoring High Risk Individuals for Disease

The methods that are provided can be used as part of a monitoring program for dogs at high risk for hemangiosarcomas and for humans at high risk for angiosarcomas (see supra). In such a program, the methods as described above are repeated at intervals determined by the responsible clinician to monitor whether there is any change in the status of the subject. In such methods, the expression data can be compared against a variety of different values. The data may be compared, for example, with a control that establishes a threshold level that provides a statistical basis for concluding whether the subject has hemangiosarcoma or angiosarcoma. Alternatively, the expression data may be compared with the expression level from the prior measurement. Depending upon the trend that is observed, the clinician may opt to simply further monitor the subject or initiate treatment.

B. Detection of Residual Disease in Individuals Undergoing Treatment.

The markers used initially to detect and diagnose HSA can also be used to monitor disease progression, in individuals being treated for the disease. Such techniques allow caregivers to monitor efficacy of treatment regimens and allow modification of those regimens based on an individual's response.

C. Identification of Cells Expressing Desired Markers

The methods that are provided herein can also be utilized to select and collect cells that express the desired markers. For example, cells that express markers characteristic of hemangiosarcoma or angiosarcoma (e.g., cells expressing a primitive hematopoietic cell marker, an endothelial cell marker but not a leukemia or leukocyte-specific cell marker) can be identified using the antibody tagging methods described above. These cells can be selected and collected using any of a variety of cell sorters that are known in the art.

Once collected, the cells may be cultured in suitable media at 37° C. for a period of time (e.g., 2 hr) to promote internalization of surface antigens with bound antibodies. The antibodies once taken up can be broken down by lysosomal or proteosomal degradation, with new synthesis or recycling to the surface of the characteristic antigens.

The collected cells can be used in a variety of other applications including, for example, to (1) identify early genetic lesions to define events in molecular progression; (2) identify genes or proteins that interact with environmental factors (e.g., cigarette smoke, other environmental carcinogens) to promote cancer; (3) derive novel diagnostic tests (e.g., new, improved antibodies); and (4) derive xenotransplant tumor models in mice (putting the human or dog tumor in an immunodeficient mouse (see, e.g., Akhtar et al, (2004) Neoplasia, 6:106-116) to test specific therapies in vivo.

X. Kits

Kits that can be used in the methods described herein are also provided. The kits in general include one or more species that can be used to detect the expression of one or more primitive hematopoietic cell markers, one or more endothelial cell markers and/or one or more leukemia or leukocyte-specific cell markers. The kits can thus be used, for example, to diagnose the presence of hemangiosarcomas in dogs and angiosarcomas in humans.

The species included in the kits that are used to detect the presence of the maker(s) can be an antibody that specifically binds to a marker, a probe that specifically hybridizes to a target sequence of a marker that encodes the marker, and/or a primer that can be utilized to specifically amplify a target sequence (e.g., a sequence that encodes a marker). The antibodies, probes and/or primers are typically stored in suitable storage containers. The antibodies, probes and/or primers that are included in a kit may be labeled. If so, they are typically differentially labeled so antibodies, probes or primers specific for different markers have different labels. If the antibodies, probes or primers are not labeled, the kits can include suitable labels such as described herein. Kits may also include instructions that provide directions on how to use the antibodies, probes and/or primers to detect expression of the markers.

One example of a kit that can be used to distinguish between a hemangiosarcoma or angiosarcoma and leukemia contains a plurality of antibodies, including: (1) at least one antibody that specifically binds to a primitive hematopoietic cell marker, (2) at least one antibody that specifically binds to an endothelial cell marker, and (3) at least one antibody that specifically binds to a leukemia marker.

A specific example of such an antibody kit is one that contains an antibody that specifically binds CD117, an antibody that specifically binds CD34, an antibody that specifically binds CD51/61 and an antibody that binds CD18, CD45, CD3, CD21, CD5 or CD11b. Other kits include the same antibodies but include an antibody that can bind more than one leukemia or leukocyte-specific cell marker selected from the group consisting of CD18, CD45, CD3, CD21, CD5 and CD11b.

Other related kits, rather than including antibodies, include probes that specifically hybridize with nucleic acids encoding these particular markers and/or primers that specifically amplify nucleic acids encoding these particular markers.

The following examples are provided to illustrate certain aspects of the methods and compositions that are provided. As such, they should not be construed to limit the scope of the claimed invention.

Example 1

Detection of Hemangiosarcomas in Dogs

I. Materials and Methods

A. Flow Cytometer

Beckman Coulter Epics XL flow cytometer, catalog #6605464 (Beckman Coulter, Inc., Hialeah, Fla.) running the Expo 32 software package, catalog #6605433 (Beckman Coulter, Inc.), or BD FACSCalibur™ flow cytometer, catalog #343020 (Becton Dickinson Immunocytometry Systems, Mountain View, Calif.) running the BD CellQuest™ software package, catalog #342182 (BD Biosciences Immunocytometry Systems).

B. Antibodies

The testing described in this example was conducted with the antibodies listed below. However, these antibodies are available in different conjugate forms to provide flexibility for multiparameter flow cytometry, and all can be conjugated to a variety of fluorochromes using the AlexaFluor technology (Molecular Probes-Invitrogen, Eugene, Oreg., see http://www.probes.com/handbook/sections/0103.html). In addition, Serotec, Inc. and BD Biosciences offer a range of canine leukocyte typing reagents that can be incorporated into the assay (for example, see world wide web-bdbiosciences.com/pdfs/brochures/03-7900030-3-A1.pdf).

a. Control antibody-1: Mouse IgG2a conjugated to phycoerythrin (PE), clone G155-178, catalog #559319, BD Pharmingen™ (San Diego, Calif.)

b. Control antibody-2: Mouse IgG1, k conjugated to fluorescein isothiocyanate (FITC), clone MOPC-2, catalog #1554679, BD Pharmingen™ (San Diego, Calif.)

c. Control antibody-3 and second-step reagent: Goat Anti-Mouse IgG & IgM (human adsorbed) conjugated to FITC, catalog #555988, BD Pharmingen™ (San Diego, Calif.)

d. Control antibody-4 and second-step reagent: Sheep Anti-Mouse IgG (whole molecule) F(ab')2 fragment, affinity isolated, conjugated to PE, catalog#P8547, Sigma-Aldrich (St. Louis, Mo.)

e. Anti-CD117 (c-Kit): clone ACK45 (Rat IgG2b, κ) conjugated to PE, catalog #553869, BD Pharmingen™ (San Diego, Calif.)

f. Anti-CD34: clone 2E9 (Ms IgG1, κ) conjugated to biotin, catalog #550427, BD Pharmingen™ (San Diego, Calif.)

g. Anti-CD51/61($\alpha_v\beta_3$ integrin): clone LM606 (Ms IgG1) conjugated to FITC, catalog #MAB1976F, Chemicon Intl., (Temecula, Calif.)

h. Anti-CD146 (MUC18, S-endo): clone P1H12 conjugated to biotin, catalog #MAB16985B, Chemicon Intl., (Temecula, Calif.)

i. Anti-CD105 (endoglin): clone 8E11(Ms IgM, κ) conjugated to FITC, catalog #9810-02, Southern Biotechnology Associates (Birmingham, Ala.)

j. Anti-CD3: clone CA17.2A12 (Ms IgG1) conjugated to FITC, catalog #MCA1774F, Serotec, Inc. (Raleigh, N.C.)

k. Anti-canine B-cells (probably CD21): clone CA2.1D6 (Ms IgG1) conjugated to PE, catalog #MCA1781PE, Serotec, Inc. (Raleigh, N.C.)

l. Anti-CD5: clone YKIX322.3 (Rat IgG2a) conjugated to FITC, catalog #MCA1037F, Serotec, Inc. (Raleigh, N.C.)

m. Anti-LFA-1 (CD11a and/or CD18):

Anti-CD11/18 (LFA-1): clone YKIX490.6.4 (Rat IgG2c) conjugated to FITC, catalog #MCA1040F, Serotec, Inc. (Raleigh, N.C.)

Anti-CD18 (integrin β2 chain): clone CA1.4E9 (Ms IgG1) unconjugated, catalog #MCA1780, Serotec, Inc. (Raleigh, N.C.)

Anti-CD11a (integrin αL): clone HI111 (Ms IgG1, κ) conjugated to PE-Cy5 (BD Cy-Chrome™), catalog #551131, BD Pharmingen™ (San Diego, Calif.)

n. Anti-CD45: clone YKIX716.13 (Rat IgG2b) conjugated to PE, catalog #MCA1042PE, Serotec, Inc. (Raleigh, N.C.)

o. Anti-CD90 (Thy-1): clone YKIX337.217 (Rat IgG2b) unconjugated, catalog #MCA1036G, Serotec, Inc. (Raleigh, N.C.)

p. Anti-CD8: clone YCATE55.9 (Rat IgG1) conjugated to PE, catalog #MCA1039PE, Serotec, Inc. (Raleigh, N.C.)

q. Anti-CD4: clone YKIX302.9 (Rat IgG2a) conjugated to FITC, catalog #MCA1038F, Serotec, Inc. (Raleigh, N.C.)

r. Anti-CD14: clone M5E2 (Ms IgG2a, κ) conjugated to PE, catalog #555398, BD Pharmingen™ (San Diego, Calif.)

s. Anti-CD133 clone 13A4 (Rat IgG1, κ) conjugated to PE, catalog #12-1331-82, eBioscience (San Diego, Calif.)

t. Labeled streptavidin secondary reagents and labeling kits:

Streptavidin-FITC (ZyMAX grade), catalog #43-8311, Zymed Laboratories (South San Francisco, Calif.)

Streptavidin-PE, catalog #15-4301, Zymed Laboratories (South San Francisco, Calif.)

Streptavidin-APC, catalog #SA1005, Caltag Laboratories (Burlingame, Calif.)

Alexa Fluor® 647 Monoclonal Antibody Labeling Kit, catalog # A-20186, Invitrogen (Carlsbad, Calif.)

Alexa Fluor® 488 Monoclonal Antibody Labeling Kit, catalog # A30006, Invitrogen (Carlsbad, Calif.)

C. Solutions a. RBC lysis buffer: 8.3 g/L of ammonium chloride ($NH_4Cl$) in 10 mM Tris, pH 7.2, catalog #R7757, Sigma-Aldrich (St. Louis, Mo.).

b. Phosphate buffered saline (PBS): 8 g/L of sodium chloride (NaCl), 0.2 g/L of potassium chloride (KCl), 1.44 g/L of sodium phosphate ($Na_2PO_4$), 0.24 g/L of potassium dihydrogen phosphate ($KH_2PO_4$).

c. Staining buffer: PBS with 0.1% (0.1 g/100 mL) of bovine serum albumin (BSA) and 0.1% sodium azide ($NaN_3$). Can substitute 0.1% fetal bovine serum (FBS) or 0.1% horse serum for BSA.

D. Dogs

Blood samples from health dogs and from dogs with biopsy-confirmed HSA, leukemia, or other splenic abnormalities (nodular hyperplasia, splenic hematoma) were obtained from a protocol reviewed and approved by the Institutional Animal Care and Use Committee and the Institutional Review Board of AMC Cancer Center. Dog owners were required to sign Informed Consent donating blood and tumor samples to Dr. Jaime Modiano at AMC Cancer Center/University of Colorado Health Science Center. Whole blood samples were submitted from veterinary clinics throughout the United States and shipped at 4° C. in EDTA using a priority overnight courier.

a. The Dal-4 cell line was derived from a male Dalmatian (see Fosmire, S. P., et al. (2004) Laboratory Investigation 84:562-572).

b. The DD-1 cell line was derived from a male Golden Retriever/Great Pyrenees mix (see Fosmire et al, tab Invest, 2004).

c. Normal blood samples (unaffected dog controls) were obtained from seven dogs.

d. Samples were obtained from three dogs with leukemia (chronic lymphocytic leukemia or acute lymphoblastic leukemia).

e. Samples from affected dogs (biopsy-confirmed hemangiosarcoma) were obtained from 10 dogs.

II. Methods

A. Sample Acquisition

Cell lines were maintained as described by Fosmire, S. P., et al. (2004) Laboratory Investigation 84:562-572. Briefly, cells were fed three times weekly and passaged when they reached approximately 80% confluence in F12K media (ATCC, Manassas, Va.) supplemented with 10% fetal bovine serum (Hyclone, Logan, Utah), endothelial growth supplements (BD Biosciences, San Jose, Calif.), and 100,000 IU/ml of high molecular weight heparin (Sigma-Aldrich, St. Louis, Mo.).

Sterile venous blood samples from normal or affected dogs were obtained at the attending veterinarians' offices with Informed Consent of the owners by jugular venipuncture using 22 gauge needles and collected into 6-ml syringes using standard procedures of veterinary care. Blood was immediately transferred into evacuated 3-ml collection tubes containing EDTA.

Sterile thoracic, pericardial, or peritoneal effusions from affected dogs with thoracic, atrial, or splenic/hepatic hemangiosarcoma were collected by thoracocentesis, pericardiocentesis, or pleurocentesis using standard procedures of veterinary care. The effusions were immediately transferred into evacuated 3-ml collection tubes containing EDTA B. Sample Preparation Cell lines were detached using 0.1 mM EDTA and sterile cell scrapers to maintain the integrity of extracellular antigens, washed in PBS, and resuspended in staining buffer at the indicated concentrations for staining. In some procedures, cells were separated using a discontinuous Ficoll-hypaque gradient. HSA cells from four cell lines (DD-1, Dal-4, CHAD-G4.1, and CHAD-B7.4) were shown to float on the Ficoll-hypaque gradient with a similar buoyant density as other blood mononuclear cells.

Blood samples were subjected to red blood cell lysis using the following procedure. Blood was transferred to 15 ml conical tubes and centrifuged at 2,000 RPM (1,600×g) for 15 min in a Sorvall RT-6000 centrifuge. Plasma was aspirated under vacuum and cells were washed in 10 volumes of PBS.

Cell suspension was again centrifuged at the same speed for 15 minutes and supernatant was aspirated under vacuum. Cells were gently resuspended in 3 volumes of RBC lysis buffer and incubated at 37° C. After 10 minutes, five volumes of PBS were added to the sample and the cells were centrifuged as above. The procedure was repeated twice. The remaining white blood cells (nucleated blood cells) were counted using an automated particle analyzer (Cell-Dyn 1200, Abbott Diagnostics, Santa Clara, Calif.), resuspended in staining buffer and divided into $3\times10^5$ to $1\times10^6$ per condition for staining.

C. Cell Labeling/Immunophenotyping

All procedures were at 4° C. (except where noted). Plates, cells and antibodies were kept on ice and centrifuged at 4° C.

Preparation of Antibodies: Total staining volume was 25 μl/sample. Directly conjugated antibodies were used at 5 μl/sample (as recommended by the manufacturers for "1 test"); negative control antibodies were used at 2 μl/sample.

Negative controls for Streptavidin-APC, Control antibody-FITC, Control antibody-PE were prepared individually, in pairs (APC-FITC, APC-PE, FITC-PE), and for three-color staining (APC-FITC-PE)

Experimental conditions included anti-CD117-PE, anti-CD34-biotin, anti-CD51/CD61-FITC, and anti-CD45-PE prepared individually, in pairs, or for three-color staining (anti-CD117, anti-CD34, anti-CD51/CD61)

Red blood cells were lysed as described above. Cells were divided into aliquots of $5\times10^5$ cells in 100 μl of staining buffer into individual wells of a 96 well, round-bottom plate and centrifuged 2 min at 1,200 RPM using a plate adaptor in the RT-6000 centrifuge. Supernatant was discarded by inverting the plate and shaking vigorously without dislodging the pellets.

The blocking step included adding 10 μg/ml of non-specific antibody (e.g., goat IgG) in 5 μl for 10 min. Primary antibodies (negative controls or test antibodies) were then added as indicated above in a total volume of 25 μl and incubated at 4° C. for 30 min.

One hundred μl of staining buffer were then added to each well with gentle agitation and the plates were centrifuged as described above. The cell pellets were washed once more in 100 μl of staining buffer.

Samples that did not require a second step reagent (directly conjugated antibodies) were resuspended in 100 μl of staining buffer and transferred to 12×75 polystyrene tubes. Each sample was fixed in 2% neutral buffered formalin (by adding an additional 350 μl of staining buffer and 150 μl of 10% formalin). Samples were kept protected from light at 4° C. until analysis (<48 hr).

Samples that required a second step reagent (e.g., streptavidin-APC or anti-mouse FITC) were kept in the 96 well plates. Streptavidin-APC was used at a concentration of 2 μg/ml in 50 μl. Anti-mouse-FITC was used at 1 μg/ml in 50 μl. Samples were incubated for 20 min at 4° C. At the end of the incubation period, 100 μl of staining buffer were added to each well with gentle agitation and the plates were centrifuged as described above. The cell pellets were washed once more in 100 μl of staining buffer.

Samples were resuspended in 100 μl of staining buffer and transferred to 12×75 polystyrene tubes. Each sample was fixed in 2% neutral buffered formalin (by adding an additional 350 μl of staining buffer and 150 μl of 10% formalin). Samples were kept protected from light at 4° C. until analysis (<48 hr).

D. Flow Cytometry

The instrument was calibrated daily as per the manufacturers' directions.

Cells were calibrated by running a positive control sample and a negative control sample to determine the extent of adjustment needed, if any, for the detectors and for color compensation.

Gates were set based on the negative control samples for cell populations based on light scatter and fluorescence emission.

Each sample was run on the "high" setting (>300 events/second) and 5000 to 20,000, or preferably, >100,000 events, were acquired in the light scatter gates.

Samples were analyzed by assessment of fluorescence for each antigen based on the whole population and based on gating of discrete subpopulations identified based on light scatter properties.

Blood from dogs with HSA, leukemia, and nodular hyperplasia was used to optimize flow cytometry conditions. Blood from fourteen dogs (seven with HSA, six normal, and one splenic E. Threshold Level The threshold for the analysis to date was based on negative controls.

A reference range can be established based on the numbers of detectable cells that have the test markers in a suitable population of disease-free, low risk dogs.

F. Controls

The controls included non-specific antibodies (to determine background staining that is not antigen-specific), blood from normal healthy dogs (to determine the extent of circulating cells that express the markers in these samples), leukemia cells (to distinguish between leukemia and hemangiosarcoma), and separation of normal cell populations and hemangiosarcoma cell populations in patient samples (see below).

III. Results

Results obtained from samples from the dogs listed above show that:

a. Canine hemangiosarcoma cells express approximately equivalent levels of CD34 and CD117;

b. Canine hemangiosarcoma cells express CD105, CD146, and CD51/CD61;

c. Canine hemangiosarcoma cells express variable levels of CD45 and CD14, which are generally distinguishable from the levels of CD45 and CD14 seen in canine leukocytes;

d. Circulating canine hemangiosarcoma cells express equivalent levels of CD34 to those seen in cultured canine hemangiosarcoma cells;

e. Canine hemangiosarcoma cells have unique light scatter patterns that are distinguishable from the light scatter seen in canine leukocytes (FIGS. 1A-1H and FIGS. 2A-2H). Canine hemangiosarcoma cells are large (they segregate to higher channels than leukocytes based on forward angle (or 0°) light scatter) and they are granular or have complex cytoplasm, resulting in right angle (or 90°) side scatter that is comparable to or higher than granulocytes (neutrophils, eosinophils, basophils).

Hemangiosarcoma cells and leukocytes or leukemia cells will be generally distinguishable based on light scatter by using a laser power setting that localizes the mean forward light scatter for the lymphoid cells to approximately channel 250 (of 1024) and the mean right angle light scatter for the lymphoid cells to approximately channel 25 (of 1024). Under these conditions, monocytes will usually localize at or near channel 400 for the mean forward light scatter and at or near channel 50 for the mean right angle light scatter; granulocytes will usually localize at or near channel 400 for the mean forward light scatter and at or near channel 300 for the mean right angle light scatter. Leukemia cells will usually localize between channels approximately 300 and approximately 1,000 for the mean forward light scatter and between channels approximately 25 and approximately 300 for the mean right angle light scatter. In contrast, hemangiosarcoma cells will usually localize between channels approximately 400 and approximately 1,000 for the mean forward light scatter and between channels approximately 300 and approximately 1,000 for the mean right angle light scatter. Certain types of leukemia cells and hemangiosarcoma cells may show overlapping light scatter properties. These include chronic granulocytic leukemia and possibly some types of myeloid leukemias such as megakaryocytic leukemia. In the subclinical stage where such circulating cells may not manifest as clinical disease, these diseases (leukemia and hemangiosarcoma) can be distinguished based on the expression of cell markers as described herein.

f. Normal canine leukocytes (FIGS. 1E and 1F) and canine leukemia cells (not shown) do not express CD51/CD61;

g. The patterns of expression of CD117/CD51/CD61 (FIGS. 1E-1H) and of CD45/CD51/CD61 (FIGS. 2E-2H) are distinct between canine leukocytes and canine hemangiosarcoma cells;

h. Blood from unaffected healthy dogs will be used to establish precise reference ranges for expression of CD34+, CD117+, CD51/CD61+, CD45, CD18+ in these cells, individually and in groups;

i. Blood from unaffected healthy dogs to which known concentrations of hemangiosarcoma cells are added will be used to define the sensitivity of the assay; and j. Blinded samples similar to those used to define the sensitivity in (g) can be used to define the specificity of the assay.

IV. Conclusions

The results obtained herein demonstrate that multiparameter flow cytometry can be used to identify canine hemangiosarcoma cells in the circulation of dogs with this disease and to distinguish these malignant cells from normal canine leukocytes.

The same approach described in this example can be used to detect and diagnose angiosarcoma in human subjects. As described supra, antibodies specific for the markers that are analyzed in the analysis are commercially available.

Example 2

Hemangiosarcoma Detection in Dogs by Determining HSA Cell Levels

The light scatter parameters of HSA cells as defined in Example 1 were used to define the flow cytometric light scatter parameters of HSA cells versus normal leukocytes to determine HSA levels in patient samples.

The percentage of cells co-expressing one or more markers of immature bone marrow precursor cells (c-KIT, CD34, CD133) and $\alpha_v\beta_3$-integrin ranged between 0.5% and 2.0% for dogs with HSA, and was generally less than 0.1% for unaffected dogs (0.03% in a dog with splenic hematoma, see FIGS. 5A-5C, except for two highly conditioned, healthy dogs that had 0.2-0.3% EPCin the circulation. The mean, median, standard deviation, and standard error of the mean for each group were 0.90, 0.93, 0.26, and 0.10 for dogs with HSA, and 0.10, 0.04, 0.13 and 0.05 for unaffected dogs. Non-parametric analyses (analysis of variance, Wilcoxon rank test, Wilcoxon two-sample test, and Kruskal-Wallis test) all indicate the two groups were significantly different from each other ($p<0.01$); working on the assumption that EPC in the circulation are rare events that follow a Poisson distribution, the results show a trend for increased frequency ($t=2.22$) of EPC in the blood from dogs with biopsy confirmed HSA.

When the same criteria were applied using antibodies against peripheral blood leukocytes (CD3, CD21, CD11b), the frequency of gated cells was also <<0.1%, whether applied to normal or leukemic white blood cells.

Analyses was done of samples in which leukocytes were excluded by using a "dump gate" for T cells (CD5), B cells (CD21), and granulocytes (CD11b) labeled with FITC. Two dogs were unaffected, while another had HSA of the right atrium. The frequency of cells obtained using this method was similar to that obtained without using the "dump gate" both for the unaffected dogs (0%, 0.01%) and for the affected dog (0.5%), although interpretation was much simpler due to the reduced background noise.

Example 3

Expression of HSA Markers in Established Cell Lines

Four established canine cell lines of HSA origin were monitored for expression of bone marrow precursor cell markers (e.g., c-KIT, CD34, CD133), using flow cytometry and/or immunofluorescence techniques described in Example 1. Differences in expression from other cell lineages of hematopoietic differentiation, as well as from mature, fully differentiated, leukocytes and vascular endothelial cells and proteins that define lineage commitment to T-lymphocytes (CD3), B-lymphocytes (CD21), granulocytes (CD11b), and vascular endothelial cells (CD105, CD146, $\alpha_v\beta_3$-integrin) are shown in Table 2.

TABLE 2

| Surface | Cell Lines | | | |
|---|---|---|---|---|
| Markers | DD-1 | Dal-4 | CHAD G4.1 | CHAD B7.4 |
| CD3 | − | − | − | − |
| CD11b | − | − | − | − |
| CD14 | +[1] | − | − | − |
| CD21 | − | − | − | − |
| CD34 | + | + | + | − |
| CD45 | + | +[2] | +[1] | +[1] |
| $\alpha_v\beta_3$-integrin (CD51/CD61) | + | + | + | + |
| CD105 | + | + | + | + |
| CD133 | + | + | + | + |
| c-KIT (CD117) | + | + | + | + |
| CD146 | + | + | + | + |

[1]Expression was only upregulated in the presence of endothelial growth factors

[2]A subpopulation of approximately 5% of the cells was positive

Figures 4A, 4B, 4C, 4D, 4E, 4F, 4G, 4H, 4I, 4J, 4K, 4L, 4M, 4N, 4O, 4P:
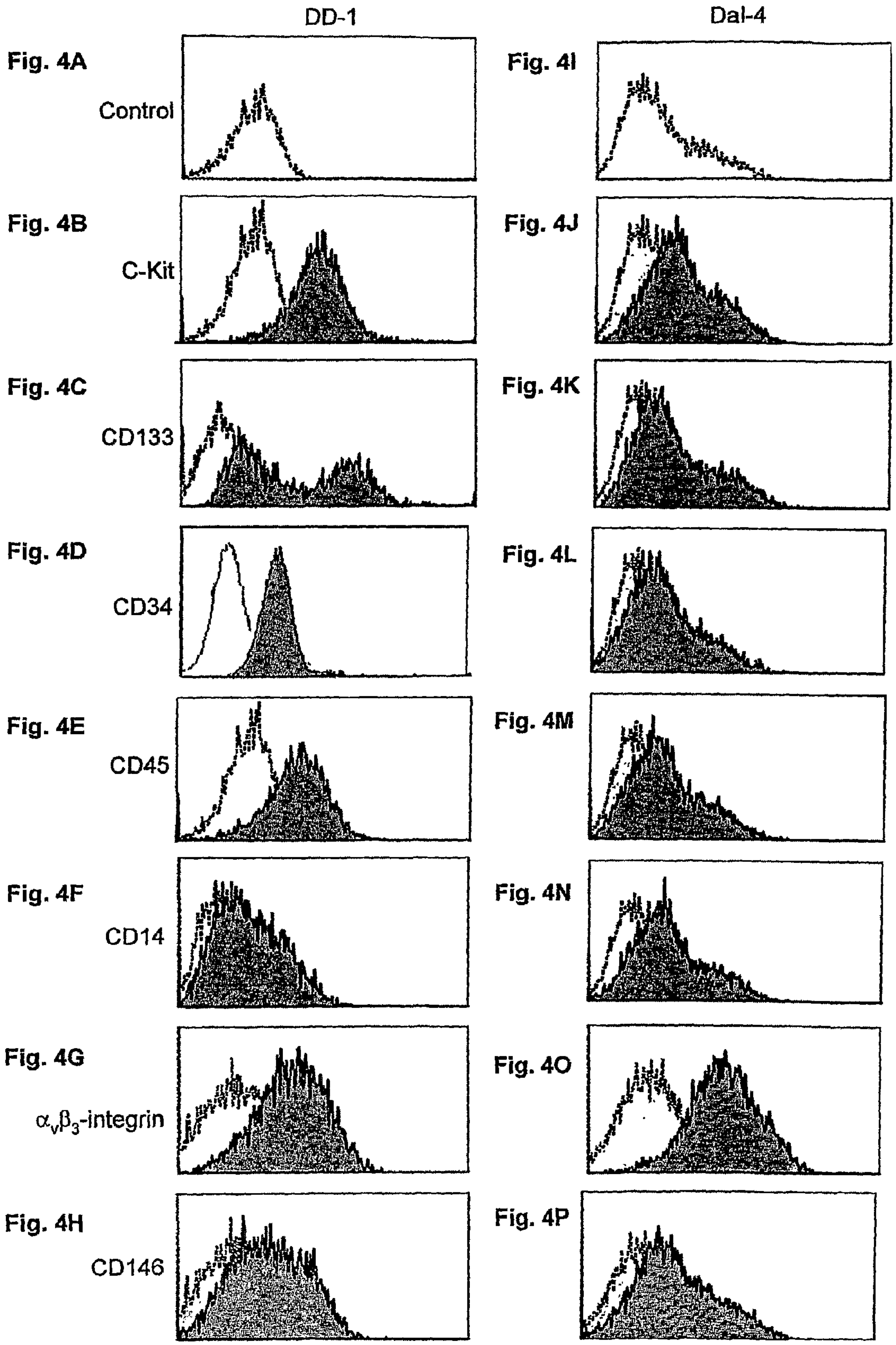
FIGS. 4A-4P show one-dimensional flow cytometry histograms for representative hemangiosarcoma cell lines, DD-1 (FIGS. 4A-4H) and Dal-4(FIGS. 4I-4P), stained using antibodies against irrelevant controls (FIGS. 4A and 4I), c-KIT (FIGS. 4B and 4J), CD133 (FIGS. 4C and 4K), CD34 (FIGS. 4D and 4L), CD45 (FIGS. 4E and 4M), CD14 (FIGS. 4F and 4N), $\alpha_v\beta_3$-integrin (FIGS. 4G and 4O), and CD146 (FIGS. 4H and 4P).

Each of the cell lines is positive for c-KIT, CD133, $\alpha_v\beta_3$-integrin, CD105 and CD146; none express prototypical leukocyte markers CD3, CD21 or CD11b, and the expression of CD34, CD45 and CD14 is variable (See, e.g., FIGS. 4A-4P). These cell lines all express CD105, CD146 and $\alpha_v\beta_3$-integrin. While other hematopoietic tumors (leukemias, mast cells tumors and multiple myeloma) can express one or more of these markers, the pattern of co-expression where cells have c-KIT/CD34/CD133 and $\alpha_v\beta_3$-integrin, but no detectable leukocyte markers (CD3, CD21, or CD11b), seems to be uniquely associated with HSA.

It is noteworthy that under conditions of logarithmic growth certain subpopulations in the cultures lacked expression of CD133, CD105, and CD146, and the density of receptor expression was also variable. HSA cell lines have also been shown to express VEGFR2. The levels of expression for CD45, CD34 and CD105 increase in DD-1 and CHAD-B7.4 cells when they are cultured in the presence of endothelial growth factors as compared to basal media (F12K media supplemented with 10% fetal bovine serum). In addition, when the lines are maintained in culture for extended periods of time (e.g., more than 10-15 passages), there is a tendency by the cells to down regulate expression of CD133, c-KIT, CD34, and CD105. For example, CD34, which was positive in Dal-4 cells and in early passage DD-1 cells, was lost in DD-1 cells after several passages (see FIGS. 4D and 4L). Various non-mutually exclusive possibilities can account for these changes: (1) expression of these proteins is unnecessary in the artificial environment of tissue culture, (2) the cell lines are genetically unstable and "drift", or (3) "stem cells" in the populations are lost at the expense of differentiated progeny.

All publications, patents and patent applications cited herein are hereby incorporated by reference in their entirety for all purposes to the same extent as if each individual publication, patent or patent application were specifically and individually.

What is claimed is:

1. A method for early detection of hemangiosarcoma in a dog, the method comprising:

(a) providing a population of cells obtained from a blood sample from the dog;

(b) determining (i) the level at which cells within the cell population concurrently express a plurality of cell markers, the plurality of cell markers comprising at least one primitive hematopoietic cell marker and at least one endothelial cell marker, and (ii) whether or not cells within the cell population express at least one leukemia cell marker or leukocyte-specific cell marker, wherein the at least one primitive hematopoietic cell marker is selected from the group consisting of CD117, CD34, and CD133;

the at least one endothelial cell marker is selected from the group consisting of CD51/CD61, CD31, CD105, CD106 CD146 and von Willebrand Factor (vWF); and the at least one leukemia cell marker or leukocyte-specific cell marker is selected from the group consisting of CD18, CD3, CD5, CD21 and CD11b; and (c) comparing the level at which cells in the cell population concurrently express the plurality of cell markers with a control level of concurrent expression of the markers, wherein (1) an increase in the expression level of the plurality of cell markers relative to the control expression level, and (2) the absence of expression of CD18, CD3, CD5, CD21 and/or CD11b collectively are an indication of hemangiosarcoma.

2. The method of claim 1, wherein the determining comprises incubating the population of cells with labeled antibodies that specifically bind the at least one primitive hematopoietic cell marker, the at least one endothelial cell marker and the at least one leukemia cell marker or leukocyte-specific cell marker under conditions such that cells expressing the markers become labeled, and wherein antibodies that bind different markers are differentially labeled; and detecting labeled cells by multiparameter flow cytometry.

3. The method of claim 2, wherein the dog is a purebred dog from a breed where the prevalence of hemangiosarcoma is high, or a mix breed dog containing predominant derivation from a breed where the prevalence of hemangiosarcoma is high.

4. The method of claim 2, wherein one or more of the antibodies is labeled using a secondary detection scheme to increase sensitivity of the method.

5. The method of claim 3, wherein the breed is selected from the group consisting of a Golden Retriever, a German Shepherd, a Portuguese Water Dog, or a Skye Terrier.

6. The method of claim 1, wherein the determining comprises determining the level at which cells in the population of cells concurrently express at least one primitive hematopoietic cell marker selected from the group consisting of CD117, CD133 and CD34.

7. The method of claim 1, wherein the determining comprises determining the level at which cells in the population of cells concurrently express at least one leukemia cell marker or leukocyte-specific cell marker selected from the group consisting of CD18, CD3, CD5, CD21 and CD11b.

8. The method of claim 1, wherein the determining comprises determining the level at which cells in the population of cells concurrently express CD117, CD34, CD51/CD61, and CD18, and/or CD3, CD5, CD21 or CD11b.

9. The method of claim 1, wherein the determining step further comprises determining the fraction of cells in the cell population that concurrently express the plurality of cell markers;

the control is a threshold level representative of the fraction of cells that currently express the plurality of cell markers in a control population; and the comparing step comprises comparing the fraction of cells in the cell population that concurrently express the plurality of cell markers with the threshold level.

10. The method of claim 9, wherein the determining step further comprises (i) incubating the population of cells with differentially labeled antibodies that specifically bind to CD117, CD34, CD51/61, and CD18 and/or CD3, CD5, CD21 or CD11b under conditions such that cells expressing CD117, CD34, CD51/61, and CD18 and/or CD3, CD5, CD21 or CD11b become labeled; and (ii) detecting labeled cells by multiparameter flow cytometry.

11. The method of claim 1, wherein the expression level of the plurality of cell markers is determined at the mRNA level.

12. The method of claim 1, wherein the expression level of the plurality of cell markers is determined at the protein level.

13. A method for assessing risk of hemangiosarcoma, the method comprising:

(a) obtaining a population of cells from a blood sample of a dog; and (b) determining the level at which cells within the cell population express at least one primitive hematopoietic cell marker, at least one endothelial cell marker and at least one leukemia cell marker or leukocyte-specific cell marker, wherein the at least one primitive hematopoietic cell marker is selected from the group consisting of CD117, CD34 and CD133;

the at least one endothelial cell marker is selected from the group consisting of CD51/CD61, CD31, CD105, CD106, CD146 and von Willebrand Factor (vWF);

the at least one leukemia cell marker or leukocyte-specific cell marker is selected from the group consisting of CD18, CD3, CD5, CD21 and CD11b; and (c) comparing the level at which cells in the cell population concurrently express the at least one primitive hematopoietic cell marker and at least one endothelial cell marker with a control level of concurrent expression of the markers and comparing the level at which the cells express the at least one leukemia or leukocyte-specific marker with a control level of the leukemia or leukocyte-specific marker and thereby assessing the risk of hemangiosarcoma.

14. The method of claim 13, wherein the determining step comprises incubating the population of cells with labeled antibodies that specifically bind the at least one primitive hematopoietic cell marker, the at least one endothelial cell marker and the at least one leukemia cell marker or leukocyte-specific cell marker under conditions such that cells expressing the markers become labeled, and wherein antibodies that bind different markers are differentially labeled; and detecting labeled cells by multiparameter flow cytometry.

* * * * *